(12) United States Patent
Wilson et al.

(10) Patent No.: US 9,133,483 B2
(45) Date of Patent: Sep. 15, 2015

(54) SIMIAN ADENOVIRUS NUCLEIC ACID AND AMINO ACID SEQUENCES, VECTORS CONTAINING SAME, AND METHODS OF USE

(71) Applicant: The Trustees of the University of Pennsylvania, Philadelphia, PA (US)

(72) Inventors: James M Wilson, Glen Mills, PA (US); Guangping Gao, Westborough, MA (US); Soumitra Roy, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/073,979

(22) Filed: Nov. 7, 2013

(65) Prior Publication Data

US 2014/0065105 A1    Mar. 6, 2014

Related U.S. Application Data

(60) Division of application No. 13/337,608, filed on Dec. 27, 2011, now Pat. No. 8,603,459, which is a division of application No. 11/820,439, filed on Jun. 19, 2007, now Pat. No. 8,105,574, which is a continuation of application No. 10/494,364, filed as application No. PCT/US02/33645 on Nov. 20, 2002, now Pat. No. 7,247,472.

(60) Provisional application No. 60/366,798, filed on Mar. 22, 2002, provisional application No. 60/331,951, filed on Nov. 21, 2001.

(51) Int. Cl.
| | |
|---|---|
| *C12N 15/861* | (2006.01) |
| *C12N 7/01* | (2006.01) |
| *C12N 15/03* | (2006.01) |
| *C12N 15/86* | (2006.01) |
| *C07K 14/005* | (2006.01) |
| *C12N 7/00* | (2006.01) |
| *A61K 39/00* | (2006.01) |
| *A61K 48/00* | (2006.01) |

(52) U.S. Cl.
CPC .............. *C12N 15/86* (2013.01); *C07K 14/005* (2013.01); *C12N 7/00* (2013.01); *A61K 39/00* (2013.01); *A61K 48/00* (2013.01); *A61K 2039/5256* (2013.01); *A61K 2039/57* (2013.01); *C12N 2710/10321* (2013.01); *C12N 2710/10322* (2013.01); *C12N 2710/10343* (2013.01); *C12N 2710/10362* (2013.01); *C12N 2710/20022* (2013.01); *C12N 2740/16122* (2013.01); *C12N 2740/17022* (2013.01); *C12N 2750/14122* (2013.01); *C12N 2760/14134* (2013.01); *C12N 2760/16134* (2013.01); *C12N 2760/20122* (2013.01); *C12N 2830/002* (2013.01); *C12N 2830/55* (2013.01)

(58) Field of Classification Search
None
See application file for complete search history.

(56) References Cited

U.S. PATENT DOCUMENTS

| | | | |
|---|---|---|---|
| 5,698,202 | A | 12/1997 | Ertl et al. |
| 5,770,442 | A | 6/1998 | Wickham |
| 5,922,315 | A | 7/1999 | Roy et al. |
| 5,972,596 | A | 10/1999 | Pavlakis et al. |
| 6,001,557 | A | 12/1999 | Wilson et al. |
| 6,019,978 | A | 2/2000 | Ertl et al. |
| 6,083,716 | A | 7/2000 | Wilson et al. |
| 6,127,525 | A | 10/2000 | Crystal et al. |
| 6,153,435 | A | 11/2000 | Crystal |
| 6,203,975 | B1 | 3/2001 | Wilson et al. |
| 6,210,663 | B1 | 4/2001 | Ertl et al. |
| 6,287,571 | B1 | 9/2001 | Ertl et al. |
| 7,247,472 | B2 | 7/2007 | Wilson |
| 7,291,498 | B2 | 11/2007 | Roy |
| 7,344,872 | B2 | 3/2008 | Gao |
| 7,491,508 | B2 | 2/2009 | Roy |
| 8,105,574 | B2 | 1/2012 | Wilson |
| 8,394,386 | B2 | 3/2013 | Wilson |
| 8,603,459 | B2 | 12/2013 | Wilson |
| 2004/0136963 | A1 | 7/2004 | Wilson et al. |
| 2004/0171807 | A1 | 9/2004 | Gao et al. |
| 2004/0241181 | A1 | 12/2004 | Ertl |
| 2006/0188527 | A1 | 8/2006 | Hoffman |
| 2007/0218536 | A1 | 9/2007 | Gao |
| 2007/0231347 | A1 | 10/2007 | Wilson |
| 2008/0241189 | A1 | 10/2008 | Wilson |
| 2009/0074810 | A1 | 3/2009 | Roy et al. |
| 2009/0208515 | A1 | 8/2009 | Ertl |
| 2009/0215871 | A1 | 8/2009 | Wilson |
| 2010/0055166 | A1 | 3/2010 | Voss |
| 2010/0150998 | A1 | 6/2010 | Cohen |

FOREIGN PATENT DOCUMENTS

| | | |
|---|---|---|
| EP | 0 787 200 B1 | 4/2005 |
| WO | WO 96/13597 A3 | 5/1996 |

(Continued)

OTHER PUBLICATIONS

GenBank: ABH01061.1, long fiber [Simian adenovirus 7], Jul. 11, 2007.*
Section 21.4 "Genome Composition and Gene Expression", Simian Virology, Voevodin et al, John Wiley & Sons, Aug. 6, 2009 pp. 409.*
Amara et al, Control of a Mucosal Challenge and Prevention of AIDS by a Multiprotein DNA/MVA Vaccine, Science, 292:69-74, (Apr. 6, 2001).
Babiuk et al, Adenoviruses as Vectors for Delivering Vaccines to Mucosal Surfaces, Journal of Biotechnology, 83:105-113, (Sep. 29, 2000).

(Continued)

*Primary Examiner* — Maria Marvich
(74) *Attorney, Agent, or Firm* — Howson & Howson LLP

(57) ABSTRACT

A recombinant vector comprises simian adenovirus sequences and a heterologous gene under the control of regulatory sequences. A cell line which expresses simian adenovirus gene(s) is also disclosed. Methods of using the vectors and cell lines are provided.

12 Claims, 2 Drawing Sheets

(56) References Cited

FOREIGN PATENT DOCUMENTS

| WO | WO-A-98/10087 | 3/1998 |
|---|---|---|
| WO | WO 99/16884 A1 | 4/1999 |
| WO | WO 00/03029 | 1/2000 |
| WO | WO 00/11140 A1 | 3/2000 |
| WO | WO 01/02607 A1 | 1/2001 |
| WO | WO 01/54719 A3 | 8/2001 |
| WO | WO 03/000283 | 1/2003 |
| WO | WO 03/000851 A2 | 1/2003 |
| WO | WO03/046124 | 6/2003 |

OTHER PUBLICATIONS

Bruce et al, Replication-deficient Recombinant Adenoviruses Expressing the Human Immunodeficiency Virus Env Antigen can Induce both Humoral and CTL Immune Responses in Mice, Journal of General Virology, 80:2621-2628, (Oct. 1999).

Cohen et al, Chimpanzee Adenovirus CV-68 Adapted as a Gene Delivery Vector Interacts with the Coxsackievirus and Adenovirus Receptor, Journal of General Virology, 83:151-155, (Jan. 2002).

Crawford-Miksza et al, Analysis of 15 Adenovirus Hexon Proteins Reveals the Location and Structure of Seven Hypervariable Regions Containing Serotype-Specific Residues, Journal of Virology, 70(3):1836-1844, (Mar. 1996).

Crawford-Miksza et al, Strain Variation in Adenovirus Serotypes 4 and 7A Causing Acute Respiratory Disease, Journal of Clinical Microbiology, 37(4):1107-1112, (Apr. 1, 1999).

De Jong et al, Detection, Typing and Subtyping of Enteric Adenoviruses 40 and 41 from Fecal Samples and Observation of Changing Incidences of Infection with These Types and Subtypes, Journal of Clinical Microbiology, 31(6):1562-1569, (Jun. 1993).

Eiz et al, Immunological Adenovirus Variant Strains of Subgenus D: Comparison of the Hexon and Fiber Sequences, Virology, 213(2): 313-320, (Nov. 1, 1995).

Ertl et al, Mucosal Vaccine to HIV-1 Gag, (Apr. 15, 2001) Abstract.

Farina et al, Replication-Defective Vector Based on a Chimpanzee Adenovirus, Journal of Virology, 75(23):11603-11613, (Dec. 2001).

Fitzgerald et al, A Simian Replication-Defective Adenoviral Recombinant Vaccine to HIV-1 Gag1, The Journal of Immunology, 170(3):1416-1422, (Feb. 1, 2003).

Gall, et al., Construction and Characterization of Hexon-Chimeric Adenoviruses: Specification of Adenovirus Serotype, Journal of Virology, 72(12):10260-10264 (Dec. 1998).

Gao et al, Autoimmune Anemia in Macaques Following Erythropoietin Gene Therapy, Abstract 341, 7th Annual Meeting of the American Society of Gene Therapy [Jun. 2-6, 2004] Minneapolis, Minnesota, (e-published—May 2, 2004).

Hashimoto et al, Induction of Protective Immunity to Anthrax Lethal Toxin with a Chimpanzee Adenovirus-Based Vaccine Carrier in the Presence of Pre-Existing Anti-Human Adenovirus Immunity, Abstract 1015, 7th Annual Meeting of the American Society of Gene Therapy [Jun. 2-6, 2004] Minneapolis, Minnesota, (e-published-May 2, 2004).

Holmgren et al, Mucosal Immunity: Implications for Vaccine Development, Immunobiol, 184:157-179, (Feb. 1992).

Kobinger et al, Pseudotyping HIV Vector with the Spike Envelope Protein of SARS-CoV fbr Studying Viral Tropism, Immunology and Gene Therapy Applications, Abstract 368, $7^{th}$ Annual Meeting of the American Society of Gene Therapy [Jun. 2-6, 2004] Minneapolis, Minnesota, (e-published—May 2, 2004).

Kobinger et al, Simian Adenoviral Vector Based-Vaccine Fully Protect Against Ebola Virus Even in the Presence of Pre-Existing Immunity to Human Adenovirus, Abstract 373, $7^{th}$ Annual Meeting of the American Society of Gene Therapy [Jun. 2-6, 2004] Minneapolis, Minnesota, (e-published—May 2, 2004).

Kobinger et al, Pharmacologically Regulated Regeneration of Functional Human Pancreatic Islets, Abstract 1053, $7^{th}$ Annual Meeting of the American Society of Gene Therapy [Jun. 2-6, 2004] Minneapolis, Minnesota, (e-published—May 2, 2004).

Lebherz et al, Nonhuman Primate Models for Retinal and Choroidal Neovascularization using AAV2-Mediated Overexpression of Vascular Endothelial Growth Factor, Abstract 218, $7^{th}$ Annual Meeting of the American Society of Gene Therapy [Jun. 2-6, 2004] Minneapolis, Minnesota, (e-published—May 2, 2004).

Lubeck et al, Immunogenicity of Recombinant Adenovirus-human Immunodeficiency Virus Vaccines in Chimpanzees following Inrranasal Administration, AIDS Res Hum Retroviruses, 10(11):1443-9, (Nov. 1994), abstract only.

Qiu et al, Evaluation of Novel Human Immunodeficiency Virus Type 1 Gag DNA Vaccines for Protein Expression in Mammalian Cells and Induction of Immune Responses, Journal of Virology, 73(11):9145-9152, (Nov. 1999).

Roy et al, Characterization of a Family of Chimpanzee Adenoviruses and Development of Molecular Clones for Gene Transfer Vectors, Human Gene Therapy, 15:519-530 (May 2004).

Roy et al, Use of Chimeric Adenoviral Vectors to Assess Capsid Neutralization Determinants, Abstract 128, $7^{th}$ Annual Meeting of the American Society of Gene Therapy [Jun. 2-6, 2004] Minneapolis, Minnesota, (c-published—May 2, 2004).

Roy et al, Complete Nucleotide Sequences and Genome Organization of Four Chimpanzee Adenoviruses, Virology, 324:361/372, (May 2004).

Roy et al, Circumvention of Immunity to the Adenovirus Major Coat Protein Hexon, Journal of Virology, 72(8): 6875-6879, (Aug. 1, 1998).

Russell et al, Update on Adenovirus and its Vectors, Journal of General Virology, 81:2573-2604, (Nov. 2000).

Santra et al, Recombinant canarypox Vaccine-Elicited CTL Specific for dominant and Subdominant Simian Immunodeficiency Virus Epitopes in Rhesus Monkeys, The Journal of Immunology, 168:1847-1853 (Feb. 2002).

Schneider et al, Inactivation of the Human Immunodeficiency Virus Type 1 Inhibitory Elements Allows Rev-Independent Expression of Gag and Gag/Protease and Particle Formation, Journal of Virology, 71(7): 4892-4903, (Jul. 1997).

Siemens, et al., Cutting edge: Restoration of the ability to generate CTL in mice immune to adenovirus by delivery of virus in a collagen-based matrix, Journal of Immunology, 166(2):731-735 (Jan. 15, 2001).

Stevens, D, American Type Culture Collection Catalogue of Strains II 4th Edition, Viruses and Antisera, p. 226, (1983).

Toes et al, Protective Anti-tumor Immunity Induced by Vaccination with Recombinant Adenoviruses Encoding Multiple Tumor-Associated Cytotoxic T Lymphocyte Epitopes in a String-of-Beads Fashion, Proceedings of the National Academy of Sciences, 94:14660-14665, (Dec. 1997).

Van Olphen et al, Development and Characterization of bovine X Human Hybrid Cell Lines that Efficiently Support the Replication of Both Wild-type Bovine and Human Adenoviruses and Those with E1 Deleted, Journal of Virology, 76(12): 5882-5892, (Jun. 2002).

Wigand et al, Chimpanzee Adenoviruses are Related to Four Subgenera of Human Adenoviruses, Intervirology, 30:1-9, (Jan. 1989).

Wu, Hongju, et al., Construction and characterization of adenovirus serotype 5 packaged by serotype 3 hexon, Journal of Virology, 76(24):12775-12782 (Dec. 2002).

Xiang et al, Novel Chimpanzee Serotype 68-Based Adenoviral Vaccine Carrier for Induction of Antibodies to a Transgene Product, Journal of Virology, 76(6):2667-2675 (Mar. 2002).

Youil et al, Hexon Gene Switch Strategy for t ie Generation of Chimeric Recombinant Adenovirus, Human Gene Therapy, 13:311-320, (Jan. 20, 2002).

Zhi et al, Comparison of Antigen-Specific Immune Responses Elicited by Recombinant Simian Adenoviral Vectors with Deletions in Either E1, or E1/E3, or E1/E4 Regions, Abstract 568, 7th Annual Meeting of the American Society of Gene Therapy [Jun. 2-6, 2004] Minneapolis, Minnesota, (e-published—May 2, 2004).

Zolla-Pazner et al, Induction of Neutralizing Antibodies to T-Cell Line Adapted and Primary Human Immunodeficiency Virus Type 1 Isolates with a Prime-Boost Vaccine Regimen in Chimpanzees, Journal of Virology, 72(2):1052-1059, (Feb. 1998).

(56) References Cited

OTHER PUBLICATIONS

Guo et al, Protein Tolerance to Random Amino Acid Change, Proceedings of National Academy of Sciences of the United States of America, 101(25):9205-9210, (Jun. 22, 2004).
Lesk and J.C. Whisstock, Prediction of Protein Function from Protein Sequence and Structure, pp. 27 and 28, downloaded Sep. 16, 2007, Abstract.
Pring-Akerblon, Hexon Protein-Human Adenovirus 4, Accession No. S57637, submitted to the EMBL Data Library, (Feb. 1995).
Roy et al, Isolation and Characterization of Adenoviruses Persistently Shed from the Gastrointestinal Tract of Non-Human Primates, PLOS, Pathogens, 5(7):1-9, (Jul. 1, 2009).
Bukh et al, Increased Mucosal CD4+ T-cell Activation Following Vaccination with an Adenoviral Vector in *Rhesus macaques*, Retrovirology, vol. 9(2) pp. 267 (Sep. 2012).
Roy et al, Adenoviruses in Fecal Samples from Asymptomatic *Rhesus macaques*, United States, Emerging Infectious Diseases, vol. 18(7):1081-1088 (Jul. 2012).
Roy et al, Construction of Gene Transfer Vectors Based on Simian Adenovirus 7, Journal of General Virology, vol. 92: 1749-1753 (May 2011).
Toogood et al, The Adenovirus Type 40 Hexon Sequence Predicted Structure and Relationship to Other Adenovirus Hexons, J. Virology, 70(12):3203-14 (Dec. 1989).
Response to Communication and Search Report dated Sep. 27, 2011, filed in EP patent application No. 10178464.3.

\* cited by examiner

FIG. 1

```
Hu5    APKGAPNPCEWDEAATALEINLEEEDDNEDEVDEQAEQQKTHVFGQAPYSGINITKEGIQIGVEGQT--
Pan-6  APKGAPNSSQWEQAKTG-------------------NGGTMETHTYGVAPMGGENITKDGLQIGTDVTANQ
Pan-5  APKGAPNTCQWTYKADG-------------------DFGTEKTYTYGNAPVQGISITKDGIQLGTDTDD--
Pan-7  APKGAPNTCQWTYKAG--------------------DFDTEKTYTYGNAPVQGISITKDGIQLGTDSDG--
Pan-9  APKGAPNTCQWTYKADG-------------------ETATEKTYTYGNAPVQGINITKDGIQLGTDTDD--

Hu5    ---PKYADKTFQPEPQIGESQWYETEIN--HAAGRVLKKTTPMKPCYGSYAKPTNENGGQGILVKQQN--G
Pan-6  NKPIYADKTFQPEPQVGEENWQETEN---FYGGRALKKDTNMKPCYGSYARPTNEKGGQAKLKVGDDGVP
Pan-5  -QPIYADKTYQPEPQVGDAEWHDITGTDEKYGGRALKPDTRMKPCYGSFAKPTNKEGGQANVKTETG--G
Pan-7  -QAIYADETYQPEPQVGDAEWHDITGTDEKYGGRALKPDTRMKPCYGSFAKPTNKEGGQANVKTETG--G
Pan-9  -QPIYADKTYQPEPQVGDAEWHDITGTDEKYGGRALKPDTRMKPCYGSFAKPTNKEGGQANVKTGTG--T

Hu5    KLESQVEMQFFSTTEATAGNGDNLTPKVVLYSEDVDIETPDTHISYMPTIKEGNSRELMGQQSMPNRPNY
Pan-6  TKEFDIDLAFFDTPGGTVNGQDEYKADIVMYTENTYLETPDTHVVYKPGKDDASSEINLVQQSMPNRPNY
Pan-5  TKEYDIDMAFFDNRSAAAAG---LAPEIVLYTENVDLETPDTHIVYKAGTDDSSSSINLGQQSMPNRPNY
Pan-7  TKEYDIDMAFFDNRSAAAAG---LAPEIVLYTENVDLETPDTHIVYKAGTDDSSSSINLGQQSMPNRPNY
Pan-9  TKEYDIDMAFFDNRSAAAAG---LAPEIVLYTENVDLETPDTHIVYKAGTDDSSSSINLGQAMPNRPNY

Hu5    IAFRDNFIGLMYYNSTGNMGVLAGQASQLNAVVDLQDRNTELSYQLLLDSIGDRTRYFSMWNQAVDSYDP
Pan-6  IGFRDNFIGLMYYNSTGNMGVLAGQASQLNAVVDLQDRNTELSYQLLLDSLGDRTRYFSMWNQAVDSYDP
Pan-5  IGFRDNFIGLMYYNSTGNMGVLAGQASQLNAVVDLQDRNTELSYQLLLDSLGDRTRYFSMWNQAVDSYDP
Pan-7  IGFRDNFIGLMYYNSTGNMGVLAGQASQLNAVVDLQDRNTELSYQLLLDSLGDRTRYFSMWNQAVDSYDP
Pan-9  IGFRDNFIGLMYYNSTGNMGVLAGQASQLNAVVDLQDRNTELSYQLLLDSLGDRTRYFSMWNQAVDSYDP

Hu5    DVRIIENHGTEDELPNYCFPLGGVINTETLITKVKPKTG-----QENGWEKDATEFSDKNEIRVGNNFAMEI
Pan-6  DVRIIENHGVEDELPNYCFPLDSGTNAAYQGVKVKDGQDGDVESEWENDDTVA-ARNQLCKGNIFAMEI
Pan-5  DVRIIENHGVEDELPNYCFPLDSGTNAAYQGVKVKDGQDGDVESEWENDDTVA-ARNQLCKGNIFAMEI
Pan-7  DVRIIENHGVEDELPNYCFPLDAVGRTDTYQGIKAN-----GDNQTTWTKDDTVN-DANELGKGNPFAMEI
Pan-9  DVRIIENHGVEDELPNYCFPLDAVGRTDTYQGIKAN-----GTDQTTWTKDDSVN-DANEIGKGNPFAMEI
```

FIG. 2

```
Pan-9 fiber knob    (1)   PD       QILAENI A L   C       I  A   SVLV  GSG-N  NP
Pan-6 fiber knob    (1)   PD       QLLSDRI A F   C       I  G   AVAA  TVGSA  NP
Ad 2 fiber knob     (1)   PD       RIHSDNI C F   V       V  A   AALA  SG--D  SS
Ad 5 fiber knob     (1)   PA       RLNA EKI A L   V       V  A   SVLA  KG--S  AP
Pan-7 fiber knob    (1)   AD       KIYSEKI A L   C       I  G   TVLA  NNG-S  NP
Pan-5 fiber knob    (1)   AD       HIYSEKI A L   C       I  G   SLIA  DTG-S  NP Pan-9 fiber knob    (50)  ITG    SSAQVFLR    AN    LTEH STLKK   GY  Q   DSIDGTP   V
Pan-6 fiber knob    (51)  IND    KSAIVFLR    SD    MSNSS MVGD   NF  E   QTTQSVA   V
Ad 2 fiber knob     (49)  MTG    ASVSIFLR    QN    MENSSL KKH   NF  N   NSTNANP   V
Ad 5 fiber knob     (49)  ISG    QSAHLIIR    EN    LNNSFLDPE    NF  N   DLTEGTA   V
Pan-7 fiber knob    (50)  ITN    STALVSLK    AS    LSSSTLDKE    NF  K   DVTPAEP   I
Pan-5 fiber knob    (50)  ITG    TTALVSLK    AN    QSSSTLDSD    NF  Q   DVTPAEA   I Pan-9 fiber knob    (100) LK      SQSSTT   NN    GQ   MN   DVSK ML T   L G   DDS ----
Pan-6 fiber knob    (101) IG      TQSKTP   NS    SQ   LT   ETTM MT T   F G   DEK-DTTP
Ad 2 fiber knob     (99)  LL      TQSQTA   NN    SQ   LH   DKTK MI T   L G   SESTETSE
Ad 5 fiber knob     (99)  LS      SHGKTA   SN    SQ   LN   DKTK VT T   L G   QET-GDTT
Pan-7 fiber knob    (100) IK      NTSAAS   SH    SQ   LN   DEAR LM I   F E   EDAT----
Pan-5 fiber knob    (100) LK      NTSGAA   SH    GK   LH   DTGK LD I   F E   SDES----

Pan-9 fiber knob    (145) NST  SMS  SYT  T-NGS YVGA TF GAN  YT      Q
Pan-6 fiber knob    (150) VST  SMT  TWQ  TGDY KDKNITFAT N  FS       Q
Pan-2 fiber knob    (149) VST  SMS  TWS  E-SGKYTTETFAT N  YT        Q
Ad 5 fiber knob     (148) PSA  SMS  SWD  S-GHNYINEIFATS  YT         Q
Pan-7 fiber knob    (146) -CT  SIT  QWK  D-STKYTGETLATS  FT         Q
Pan-5 fiber knob    (146) -CT  CIN  QWQ  G-ADQYKNETLAVS  FT         K
```

SIMIAN ADENOVIRUS NUCLEIC ACID AND AMINO ACID SEQUENCES, VECTORS CONTAINING SAME, AND METHODS OF USE

CROSS-REFERENCE TO RELATED APPLICATION

This application is a divisional of U.S. patent application Ser. No. 13/337,608, filed Dec. 27, 2011, now U.S. Pat. No. 8,603,458, which is a divisional of U.S. patent application Ser. No. 11/820,439, filed Jun. 19, 2007, now U.S. Pat. No. 8,105,574, which a continuation of U.S. patent application Ser. No. 10/494,364, filed May 12, 2004, now U.S. Pat. No. 7,247,472, which is a 371 of PCT/US02/33645, filed Nov. 20, 2002, which claims the benefit under 35 USC 119(e) of U.S. Provisional Patent Application No. 60/366,798, filed Mar. 22, 2002, and U.S. Provisional Patent Application No. 60/331,951, filed Nov. 21, 2001.

INCORPORATION-BY-REFERENCE OF MATERIAL SUBMITTED IN ELECTRONIC FORM

Applicant hereby incorporates by reference the Sequence Listing material filed in electronic form herewith. This file is labeled "O2677D1_Sequence_ST25.txt".

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (November 2000)]. The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Recombinant adenoviruses have been described for delivery of molecules to host cells. See, U.S. Pat. No. 6,083,716, which describes the genome of two chimpanzee adenoviruses.

What is needed in the art are more effective vectors which avoid the effect of pre-existing immunity to selected adenovirus serotypes in the population and/or which are useful for repeat administration and for titer boosting by second vaccination, if required.

SUMMARY OF THE INVENTION

The present invention provides the isolated nucleic acid sequences and amino acid sequences of six simian adenoviruses, vectors containing these sequences, and cell lines expressing simian adenovirus genes. Also provided are a number of methods for using the vectors and cells of the invention.

The methods of the invention involve delivering one or more selected heterologous gene(s) to a mammalian patient by administering a vector of the invention. Because the various vector constructs are derived from simian rather than from human adenoviruses, the immune system of the non-simian human or veterinary patient is not primed to respond immediately to the vector as a foreign antigen. Use of the compositions of this invention thus permits a more stable expression of the selected transgene when administered to a non-simian patient. Use of the compositions of this invention for vaccination permits presentation of a selected antigen for the elicitation of protective immune responses. Without wishing to be bound by theory, the ability of the adenoviruses of the invention to transduce human dendritic cells is at least partially responsible for the ability of the recombinant constructs of the invention to induce an immune response. The recombinant simian adenoviruses of this invention may also be used for producing heterologous gene products in vitro. Such gene products are themselves useful in a variety for a variety of purposes such as are described herein.

These and other embodiments and advantages of the invention are described in more detail below.

BRIEF DESCRIPTION OF THE DRAWINGS

FIG. 1 provides an alignment of the amino acid sequences of the L1 and a portion of the L2 loops of the capsid protein hexon of the chimpanzee adenovirus C1 [SEQ ID NO:13], chimpanzee adenovirus C68 (Pan-9) [SEQ ID NO:14], and the novel Pan5 [SEQ ID NO:15], Pan6 [SEQ ID NO: 16] and Pan7 [SEQ ID NO: 17] chimpanzee adenovirus sequences of the invention. The intervening conserved region is part of the pedestal domain conserved between adenovirus serotypes.

FIG. 2 provides an alignment of the amino acid sequences of the fiber knob domains of chimpanzee C68 (Pan-9) [SEQ ID NO:18], Pan-6 [SEQ ID NO:19], Pan-7 [SEQ ID NO:20], and Pan-5 [SEQ ID NO:21] and the human adenoviruses serotypes 2 [SEQ ID NO:22] and 5 [SEQ ID NO:23].

DETAILED DESCRIPTION OF THE INVENTION

The invention provides novel nucleic acid and amino acid sequences from Ad Pan5 [SEQ ID NO:1-4, 15 and 21], Ad Pan6 [SEQ ID NO: 5-8, 16, 19], and Ad serotype Pan7 [SEQ ID NO: 9-12, 17, 20], which were originally isolated from chimpanzee lymph nodes. In several instances throughout the specification, these adenoviruses are alternatively termed herein C5, C6 and C7, respectively. Also provided are sequences from adenovirus SV1 [SEQ ID NO: 24-28], which was originally isolated from the kidney cells of cynomolgus monkey. The invention also provides sequences of adenoviruses SV-25 [SEQ ID NO:29-33] and SV-39 [SEQ ID NO: 34-37], which were originally isolated from rhesus monkey kidney cells.

The present invention provides novel adenovirus vectors and packaging cell lines to produce those vectors for use in the in vitro production of recombinant proteins or fragments or other reagents. The invention further provides compositions for use in delivering a heterologous molecule for therapeutic or vaccine purposes. Such therapeutic or vaccine compositions contain the adenoviral vectors carrying an inserted heterologous molecule. In addition, novel sequences of the invention are useful in providing the essential helper functions required for production of recombinant adeno-associated viral (AAV) vectors. Thus, the invention provides helper constructs, methods and cell lines which use these sequences in such production methods.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

I. The Simian Adenovirus Sequences

The invention provides nucleic acid sequences and amino acid sequences of Pan5, Pan6, Pan7, SV1, SV25 and SV39, which are isolated from the other viral material with which they are associated in nature.

A. Nucleic Acid Sequences

The Pan5 nucleic acid sequences of the invention include nucleotides 1 to 36462 of SEQ ID NO:1. The Pan6 nucleic acid sequences of the invention include nucleotides 1 to 36604 of SEQ ID NO: 5. The Pan7 nucleic acid sequences of the invention include nucleotides 1 to 36535 of SEQ ID NO: 9. The SV1 nucleic acid sequences of the invention include nucleotides 1 to 34264 of SEQ ID NO: 24. The SV25 nucleic acid sequences of the invention include nucleotides 1 to 31044 of SEQ ID NO: 29. The SV39 nucleic acid sequences of the invention include nucleotides 1 to 34115 of SEQ ID NO: 34. See, Sequence Listing, which is incorporated by reference herein.

The nucleic acid sequences of the invention further encompass the strand which is complementary to the sequences of SEQ ID NO: 5, 9, 24, 29 and 34, as well as the RNA and cDNA sequences corresponding to the sequences of these sequences figures and their complementary strands. Further included in this invention are nucleic acid sequences which are greater than 95 to 98%, and more preferably about 99 to 99.9% homologous or identical to the Sequence Listing. Also included in the nucleic acid sequences of the invention are natural variants and engineered modifications of the sequences provided in SEQ ID NO: 5, 9, 24, 29 and 34 and their complementary strands. Such modifications include, for example, labels that are known in the art, methylation, and substitution of one or more of the naturally occurring nucleotides with a degenerate nucleotide.

The invention further encompasses fragments of the sequences of Pan5, Pan6, Pan7, SV1, SV25 and SV39, their complementary strand, cDNA and RNA complementary thereto. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables below.

The following tables provide the transcript regions and open reading frames in the simian adenovirus sequences of the invention. For certain genes, the transcripts and open reading frames (ORFs) are located on the strand complementary to that presented in SEQ ID NO: 5, 9, 24, 29 and 34. See, e.g., E2b, E4 and E2a. The calculated molecular weights of the encoded proteins are also shown. Note that the E1a open reading frame Pan5 [nt 576-1436 of SEQ ID NO:1], Pan6 [nt 576 to 1437 of SEQ ID NO: 5] and Pan7 [nt 576 to 1437 of SEQ ID NO: 9] contain internal splice sites. These splice sites are noted in the following tables.

| Ad Pan-5 [SEQ ID NO: 1] | | | | |
|---|---|---|---|---|
| Regions | | Start (nt) | End (nt) | M.W. (Daltons) |
| ITR | | 1 | 120 | — |
| E1a | Transcript | 478 | | — |
| | 13S | 576-664, 1233-1436 | | 28120 |
| | 12S | 576-1046, 1233-1436 | | 24389 |
| | 9S | 576-644, 1233-1436 | | 9962 |
| | Transcript | | 1516 | — |
| E1b | Transcript | 1552 | | — |
| | Small T | 1599 | 2171 | 22317 |
| | Large T | 1904 | 3412 | 55595 |
| | IX | 3492 | 3920 | 14427 |
| | Transcript | | 3959 | — |
| E2b | Transcript | 10349 | | — |
| | PTP | 10349 | 8451 | 72930 |
| | Polymerase | 8448 | 5083 | 127237 |
| | IVa2 | 5604 | 3980 | 50466 |
| | Transcript | | 3960 | — |
| 28.1 kD | | 5155 | 5979 | 28141 |
| Agnoprotein | | 7864 | 8580 | 25755 |
| L1 | Transcript | 10849 | | — |
| | 52/55D | 10851 | 12025 | |
| | IIIa | 12050 | 13819 | 65669 |
| | Transcript | | 13832 | — |
| | Transcript | 13894 | | — |
| L2 | Penton | 13898 | 15490 | 59292 |
| | VII | 15494 | 16078 | 21478 |
| | V | 16123 | 17166 | 39568 |
| | Mu | 17189 | 17422 | 8524 |
| | transcript | | 17442 | — |
| | Transcript | 17488 | | — |
| L3 | VI | 17491 | 18222 | 26192 |
| | Hexon | 18315 | 21116 | 104874 |
| | Endoprotease | 20989 | 21783 | 28304 |
| | transcript | | 21811 | — |
| E2a | Transcript | 26782 | | — |
| | DBP | 23386 | 21845 | 57358 |
| | transcript | | 21788 | — |
| L4 | Transcript | 23406 | | — |
| | 100 kD | 23412 | 25805 | 88223 |
| | 33 kD homolog | 25525 | 26356 | 24538 |
| | VIII | 26428 | 27111 | 24768 |
| | transcript | | 27421 | — |
| E3 | Transcript | 26788 | | — |
| | Orf #1 | 27112 | 27432 | 12098 |
| | Orf #2 | 27386 | 28012 | 23040 |
| | Orf #3 | 27994 | 28527 | 19525 |
| | Orf #4 | 28557 | 29156 | 22567 |
| | Orf #5 | 29169 | 29783 | 22267 |
| | Orf #6 | 29798 | 30673 | 31458 |
| | Orf #7 | 30681 | 30956 | 10477 |
| | Orf #8 | 30962 | 31396 | 16523 |
| | Orf #9 | 31389 | 31796 | 15236 |
| | transcript | | 31837 | — |
| L5 | Transcript | 32032 | | — |
| | Fiber | 32035 | 33372 | 47670 |
| | transcript | | 33443 | — |
| E4 | Transcript | 36135 | | — |
| | Orf 7 | 33710 | 33462 | 9191 |
| | Orf 6 | 34615 | 33710 | 35005 |
| | Orf 4 | 34886 | 34521 | 13878 |
| | Orf 3 | 35249 | 34896 | 13641 |
| | Orf 2 | 35635 | 35246 | 14584 |
| | Orf 1 | 36050 | 35676 | 13772 |
| | Transcript | | 33437 | — |
| ITR | | 36343 | 36462 | — |

| Ad Pan-6 [SEQ ID NO: 5] | | | | |
|---|---|---|---|---|
| Regions | | Start (nt) | End (nt) | M.W. (Daltons) |
| ITR | | 1 | 123 | — |
| E1a | transcript | 478 | | — |
| | 13S | 576-1143, 1229-1437 | | 28291 |
| | 12S | 576-1050, 1229-1437 | | 24634 |
| | 9S | 576-645, 1229-1437 | | 10102 |
| | transcript | | 1516 | — |
| E1b | transcript | 1553 | | — |
| | Small T | 1600 | 2172 | 22315 |
| | Large T | 1905 | 3413 | 55594 |
| | IX | 3498 | 3926 | 14427 |
| | transcript | | 3965 | — |
| E2b | transcript | 10341 | | — |
| | PTP | 10340 | 8451 | 72570 |
| | Polymerase | 8445 | 5089 | 126907 |
| | IVa2 | 5610 | 3986 | 50452 |
| | transcript | | 3966 | — |
| L1 | transcript | 10838 | | — |
| | 52/55 kD | 10840 | 12012 | 44205 |
| | IIIa | 12036 | 13799 | 65460 |
| | Transcript | | 13812 | — |
| 28.1 kd | | 5161 | 5985 | 28012 |
| Agnoprotein | | 7870 | 8580 | 25382 |
| L2 | transcript | 13874 | | — |
| | Penton | 13878 | 15467 | 59314 |
| | VII | 15471 | 16055 | 21508 |
| | V | 16100 | 17137 | 39388 |
| | Mu | 17160 | 17393 | 8506 |
| | transcript | | 17415 | — |
| L3 | transcript | 17466 | | — |
| | VI | 17469 | 18188 | 25860 |
| | Hexon | 18284 | 21112 | 106132 |
| | Endoprotease | 21134 | 21754 | 23445 |
| | transcript | | 21803 | — |
| E2a | transcript | 26780 | | — |
| | DBP | 23375 | 21837 | 57299 |
| | transcript | | 21780 | — |
| L4 | Transcript | 23398 | | — |
| | 100 kD | 23404 | 25806 | 88577 |
| | 33 kD homolog | 25523 | 26357 | 24609 |
| | VIII | 26426 | 27109 | 24749 |
| | transcript | | 27419 | — |
| E3 | transcript | 26786 | | — |
| | Orf #1 | 27110 | 27430 | 12098 |
| | Orf #2 | 27384 | 28007 | 22880 |
| | Orf #3 | 27989 | 28519 | 19460 |
| | Orf #4 | 28553 | 29236 | 25403 |
| | Orf #5 | 29249 | 29860 | 22350 |
| | Orf #6 | 29875 | 30741 | 31028 |
| | Orf #7 | 30749 | 31024 | 10469 |
| | Orf #8 | 31030 | 31464 | 16540 |
| | Orf #9 | 31457 | 31864 | 15264 |
| | transcript | | 31907 | — |
| L5 | transcript | 32159 | | — |
| | Fiber | 32162 | 33493 | 47364 |
| | transcript | | 33574 | — |
| E4 | transcript | 36276 | | — |
| | Orf 7 | 33841 | 33593 | 9177 |
| | Orf 6 | 34746 | 33841 | 35094 |
| | Orf 4 | 35017 | 34652 | 13937 |
| | Orf 3 | 35380 | 35027 | 13627 |
| | Orf 2 | 35766 | 35377 | 14727 |
| | Orf 1 | 36181 | 35807 | 13739 |
| | transcript | | 33558 | — |
| ITR | | 36482 | 36604 | — |

| Ad Pan-7 [SEQ ID NO: 9] | | | | |
|---|---|---|---|---|
| Regions | | Start (nt) | End (nt) | M.W. (Daltons) |
| ITR | | 1 | 132 | — |
| E1a | transcript | 478 | | — |
| | 13S | 576-1143, 1229-1437 | | 28218 |
| | 12S | 576-1050, 1229-1437 | | 24561 |

-continued

| Ad Pan-7 [SEQ ID NO: 9] | | | |
|---|---|---|---|
| Regions | Start (nt) | End (nt) | M.W. (Daltons) |
| 9S | 576-645, 1229-1437 | | 10102 |
| transcript | | 1516 | — |
| E1b transcript | 1553 | | — |
| Small T | 1600 | 2178 | 22559 |
| LargeT | 1905 | 3419 | 55698 |
| IVa2 | 3992 | 5616 | 50210 |
| transcript | | 3971 | — |
| E2b transcript | 10341 | | — |
| PTP | 10340 | 8457 | 72297 |
| Polymerase | 8451 | 5095 | 126994 |
| IX | 3504 | 3932 | 14441 |
| transcript | | 3972 | — |
| 28.1 kD | 5167 | 5991 | 28028 |
| Agnoprotein | 7876 | 8586 | 25424 |
| L1 transcript | 10834 | | |
| 52/55 kD | 10836 | 12011 | 44302 |
| IIIa | 12035 | 13795 | 65339 |
| transcript | | 13808 | — |
| L2 transcript | 13870 | | — |
| Penton | 13874 | 15469 | 59494 |
| VII | 15473 | 16057 | 21339 |
| V | 16102 | 17139 | 39414 |
| Mu | 17167 | 17400 | 8506 |
| transcript | | 17420 | — |
| L3 transcript | 17467 | | — |
| VI | 17470 | 18198 | 26105 |
| Hexon | 18288 | 21086 | 104763 |
| Endoprotease | 21106 | 21732 | 23620 |
| transcript | | 21781 | — |
| E2a transcript | 26764 | | — |
| DBP | 23353 | 21815 | 57199 |
| transcript | | 21755 | — |
| L4 transcript | 23370 | | — |
| 100 kD | 23376 | 25781 | 88520 |
| 33 kD | 25489 | 26338 | 25155 |
| homolog | | | |
| VIII | 26410 | 27093 | 24749 |
| transcript | | 27403 | — |
| E3 transcript | 26770 | | — |
| Orf #1 | 27094 | 27414 | 12056 |
| Orf #2 | 27368 | 27988 | 22667 |
| Orf #3 | 27970 | 28500 | 19462 |
| Orf #4 | 28530 | 29150 | 22999 |
| Orf #5 | 29163 | 29777 | 22224 |
| Orf #6 | 29792 | 30679 | 32153 |
| Orf #7 | 30687 | 30962 | 10511 |
| Orf #8 | 30968 | 31399 | 16388 |
| Orf #9 | 31392 | 31799 | 15205 |
| transcript | | 31842 | — |
| L5 transcript | 32091 | | — |
| Fiber | 32094 | 33425 | 47344 |
| transcript | | 33517 | — |
| E4 transcript | 36208 | | — |
| Orf 7 | 33784 | 33536 | 9191 |
| Orf 6 | 34689 | 33784 | 35063 |
| Orf 4 | 34960 | 34595 | 13879 |
| Orf 3 | 35323 | 34970 | 13641 |
| Orf 2 | 35709 | 35320 | 14644 |
| Orf 1 | 36123 | 35749 | 13746 |
| transcript | | 33501 | — |
| ITR | 36404 | 36535 | — |

| | Ad SV-1 [SEQ ID NO: 24] | | Ad SV-25 [SEQ ID NO: 29] | | Ad SV-39 [SEQ ID NO: 34] | |
|---|---|---|---|---|---|---|
| Region | Start | End | Start | End | Start | End |
| ITR | 1 | 106 | 1 | 133 | 1 | 150 |
| E1a | 352 | 1120 | — | — | 404 | 1409 |
| E1b | 1301 | 2891 | 359 | 2273 | 1518 | 3877 |
| E2b | 9257 | 2882 | 9087 | 2754 | 10143 | 3868 |
| E2a | 24415 | 20281 | 24034 | 20086 | 25381 | 21228 |
| E3 | 24974 | 27886 | 24791 | 25792 | 25790 | 29335 |
| E4 | 33498 | 30881 | 30696 | 28163 | 33896 | 31157 |
| ITR | 34145 | 34264 | 30912 | 31044 | 33966 | 34115 |
| ITR | 1 | 106 | 1 | 133 | 1 | 150 |
| L1 | 9513 | 12376 | 9343 | 12206 | 10416 | 13383 |
| L2 | 12453 | 15858 | 12283 | 15696 | 13444 | 16877 |
| L3 | 15910 | 20270 | 15748 | 20080 | 17783 | 21192 |
| L4 | 21715 | 25603 | 21526 | 25420 | 22659 | 26427 |
| L5 | 28059 | 30899 | 25320 | 28172 | 29513 | 31170 |
| ITR | 34145 | 34264 | 30912 | 31044 | 33966 | 34115 |

| | | Ad SV-1, SEQ ID NO: 24 | | |
|---|---|---|---|---|
| | protein | Start | End | M.W. |
| ITR | | 1 | 106 | — |
| E1a | 13S | 459 | 953 | 18039 |
| | 12S | | | |
| E1b | Small T | | | |
| | LargeT | 1301 | 2413 | 42293 |
| | IX | 2391 | 2885 | 16882 |
| E2b | IVa2 | 4354 | 2924 | 54087 |
| | Polymerase | 6750 | 4027 | 102883 |
| | PTP | 9257 | 7371 | 72413 |
| | Agno-protein | 6850 | 7455 | 20984 |
| L1 | 52/55 kD | 9515 | 10642 | 42675 |
| | IIIa | 10663 | 12372 | 636568 |
| L2 | Penton | 12454 | 13965 | 56725 |
| | VII | 13968 | 14531 | 20397 |
| | V | 14588 | 15625 | 39374 |
| | Mu | 15645 | 15857 | 7568 |
| L3 | VI | 15911 | 16753 | 30418 |
| | Hexon | 16841 | 19636 | 104494 |
| | Endoprotease | 19645 | 20262 | 23407 |
| 2a | DBP | 21700 | 20312 | 52107 |
| L4 | 100 kD | 21721 | 24009 | 85508 |
| | VIII | 24591 | 25292 | 25390 |
| E3 | Orf #1 | 25292 | 25609 | 11950 |
| | Orf #2 | 25563 | 26081 | 18940 |
| | Orf #3 | 26084 | 26893 | 30452 |
| | Orf #4 | 26908 | 27180 | 10232 |
| | Orf #5 | 27177 | 17512 | 12640 |
| | Orf #6 | 27505 | 27873 | 13639 |
| L5 | Fiber #2 | 28059 | 29150 | 39472 |
| | Fiber #1 | 29183 | 30867 | 61128 |
| E4 | Orf 7 | 31098 | 30892 | 7837 |
| | Orf 6 | 31982 | 31122 | 33921 |
| | Orf 4 | 32277 | 31915 | 14338 |
| | Orf 3 | 32629 | 32279 | 13386 |
| | Orf 2 | 33018 | 32626 | 14753 |
| | Orf 1 | 33423 | 33043 | 14301 |
| ITR | | 34145 | 34264 | |

| | | Ad SV-25, SEQ ID NO: 29 | | | Ad SV-39, SEQ ID NO: 34 | | |
|---|---|---|---|---|---|---|---|
| | protein | Start | End | M.W. | Start | End | M.W. |
| ITR | | 1 | 133 | — | 1 | 150 | |
| E1a | 13S | | | | 492 | 1355 | 28585 |
| | 12S | | | | 492 | 1355 | 25003 |
| E1b | Small T | 478 | 1030 | 20274 | 1518 | 2075 | 21652 |
| | Large T | 829 | 2244 | 52310 | 1823 | 3349 | 55534 |
| | IX | 2306 | 2716 | 13854 | 3434 | 3844 | 14075 |
| E2b | IVa2 | 4208 | 2755 | 54675 | 3912 | 5141 | 46164 |
| | Poly-merase | 6581 | 3858 | 102839 | 7753 | 5033 | 103988 |
| | PTP | 9087 | 7207 | 71326 | 10143 | 8335 | 69274 |

-continued

| | protein | Ad SV-25, SEQ ID NO: 29 | | | Ad SV-39, SEQ ID NO: 34 | | |
|---|---|---|---|---|---|---|---|
| | | Start | End | M.W. | Start | End | M.W. |
| | Agno-protein | 6681 | 7139 | 16025 | — | — | — |
| L1 | 52/55 kD | 9345 | 10472 | 42703 | 10418 | 11608 | 44232 |
| | IIIa | 10493 | 12202 | 63598 | 11574 | 13364 | 66078 |
| L2 | Penton | 12284 | 13801 | 56949 | 13448 | 14959 | 56292 |
| | VII | 13806 | 14369 | 20369 | 14960 | 15517 | 20374 |
| | V | 14426 | 15463 | 39289 | 15567 | 16628 | 39676 |
| | Mu | 15483 | 15695 | 7598 | 16650 | 16871 | 7497 |
| L3 | VI | 15749 | 16591 | 30347 | 16925 | 17695 | 28043 |
| | Hexon | 16681 | 19446 | 10435 | 17785 | 20538 | 102579 |
| | Endo-protease | 19455 | 20072 | 23338 | 20573 | 21181 | 22716 |
| 2a | DBP | 21511 | 20123 | 52189 | 22631 | 21231 | 53160 |
| L4 | 100 kD | 21532 | 23829 | 85970 | 22659 | 25355 | 100362 |
| | VIII | 24408 | 25109 | 25347 | 25410 | 26108 | 25229 |
| E3 | Orf #1 | 25109 | 25426 | 11890 | 26375 | 27484 | 42257 |
| | Orf #2 | | | | 27580 | 28357 | 29785 |
| | Orf #3 | | | | 28370 | 28645 | 10514 |
| | Orf #4 | | | | 28863 | 29333 | 18835 |
| | Orf #5 | | | | | | |
| | Orf #6 | | | | | | |
| L5 | Fiber #2 | 25380 | 26423 | 37529 | | | |
| | Fiber #1 | 26457 | 28136 | 60707 | 29515 | 31116 | 56382 |
| E4 | Orf 7 | | | | 31441 | 31118 | 11856 |
| | Orf 6 | 29255 | 28395 | 33905 | 32292 | 31438 | 33437 |
| | Orf 4 | 29550 | 29188 | 14399 | 32587 | 32222 | 13997 |
| | Orf 3 | 29902 | 29552 | 13284 | 32954 | 32607 | 13353 |
| | Orf 2 | 30291 | 29899 | 14853 | 33348 | 32959 | 14821 |
| | Orf 1 | 30316 | 30696 | 14301 | 33764 | 33378 | 14235 |
| ITR | | 30912 | 31044 | | 33966 | 34115 | |

The Pan5, Pan6, Pan7, SV1, SV25 and SV39 adenoviral nucleic acid sequences are useful as therapeutic agents and in construction of a variety of vector systems and host cells. As used herein, a vector includes any suitable nucleic acid molecule including, naked DNA, a plasmid, a virus, a cosmid, or an episome. These sequences and products may be used alone or in combination with other adenoviral sequences or fragments, or in combination with elements from other adenoviral or non-adenoviral sequences. The adenoviral sequences of the invention are also useful as antisense delivery vectors, gene therapy vectors, or vaccine vectors. Thus, the invention further provides nucleic acid molecules, gene delivery vectors, and host cells which contain the Ad sequences of the invention.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E4ORF6 region.

In addition, the adenoviral gene sequences and fragments thereof are useful for providing the helper functions necessary for production of helper-dependent viruses (e.g., adenoviral vectors deleted of essential functions or adeno-associated viruses (AAV)). For such production methods, the simian adenoviral sequences of the invention are utilized in such a method in a manner similar to those described for the human Ad. However, due to the differences in sequences between the simian adenoviral sequences of the invention and those of human Ad, the use of the sequences of the invention essentially eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258,595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The simian adenoviral gene sequences of the invention which provide the necessary helper functions (e.g., E1a, E1b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the adenoviral sequences of the invention may be utilized in these rAAV production methods.

Alternatively, recombinant adenoviral simian vectors of the invention may be utilized in these methods. Such recombinant adenoviral simian vectors may include, e.g., a hybrid chimp Ad/AAV in which chimp Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or gene sequences of the invention will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an adenovirus E1a protein of the invention may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, the Pan5, Pan6, Pan7, SV1, SV25 and/or SV39 simian Ad genomes of the invention can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of naked DNA, a plasmid, a virus or any other genetic element.

B. Simian Adenoviral Proteins of the Invention

The invention further provides gene products of the above adenoviruses, such as proteins, enzymes, and fragments thereof, which are encoded by the adenoviral nucleic acids of the invention. The invention further encompasses Pan5, Pan6 and Pan7, SV1, SV25 and SV39 proteins, enzymes, and fragments thereof, having the amino acid sequences encoded by these nucleic acid sequences which are generated by other methods. Such proteins include those encoded by the open reading frames identified in the tables above, in FIGS. 1 and 2, and fragments thereof.

Thus, in one aspect, the invention provides unique simian adenoviral proteins which are substantially pure, i.e., are free of other viral and proteinaceous proteins. Preferably, these proteins are at least 10% homogeneous, more preferably 60% homogeneous, and most preferably 95% homogeneous.

In one embodiment, the invention provides unique simian-derived capsid proteins. As used herein, a simian-derived capsid protein includes any adenoviral capsid protein that contains a Pan5, Pan6, Pan7, SV1, SV25 or SV39 capsid protein or a fragment thereof, as defined above, including, without limitation, chimeric capsid proteins, fusion proteins, artificial capsid proteins, synthetic capsid proteins, and recombinantly capsid proteins, without limitation to means of generating these proteins.

Suitably, these simian-derived capsid proteins contain one or more Pan5, Pan6, Pan7, SV1, SV25 or SV39 regions or fragments thereof (e.g., a hexon, penton, fiber or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e., a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotypes which may be of human or non-human origin. Such Ad may be obtained from a variety of sources including the ATCC, commercial and academic sources, or the sequences of the Ad may be obtained from GenBank or other suitable sources.

The amino acid sequences of the simian adenoviruses penton proteins of the invention are provided herein. The AdPan5 penton protein is provided in SEQ ID NO:2. The AdPan7 penton is provided in SEQ ID NO:6. The AdPan6 penton is provided in SEQ ID NO:10. The SV1 penton is provided in SEQ ID NO:25. The SV25 penton protein is provided in SEQ ID NO:30. The SV39 penton is provided in SEQ ID NO:35. Suitably, any of these penton proteins, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above and in SEQ ID NO:2; SEQ ID NO:6; SEQ ID NO:25; SEQ ID NO:30, or SEQ ID NO:35. Other suitable fragments include shorter internal, C-terminal, or N-terminal fragments. Further, the penton protein may be modified for a variety of purposes known to those of skill in the art.

The invention further provides the amino acid sequences of the hexon protein of Pan5 [SEQ ID NO:3], Pan6 [SEQ ID NO:7], Pan 7 [SEQ ID NO:11], SV1 [SEQ ID NO:26], SV25 [SEQ ID NO:31], and/or SV39 [SEQ ID NO:36]. Suitably, this hexon protein, or unique fragments thereof, may be utilized for a variety of purposes. Examples of suitable fragments include the hexon having N-terminal and/or C-terminal truncations of about 50, 100, 150, 200, 300, 400, or 500 amino acids, based upon the amino acid numbering provided above and in SEQ ID NO: 3, 7, 11, 26, 31 and 36. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; and about 404 to about 430 of the simian hexon proteins, with reference to SEQ ID NO: 3, 7, 11, 26, 31 or 36. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one example, it may be desirable to generate an adenovirus having an altered hexon protein utilizing the sequences of a hexon protein of the invention. One suitable method for altering hexon proteins is described in U.S. Pat. No. 5,922, 315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of the invention (e.g. Pan7). In one embodiment, a loop region of the Pan7 hexon protein is replaced by a loop region from another adenovirus serotype. In another embodiment, the loop region of the Pan7 hexon is used to replace a loop region from another adenovirus serotype. Suitable adenovirus serotypes may be readily selected from among human and non-human serotypes, as described herein. Pan7 is selected for purposes of illustration only; the other simian Ad hexon proteins of the invention may be similarly altered, or used to alter another Ad hexon. The selection of a suitable serotype is not a limitation of the present invention. Still other uses for the hexon protein sequences of the invention will be readily apparent to those of skill in the art.

The invention further encompasses the fiber proteins of the simian adenoviruses of the invention. The fiber protein of AdPan 5 has the amino acid sequence of SEQ ID NO:4. The fiber protein AdPan6 has the amino acid sequence of SEQ ID NO: 8. The fiber protein of AdPan7 has the amino acid sequence of SEQ ID NO: 12. SV-1 has two fiber proteins; fiber 2 has the amino acid sequence of SEQ ID NO:27 and fiber 1 has the amino acid sequence of SEQ ID NO:28. SV-25 also has two fiber proteins; fiber 2 has the amino acid sequence of SEQ ID NO:32 and fiber 1 has the amino acid sequence of SEQ ID NO:33. The fiber protein of SV-39 has the amino acid sequence of SEQ ID NO:37.

Suitably, this fiber protein, or unique fragments thereof, may be utilized for a variety of purposes. One suitable fragment is the fiber knob, which spans about amino acids 247 to 425 of SEQ ID NO: 4, 8, 12, 28, 32, 33 and 37. See FIG. 2. Examples of other suitable fragments include the fiber having N-terminal and/or C-terminal truncations of about 50, 100, 150, or 200 amino acids, based upon the amino acid numbering provided above and in SEQ ID NO: 4, 8, 12, 28, 32, 33 and 37. Still other suitable fragments include internal fragments. Further, the fiber protein may be modified using a variety of techniques known to those of skill in the art.

The invention further encompasses unique fragments of the proteins of the invention which are at least 8 amino acids in length. However, fragments of other desired lengths can be readily utilized. In addition, the invention encompasses such modifications as may be introduced to enhance yield and/or expression of a Pan5, Pan6, Pan7, SV1, SV25 or SV39 gene product, e.g., construction of a fusion molecule in which all or a fragment of the Pan5, Pan6, Pan7, SV1, SV25 or SV39 gene product is fused (either directly or via a linker) with a fusion partner to enhance. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. The invention further encompasses proteins having at least about 95% to 99% identity to the Pan5, Pan6, Pan7, SV1, SV25 or SV39 proteins provided herein.

As described herein, vectors of the invention containing the adenoviral capsid proteins of the invention are particularly well suited for use in applications in which the neutralizing antibodies diminish the effectiveness of other Ad serotype based vectors, as well as other viral vectors. The rAd vectors of the invention are particularly advantageous in readministration for repeat gene therapy or for boosting immune response (vaccine titers).

Under certain circumstances, it may be desirable to use one or more of the Pan5, Pan6, Pan7, SV1, SV25 and/or SV39 gene products (e.g., a capsid protein or a fragment thereof) to generate an antibody. The term "an antibody," as used herein, refers to an immunoglobulin molecule which is able to specifically bind to an epitope. Thus, the antibodies of the invention bind, preferably specifically and without cross-reactivity, to a Pan5, Pan6, Pan7, SV1, SV25 or SV39 epitope. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods know in the art. Suitable antibodies may be generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 Science, 233:747-753; Queen et al., 1989 Proc. Nat'l. Acad. Sci. USA, 86:10029-10033; PCT Patent Application No. PCT/WO9007861; and Riechmann et al., Nature, 332:323-327 (1988); Huse et al, 1988a Science, 246:1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; and Bird et al., 1988, Science 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 J. Am. Soc. Microbiol., Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a Pan5, Pan6, Pan7, SV1, SV25 or SV39 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods of this invention are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of the invention may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, J. Am. Chem. Soc., 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe L K, et al, *Gene Ther.* 2001 May; 8(10):795-803 and Medina-Kauwe L K, et al, *Gene Ther.* 2001 December; 8(23): 1753-1761. Alternatively, the amino acid sequences of simian Ad protein IX may be utilized for targeting vectors to a cell surface receptor, as described in US Patent Appln 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other adenoviral proteins of the invention may be used as alone, or in combination with other adenoviral protein, for a variety of purposes which will be readily apparent to one of skill in the art. In addition, still other uses for the adenoviral proteins of the invention will be readily apparent to one of skill in the art.

II. Recombinant Adenoviral Vectors

The compositions of this invention include vectors that deliver a heterologous molecule to cells, either for therapeutic or vaccine purposes. As used herein, a vector may include any genetic element including, without limitation, naked DNA, a phage, transposon, cosmid, episome, plasmid, or a virus. Such vectors contain simian adenovirus DNA of Pan5, Pan6, Pan7, SV1, SV25 and/or SV39 and a minigene. By "minigene" is meant the combination of a selected heterologous gene and the other regulatory elements necessary to drive translation, transcription and/or expression of the gene product in a host cell.

Typically, an adenoviral vector of the invention is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of such as the site of a functional E1 deletion or functional E3 deletion, among others that may be selected. The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' inverted terminal repeat (ITR) sequences (which functions as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene is located between the 5' and 3' adenoviral sequences. Any adenoviral vector of the invention may also contain additional adenoviral sequences.

Suitably, these adenoviral vectors of the invention contain one or more adenoviral elements derived from an adenoviral genome of the invention. In one embodiment, the vectors contain adenoviral ITRs from Pan5, Pan6, Pan7, SV1, SV25 or SV39 and additional adenoviral sequences from the same adenoviral serotype. In another embodiment, the vectors contain adenoviral sequences that are derived from a different adenoviral serotype than that which provides the ITRs. As defined herein, a pseudotyped adenovirus refers to an adenovirus in which the capsid protein of the adenovirus is from a different serotype than the serotype which provides the ITRs. The selection of the serotype of the ITRs and the serotype of any other adenoviral sequences present in vector is not a limitation of the present invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other simian or from human adenoviruses are described in the published literature [see, for example, U.S. Pat. No. 5,240,846]. The DNA sequences of a number of adenovirus types are available from GenBank, including type Ad5 [GenBank Accession No. M73260]. The adenovirus sequences may be obtained from any known adenovirus serotype, such as serotypes 2, 3, 4, 7, 12 and 40, and further including any of the presently identified human types. Similarly adenoviruses known to infect non-human animals (e.g., simians) may also be employed in the vector constructs of this invention. See, e.g., U.S. Pat. No. 6,083, 716.

The viral sequences, helper viruses, if needed, and recombinant viral particles, and other vector components and sequences employed in the construction of the vectors described herein are obtained as described above. The DNA sequences of the Pan5, Pan6, Pan7, SV1, SV25 and/or SV39 simian adenovirus sequences of the invention are employed to construct vectors and cell lines useful in the preparation of such vectors.

Modifications of the nucleic acid sequences forming the vectors of this invention, including sequence deletions, insertions, and other mutations may be generated using standard molecular biological techniques and are within the scope of this invention.

A. The "Minigene"

The methods employed for the selection of the transgene, the cloning and construction of the "minigene" and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al., *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)]. Other systems include the FK506 dimer, VP16 or p65 using castradiol, diphenol murislerone, the RU486-inducible system [Wang et al, *Nat. Biotech.*, 15:239-243 (1997) and Wang et al, *Gene Ther.,* 4:432-441 (1997)] and the rapamycin-inducible system [Magari et al, *J. Clin. Invest.*, 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal ∃-actin, myosin light chain 2A, dystrophin, muscle creatine kinase, as well as synthetic muscle promoters with activities higher than naturally occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

III. Production of the Recombinant Viral Particle

In one embodiment, the simian adenoviral plasmids (or other vectors) are used to produce recombinant adenoviral particles. In one embodiment, the recombinant adenoviruses are functionally deleted in the E1a or E1b genes, and optionally bearing other mutations, e.g., temperature-sensitive mutations or deletions in other genes. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In the construction of useful simian adenovirus vectors for delivery of a gene to the human (or other mammalian) cell, a range of adenovirus nucleic acid sequences can be employed in the vectors. For example, all or a portion of the adenovirus delayed early gene E3 may be eliminated from the simian adenovirus sequence which forms a part of the recombinant virus. The function of simian E3 is believed to be irrelevant to the function and production of the recombinant virus particle. Simian adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and IVa$_2$ may be useful for some purposes. Other deletions may be made in the other structural or non-structural adenovirus genes. The above discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the simian adenovirus gene content of the viral vectors employed to carry the minigene, a helper adenovirus or non-replicating virus fragment may be necessary to provide sufficient simian adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264:16985-16987 (1989); K. J. Fisher and J. M. Wilson, *Biochem. J.*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant simian adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from Pan5, Pan6, Pan7, SV1, SV25 or SV39 under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired AdPan5, Pan6, Pan7, SV1, SV25 or SV39 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant simian adenovirus E1 deleted vectors. Additionally, or alternatively, the invention provides cell lines that express one or more simian adenoviral gene products, e.g., E1a, E1b, E2a, and/or E4 ORF6, can be constructed using essentially the same procedures for use in the generation of recombinant simian viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), Hum Gene Ther, 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant simian adenoviruses are useful in transferring a selected transgene to a selected cell. In in vivo experiments with the recombinant virus grown in the packaging cell lines, the E1-deleted recombinant simian adenoviral vectors of the invention demonstrate utility in transferring a transgene to a non-simian, preferably a human, cell.

IV. Use of the Recombinant Adenovirus Vectors

The recombinant simian adenovirus vectors of the invention are useful for gene transfer to a human or non-simian veterinary patient in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A Pan5, Pan6, Pan7, SV1, SV25 or SV39-derived recombinant simian adenoviral vector of the invention provides an efficient gene transfer vehicle that can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the Pan 5, Pan6, Pan7, SV1, SV25, or SV39 recombinant adenoviral vectors of the invention will be utilized for delivery of therapeutic or immunogenic molecules, as described below. It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first simian capsid, delivery with a rAd with a second simian capsid, and delivery with a third simian capsid. A variety of other regimens which use the Ad capsids of the invention alone, in combination with one another, or in combination with other Ad serotypes will be apparent to those of skill in the art. Optionally, such a regimen may involve administration of rAd with capsids of other non-human primate adenoviruses, human adenoviruses, or artificial serotypes such as are described herein. Each phase of the regimen may involve administration of a series of injections (or other delivery routes) with a single Ad serotype capsid followed by a series with another Ad serotype capsid. Alternatively, the recombinant Ad vectors of the invention may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the above-described recombinant vectors are administered to humans according to published methods for gene therapy. A simian viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The simian adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 µL to about 100 mL of a carrier containing concentrations of from about $1 \times 10^6$ to about $1 \times 10^{15}$ particles, about $1 \times 10^{11}$ to $1 \times 10^{13}$ particles, or about $1 \times 10^9$ to $1 \times 10^{12}$ particles virus. Dosages will range depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be delivered. In another example, a suitable human or veterinary dosage may be in the range of about $1 \times 10^{11}$ to about $1 \times 10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector. A variety of useful immune modulators and dosages for use of same are disclosed, for example, in Yang et al., *J. Virol.*, 70(9) (September, 1996); International Patent Application No. WO96/12406, published May 2, 1996; and International Patent Application No. PCT/US96/03035, all incorporated herein by reference.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor (TGF), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZFS, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The simian adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a Pan5, Pan6, Pan7, SV1, SV25 or SV39 simian adenoviral vector, followed by re-administration with a vector from the same serotype adenovirus. Particularly desirable regimens involve administration of a Pan5, Pan6, Pan7, SV1, SV25 or SV39 simian adenoviral vector of the invention, in which the serotype of the viral vector delivered in the first administration differs from the serotype of the viral vector utilized in one or more of the subsequent administrations. For example, a therapeutic regimen involves administration of a Pan5, Pan6, Pan7, SV1, SV25 or SV39 vector and repeat administration with one or more adenoviral vectors of the same or different serotypes. In another example, a therapeutic regimen involves administration of an adenoviral vector followed by repeat administration with a Pan5, Pan6, Pan7, SV1, SV25 or SV39 vector of the invention which differs from the serotype of the first delivered adenoviral vector, and optionally further administration with another vector which is the same or, preferably, differs from the serotype of the vector in the prior administration steps. These regimens are not limited to delivery of adenoviral vectors constructed using the Pan5, Pan6, Pan7, SV1, SV25 or SV39 simian serotypes of the invention. Rather, these regimens can readily utilize vectors other adenoviral serotypes, including, without limitation, other simian adenoviral serotypes (e.g., Pan9 or C68, C1, etc), other non-human primate adenoviral serotypes, or human adenoviral serotypes, in combination with one or more of the Pan5, Pan6, Pan7, SV1, SV25 or SV39 vectors of the invention. Examples of such simian, other non-human primate and human adenoviral serotypes are discussed elsewhere in this document. Further, these therapeutic regimens may involve either simultaneous or sequential delivery of Pan 5, Pan6, Pan7, SV1, SV25, and/or SV39 adenoviral vectors of the invention in combination with non-adenoviral vectors, non-viral vectors, and/or a variety of other therapeutically useful compounds or molecules. The present invention is not limited to these therapeutic regimens, a variety of which will be readily apparent to one of skill in the art.

B. Ad-Mediated Delivery of Immunogenic Transgenes

The recombinant simian adenoviruses may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. The present invention provides a recombinant simian Ad that can contain in any of its adenovirus sequence deletions a gene encoding a desired immunogen. The simian adenovirus is likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g. adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant adenoviruses of this invention are expected to be highly efficacious at inducing cytolytic T cells and antibodies to the inserted heterologous antigenic protein expressed by the vector.

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, J. Virol., 75(5): 2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); brucella; *Franisella tularensis* (which causes tularemia); yersinia (pasteurella); streptobacillus moniliformis and spirillum; Gram-positive bacilli include listeria monocytogenes; erysipelothrix rhusiopathiae; *Corynebacterium diphtheria* (diphtheria); cholera; *B. anthracia* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); Brucella species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In RA, several specific variable regions of TCRs which are involved in the disease have been characterized. These TCRs include V-3, V-14, V-17 and V$\alpha$-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and V$\alpha$-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and V$\alpha$-16, V$\alpha$-3C, V$\alpha$-7, V$\alpha$-14, V$\alpha$-15, V$\alpha$-16, V$\alpha$-28 and V$\alpha$-12. Thus, delivery of a recombinant simian adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the recombinant simian adenoviral vectors of the invention may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to second, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a recombinant simian adenoviral vector of the invention to boost the immune response to a vector (either viral or DNA-based) carrying an antigen, or a protein. In still another alternative, an immunization regimen involves administration of a protein followed by booster with a vector encoding the antigen.

In one embodiment, the invention provides a method of priming and boosting an immune response to a selected antigen by delivering a plasmid DNA vector carrying said antigen, followed by boosting with a recombinant simian adenoviral vector of the invention. In one embodiment, the prime-boost regimen involves the expression of multiproteins from the prime and/or the boost vehicle. See, e.g., R. R. Amara, *Science*, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant adenovirus construct of the invention. Still other regimens are described in WO 99/16884 and WO 01/54719.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The invention is not limited to the amount or situs of injection(s) or to the pharmaceutical carrier. Rather, the regimen may involve a priming and/or boosting step, each of which may include a single dose or dosage that is administered hourly, daily, weekly or monthly, or yearly. As an example, the mammals may receive one or two doses containing between about 10 µg to about 50 µg of plasmid in carrier. A desirable amount of a DNA composition ranges between about 1 µg to about 10,000 µg of the DNA vector. Dosages may vary from about 1 µg to 1000 µg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the simian adenoviral vectors of the invention are also well suited for use in a variety of other immunization and therapeutic regimens. Such regimens may involve delivery of simian adenoviral vectors of the invention simultaneously or sequentially with Ad vectors of different serotype capsids, regimens in which adenoviral vectors of the invention are delivered simultaneously or sequentially with non-Ad vectors, regimens in which the adenoviral vectors of the invention are delivered simultaneously or sequentially with proteins, peptides, and/or other biologically useful therapeutic or immunogenic compounds. Such uses will be readily apparent to one of skill in the art.

The following examples illustrate the cloning of the simian adenoviruses and the construction of exemplary recombinant adenovirus vectors of the present invention. These examples are illustrative only, and do not limit the scope of the present invention.

EXAMPLE 1

Viral Propagation

The Pan5 [ATCC Accession No. VR-591], Pan6 [ATCC Accession No. VR-592], and Pan7 [ATCC Accession No. VR-593] viruses, originally isolated from lymph nodes from chimpanzees, were propagated in 293 cells [ATCC CRL1573]. Typically, these cells are cultured in Dulbecco's Modified Eagles Medium (DMEM; Sigma, St. Louis, Mo.) supplemented with 10% fetal calf serum (FCS) [Sigma or Hyclone, Logan, Utah] and 1% Penicillin-Streptomycin (Sigma). Infection of 293 cells is carried out in DMEM supplemented with 2% FCS for the first 24 hours, after which FCS is added to bring the final concentration to 10%. Infected cells are harvested when 100% of the cells exhibit virus-induced cytopathic effect (CPE), and are then collected, and concentrated by centrifugation. Cell pellets are resuspended in 10 mM Tris (pH 8.0), and lysed by 3 cycles of freezing and thawing. Virus preparations are obtained following two ultra centrifugation steps on cesium chloride density gradients and stocks of virus are diluted to 1 to $5\times10^{12}$ particles/ml in 10 mM Tris/100 mM NaCl/50% glycerol and stored at −70° C.

The ability of 293 cells to propagate these adenoviruses exceeded expectations which were based on knowledge of other non-human adenovirus serotypes.

| Virus | Yield (virus particles produced in $8 \times 10^8$ cells) |
| --- | --- |
| Pan5 | $8.8 \times 10^{13}$ |
| Pan6 | $1.6 \times 10^{14}$ |
| Pan7 | $8.8 \times 10^{13}$ |

EXAMPLE 2

Characterization of Viral Genomic DNA

Genomic DNA was isolated from the purified virus preparations of Example 1 and digested with HindIII or BamHI restriction enzymes following the manufacturers' recommendations. The results (not shown) revealed that that the Pan5, Pan6, Pan7 genomes of the invention and the published Pan 9 (C68) genome show different restriction patterns, and thus, are distinct from each other.

The nucleotide sequences of Pan5, Pan6 and Pan7 were determined. The nucleotide sequence of the top strand of Pan5 DNA is reported in SEQ ID NO: 1. The nucleotide sequence of the top strand of Pan6 DNA is reported in SEQ ID NO: 5. The nucleotide sequence of the top strand of Pan7 DNA is reported in SEQ ID NO: 9.

Regulatory and coding regions in the viral DNA sequences were identified by homology to known adenoviral sequences using the "Clustal W" program described above at conventional settings. See the tables above providing the adenoviral sequences. Open reading frames were translated and the predicted amino acid sequences examined for homology to previously described adenoviral protein sequences, Ad4, Ad5, Ad7, Ad12, and Ad40.

Analysis of the sequence revealed a genome organization that is similar to that present in human adenoviruses, with the greatest similarity to human Ad4. However, substantial differences in the hexon hypervariable regions were noted between the chimpanzee adenoviruses and other known adenoviruses, including AdHu4. These differences fit well with the serological cross-reactivity data that has been obtained (see below).

An alignment of a portion of the hexon sequences is shown in FIG. 1. The portion shown is from the region of the hexon that corresponds to the outwardly disposed extended loops DE1 and FG1 where the most variability between serotypes is observed. An intervening portion that contributes to the base of the hexon (corresponding to residues 308-368 of the published AdC68 sequence; U.S. Pat. No. 6,083,716), and is highly conserved between serotypes, is also present. The following table summarizes the pair-wise comparisons of the amino acids in the hexon proteins.

| Comparison | | Hexon amino-acid |
| --- | --- | --- |
| #1 | #2 | Similarity (%) |
| AdC5 | AdC7 | 99.0 |
| AdC5 | AdC68 | 98.3 |
| AdC5 | AdC6 | 88.0 |
| AdC5 | AdC1 | 84.9 |
| AdC6 | AdC7 | 87.7 |
| AdC6 | AdC68 | 87.3 |
| AdC6 | AdC1 | 84.9 |
| AdC7 | AdC68 | 97.5 |
| AdC7 | AdC1 | 84.8 |
| AdC68 | AdC1 | 84.9 |

Analysis of the fiber knob domain (which is responsible for receptor binding) of the chimpanzee adenoviruses shows an overall similarity in structure (FIG. 2).

The degree of sequence similarity between the E1 proteins of huAd5 and C68 (see Tables below) is similar to that between huAd5 and Pan-5, Pan-6, and Pan-7.

| Comparison | | E1a (13S) amino-acid |
| --- | --- | --- |
| #1 | #2 | identity (%) |
| AdHu5 | AdC5 | 36.6 |
| AdHu5 | AdC6 | 28.5 |
| AdHu5 | AdC7 | 34.9 |
| AdHu5 | AdC68 | 35.6 |
| AdHu5 | AdC1 | 35.6 |
| AdC5 | AdC6 | 68.3 |

-continued

| Comparison | | E1a (13S) amino-acid |
|---|---|---|
| #1 | #2 | identity (%) |
| AdC5 | AdC7 | 96.9 |
| AdC5 | AdC68 | 80.4 |
| AdC5 | AdC1 | 51.3 |
| AdC6 | AdC7 | 69.3 |
| AdC6 | AdC68 | 59.4 |
| AdC6 | AdC1 | 37.7 |
| AdC7 | AdC68 | 81.5 |
| AdC7 | AdC1 | 51.0 |
| AdC68 | AdC1 | 54.9 |

| | Sequence Identity with human Ad5 | |
|---|---|---|
| | E1b Small T Protein | E1b Large T Protein |
| C68 | 47.3% | 55.8% |
| Pan-5 | 43.2% | 54.5% |
| Pan-6 | 45.3% | 54.5% |
| Pan-7 | 46.4% | 53.8% |

Replication-defective versions of AdC5, AdC6 and AdC7 were created by molecular cloning methods described in the following examples in which minigene cassettes were inserted into the place of the E1a and E1b genes. The molecular clones of the recombinant viruses were rescued and grown up in 293 cells for large-scale purification using the published CsCl sedimentation method [K. Fisher et al., J. Virol., 70:520 (1996)]. Vector yields were based on 50 plate (150 mm) preps in which approximately $1 \times 10^9$ 293 cells were infected with the corresponding viruses. Yields were determined by measuring viral particle concentrations spectrophotometrically. After having constructed E1-deleted vectors, it was determined that HEK 293 cells (which express human adenovirus serotype 5 E1 functions) trans-complement the E1 deletions of the novel viral vectors and allow for the production of high titer stocks. Examples of virus yields for a few of these recombinant viruses are shown in the table below.

The transgenes for these vectors, β-galactosidase (LacZ), green fluorescent protein (GFP), alpha-1-anti-trypsin (A1AT), ebola glycoprotein (ebo), a soluble ebola glycoprotein variant lacking the transmembrane and cytoplasmic domains (sEbo), and three deletion mutants of the ebola glycoprotein (EboΔ2, EboΔ3, and EboΔ4), were expressed by the cytomegalovirus promoter (CMV). In the following table, ND indicates that the study has not yet been done.

| | Viral backbone/Vector yield (Viral particles × $10^{13}$) | | | |
|---|---|---|---|---|
| Transgene | AdHu5 | AdC7 | AdC68 | AdC6 |
| CMVLacZ | 1.5 | 1.4 | 3.3 | 6.1 |
| CMVGFP | 2.5 | 3.6 | 8 | 10 |
| CMVA1AT | 3.7 | 6 | 10 | ND |
| CMVEbo | 1.1 | 4.3 | ND | ND |
| CMVsEbo | 4.9 | 5.4 | ND | ND |
| CMVEboΔ2 | 1 | 9.3 | ND | ND |
| CMVEboΔ3 | 0.8 | 9.5 | ND | ND |
| CMVEboΔ4 | 1.4 | 6.2 | ND | ND |

The ability of human adenovirus E1 to trans-complement the E1-deleted chimpanzee viruses of the invention is highly advantageous, as it permits the production of E1-deleted chimpanzee adenoviral vectors of the invention, while reducing or eliminating the risk of homologous recombination due to the differences in sequences between human Ad and the chimpanzee adenoviruses described herein.

EXAMPLE 3

Serological Studies of Pan 5, 6, and 7 Viruses

Because of the differences in the hexon hypervariable region, it was anticipated that the C5, C6, and C7 viruses would be serologically distinct from human adenoviruses, including AdHu4.

1. Cross-Reactivity of Wild-Type Viruses

For screening of wild-type viruses in order to make a determination of antibody cross-reactivity, the replication competent viruses were used and inhibition of cytopathic effects (CPE) was measured. Briefly, preparations of adenoviruses (Adhu5, Pan-5, Pan-6, Pan-7 and AdC68) stored at $5 \times 10^{12}$ particles/ml were diluted 1/600 for the assays. This concentration of virus was selected since it results in 100% CPE within 48 hours in the absence of neutralization. Prior to adding the virus to 293 cells ($4 \times 10^4$ cells/well in a 96 well dish), 1:20 dilutions of sera were added. The assay is read as the presence or absence of CPE; full neutralization would read as no cytopathic effect. The results are summarized in the Table below. The fact that 9/36 human sera neutralized Adhu5 induced CPE is consistent with previous estimates of neutralizing antibodies in the human population. The numbers indicate the total individuals who showed neutralization (numerator) versus the total number screened (denominator). ND=not determined

| | Neutralization by 1/20 diln of serum | | |
|---|---|---|---|
| | Human (N = 36) | Rhesus (N = 52) | Chimpanzee (N = 20) |
| Adhu5 | 9/36 | ND | ND |
| AdC68 | 1/36 | 0/52 | 12/20 |
| Pan 5 | 0/36 | 0/52 | 10/20 |
| Pan 6 | 0/36 | 0/52 | 9/20 |
| Pan 7 | 0/36 | 0/52 | 12/20 |

Of all human sera screened, 35/36 were negative for neutralization to AdC68 while 36/36 were negative for neutralization to Pan-5, Pan-6 and Pan-7. Of 52 rhesus monkeys screened, none showed neutralization to any chimpanzee adenovirus; rhesus monkey is the preferred pre-clinical model for evaluating HIV vaccines. Between 9 to 12 out of 20 chimpanzees had substantial neutralization to one or another of the chimpanzee adenoviruses consistent with the fact these are indeed endemic chimpanzee-specific pathogens. Interestingly, there are chimpanzees with neutralizing antibodies only to Pan-5, Pan-6 or AdC68 supporting the hypothesis that several of these chimpanzee adenoviral vectors will not cross neutralize each other and are distinct serotypes.

The same assay was carried out for 20 chimpanzee serum samples. Fifty percent (50%) of the samples reacted serologically, in different degrees to Pan5; 40% to Pan6; 55% to Pan7 and 60% to C68. Among the positive serum samples, one of them had strong neutralizing activity to all four chimp viruses.

2. Cross-Neutralization with Recombinant Viruses

High-titer polyclonal antibodies were obtained to each of the simian adenoviruses in order to more precisely gauge the degree of cross-neutralization among the different serotypes.

This was done by intramuscular immunization of rabbits using a recombinant virus containing GFP based on previously the described C68 chimpanzee adenovirus as an adjuvant. The serum was then used to assay for neutralizing activity against each of the three chimpanzee adenoviruses of the invention, AdC5, AdC6 and AdC7. A rabbit was injected with $5\times10^{12}$ viral particle per kg of C68CMVGFP vector intramuscularly and boosted 5 weeks later using the same dose. A bleed collected at the 9 week time point revealed extremely potent neutralizing activity against C68 as well as Pan-5 and Pan-7 but not against Pan-6 (see Table below), indicating that the administration of a C68 (or Pan-5 and Pan-7) based vaccine could be effectively followed by a boost using a vector based on Pan-6. However, it has been found that this level of inter-relatedness does not necessarily prevent with re-administration in a setting where antiviral antibody titers were not as high as was achieved in this rabbit. In the following table, + indicates 33% CPE; ++ indicates 66% CPE; +++ indicates 100% CPE.

| Infection on 293 cells with virus: | | | | | |
|---|---|---|---|---|---|
| Pan5 | Pan6 | Pan7 | Pan9 (C68) | C68 GFP | Serum Dilution |
| − | +++ | − | − | − | 1/20 |
| − | +++ | − | − | − | 1/40 |
| − | +++ | − | − | − | 1/80 |
| − | +++ | − | − | − | 1/160 |
| − | +++ | − | − | − | 1/320 |
| − | +++ | − | − | − | 1/640 |
| − | +++ | − | − | − | 1/1,280 |
| − | +++ | − | − | − | 1/2,560 |
| − | +++ | − | − | − | 1/5,120 |
| + | +++ | − | − | − | 1/10,240 |
| + | +++ | ++ | − | − | 1/20,480 |
| ++ | +++ | +++ | − | − | 1/40,960 |
| ++ | +++ | +++ | + | + | 1/81,920 |
| +++ | +++ | +++ | ++ | ++ | 1/163,840 |
| +++ | +++ | +++ | +++ | +++ | 1/327,680 |
| +++ | +++ | +++ | +++ | +++ | 1/665,360 |
| +++ | +++ | +++ | +++ | +++ | 1/1,310,720 |
| +++ | +++ | +++ | +++ | +++ | 1/2,621,440 |

3. Quantitative Assay for Detection of Neutralizing Antibody

The result was validated by a more quantitative-based assay for detecting neutralizing antibody, which is based on transduction of a GFP vector. Briefly, groups of C57BL/6 mice were immunized intramuscularly or intravenously with $5.0\times10^{10}$ particles/ml Pan5, Pan6, Pan7 or C68. Sera from day 28 bleeds were tested for cross-neutralizing activity against C68CMVEGFP at dilutions of 1/20 and 1/80. In summary, when a pharmaceutical preparation of human immunoglobulin was tested for serological reactions to Pan 5, 6, and 7, and C68, some low levels of neutralizing activities against Pan 7 and C68 were detected. No neutralizing activity against Pan5 or Pan6 was detected. Serum samples from 36 human subjects were run for the same assay. Serum samples were tested at a 1/20 dilution. The results indicated that only one individual has clear neutralizing activity to C68. No neutralizing activity to Pan5, Pan6 or Pan7 was detected.

4. In Vitro Cross-Neutralization

Cross-neutralization of the simian adenoviruses by high-titer rabbit polyclonal antibodies raised against each of the adenoviruses Pan-5, Pan-6, Pan-7, and C68 was tested.

Rabbits were immunized with intra-muscular injections of $10^{13}$ particles of each of the chimpanzee adenoviruses and boosted 40 days later with the same dose with incomplete Freund's adjuvant. Sera were analyzed or the presence of neutralizing antibodies by incubating serial two-fold dilutions with $10^9$ genome copies of each of the appropriate chimpanzee adenovirus vector expressing GFP and testing for the attenuation of GFP expression when applied to 293 cells. The serum dilution which produced a 50% reduction of GFP expression was scored as the neutralizing antibody titer against that particular virus.

The results are shown in the Table. The data are consistent with the expectation from sequence analysis of the hexon amino-acid sequences, which indicated that Ad Pan-6 was likely to be the most serologically distinct compared to the other chimpanzee adenoviruses.

| Serum from rabbit immunized with: | Infection of 293 cells with $10^9$ genome copies of | | | |
|---|---|---|---|---|
| | Ad Pan-5 | Ad Pan-6 | Ad Pan-7 | Ad C68 |
| Ad Pan-5 | 1/5120 | <1/20 | 1/2560 | 1/2560 |
| Ad Pan-6 | No neutralization | 1/20,480 | <1/20 | <1/20 |
| Ad Pan-7 | 1/2560 | 1/160 | 1/163,840 | 1/2560 |
| Ad C68 | No neutralization | <1/20 | <1/20 | 1/5120 |

In order to determine whether antibodies cross-reacting with the simian adenoviruses were likely to be of low prevalence in humans, simian adenoviruses SV1, SV39, and SV25 were tested for their ability to withstand neutralization when incubated with commercially available pooled human immunoglobulins (Ig). The same assay was also performed with Adhu5 and the chimpanzee adenoviruses Pan-5, Pan-6, Pan-7, and C68. In a further study, sera from mice has been immunized with one of the chimpanzee adenoviruses C5, C6, C7, and C68 and their ability to cross-neutralize the simian adenoviruses SV-15, SV-23, SA-17, and Baboon Adenovirus has been tested. No cross-reactivity was observed in any case.

EXAMPLE 4

Generation of Recombinant E1-Deleted Pan5 Vector

A modified pX plasmid was prepared by destroying the FspI site in the bla gene region of pX (Clontech) by site-directed mutagenesis. The resulting modified plasmid, termed pX', is a circular plasmid of 3000 bp which contains an f1 ori and an ampicillin resistance gene (AmpR-cds).

A. Production of Pan-5 Adenovirus Plasmid

A polylinker for sequential cloning of the Pan5 DNA fragments into pX' is created. The polylinker is substituted for the existing pX' polylinker following digestion with MluI and EcoRI. The blunt-FseI fragment of the Pan 5 is inserted into the SmaI and FseI sites of the polylinker. This fragment contains the 5' end of the adenoviral genome (bp 1 to 3606, SEQ ID NO:1). The SnaBI-FspI fragment of Pan 5 (bp 455 to 3484, SEQ ID NO:1) is replaced with a short sequence flanked by I-Ceu and PI-Sce sites from pShuttle (Clontech), to eliminate the E1 region of the adenoviral genome. The EcoRI-blunt fragment of Pan5 (bp 28658 to 36462, SEQ ID NO:1) is inserted into the EcoRI and EcoRV sites of the polylinker (to provide the 3' end of the adenoviral genome); the FseI-MluI fragment (bp 3606 to 15135, SEQ ID NO:1) is inserted into the polylinker; and the MluI-EcoRI fragment is inserted into the polylinker (bp 15135 to 28658, SEQ ID NO:1). Optionally, a desired transgene is inserted into I-CeuI and PI-SceI sites of the newly created pX'Pan5)E1 vector.

B. Alternative Method of Generating pX'Pan5)E1.

The initial plasmid pX is derived from pAdX adenovirus plasmid available from Clontech, as described above. Thereafter, a PacI-XhoI region of pX' was deleted and the blunt-ended Pan5 polylinker was inserted into the FspI site to generate pX'PLNK (2994 bp). The 5' end-FseI region of Pan 5 (bp 1-3607, SEQ ID NO:1) was inserted into SmaI and FseI sites of pX'LNK to generate the pX'Pan5-5' plasmid (6591 bp). The SnaBi-NdeI region of pX'Pan5-5' was excised and replaced with the Ceu/Sce cassette, which had been PCR amplified from pRCS to create pX'Pan5-5')E1 (4374 bp). Briefly, a sequence containing I-CeuI and PI-SceI rare cutter sites was PCR amplified from pRCS (3113 bp). The 3' PCR primer was introduced an NdeI site into the PCR product.

To extend the Pan5 DNA in pX'Pan5-5')E1 (4374 bp), the FseI-MluI region of Pan 5 (bp 3607-15135, SEQ ID NO:1) is added, to create pX'Pan5-5'Mlu (15900 bp). The remaining MluI-3' end of the Pan5 sequence (bp 15135-36462, SEQ ID NO:1) is added to the vector between the MluI and EcoRV sites of the vector polylinker to form pX'Pan5)E1 which contains the full-length Pan5 sequence containing a deletion in the E1 region.

C. Generation of Recombinant Viruses

To generate the recombinant adenoviruses from pX'Pan5)E1, the plasmid is co-transfected with a helper expressing E1, or from an E1-expressing packaging cell line, such as 293 cell line or a cell line prepared as described herein. The expression of E1 in the packaging cell permits the replication and packaging of the Pan5)E1 into a virion capsid. In another embodiment, the packaging cell transfected with pX'Pan5)E1 is transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus.

Transfection is followed by an agar overlay for 2 weeks, after which the viruses are plaqued, expanded and screened for expression of the transgene. Several additional rounds of plaque purification are followed by another expansion of the cultures. Finally the cells are harvested, a virus extract prepared and the recombinant chimpanzee adenovirus containing the desired transgene is purified by buoyant density ultracentrifugation in a CsCl gradient or by alternative means known to those of skill in the art.

EXAMPLE 5

Generation of Recombinant E1-Deleted Pan6 Vector

A. Strategy for Construction of Pan-6 Adenoviral Plasmid
1. Cloning of Terminal Fragments Pan 6 virus is deproteinated by pronase and proteanase K treatment and phenol extraction. Synthetic 12 bp Pme I linkers are ligated onto the viral DNA as described by Berkner and Sharp, *Nucleic Acids Research*, 11: 6003 (1983). The viral DNA is then digested with Xba I to isolate a 5' terminal fragment (6043 bp). The Ad6 XbaI 5' fragment is then ligated into pX link at Sma I and Xba I sites to form pX-AdPan6-0-16.5. The viral DNA with Pme I linkers is also digested with Pac I to isolate the 6475 bp 3' terminal fragment and cloned into pX link at Pac I and Sma I sites, resulting in pXAdPan6-82-100.

2. Deletion of E1 from the 5' Clone

To delete E1 (m.u.1.2-9), the BsiWi-Xba I fragment in pX-AdPan6-0-16.5 is replaced with a PCR fragment spanning m.u.9-16.7 fragment treated with BsiWi and Xba I, leading to pX-Ad-Pan6 m.u.0-1, 9-16.5.

3. Fusion of 5' and 3' Clones and to Create an Anchor Site to Accept the Middle Hind III Fragment First, the 5' clone, pX-Ad-Pan6 m.u.0-1, 9-16.5, is further expanded by inserting the $2^{nd}$ Xba I fragment (4350 bp, m.u.16.5-28) from Pan 6 genome into the Xba I site in the pX-Ad-Pan6 m.u.0-1, 9-16.5. This construct is named pXAd-Pan6-mu 0-1, 9-28.

Second, the 3' clone is also expanded by inserting the 15026 bp Mlu I/Pac I fragment covering m.u.41-82 from Pan 6 genome into the Mlu I/Pac I sites of pXAdPan6-82-100, generating pXAdPan6-m.u.41-100.

Then, a 8167 bp Hind III/Eco 47111 Pan 6 fragment is isolated from pXAd-Pan6-mu 0-1, 9-28 and subcloned into pXAdPan6-m.u.41-100 at Hind III and Xba I blunt sites. This 5' and 3' fusion clone is called pXAdPan6mu0-1, 9-19.5, 64-100.

4. Drop of the Middle Fragment of the Genome into the Fusion Clone

A 16335 bp Hind III fragment (m.u.19.5-64) from Pan 6 is inserted into Hind III site of pXAdPan6mu0-1, 9-19.5, 64-100 to form pXAdPan6-0-1, 9-100.

5. Introduction of a PKGFP Selective Marker into the Final Construct for Direct Cloning the Gene of Interest and Green/White Selection of Recombinant Transformants.

A minigene cassette that expresses GFP under a lac promoter and is flanked with recognition sites of rare intron encoding restriction enzymes, PI-Sce I and I-Ceu I, was isolated from pShuttle-pkGFP (bare) by Sap I and Dra III digestions followed by filling-in reaction. The pShuttle-pkGFP (bare) plasmid is 4126 bp in length, and contains a ColE1-Ori, a kanamycin resistance gene, plac, a LacZ promoter-GFP-mut3-1 cds (Clontech), and a GFPmut3-1 cds (Clontech). This cassette is subcloned into Srf I cut and blunted pXAd-Pan6-0-1, 9-100. This final construct is called pX-Pan6-pkGFP mu.0-1, 9-100, which is useful for generating recombinant E1-deleted Pan 6 molecular clones carrying genes of interest by direct ligation and green/white selection in combination with the generic pShuttlepkGFP vectors.

B. Alternative Strategy for Generation of Pan-6 Plasmid
1. Cloning of 5' Terminal Fragment The Pan 6 virus is deproteinated by pronase and proteanase K treatment and phenol extraction as described above and synthetic 12 bp Pme I linkers are ligated onto the viral DNA as described. The AdPan6 5' XbaI fragment is isolated and ligated into pX to form pX-AdPan6-0-16.5 (9022 bp) as described in Part A above.

2. Deletion of E1 from the 5' Clone

To delete E1 (m.u. 1.2-9), pX-AdPan6-0-16.5 is digested with SnaBI and NdeI to remove the regions encoding the E1a and E1b proteins (3442-6310 bp). This vector is subsequently digested with BsiWI in preparation for blunting with the minigene cassette carrying a selective marker.

3. Introduction of a Selective Marker

A minigene cassette that expressed GFP under a lac promoter and which is flanked with recognition sites of rare intron encoding restriction enzymes, PI-XceI and I-CeuI, was isolated from pShuttle-pkGFP as described above. The DraIII-SapI fragment is then ligated with the digested pX-AdPan6-0-16.5 to form pX-AdPan6 MU 0-16.5)E1 (7749 bp).

4. Extension of Pan-6 Adenoviral Sequences pX-AdPan6 MU 0-16.5)E1 was subjected to XbaI digestion to permit insertion of an XbaI-RsrII linker. An XbaI/RsrII digestion fragment from the AdPan6 genome was isolated (mu 28-100, 26240 bp) and ligated into the Xba/RsrII-digested pX-AdPan6 MU 0-16.5)E1 to provide pX-AdPan6 MU 0-1, 9-16.5, 28-100. A second XbaI fragment from the Pan6 genome (mu 16.5-28, 4350 bp) is then ligated into this plasmid to form pX-AdPan6 MU 0-1, 9-100 (38551 bp).

C. Generation of Recombinant Adenoviruses

To generate the recombinant adenoviruses from a E1-deleted Pan6 plasmid prepared as described in Parts A or b, the plasmid is co-transfected with a helper expressing E1, or from an E1-expressing packaging cell line, such as 293 cell line or a cell line prepared as described herein. The expression of E1 in the packaging cell permits the replication and packaging of the Pan6-pkGFP mu.0-1, 9-100 into a virion capsid. Alternatively, the packaging cell transfected with pX-Pan6-pkGFP mu.0-1, 9-100 is transfected with an adenovirus vector as described above bearing another transgene of interest.

EXAMPLE 6

Generation of Recombinant E1-Deleted Pan7 Vector

A. Generation of Pan7 Plasmids

A synthetic linker containing the restriction sites PacI-SmaI-FseI-MluI-EcoRV-PacI was cloned into pBR322 that was cut with EcoRI and NdeI. The left end (bp1 to 3618) of Ad Pan7 was cloned into the linker between the SmaI and FseI sites. The adenovirus E1 was then excised from the cloned left end by cutting with SnaBI and NdeI and inserting an I-CeuI-GFP-PI-SceI cassette from pShuttle (Clontech) in its place. The resulting plasmid was cut with FseI and MluI and Ad Pan7 fragment FseI (bp 3618) to MluI (bp 155114 was inserted to extend the left end. The construct (pPan7pGFP) was completed by inserting the 21421 bp Ad Pan7 right end fragment from the MluI site (bp 15114) into the above plasmid between MluI and EcoRV to generate a complete molecular clone of E1 deleted adenovirus Pan7 suitable for the generation of recombinant adenoviruses. Optionally, a desired transgene is inserted into the I-CeuI and PI-SceI sites of the newly created pPan7 vector plasmid.

B. Construction of E1-Deleted Pan7 Viral Vectors

To generate the recombinant adenoviruses from pPan7)E1, the plasmid is co-transfected with a helper expressing E1, or from an E1-expressing packaging cell line, such as 293 cell line or a cell line prepared as described herein. The expression of E1 in the packaging cell permits the replication and packaging of the Pan7)E1 into a virion capsid. In another embodiment, the packaging cell transfected with pX'Pan7)E1 is transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus. Transfection and purification is as described above.

EXAMPLE 7

Generation of Plasmid Vectors Expressing the E1 Genes

Plasmid vectors are constructed which encode the Pan5 E1 region gene, and these plasmids are used to generate stable cell lines expressing viral E1 proteins.

The E1 region of Pan5 is cloned into pX', essentially as described in Example 4 above, prior to replacement of this region with the fragment from pShuttle (Clontech). The expression plasmid contains the Pan5 adenoviral genome sequence spanning at least by 1 to 3959 in the Pan5 genomic sequence. Thus, the expression plasmid contains the sequence encoding E1a and E1b of chimpanzee Ad Pan5 under the control of a heterologous promoter. Similar expression plasmids can be generated using the Ad Pan6 and AdPan 7 E1 regions, identified in the tables above.

EXAMPLE 8

Generation of Cell Lines Expressing Chimpanzee Adenovirus E1 Proteins

Cell lines expressing viral E1 proteins are generated by transfecting HeLa (ATCC Acc. No. CCL2) with the plasmid of Example 6. These cell lines are useful for the production of E1-deleted recombinant chimpanzee adenoviruses by co-transfection of genomic viral DNA and the expression plasmids described above. Transfection of these cell lines, as well as isolation and purification of recombinant chimpanzee adenoviruses therefrom are performed by methods conventional for other adenoviruses, i.e., human adenoviruses [see, e.g., Horwitz, cited above and other standard texts].

A. Cell Lines Expressing Pan5 E1 Proteins

HeLa cells in 10 cm dishes are transfected with 10 μg of pX-Pan51-E1 DNA using a Cellphect™ kit (Pharmacia, Uppsala, Sweden) and following the manufacturer's protocol. 22 hours post-transfection, the cells are subjected to a three minute glycerol shock (15% glycerol in Hepes Buffered Saline, pH 7.5) washed once in DMEM (HeLa) or F12K (A549; Life Technologies, Inc., Grand Island, N.Y.) media supplemented with 10% FCS, 1% Pen-Strep, then incubated for six hours at 37° C. in the above described media. The transfected cells are then split into duplicate 15 cm plates at ratios of 1:20, 1:40, 1:80, 1:160, and 1:320. Following incubation at 37° C. overnight, the media is supplemented with G418 (Life Technologies, Inc.) at a concentration of 1 μg/ml. The media is replaced every 5 days and clones are isolated 20 days post-transfection.

HeLa E1 cell clones are isolated and assayed for their ability to augment adeno-associated virus (AAV) infection and expression of recombinant LacZ protein as described below.

B. AAV Augmentation Assay for Screening E1 Expressing Cell Lines

AAV requires adenovirus-encoded proteins in order to complete its life cycle. The adenoviral E1 proteins as well as the E4 region-encoded ORF6 protein are necessary for the augmentation of AAV infection. An assay for E1 expression based on AAV augmentation is used. Briefly, the method for identifying adenoviral E1-expressing cells comprises the steps of infecting in separate cultures a putative adenovirus E1-expressing cell and a cell containing no adenovirus sequence, with both an adeno-associated virus (AAV) expressing a marker gene and an AAV expressing the ORF6 of the E4 gene of human adenovirus, for a suitable time. The marker gene activity in the resulting cells is measured and those cells with significantly greater measurable marker activity than the control cells are selected as confirmed E1-expressing cells. In the following experiment, the marker gene is a lacZ gene and the marker activity is the appearance of blue stain.

For example, the cell lines described above, as well as untransfected control cells (HeLa) are infected with 100 genomes per cell of an AAV vector bearing a marker gene, e.g., AV.LacZ [K. Fisher et al., J. Virol., 70:520 (1996)] and an AAV vector expressing the ORF6 region of human 5 (AV.orf6). The DNA sequence of the plasmid generates a novel recombinant adeno-associated virus (rAAV) containing the LacZ transgene and the Ad E4 ORF 6, which is an open reading frame whose expression product facilitates single-stranded (ss) to double-stranded (ds) conversion of rAAV genomic DNA. These vectors are incubated in medium containing 2% FCS and 1% Pen-Strep at 37° C. for 4 hours, at which point an equal volume of medium containing 10% FCS is added. It should be understood by one of skill in the art that any marker gene (or reporter gene) may be employed in the first AAV vector of this assay, e.g., alkaline phosphatase, luciferase, and others. An antibody-enzyme assay can also be used to quantitate levels of antigen, where the marker expresses an antigen. The assay is not limited by the identity of the marker gene. Twenty to twenty-four hours post-infection, the cells are stained for LacZ activity using standard methods. After 4 hours the cells are observed microscopically and cell lines with significantly more blue cells than the A549 or HeLa cell controls are scored as positive.

EXAMPLE 9

Delivery of Transgene to Host Cell

The resulting recombinant chimpanzee adenovirus described in Example 4, 5 or 6 above is then employed to deliver the transgene to a mammalian, preferably human, cell. For example, following purification of the recombinant virus, human embryonic kidney 293 cells are infected at an MOI of 50 particles per cell. GFP expression was documented 24 hours post-infection.

A. Gene Transfer in Mouse Models Via Pan-6, Pan-7, and Pan-9 Vectors

Gene transfer efficiencies and toxicological profile of recombinant chimpanzee adenoviruses were compared in mouse liver directed gene transfer, mouse lung directed gene transfer, and mouse muscle directed gene transfer.

E1-deleted adenoviral vectors containing LacZ under the control of the CMV promoter were constructed using the techniques herein for human Ad5, chimpanzee Pan 6, chimpanzee Pan 7 and chimpanzee Pan 9 (C68). The vectors were delivered to immune-deficient NCR nude mice (80 for each study) as follows. For the liver study, 100 µl ($1\times10^{11}$ particles) were injected into the tail vein. For the lung study, 50 µl ($5\times10^{10}$ particles) were delivered intratracheally. For the muscle study, 25 µl ($5\times10^{10}$ particles) were injected into tibialis anterior. The mice were sacrificed on days 3, 7, 14 and 28 post-vector injection (5 animals per group at each time point). At each necropsy, the liver/lung/muscle tissue was harvested and prepared for cryoblocks and paraffin embedding. The cryoblocks were sectioned for X-gal staining and the paraffin sections are H&E stained for histopathic analysis. At each time point, terminal bleeding was performed. Serum samples were subjected to liver function tests.

It was observed in this experiment the chimpanzee adenoviruses Pan-6, Pan-7, and Pan-9 were less efficient than huAd5 in gene transfer to the liver and to the lung. However, this may be desirable in certain circumstances, to reduce liver toxicity observed for huAd5. The gene transfer efficiency in muscle varied less between serotypes.

B. Mouse Study to Feasibility of Re-Administration of Adenovirus Vectors by Serotype Switching Between Adhu5, Pan-6, Pan-7, and Pan-9 Vectors Mice were administered (C57/Bl6; 4/group) LacZ vectors based on huAd5, Pan-6, Pan-7, and Pan-9 (H5.040CMVLacZ, Pan6.000CMVLacZ, Pan7.000CMVLacZ, Pan9.000CMVLacZ; $10^{11}$ particles/injection) by tail vein. Thirty days later the mice were re-administered adenovirus vectors expressing α1-antitrypsin (H5.040CMVhA1AT, Pan6.000CMVhA1AT, $1\times10^{11}$ particles, Pan7.000CMVhA1AT, Pan9.000CMVhA1AT, $10^{11}$ particles/injection). Successful transduction by the re-administered vector is monitored by measuring serum α1-antitrypsin on days 3 and 7, following re-administration.

The ability of adenovirus vectors based on huAd5, Pan-6, Pan-7, and Pan-9 respectively to transduce the livers of mice in the presence of neutralizing antibodies to the other serotypes was determined. The results are tabulated here.

| $1^{st}$ injection | $2^{nd}$ injection | Cross-neutralization |
|---|---|---|
| Adhu5 | Adhu5 | Yes (+ve control) |
| | Pan-6 | No |
| | Pan-7 | No |
| | Pan-9 (C68) | No |
| Pan-6 | Adhu5 | No |
| | Pan-6 | Yes (+ve control) |
| | Pan-7 | Yes |
| | Pan-9 (C68) | No |
| Pan-7 | Adhu5 | No |
| | Pan-6 | Yes |
| | Pan-7 | Yes (+ve control) |
| | Pan-9 (C68) | Yes |
| Pan-9 (C68) | Adhu5 | No |
| | Pan-6 | No |
| | Pan-7 | Yes |
| | Pan-9 (C68) | Yes (+ve control) |

Ability of vectors to transduce murine liver in the presence of neutralizing antibodies to other serotypes.

Thus, immunization with huAd5 does not prevent re-administration with either of the chimpanzee adenovirus vectors Pan-6, Pan-7, or Pan-9 (C68). This experiment also appears to indicate that Pan-7 is between Pan-6 and Pan-9 in the spectrum of antigenic relatedness and cross-reacts with both; however Pan-6 and Pan-9 do not neutralize each other. This is a surprising result based on homology comparisons, which indicates that Pan-6 is quite distinct from Pan-7 and Pan-9. Evaluation of antisera generated against Pan-9 indicated no cross-neutralization against Pan-6 but some neutralization against Pan-7, arguing that Pan-6 is distinct from the others.

EXAMPLE 10

Generation of Recombinant E1-Deleted SV-25 Vector

A plasmid was constructed containing the complete SV-25 genome except for an engineered E1 deletion. At the site of the E1 deletion recognition sites for the restriction enzymes I-CeuI and PI-SceI which would allow insertion of transgene from a shuttle plasmid where the transgene expression cassette is flanked by these two enzyme recognition sites were inserted.

A synthetic linker containing the restriction sites SwaI-SnaBI-SpeI-AflII-EcoRV-SwaI was cloned into pBR322 that was cut with EcoRI and NdeI. This was done by annealing together two synthetic oligomers SV25T (5'-AAT TTA AAT ACG TAG CGC ACT AGT CGC GCT AAG CGC GGA TAT CAT TTA AA-3', SEQ ID NO: 38) and SV25B (5'-TAT TTA AAT GAT ATC CGC GCT AAG CGC GGA CTA GTG CGC TAC GTA TTT A-3', SEQ ID NO:39) and inserting it into pBR322 digested with EcoRI and NdeI. The left end (bp1 to 1057, SEQ ID NO:29) of Ad SV25 was cloned into the above linker between the SnaBI and SpeI sites. The right end (bp28059 to 31042, SEQ ID NO: 29) of Ad SV25 was cloned into the linker between the AflII and EcoRV sites. The adenovirus E1 was then excised between the EcoRI site (bp 547) to XhoI (bp 2031) from the cloned left end as follows. A PCR generated I-CeuI-PI-SceI cassette from pShuttle (Clontech) was inserted between the EcoRI and SpeI sites. The 10154 bp XhoI fragment of Ad SV-25 (bp2031 to 12185, SEQ ID NO:29) was then inserted into the SpeI site. The resulting plasmid was digested with HindIII and the construct (pSV25) was completed by inserting the 18344 bp Ad SV-25 HindIII fragment (bp11984 to 30328, SEQ ID NO:29) to generate a complete molecular clone of E1 deleted adenovirus SV25 suitable for the generation of recombinant adenoviruses. Optionally, a desired transgene is inserted into the I-CeuI and PI-SceI sites of the newly created pSV25 vector plasmid.

To generate an AdSV25 carrying a marker gene, a GFP (green fluorescent protein) expression cassette previously cloned in the plasmid pShuttle (Clontech) was excised with the restriction enzymes I-CeuI and PI-SceI and ligated into pSV25 (or another of the Ad chimp plasmids described herein) digested with the same enzymes. The resulting plasmid (pSV25GFP) was digested with SwaI to separate the bacterial plasmid backbone and transfected into the E1 complementing cell line HEK 293. About 10 days later, a cytopathic effect was observed indicating the presence of replicative virus. The successful generation of an Ad SV25 based adenoviral vector expressing GFP was confirmed by applying the supernatant from the transfected culture on to fresh cell cultures. The presence of secondarily infected cells was determined by observation of green fluorescence in a population of the cells.

EXAMPLE 11

Construction of E3 Deleted Pan-5, Pan-6, Pan-7 and C68 Vectors

In order to enhance the cloning capacity of the adenoviral vectors, the E3 region can be deleted because this region encodes genes that are not required for the propagation of the virus in culture. Towards this end, E3-deleted versions of Pan-5, Pan-6, Pan-7, and C68 have been made (a 3.5 kb Nru-AvrII fragment containing E31-9 is deleted).

A. E3 Deleted Pan5 Based Vector

E1-deleted pPan5-pkGFP plasmid was treated with Avr II endonuclease to isolate a 5.8 kb fragment containing the E3 region and re-circulate pPan5-pkGFP with Avr II deletion to form construct pPan5-pkGFP-E3-Avr II. Subsequently, the 5.8 kb Avr II fragment was subcloned into pSL-Pan5-E3-Avr II for a further deletion of E3 region by Nru I digestion. This led to a plasmid pSL-Pan5-E3-deletion. The final construct pPan5-E3-pkGFP was produced by removing a 4.3 kb Avr II/Spe I fragment from pSL-Pan5-E3-deletion plasmid and inserting into pPan5-pkGFP-E3-Avr II at Avr II site. In this final construct, a 3.1 kb deletion in E3 region was accomplished.

B. E3 Deletion in Pan6 Based Vector

E1-deleted pPan6-pkGFP molecular clone was digested with Sbf I and Not I to isolate 19.3 kb fragment and ligated back at Sbf I site. The resulting construct pPan6-Sbf I-E3 was treated with Eco 47 III and Swa I, generating pPan6-E3. Finally, 21 kb Sbf I fragment from Sbf I digestion of pPan6-pkGFP was subcloned into pPan6-E3 to create pPan6-E3-pkGFP with a 4 kb deletion in E3.

C. E3 Deleted Pan7 and Pan9 Vectors

The same strategy was used to achieve E3 deletions in both vectors. First, a 5.8 kb Avr II fragment spanning the E3 region was subcloned pSL-1180, followed by deletion of E3 by Nru I digestion. The resulting plasmids were treated with Spe I and Avr II to obtain 4.4 kb fragments and clone into pPan7-pkGFP and pPan9-pkGFP at Avr II sites to replace the original E3 containing Avr II fragments, respectively. The final pPan7-E3-pkGFP and pPan9-E3-pkGFP constructs have 3.5 kb E3-deletions.

EXAMPLE 12

Construction of E3- and E4-Deleted Pan-7 Vector

Although the deletion of the E1 region of adenoviruses (first generation adenovirus vectors) renders them replication-incompetent, expression of the adenoviral vector backbone genes is not fully abolished. Deletion of the E4 region considerably attenuates this residual gene expression and may confer a safety advantage. An E4-deleted Pan-7 vector containing a 2.5 kb deletion (a PvuII-AgeI fragment containing E4ORF1-ORF7 is deleted) has been constructed. High titer stocks of this virus were generated using a HEK 293-based cell line, which in addition to E1, expresses an essential E4 gene (orf 6).

1. E4 Deletion in the Molecular Clone of Pan7

A 19 kb Xba I fragment was deleted from pPan7-pkGFP to create pPan7-Xba I from which a 2.5 kb E4 fragment was deleted by Age I and Pvu II partial digestion, resulting in pPan7-Xba I-E4. pPan7-E4-pkGFP plasmid was generated from pPan7-Xba I-E4 in two sequential cloning steps, adding 19 kb Xba I and 15 kb I-Ceu I/Mlu I fragments, both of which came from pPan7-pkGFP construct.

2. Introduction of E3 and E4 Deletions in Pan9 Vector

A 11 kb plasmid, pPan9-EcoRI, containing E4 region was created by retrieving 11 kb EcoRI fragment from pPan9 pkGFP after EcoRI digestion and self-ligation. E4 region was deleted from this construct by Age I digestion/filled in and Pvu II partial digestion and self-ligation to generate pPan9-EcoR I-E4. A 23 kb EcoR I fragment was isolated from pPan9-pkGFP and inserted into pPan9-EcoR I-E4 at EcoR I site, followed by adding 5.8 kb Avr II fragment from pPan9-pkGFP, to form the final product pPan9-E3-E4-pkGF. Compared to the genome size of wild type Pan9, this E1-E3-E4-deleted vector could have a transgene capacity up to 8 kb.

3. Introduction of Minigene Cassettes with Genes of Interest Including Reporter Genes, Glyco- and Nuclear Proteins of Ebo into Molecular Clones of Pan Vectors A highly efficient direct cloning and green/white selection procedure was employed for creating molecular clones of recombinant viruses. Briefly, genes of interest were cloned into pShuttlepkGFP by screening white colonies for recombinants. Subsequently, the minigene cassettes were transferred into chimpanzee adenovirus backbone plasmids, pPanX-pkGFP with various deletions, easily by swapping with pkGFP cassette at I-Ceu I and PI-Sce I sites and screening a few white colonies for correct recombinants.

4. Rescue of Molecular Clones of Pan Vectors with Multiple Deletions in Early Regions and Virus Propagation For rescue of E1-E3-deleted molecular clones of chimpanzee adenovirus vectors, the clones were linearized with appropriate restriction enzymes and transfected into regular 293 cells. Once a full cytopathic effect (CPE) observed in the transfected cells, crude lysate was harvested and expanded in 293 cells to large-scale infections. The viruses were purified by CsCl sedimentation method.

For E1-E4 and E1-E3-E4-deleted Pan vectors, 10-3 cells, a 293-based E1-E4-complementing cell line, were used for rescue and propagation of vectors. E4 ORF6 gene expression in 10-3 cells was induced by addition of 150 μM ZnSO$_4$ to the culture medium.

EXAMPLE 13

Vaccination with Adenovirus Vectors Expressing Wild Type and Variant EboZ GP AdHu5 or AdC7 vectors expressing Ebola envelope chimeras were produced for in vivo immunization experiments in C57BL/6 mice. Recombinant viruses with different viral backbones were created by molecular cloning method in which the minigene cassettes were inserted into the place of E1-deletions. The molecular clones of all recombinant viruses were rescued and grown up in 293 cells for large-scale purification using CsCl sedimentation method. Five EboZ variants encoded by AdHu5 or AdPan7 (C7) were selected and produced to evaluate their relative immunogenicity following an intramuscular Ad injection. The wt Ebo, a soluble Ebo variant, EboΔ1, EboΔ2, EboΔ3, EboΔ4, EboΔ5S, EboΔ6S, EboΔ7S and EboΔ8S were evaluated in the initial vaccine studies. For the data summarized in the following table, the number of viral particles (per ml or total) produced and amplified from infected 293 cells was established by spectrophotometry reading.

TABLE

Production of Adhu5 or AdC7 Adenoviral vector encoding EboZ variant.

| Gene | HuAd5 | | AdC7 | |
| --- | --- | --- | --- | --- |
| | Titer (VP × $10^{12}$/ml) | Total yield (VP × $10^{12}$) | Titer (VP × $10^{12}$/ml) | Total yield (VP × $10^{12}$) |
| Ebo wt | 2.6 | 12 | 4.3 | 43 |
| EboS | 4.9 | 49 | 4.6 | 55 |
| EboΔ2 | 2.1 | 9 | 5.8 | 93 |
| EboΔ3 | 1.7 | 8 | 5.3 | 95 |
| EboΔ4 | 3 | 12 | 4.1 | 62 |

Vector was administered intramuscularly ($10^{11}$ genome copies/cell) in C57BL/6 mice and the presence of virus neutralizing antibody (VNA0 was evaluated 28 days later as a first measure of an immune response generated against the Ebola envelope glycoprotein. VNA is defined here as serum antibody able to inhibit transduction of HeLa cells mediated by HIV-based vector pseudotyped with the wild-type Ebola envelope.

VNA to the EboZ pseudotypes was detected with AdPan7 (C7) yielding higher titers than AdHu5. The EboZΔ3 elicited the highest VNA in terms of the transgene targets. For the data summarized in the following table, neutralizing antibody titers to HIV-EboZ-GFP pseudotypes (reciprocal dilution) are provided (N=5 animals/group).

| | VNA Titers | | |
| --- | --- | --- | --- |
| | EboZ wildtype | EboZs | EboZΔ3 |
| AdHu5 | 12 | 16 | 12 |
| AdC7 | 44 | 12 | 140 |

EXAMPLE 14

Pan7-Mediated Expression of Ebola Proteins

Mouse studies to evaluate Pan-7 vectors expressing Ebola envelope proteins and the Ebola nuclear antigen have been initiated. These are directed towards evaluation of neutralizing antibodies in C57Bl/6 mice injected intramuscularly (IM) with Adhu5 or Pan-7 expressing each of 4 Ebola env constructs.

A. Evaluation of CTL from C57Bl/6 Mice Injected IM with Adhu5 or Pan-7 Expressing the Ebola Env Constructs.

1. Challenge Experiment in Mice with Ebola Virus.

Neutralizing antibody (NAB) responses to the Ebola envelope were analyzed by looking at immunized mouse sera mediated neutralization of a lentiviral (HIV) vector pseudotyped with the several constructs (eEbo, NTD2, NTD3, NTD4) of the Ebola envelope glycoprotein. C57BL/6 or BALB/c mice received a single intramuscular injection of $5\times10^{10}$ particles per mouse of C7 (Ad Pan-7) encoding Ebola envelope variant. Neutralizing antibody was evaluated 30 days post-vaccination. Briefly, Ebola Zaire pseudotyped HIV vector encoding for β-galactosidase (EboZ-HIV-LacZ) was incubated for 2 hr at 37° C. with different dilution of heat inactivated mouse serum. Following the incubation with serum, EboZ-HIV-LacZ was then used to infect HeLa cells for 16 hr at 37° C. Infectivity was revealed by X-gal staining of transduced HeLa cells positive for β-galactosidase. Neutralizing titer represent the serum reciprocal dilution where a 50% decrease in the number of β-galactosidase positive blue cells was observed. Sera were collected 30 days post-immunization, which consisted in a single intramuscular (I.M.) administration of $5\times10^{10}$ particles/animal. Neutralizing antibody to Ebola pseudotyped HIV could be detected from all groups with antibody titers ranging from 20 for Ad-EboZ (Adhu5 expressing EboZ), Ad-NTD3 (Adhu5 expressing NTD3) and C7-sEbo (Ad Pan-7 expressing soluble EboZ) to over 130 for C7-NTD3 (Ad Pan-7 expressing soluble NTD3) and C7-NTD4 (Ad Pan-7 expressing soluble NTD3). The same immunization strategy in BALB/c mice resulted in lower neutralizing antibody titers for Ad- and C7-NTD2, and NTD4.

B. Cellular Immune Response

The cellular immune response to the Ebola envelope in C57BL/6 mice was evaluated 8 days after a single I.M. administration of $5\times10^{10}$ particles of C7-LacZ or C7-Ebola envelope variant per animal. Mice were vaccinated I.M. with $5\times10^{10}$ particles of C7 encoding LacZ or Ebola envelope variant. Splenic lymphocytes from immunized mice were collected 8 days post vaccination and stimulated in vitro with feeder cells (splenic lymphocytes from untreated mice infected with human Adenovirus serotype 5 encoding for the wild-type Ebola envelope and irradiated). Standard 5-hr CTL assays were performed using $^{51}$Cr-labeled syngenic C57 cells transfected with an expressor of EboZ.

A positive MHC-restricted cytotoxic T lymphocyte (CTL) response was observed from all AdPan-7 encoding for Ebola envelope variants with a higher response from NTD2, NTD3 or NTD4 immunized mice. Indeed, effector cells from C7 encoding Ebola envelope variant immunized mice recognized EboZ transfected target cells and gave recall CTL responses up to 30% specific lysis. Less than 5% lysis was seen with effector cells from naïve or LacZ immunized control mice confirming that lysis was specific for Ebola envelope antigens.

C. Protection Studies

The most direct means of evaluating C7 (Ad Pan-7) encoding for the EboZ variants as a successful vaccine in mice was to assess protection against weight loss and death following lethal challenge with mouse adapted Ebola Zaire virus. BALB/c mice were immunized with a single dose of $5\times10^{10}$ particles per animal as performed previously and vaccinated animals were challenged with 200 $LD_{50}$ of mouse adapted Ebola Zaire 21 days later. All control mice (vehicle and C7-LacZ) died between day 5 to day 9 post-challenge. In contrast, all vaccinated mice but one, (from the C7-sEbo group), survived the challenge with Ebola Zaire.

Weight loss was observed from mice vaccinated with C7-sEbo from day 4 to day 7. Signs of illness such as pilo-erection and from light to severe lethargy were also noted from mice vaccinated with C7-sEbo, NTD2 and NTD3 between day 4 to day 7. Mice immunized with C7-EboZ and C7-NTD4 did not show sign of illness. Overall, a single dose of C7-EboZ and C7-NTD4 completely protected immunized mice from illness and death possibly due to a significant T cell mediated immunity.

All documents recited above are incorporated herein by reference, as are priority applications, U.S. patent application Ser. No. 13/337,608, filed Dec. 27, 2011, U.S. patent application Ser. No. 11/840,439, filed Jun. 19, 2007, now U.S. Pat. No. 8,105,574, U.S. patent application Ser. No. 10/494,364, filed May 12, 2004, now U.S. Pat. No. 7,247,472, issued Jul. 24, 2007, which is a 371 of PCT/US02/33645, filed Nov. 20, 2002, which claims the benefit under 35 USC 119(e) of U.S. Provisional Patent Application No. 60/366,798, filed Mar. 22, 2002 and U.S. Provisional Patent Application No. 60/331,951, filed Nov. 21, 2001, now expired. Numerous modifications and variations of the present invention are included in the scope of the above-identified specification and are expected to be obvious to one of skill in the art. Such modifications and alterations to the compositions and processes of the present invention, such as selections of different minigenes or selection or dosage of the vectors or immune modulators are believed to be within the scope of the claims appended hereto.

What is claimed is:

1. A recombinant adenovirus having an adenovirus capsid comprising a SV25 hexon protein having the amino acid sequence of SEQ ID NO:34, said capsid having packaged therein a nucleic acid sequence comprising (a) an adenovirus 5' inverted terminal repeat sequence, (b) a nucleotide sequence heterologous to SV25 encoding a therapeutic or immunogenic product operably linked to expression control sequences which direct transcription, translation, and/or expression thereof in a host cell, and (c) an adenovirus 3' inverted terminal repeat sequence.

2. The recombinant adenovirus according to claim 1, wherein the capsid further comprises a SV25 fiber protein.

3. The recombinant adenovirus according to claim 2, wherein the adenovirus fiber protein has the sequence of SEQ ID NO:36.

4. The recombinant adenovirus according to claim 2, wherein the adenovirus fiber protein has the sequence of SEQ ID NO: 35.

5. The recombinant adenovirus according to claim 1, wherein the capsid further comprises a SV25 penton protein.

6. The recombinant adenovirus according to claim 5, wherein the adenovirus SV25 penton protein has the sequence of SEQ ID NO: 33.

7. The recombinant adenovirus according to claim 1, wherein the adenovirus capsid further comprises an adenovirus capsid protein heterologous to SV25.

8. The recombinant adenovirus according to claim 7, wherein the heterologous adenovirus capsid protein is selected from one or more of (a) a penton protein, (b) a fiber protein, (c) a protein of the adenovirus L1 region selected from the 28.1 kD protein, polymerase, agnoprotein, 52/55 kD protein, and/or IIIa protein; (d) a protein of the adenovirus L2 region selected from the VII, VI, and/or Mu proteins; (e) a protein of the adenovirus L3 region selected from the VI and/or endoprotease; and (f) a protein of the adenovirus L4 region selected from the 100 kD protein, the 33 kD homolog, and/or VIII.

9. The recombinant adenovirus according to claim 1, wherein the recombinant adenovirus is a pseudotyped adenovirus wherein the adenovirus 5' inverted terminal repeat and the adenovirus 3' inverted terminal repeat are heterologous to SV25.

10. The recombinant adenovirus according to claim 1, wherein said adenovirus comprises minimal genomic adenovirus sequences which lacks all or a part of the E1 gene.

11. The recombinant adenovirus according to claim 1, wherein said capsid further comprises one or more adenovirus capsid proteins selected from the group consisting of:
(a) a protein of the adenovirus L1 region selected from the 28.1 kD protein, polymerase, agnoprotein, 52/55 kD protein, and/or Ma protein of SV25;
(b) a protein of the adenovirus L2 region selected from the VII, VI, and/or Mu proteins of SV25;
(c) a protein of the adenovirus L3 region selected from the VI and/or endoprotease of SV25;
(d) a protein of the adenovirus L4 region selected from the 100 kD protein, the 33 kD homolog, and/or VIII of SV25.

12. A composition comprising the adenovirus according to claim 1 and a pharmaceutically acceptable carrier.

* * * * *

UNITED STATES PATENT AND TRADEMARK OFFICE
CERTIFICATE OF CORRECTION

PATENT NO. : 9,133,483 B2
APPLICATION NO. : 14/073979
DATED : September 15, 2015
INVENTOR(S) : James M. Wilson et al.

It is certified that error appears in the above-identified patent and that said Letters Patent is hereby corrected as shown below:

In The Claims

In claim 11, line 6 (column 372, line 14), replace the word "Ma" with "IIIa" as follows:

-- protein, and/or IIIa protein of SV25 --

Signed and Sealed this
Fifteenth Day of March, 2016

Michelle K. Lee
*Director of the United States Patent and Trademark Office*

SEQUENCE LISTING

```
<160> NUMBER OF SEQ ID NOS: 43

<210> SEQ ID NO 1
<211> LENGTH: 36462
<212> TYPE: DNA
<213> ORGANISM: chimpanzee adenovirus serotype Pan5
<220> FEATURE:
<221> NAME/KEY: CDS
<222> LOCATION: (13898)..(15490)
<223> OTHER INFORMATION: L2 Penton
<220> FEATURE:
<221> NAME/KEY: CDS
<222> LOCATION: (18315)..(21116)
<223> OTHER INFORMATION: L3 Hexon
<220> FEATURE:
<221> NAME/KEY: CDS
<222> LOCATION: (32035)..(33372)
<223> OTHER INFORMATION: L5 Fiber

<400> SEQUENCE: 1
catcatcaat aatataccto aaactttttgg tgcgcgttaa tatgcaaatg aggtatttga      60
atttggggat gcggggcggt gattggctgc gggagcggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaacggg ccatttttcgc gcgaaaactg      300 aatgaggaag tgaaaatctg agtaattccg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgtaggt gtcagctgat cgccagggta     480
tttaaacctg cgctctctag tcaagaggcc actcttgagt gccagcgagt agagtttttct     540 cctccgcgcc gcgagtcaga tctacacttt gaaagatgag gcacctgaga gacctgcccg     600
gtaatgtttt cctggctact gggaacgaga ttctggaact ggtggtggac gccatgatgg     660
gtgacgaccc tccggagccc cctaccccat ttgaagcgcc ttcgctgtac gatttgtatg     720
atctggaggt ggatgtgccc gagaacgacc ccaacgagga ggcggtgaat gatttgttta     780
gcgatgccgc gctgctggct gccgagcagg ctaatacgga ctctggctca gacagcgatt     840
cctctctcca taccccgaga cccggcagag gtgagaaaaa gatccccgag cttaaagggg     900
aagagctcga cctgcgctgc tatgaggaat gcttgcctcc gagcgatgat gaggaggacg     960
```

```
aggaggcgat tcgagctgca gcgaaccagg gagtgaaaac agcgagcgag ggctttagcc    1020
tggactgtcc tactctgccc ggacacggct gtaagtcttg tgaatttcat cgcatgaata    1080
ctggagataa gaatgtgatg tgtgccctgt gctatatgag agcttacaac cattgtgttt    1140
acagtaagtg tgattaactt tagctgggga ggcagagggt gactgggtgc tgactggttt    1200
atttatgtat atgtttttta tgtgtaggtc ccgtctctga cgtagatgag accccccacta   1260 cagagtgcat ttcatcaccc ccagaaattg gcgaggaacc gcccgaagat attattcata    1320
gaccagttgc agtgagagtc accgggcgta gagcagctgt ggagagtttg atgacttgc     1380 tacagggtgg ggatgaacct ttggacttgt gtacccggaa acgccccagg cactaagtgc    1440
cacacatgtg tgtttactta aggtgatgtc agtatttata gggtgtggag tgcaataaaa    1500
tccgtgttga ctttaagtgc gtggtttatg actcaggggt ggggactgtg ggtatataag    1560
caggtgcaga cctgtgtggt cagttcagag caggactcat ggagatctgg acagtcttgg    1620
aagactttca ccagactaga cagctgctag agaactcatc ggagggagtc tcttacctgt    1680
ggagattctg cttcggtggg cctctagcta agctagtcta tagggccaag caggattata    1740
aggatcaatt tgaggatatt ttgagagagt gtcctggtat ttttgactct ctcaacttgg    1800
gccatcagtc tcactttaac cagagtattc tgagagccct tgacttttct actcctggca    1860
gaactaccgc cgcggtagcc ttttttgcct ttatccttga caaatggagt caagaaaccc    1920
atttcagcag ggattaccgt ctggactgct tagcagtagc tttgtggaga acatggaggt    1980
gccagcgcct gaatgcaatc tccggctact tgccagtaca gccggtagac acgctgagga    2040
tcctgagtct ccagtcaccc caggaacacc aacgccgcca gcagccgcag caggagcagc    2100
agcaagagga ggaccgagaa gagaacctga gagccggtct ggaccctccg gtggcggagg    2160
aggaggagta gctgacttgt ttcccgagct gcgccgggtg ctgactaggt cttccagtgg    2220 acggagagg gggattaagc gggagaggca tgaggagact agccacagaa ctgaactgac     2280
tgtcagtctg atgagtcgca ggcgcccaga atcggtgtgg tggcatgagg tgcagtcgca    2340
ggggatagat gaggtctcag tgatgcatga gaaatattcc ctagaacaag tcaagacttg    2400
ttggttggag cccgaggatg attgggaggt agccatcagg aattatgcca agctggctct    2460
gaggccagac aagaagtaca agattaccaa actgattaat atcagaaaatt cctgctacat    2520 ttcagggaat ggggccgagg tggagatcag tacccaggag agggtggcct tcagatgctg    2580
catgatgaat atgtacccgg gggtggtggg catggaggga gtcacccttta tgaacgcgag    2640 gttcaggggg gatgggtata atgggtggt ctttatggcc aacaccaagc tgacagtgca     2700
cggatgctcc ttcttttggct tcaataacat gtgcattgag gcctggggca gtgtttcagt    2760
gaggggatgc agttttttcag ccaactggat gggggtcgtg gcagaaccca agagcatggt    2820
gtcagtgaag aaatgcctgt tcgagaggtg ccacctgggg gtgatgagcg agggcgaagc    2880
caaagtcaaa cactgcgcct ctaccgagac gggctgcttt gtactgatca agggcaatgc    2940
caaagtcaag cataatatga tctgtggggc ctcggatgag cgcggctacc agatgctgac    3000
ctgcgccggt gggaacagcc atatgctagc caccgtgcat gtggcctcgc accccgcaa     3060 gacatggccc gagttcgagc acaacgtcat gacccgctgc aatgtgcacc tggggtcccg    3120
ccgaggcatg ttcatgccct accagtgcaa catgcaattt gtgaaggtgc tgctggagcc    3180
cgatgccatg tccagagtga gcctgacggg ggtgtttgac atgaatgtgg agctgtggaa    3240
aattctgaga tatgatgaat ccaagaccag gtgccgggcc tgcgaatgcg gaggcaagca    3300
```

```
cgccaggctt cagcccgtgt gtgtggaggt gacggaggac ctgcgacccg atcatttggt    3360
gttgtcctgc aacgggacgg agttcggctc agcggggaa gaatctgact agagtgagta    3420
gtgtttggga ctgggtggga gcctgcatga tgggcagaat gactaaaatc tgtgttttc    3480 tgcgcagcag catgagcgga agcgcctcct ttgaggagg ggtattcagc ccttatctga    3540
cggggcgtct cccctcctgg gcgggagtgc gtcagaatgt gatgggatcc acggtggacg    3600 gccgcccgt gcagcccgcg aactcttcaa ccctgaccta cgcgaccctg agctcctcgt    3660
ccgtggacgc agctgccgcc gcagctgctg cttccgccgc cagcgccgtg cgcggaatgg    3720
ccctgggcgc cggctactac agctctctgg tggccaactc gagttccacc aataatcccg    3780
ccagcctgaa cgaggagaag ctgctgctgc tgatggccca gctcgaggcc ctgacccagc    3840
gcctgggcga gctgacccag caggtggctc agctgcaggc ggagacgcgg gccgcggttg    3900
ccacggtgaa aaccaaataa aaaatgaatc aataaataaa cggagacggt tgttgatttt    3960
aacacagagt cttgaatctt tatttgattt ttcgcgcgcg gtaggccctg gaccaccggt    4020
ctcgatcatt gagcacccgg tggatctttt ccaggacccg gtagaggtgg gcttggatgt    4080
tgaggtacat gggcatgagc ccgtcccggg ggtggaggta gctccattgc agggcctcgt    4140 gctcggggt ggtgttgtaa atcacccagt catagcaggg gcgcagggcg tggtgctgca    4200
cgatgtcctt gaggaggaga ctgatggcca cgggcagccc cttggtgtag gtgttgacga    4260
acctgttgag ctgggaggga tgcatgcggg gggagatgag atgcatcttg gcctggatct    4320
tgagattggc gatgttcccg cccagatccc gccgggggtt catgttgtgc aggaccacca    4380
gcacggtgta tccggtgcac ttgggggaatt tgtcatgcaa cttggaaggg aaggcgtgaa    4440
agaatttgga gacgcccttg tgaccgccca ggttttccat gcactcatcc atgatgatgg    4500
cgatgggccc gtgggcggcg gcttgggcaa agacgtttcg ggggtcggac acatcgtagt    4560
tgtggtcctg ggtgagctcg tcataggcca ttttaatgaa tttggggcgg agggtgcccg    4620
actgggggac gaaggtgccc tcgatcccgg gggcgtagtt gccctcgcag atctgcatct    4680
cccaggcctt gagctcggag gggggatca tgtccacctg cggggcgatg aaaaaaacgg    4740
tttccggggc gggggagatg agctgggccg aaagcaggtt ccggagcagc tgggacttgc    4800
cgcagccggt ggggccgtag atgaccccga tgaccggctg caggtggtag ttgagggaga    4860
gacagctgcc gtcctcgcgg aggagggggg ccacctcgtt catcatctcg cgcacatgca    4920
tgttctcgcg cacgagttcc gccaggaggc gctcgccccc aagcgagagg agctcttgca    4980
gcgaggcgaa gttttttcagc ggcttgagcc cgtcggccat gggcattttg gagagggtct    5040
gttgcaagag ttccagacgg tcccagagct cggtgatgtg ctctagggca tctcgatcca    5100
gcagacctcc tcgtttcgcg ggttgggcg actgcgggag tagggcacca ggcgatgggc    5160
gtccagcgag gccagggtcc ggtccttcca ggggcgcagg gtccgcgtca gcgtggtctc    5220
cgtcacggtg aaggggtgcg cgccgggctg ggcgcttgcg agggtgcgct tcaggctcat    5280
ccggctggtc gagaaccgct cccggtcggc gccctgcgcg tcggccaggt agcaattgag    5340
catgagttcg tagttgagcg cctcggccgc gtggcccttg gcgcggagct tacctttgga    5400
agtgtgtccg cagacgggac agaggaggga cttgagggcg tagagcttgg gggcgaggaa    5460
gacggactcg ggggcgtagg cgtccgcgcc gcagctggcg cagacggtct cgcactccac    5520
gagccaggtg aggtctggcc ggtcggggtc aaaaacgagg tttcctccgt gcttttttgat    5580 gcgtttctta cctctggtct ccatgagctc gtgtccccgc tgggtgacaa agaggctgtc    5640
cgtgtccccg tagaccgact ttatgggccg gtcctcgagc ggggtgccgc ggtcctcgtc    5700
```

-continued

```
gtagaggaac cccgcccact ccgagacgaa ggcccgggtc caggccagca cgaaggaggc    5760
cacgtgggag gggtagcggt cgttgtccac cagcgggtcc accttctcca gggtatgcaa    5820
gcacatgtcc ccctcgtcca catccaggaa ggtgattggc ttgtaagtgt aggccacgtg    5880
accgggggtc ccggccgggg gggtataaaa gggggcgggc ccctgctcgt cctcactgtc    5940
ttccggatcg ctgtccagga gcgccagctg ttggggtagg tattccctct cgaaggcggg    6000
catgacctcg gcactcaggt tgtcagtttc tagaaacgag gaggatttga tattgacggt    6060
gccgttggag acgcctttca tgagcccctc gtccatctgg tcagaaaaga cgatcttttt    6120
gttgtcgagc ttggtggcga aggagccgta gagggcgttg gagagcagct ggcgatgga    6180 gcgcatggtc tggttctttt ccttgtcggc gcgctccttg gcggcgatgt tgagctgcac    6240
gtactcgcgc gccacgcact tccattcggg gaagacggtg gtgagcttgt cgggcacgat    6300
tctgacccgc cagccgcggt tgtgcagggt gatgaggtcc acgctggtgg ccacctcgcc    6360
gcgcaggggc tcgttggtcc agcagaggcg cccgcccttg cgcgagcaga agggggggcag    6420 cgggtccagc atgagctcgt cgggggggtc ggcgtccacg gtgaagatgc cgggcaggag    6480
ctcggggtcg aagtagctga tgcaggtgcc cagatcgtcc agcgccgctt gccagtcgcg    6540
cacggccagc gcgcgctcgt aggggctgag gggcgtgccc cagggcatgg ggtgcgtgag    6600
cgcggaggcg tacatgccgc agatgtcgta gacgtagagg ggctcctcga ggacgccgat    6660
gtaggtgggg tagcagcgcc ccccgcggat gctggcgcgc acgtagtcgt acagctcgtg    6720
cgagggcgcg aggagcccgg tgccgaggtt ggagcgctgc ggcttttcgg cgcggtagac    6780
gatctggcgg aagatggcgt gggagttgga ggagatggtg ggcctctgga agatgttgaa    6840
gtgggcgtgg ggcagtccga ccgagtccct gatgaagtgg gcgtaggagt cctgcagctt    6900
ggcgacgagc tcggcggtga cgaggacgtc cagggcgcag tagtcgaggg tctcttggat    6960
gatgtcgtac ttgagctggc ccttctgctt ccacagctcg cggttgagaa ggaactcttc    7020
gcggtccttc cagtactctt cgagggggaa cccgtcctga tcggcacggt aagagcccac    7080
catgtagaac tggttgacgg ccttgtaggc gcagcagccc ttctccacgg ggagggcgta    7140
agcttgcgcg gccttgcgca gggaggtgtg ggtgagggcg aaggtgtcgc gcaccatgac    7200
cttgaggaac tggtgcttga agtcgaggtc gtcgcagccg ccctgctccc agagctggaa    7260
gtccgtgcgc ttcttgtagg cggggttggg caaagcgaaa gtaacatcgt tgaagaggat    7320
cttgcccgcg cggggcatga agttgcgagt gatgcggaaa ggctggggca cctcggcccg    7380
gttgttgatg acctgggcgg cgaggacgat ctcgtcgaag ccgttgatgt tgtgcccgac    7440
gatgtagagt tccacgaatc gcgggcggcc cttgacgtgg ggcagcttct tgagctcgtc    7500
gtaggtgagc tcggcgggt cgctgaggcc gtgctgctcg agggcccagt cggcgaggtg    7560
ggggttggcg ccgaggaagg aagtccagag atccacggcc agggcggtct gcaagcggtc    7620
ccggtactga cggaactgct ggcccacggc cattttttcg ggggtgacgc agtagaaggt    7680 gcggggggtcg ccgtgccagc ggtcccactt gagctggagg gcgaggtcgt gggcgagctc    7740
gacgagcggc gggtccccgg agagtttcat gaccagcatg aagggacga gctgcttgcc    7800 gaaggacccc atccaggtgt aggtttccac gtcgtaggtg aggaagagcc tttcggtgcg    7860
aggatgcgag ccgatgggga agaactggat ctcctgccac cagttggagg aatggctgtt    7920
gatgtgatgt aagtagaaat gccgacgcg cgccgagcac tcgtgcttgt gtttatacaa    7980
gcgtccgcag tgctcgcaac gctgcacggg atgcacgtgc tgcacgagct gtacctgggt    8040
```

```
tcctttgacg aggaatttca gtgggcagtg gagcgctggc ggctgcatct ggtgctgtac    8100
tacgtcctgg ccatcggcgt ggccatcgtc tgcctcgatg gtggtcatgc tgacgaggcc    8160
gcgcgggagg caggtccaga cctcggctcg gacgggtcgg agagcgagga cgagggcgcg    8220
caggccggag ctgtccaggg tcctgagacg ctgcggagtc aggtcagtgg gcagcggcgg    8280
cgcgcggttg acttgcagga gcttttccag ggcgcgcggg aggtccagat ggtacttgat    8340
ctccacggcg ccgttggtgg cgacgtccac ggcttgcagg gtcccgtgcc cctggggcgc    8400
caccaccgtg ccccgtttct tcttgggtgc tggcggcggc ggctccatgc ttagaagcgg    8460
cggcgaggac gcgcgccggg cggcaggggc ggctcggggc ccggaggcag gggcggcagg    8520
ggcacgtcgg cgccgcgcgc gggcaggttc tggtactgcg cccggagaag actggcgtga    8580
gcgacgacgc gacggttgac gtcctggatc tgacgcctct gggtgaaggc cacgggaccc    8640
gtgagtttga acctgaaaga gagttcgaca gaatcaatct cggtatcgtt gacggcggcc    8700
tgccgcagga tctcttgcac gtcgcccgag ttgtcctggt aggcgatctc ggtcatgaac    8760
tgctcgatct cctcctcctg aaggtctccg cgaccggcgc gctcgacggt ggccgcgagg    8820
tcgttggaga tgcggcccat gagctgcgag aaggcgttca tgccggcctc gttccagacg    8880
cggctgtaga ccacggctcc gtcggggtcg cgcgcgcgca tgaccacctg ggcgaggttg    8940
agctcgacgt ggcgcgtgaa gaccgcgtag ttgcagaggc gctggtagag gtagttgagc    9000
gtggtggcga tgtgctcggt gacgaagaag tacatgatcc agcggcggag cggcatctcg    9060
ctgacgtcgc ccagggcttc caagcgctcc atggcctcgt agaagtccac ggcgaagttg    9120
aaaaactggg agttgcgcgc cgagacggtc aactcctcct ccagaagacg gatgagctcg    9180
gcgatggtgg cgcgcacctc gcgctcgaag gccccggggg gctcctcttc ttccatctcc    9240
tcctcctctt ccatctcctc cactaacatc tcttctactt cctcctcagg aggcggcggc    9300
ggggggagggg ccctgcgtcg ccggcggcgc acgggcagac ggtcgatgaa gcgctcgatg    9360
gtctccccgc gccggcgacg catggtctcg gtgacggcgc gcccgtcctc gcggggccgc    9420
agcgtgaaga cgccgccgcg catctccagg tggccgccgg ggggtctcc gttgggcagg    9480
gagagggcgc tgacgatgca tcttatcaat tggcccgtag ggactccgcg caaggacctg    9540
agcgtctcga gatccacggg atccgaaaac cgctgaacga aggcttcgag ccagtcgcag    9600
tcgcaaggta ggctgagccc ggtttcttgt tcttcgggta tttggtcggg aggcgggcgg    9660
gcgatgctgc tggtgatgaa gttgaagtag gcggtcctga gacggcggat ggtggcgagg    9720
agcaccaggt ccttgggccc ggcttgctgg atgcgcagac ggtcggccat gccccaggcg    9780
tggtcctgac acctggcgag gtccttgtag tagtcctgca tgagccgctc cacgggcacc    9840
tcctcctcgc ccgcgcggcc gtgcatgcgc gtgagcccga acccgcgctg cggctggacg    9900
agcgccaggt cggcgacgac gcgctcggcg aggatggcct gctggatctg ggtgagggtg    9960
gtctggaagt cgtcgaagtc gacgaagcgg tggtaggctc cggtgttgat ggtgtaggag   10020
cagttggcca tgacggacca gttgacggtc tggtggccgg ggcgcacgag ctcgtggtac   10080
ttgaggcgcg agtaggcgcg cgtgtcgaag atgtagtcgt tgcaggtgcg cacgaggtac   10140
tggtatccga cgaggaagtg cggcggcggc tggcggtaga gcggccatcg ctcggtggcc   10200
ggggcgccgg gcgcgaggtc ctcgagcatg aggcggtggt agccgtagat gtacctggac   10260
atccaggtga tgccggcggc ggtggtggag gcgcgcggga actcgcggac gcggttccag   10320
atgttgcgca gcggcaggaa gtagttcatg gtggccgcgg tctggcccgt gaggcgcgcg   10380
cagtcgtgga tgctctagac atacgggcaa aaacgaaagc ggtcagcggc tcgactccgt   10440
```

```
ggcctggagg ctaagcgaac gggttgggct gcgcgtgtac cccggttcga gtccctgctc   10500
gaatcaggct ggagccgcag ctaacgtggt actggcactc ccgtctcgac caagcctgc    10560 taacgaaacc tccaggatac ggaggcgggt cgttttggcc attttcgtca ggccggaaat   10620
gaaactagta agcgcggaaa gcggccgtcc gcgatggctc gctgccgtag tctggagaaa   10680
gaatcgccag ggttgcgttg cggtgtgccc cggttcgagc ctcagcgctc ggcgccggcc   10740
ggattccgcg ctaacgtgg gcgtggctgc cccgtcgttt ccaagacccc ttagccagcc    10800
gacttctcca gttacggagc gagcccctct ttttcttgtg tttttgccag atgcatcccg   10860
tactgcggca gatgcgcccc caccctccac cacaaccgcc cctaccgcag cagcagcaac   10920
agccggcgct tctgccccg ccccagcagc agcagccagc cactaccgcg cggccgccg     10980 tgagcggagc cggcgttcag tatgacctgg ccttggaaga gggcgagggg ctggcgcggc   11040
tgggggcgtc gtcgccggag cggcacccgc gcgtgcagat gaaaagggac gctcgcgagg   11100
cctacgtgcc caagcagaac ctgttcgaga caggagcgg cgaggagccc gaggagatgc    11160
gcgcctcccg cttccacgcg gggcgggagc tgcggcgcgg cctggaccga aagcgggtgc   11220
tgagggacga ggatttcgag gcggacgagc tgacggggat cagccccgcg cgcgcgcacg   11280
tggccgcggc caacctggtc acggcgtacg agcagaccgt gaaggaggag agcaacttcc   11340
aaaaatcctt caacaaccac gtgcgcacgc tgatcgcgcg cgaggaggtg accctgggcc   11400
tgatgcacct gtgggacctg ctggaggcca tcgtgcagaa ccccacgagc aagccgctga   11460
cggcgcagct gtttctggtg gtgcagcaca gtcgggacaa cgagacgttc agggaggcgc   11520
tgctgaatat caccgagccc gagggccgct ggctcctgga cctggtgaac attctgcaga   11580
gcatcgtggt gcaggagcgc gggctgccgc tgtccgagaa gctggcggcc atcaacttct   11640
cggtgctgag cctgggcaag tactacgcta ggaagatcta caagacccg tacgtgccca    11700 tagacaagga ggtgaagatc gacgggtttt acatgcgcat gaccctgaaa gtgctgaccc   11760
tgagcgacga tctgggggtg taccgcaacg acaggatgca ccgcgcggtg agcgccagcc   11820
gccggcgcga gctgagcgac caggagctga tgcacagcct gcagcgggcc ctgaccgggg   11880
ccgggaccga ggggagagc tactttgaca tgggcgcgga cctgcgctgg cagcctagcc    11940
gccgggcctt ggaagctgcc ggcggttccc cctacgtgga ggaggtggac gatgaggagg   12000
aggagggcga gtacctggaa gactgatggc gcgaccgtat ttttgctaga tgcagcaaca   12060
gccaccgccg cctcctgatc ccgcgatgcg ggcggcgctg cagagccagc cgtccggcat   12120
taactcctcg gacgattgga cccaggccat gcaacgcatc atggcgctga cgacccgcaa   12180
tcccgaagcc tttagacagc agcctcaggc caaccgactc tcggccatcc tggaggccgt   12240
ggtgccctcg cgctcgaacc ccacgcacga aaggtgctg gccatcgtga acgcgctggt    12300
ggagaacaag gccatccgcg gcgacgaggc cgggctggtg tacaacgcgc tgctggagcg   12360
cgtgccccgc tacaacagca ccaacgtgca gacgaacctg accgcatgg tgaccgcgt     12420 gcgcgaggcg gtgtcgcagc gcgagcggtt ccaccgcgag tcgaacctgg gctccatggt   12480
ggcgctgaac gccttcctga gcacgcagcc cgccaacgtg cccgggggcc aggaggacta   12540
caccaacttc atcagcgcgc tgcggctgat ggtggccgag gtgccccaga gcgaggtgta   12600
ccagtcgggg ccggactact tcttccagac cagtcgccag ggcttgcaga ccgtgaacct   12660
gagccaggct ttcaagaact tgcagggact gtggggcgtg caggcccgg tcggggaccg    12720 cgcgacggtg tcgagcctgc tgacgccgaa ctcgcgcctg ctgctgctgc tggtggcgcc   12780
```

-continued

```
cttcacggac agcggcagcg tgagccgcga ctcgtacctg ggctacctgc ttaacctgta    12840
ccgcgaggcc atcgggcagg cgcacgtgga cgagcagacc taccaggaga tcacccacgt    12900
gagccgcgcg ctgggccagg aggacccggg caacctggag gccaccctga acttcctgct    12960
gaccaaccgg tcgcagaaga tcccgcccca gtacgcgctg agcaccgagg aggagcgcat    13020
cctgcgctac gtgcagcaga gcgtggggct gttcctgatg caggaggggg ccacgcccag    13080
cgccgcgctc gacatgaccg cgcgcaacat ggagcccagc atgtacgccc gcaaccgccc    13140
gttcatcaat aagctgatgg actacttgca tcgggcggcc gccatgaact cggactactt    13200
taccaacgcc atcttgaacc cgcactggct cccgccgccc gggttctaca cgggcgagta    13260
cgacatgccc gaccccaacg acgggttcct gtgggacgac gtggacagca gcgtgttctc    13320
gccgcgcccc accaccacca ccgtgtggaa gaaagagggc ggggaccggc ggccgtcctc    13380
ggcgctgtcc ggtcgcgcgg gtgctgccgc ggcggtgccc gaggccgcca gccccttccc    13440
gagcctgccc ttttcgctga acagcgtgcg cagcagcgag ctgggtcggc tgacgcggcc    13500
gcgcctgctg ggcgaggagg agtacctgaa cgactccttg cttcggcccg agcgcgagaa    13560
gaacttcccc aataacggga tagagagcct ggtggacaag atgagccgct ggaagacgta    13620
cgcgcacgag cacaggacg agccccgagc tagcagcagc accggcgcca cccgtagacg    13680
ccagcggcac gacaggcagc ggggtctggt gtgggacgat gaggattccg ccgacgacag    13740
cagcgtgttg gacttgggtg ggagtggtgg tggtaacccg ttcgctcacc tgcgcccccg    13800
tatcgggcgc ctgatgtaag aatctgaaaa aataaaagac ggtactcacc aaggccatgg    13860
cgaccagcgt gcgttcttct ctgttgtttg tagtagt atg atg agg cgc gtg tac    13915
                                        Met Met Arg Arg Val Tyr
                                         1               5 ccg gag ggt cct cct ccc tcg tac gag agc gtg atg cag cag gcg gtg    13963
Pro Glu Gly Pro Pro Pro Ser Tyr Glu Ser Val Met Gln Gln Ala Val
             10                  15                  20 gcg gcg gcg atg cag ccc ccg ctg gag gcg cct tac gtg ccc ccg cgg    14011
Ala Ala Ala Met Gln Pro Pro Leu Glu Ala Pro Tyr Val Pro Pro Arg
         25                  30                  35 tac ctg gcg cct acg gag ggg cgg aac agc att cgt tac tcg gag ctg    14059
Tyr Leu Ala Pro Thr Glu Gly Arg Asn Ser Ile Arg Tyr Ser Glu Leu
     40                  45                  50 gca ccc ttg tac gat acc acc cgg ttg tac ctg gtg gac aac aag tcg    14107
Ala Pro Leu Tyr Asp Thr Thr Arg Leu Tyr Leu Val Asp Asn Lys Ser
55                  60                  65                  70 gcg gac atc gcc tcg ctg aac tac cag aac gac cac agc aac ttc ctg    14155
Ala Asp Ile Ala Ser Leu Asn Tyr Gln Asn Asp His Ser Asn Phe Leu
                 75                  80                  85 acc acc gtg gtg cag aac aac gat ttc acc ccc acg gag gcc agc acc    14203
Thr Thr Val Val Gln Asn Asn Asp Phe Thr Pro Thr Glu Ala Ser Thr
             90                  95                 100 cag acc atc aac ttt gac gag cgc tcg cgg tgg ggc ggc cag ctg aaa    14251
Gln Thr Ile Asn Phe Asp Glu Arg Ser Arg Trp Gly Gly Gln Leu Lys
        105                 110                 115 acc atc atg cac acc aac atg ccc aac gtg aac gag ttc atg tac agc    14299
Thr Ile Met His Thr Asn Met Pro Asn Val Asn Glu Phe Met Tyr Ser
    120                 125                 130 aac aag ttc aag gcg cgg gtg atg gtc tcg cgc aag acc ccc aac ggg    14347
Asn Lys Phe Lys Ala Arg Val Met Val Ser Arg Lys Thr Pro Asn Gly
135                 140                 145                 150 gtc aca gta aca gat ggt agt cag gac gag ctg acc tac gag tgg gtg    14395
Val Thr Val Thr Asp Gly Ser Gln Asp Glu Leu Thr Tyr Glu Trp Val
                155                 160                 165
```

```
gag ttt gag ctg ccc gag ggc aac ttc tcg gtg acc atg acc atc gat    14443
Glu Phe Glu Leu Pro Glu Gly Asn Phe Ser Val Thr Met Thr Ile Asp
            170                 175                 180 ctg atg aac aac gcc atc atc gac aac tac ttg gcg gtg ggg cgg cag    14491
Leu Met Asn Asn Ala Ile Ile Asp Asn Tyr Leu Ala Val Gly Arg Gln
        185                 190                 195 aac ggg gtg ctg gag agc gac atc ggc gtg aag ttc gac acg cgc aac    14539
Asn Gly Val Leu Glu Ser Asp Ile Gly Val Lys Phe Asp Thr Arg Asn
    200                 205                 210 ttc cgg ctg ggc tgg gac ccc gtg acc gag ctg gtg atg ccg ggc gtg    14587
Phe Arg Leu Gly Trp Asp Pro Val Thr Glu Leu Val Met Pro Gly Val
215                 220                 225                 230 tac acc aac gag gcc ttc cac ccc gac atc gtc ctg ctg ccc ggc tgc    14635
Tyr Thr Asn Glu Ala Phe His Pro Asp Ile Val Leu Leu Pro Gly Cys
                235                 240                 245 ggc gtg gac ttc acc gag agc cgc ctc agc aac ctg ctg ggc atc cgc    14683
Gly Val Asp Phe Thr Glu Ser Arg Leu Ser Asn Leu Leu Gly Ile Arg
            250                 255                 260 aag cgg cag ccc ttc cag gag ggc ttc cag atc ctg tac gag gac ctg    14731
Lys Arg Gln Pro Phe Gln Glu Gly Phe Gln Ile Leu Tyr Glu Asp Leu
        265                 270                 275 gag ggg ggc aac atc ccc gcg ctg ctg gac gtg gac gcc tac gag aaa    14779
Glu Gly Gly Asn Ile Pro Ala Leu Leu Asp Val Asp Ala Tyr Glu Lys
    280                 285                 290 agc aag gag gat agc gcc gcc gcg acc gca gcc gtg gcc acc gcc        14827
Ser Lys Glu Asp Ser Ala Ala Ala Thr Ala Ala Val Ala Thr Ala
295                 300                 305                 310 tct acc gag gtg cgg ggc gat aat ttt gct agc gcc gcg aca ctg gca    14875
Ser Thr Glu Val Arg Gly Asp Asn Phe Ala Ser Ala Ala Thr Leu Ala
            315                 320                 325 gcg gcc gag gcg gct gaa acc gaa agt aag ata gtg atc cag ccg gtg    14923
Ala Ala Glu Ala Ala Glu Thr Glu Ser Lys Ile Val Ile Gln Pro Val
        330                 335                 340 gag aag gac agc aag gag agg agc tac aac gtg ctc gcg gac aag aaa    14971
Glu Lys Asp Ser Lys Glu Arg Ser Tyr Asn Val Leu Ala Asp Lys Lys
    345                 350                 355 aac acc gcc tac cgc agc tgg tac ctg gcc tac aac tac ggc gac ccc    15019
Asn Thr Ala Tyr Arg Ser Trp Tyr Leu Ala Tyr Asn Tyr Gly Asp Pro
360                 365                 370 gag aag ggc gtg cgc tcc tgg acg ctg ctc acc acc tcg gac gtc acc    15067
Glu Lys Gly Val Arg Ser Trp Thr Leu Leu Thr Thr Ser Asp Val Thr
            375                 380                 385                 390 tgc ggc gtg gag caa gtc tac tgg tcg ctg ccc gac atg atg caa gac    15115
Cys Gly Val Glu Gln Val Tyr Trp Ser Leu Pro Asp Met Met Gln Asp
        395                 400                 405 ccg gtc acc ttc cgc tcc acg cgt caa gtt agc aac tac ccg gtg gtg    15163
Pro Val Thr Phe Arg Ser Thr Arg Gln Val Ser Asn Tyr Pro Val Val
    410                 415                 420 ggc gcc gag ctc ctg ccc gtc tac tcc aag agc ttc ttc aac gag cag    15211
Gly Ala Glu Leu Leu Pro Val Tyr Ser Lys Ser Phe Phe Asn Glu Gln
425                 430                 435 gcc gtc tac tcg cag cag ctg cgc gcc ttc acc tcg ctc acg cac gtc    15259
Ala Val Tyr Ser Gln Gln Leu Arg Ala Phe Thr Ser Leu Thr His Val
            440                 445                 450 ttc aac cgc ttc ccc gag aac cag atc ctc gtt cgc ccg ccc gcg ccc    15307
Phe Asn Arg Phe Pro Glu Asn Gln Ile Leu Val Arg Pro Pro Ala Pro
455                 460                 465                 470 acc att acc acc gtc agt gaa aac gtt cct gct ctc aca gat cac ggg    15355
Thr Ile Thr Thr Val Ser Glu Asn Val Pro Ala Leu Thr Asp His Gly
```

|     |     |     |     |     |     |     |     |     |     |     |     |     |     |       |
| --- | --- | --- | --- | --- | --- | --- | --- | --- | --- | --- | --- | --- | --- | ----- |
|     |     |     | 475 |     |     |     | 480 |     |     |     | 485 |     |     |       |
| acc | ctg | ccg | ctg | cgc | agc | agt | atc | cgg | gga | gtc | cag | cgc | gtg | acc gtc | 15403 |
| Thr | Leu | Pro | Leu | Arg | Ser | Ser | Ile | Arg | Gly | Val | Gln | Arg | Val | Thr Val |  |
|     |     | 490 |     |     |     |     | 495 |     |     |     |     | 500 |     |       |
| act | gac | gcc | aga | cgc | cgc | acc | tgc | ccc | tac | gtc | tac | aag | gcc | ctg ggc | 15451 |
| Thr | Asp | Ala | Arg | Arg | Arg | Thr | Cys | Pro | Tyr | Val | Tyr | Lys | Ala | Leu Gly |  |
|     |     |     | 505 |     |     |     |     | 510 |     |     |     |     | 515 |       |
| gta | gtc | gcg | ccg | cgc | gtc | ctc | tcg | agc | cgc | acc | ttc | taa | aaaatgtcca |   | 15500 |
| Val | Val | Ala | Pro | Arg | Val | Leu | Ser | Ser | Arg | Thr | Phe |     |     |       |
|     | 520 |     |     |     |     | 525 |     |     |     |     | 530 |     |     |       | ttctcatctc gcccagtaat aacaccggtt ggggcctgcg cgcgcccagc aagatgtacg 15560
gaggcgctcg ccaacgctcc acgcaacacc ccgtgcgcgt gcgcgggcac ttccgcgctc 15620
cctgggcgc cctcaagggc cgcgtgcgct cgcgcaccac cgtcgacgac gtgatcgacc 15680
aggtggtggc cgacgcgcgc aactacacgc ccgccgccgc gcccgtctcc accgtggacg 15740
ccgtcatcga cagcgtggtg gccgacgcgc gccggtacgc ccgcgccaag agccggcggc 15800
ggcgcatcgc ccggcggcac cggagcaccc ccgccatgcg cgcggcgcga gccttgctgc 15860
gcagggccag cgcacgggga cgcagggcca tgctcagggc ggccagacgc gcggcctccg 15920
gcagcagcag cgccggcagg acccgcagac gcgcggccac ggcggcggcg gcggccatcg 15980
ccagcatgtc ccgcccgcgg cgcggcaacg tgtactgggt gcgcgacgcc gccaccggtg 16040
tgcgcgtgcc cgtgcgcacc cgcccccctc gcacttgaag atgctgactt cgcgatgttg 16100
atgtgtccca gcggcgagga ggatgtccaa gcgcaaattc aaggaagaga tgctccaggt 16160
catcgcgcct gagatctacg gcccggcggc ggtgaaggag aaagaaagc cccgcaaact 16220
gaagcgggtc aaaaaggaca aaaggagga ggaagatgtg gacggactgg tggagtttgt 16280
gcgcgagttc gcccccggc ggcgcgtgca gtggcgcggg cggaaagtga accggtgct 16340
gcgacccggc accacggtgg tcttcacgcc cggcgagcgt tccggctccg cctccaagcg 16400
ctcctacgac gaggtgtacg gggacgagga catcctcgag caggcggccg aacgtctggg 16460
cgagtttgct tacggcaagc gcagccgccc cgcgcccttg aaagaggagg cggtgtccat 16520
cccgctggac cacggcaacc ccacgccgag cctgaagccg gtgaccctgc agcaggtgct 16580
gcctggtgcg gcgccgcgcc ggggcttcaa gcgcgagggc ggcgaggatc tgtacccgac 16640
catgcagctg atggtgccca gcgccagaa gctggaggac gtgctggagc acatgaaggt 16700
ggaccccgag gtgcagcccg aggtcaaggt gcggcccatc aagcaggtgg ccccggggcct 16760
gggcgtgcag accgtggaca tcaagatccc cacggagccc atggaaacgc agaccgagcc 16820
cgtgaagccc agcaccagca ccatggaggt gcagacggat ccctggatgc cggcaccggc 16880
ttccaccacc cgccgaagac gcaagtacg cgcggccagc ctgctgatgc caactacgc 16940
gctgcatcct tccatcatcc ccacgccggg ctaccgcggc acgcgcttct accgcggcta 17000
caccagcagc cgccgccgca agaccaccac ccgccgccgc cgtcgtcgca cccgccgcag 17060
cagcaccgcg acttccgccg ccgccctggt gcggagagtg taccgcagcg ggcgcgagcc 17120
tctgaccctg ccgcgcgcgc gctaccaccc gagcatcgcc atttaactac cgcctcctac 17180
ttgcagatat ggccctcaca tgccgcctcc gcgtccccat tacgggctac cgaggaagaa 17240
agccgcgccg tagaaggctg acggggaacg ggctgcgtcg ccatcaccac cggcggcggc 17300
gcgccatcag caagcggttg gggggaggct tcctgcccgc gctgatgccc atcatcgccg 17360
cggcgatcgg ggcgatcccc ggcatagctt ccgtggcggt gcaggcctct cagcgccact 17420
gagacacagc ttggaaaaatt tgtaataaaa aatggactga cgctcctggt cctgtgatgt 17480

-continued

```
gtgttttag atggaagaca tcaatttttc gtccctggca ccgcgacacg gcacgcggcc    17540
gtttatgggc acctggagcg acatcggcaa cagccaactg aacggggggcg ccttcaattg   17600 gagcagtctc tggagcgggc ttaagaattt cgggtccacg ctcaaaacct atggcaacaa   17660
ggcgtggaac agcagcacag ggcaggcgct gagggaaaag ctgaaagagc agaacttcca   17720
gcagaaggtg gtcgatggcc tggcctcggg catcaacggg gtggtggacc tggccaacca   17780
ggccgtgcag aaacagatca acagccgcct ggacgcggtc ccgcccgcgg ggtccgtgga   17840
gatgccccag gtggaggagg agctgcctcc cctggacaag cgcggcgaca gcgaccgcg    17900 tcccgacgcg gaggagacgc tgctgacgca cggacgag ccgcccgt acgaggaggc      17960 ggtgaaactg ggtctgccca ccacgcggcc cgtggcgcct ctggccaccg gggtgctgaa   18020
acccagcagc agcagcagcc agcccgcgac cctggacttg cctccgcctg cttcccgccc   18080
ctccacagtg gctaagcccc tgccgccggt ggccgtcgcg tcgcgcgccc ccgaggccg    18140 cccccaggcg aactggcaga gcactctgaa cagcatcgtg gtctgggag tgcagagtgt   18200 gaagcgccgc cgctgctatt aaaagacact gtagcgctta acttgcttgt ctgtgtgtat   18260
atgtatgtcc gccgaccaga aggaggagga agaggcgcgt cgccgagttg caag atg    18317
                                                                Met
gcc acc cca tcg atg ctg ccc cag tgg gcg tac atg cac atc gcc gga    18365
Ala Thr Pro Ser Met Leu Pro Gln Trp Ala Tyr Met His Ile Ala Gly
        535             540                 545 cag gac gct tcg gag tac ctg agt ccg ggt ctg gtg cag ttc gcc cgc    18413
Gln Asp Ala Ser Glu Tyr Leu Ser Pro Gly Leu Val Gln Phe Ala Arg
            550                 555                 560 gcc aca gac acc tac ttc agt ctg ggg aac aag ttt agg aac ccc acg    18461
Ala Thr Asp Thr Tyr Phe Ser Leu Gly Asn Lys Phe Arg Asn Pro Thr
        565                 570                 575 gtg gcg ccc acg cac gat gtg acc acc gac cgc agc cag cgg ctg acg    18509
Val Ala Pro Thr His Asp Val Thr Thr Asp Arg Ser Gln Arg Leu Thr
580                 585                 590                 595 ctg cgc ttc gtg ccc gtg gac cgc gag gac aac acc tac tcg tac aaa    18557
Leu Arg Phe Val Pro Val Asp Arg Glu Asp Asn Thr Tyr Ser Tyr Lys
                600                 605                 610 gtg cgc tac acg ctg gcc gtg ggc gac aac cgc gtg ctg gac atg gcc    18605
Val Arg Tyr Thr Leu Ala Val Gly Asp Asn Arg Val Leu Asp Met Ala
            615                 620                 625 agc acc tac ttt gac atc cgc ggc gtg ctg gat cgg ggc cct agc ttc    18653
Ser Thr Tyr Phe Asp Ile Arg Gly Val Leu Asp Arg Gly Pro Ser Phe
        630                 635                 640 aaa ccc tac tcc ggc acc gct tac aac agc ctg gct ccc aag gga gcg    18701
Lys Pro Tyr Ser Gly Thr Ala Tyr Asn Ser Leu Ala Pro Lys Gly Ala
    645                 650                 655 ccc aac act tgc cag tgg aca tat aaa gct gat ggt gat act ggt aca    18749
Pro Asn Thr Cys Gln Trp Thr Tyr Lys Ala Asp Gly Asp Thr Gly Thr
660                 665                 670                 675 gaa aaa acc tat aca tat gga aat gcg cct gtg caa ggc att agt att    18797
Glu Lys Thr Tyr Thr Tyr Gly Asn Ala Pro Val Gln Gly Ile Ser Ile
                680                 685                 690 aca aaa gat ggt att caa ctt gga act gac act gat cag ccc att       18845
Thr Lys Asp Gly Ile Gln Leu Gly Thr Asp Thr Asp Asp Gln Pro Ile
            695                 700                 705 tat gca gat aaa act tat caa cca gag cct caa gtg ggt gat gct gaa   18893
Tyr Ala Asp Lys Thr Tyr Gln Pro Glu Pro Gln Val Gly Asp Ala Glu
        710                 715                 720 tgg cat gac atc act ggt act gat gaa aaa tat gga ggc aga gct ctc    18941
Trp His Asp Ile Thr Gly Thr Asp Glu Lys Tyr Gly Gly Arg Ala Leu
```

-continued

```
                Trp His Asp Ile Thr Gly Thr Asp Glu Lys Tyr Gly Gly Arg Ala Leu
                    725                 730                 735 aag cct gac acc aaa atg aag ccc tgc tat ggt tct ttt gcc aag cct       18989
Lys Pro Asp Thr Lys Met Lys Pro Cys Tyr Gly Ser Phe Ala Lys Pro
740                 745                 750                 755 acc aat aaa gaa gga ggt cag gca aat gtg aaa acc gaa aca ggc ggt       19037
Thr Asn Lys Glu Gly Gly Gln Ala Asn Val Lys Thr Glu Thr Gly Gly
                760                 765                 770 acc aaa gaa tat gac att gac atg gca ttc ttc gat aat cga agt gca       19085
Thr Lys Glu Tyr Asp Ile Asp Met Ala Phe Phe Asp Asn Arg Ser Ala
            775                 780                 785 gct gcg gct ggc ctg gcc cca gaa att gtt ttg tat act gag aat gtg       19133
Ala Ala Ala Gly Leu Ala Pro Glu Ile Val Leu Tyr Thr Glu Asn Val
        790                 795                 800 gat ctg gaa act cca gat act cat att gta tac aag gcg ggc aca gat       19181
Asp Leu Glu Thr Pro Asp Thr His Ile Val Tyr Lys Ala Gly Thr Asp
    805                 810                 815 gac agc agc tct tct atc aat ttg ggt cag cag tcc atg ccc aac aga       19229
Asp Ser Ser Ser Ser Ile Asn Leu Gly Gln Gln Ser Met Pro Asn Arg
820                 825                 830                 835 ccc aac tac att ggc ttt aga gac aac ttt atc ggg ctc atg tac tac       19277
Pro Asn Tyr Ile Gly Phe Arg Asp Asn Phe Ile Gly Leu Met Tyr Tyr
                840                 845                 850 aac agc act ggc aac atg ggc gtg ctg gct ggt cag gcc tcc cag ctg       19325
Asn Ser Thr Gly Asn Met Gly Val Leu Ala Gly Gln Ala Ser Gln Leu
            855                 860                 865 aat gct gtg gtg gac ttg cag gac aga aac act gaa ctg tcc tac cag       19373
Asn Ala Val Val Asp Leu Gln Asp Arg Asn Thr Glu Leu Ser Tyr Gln
        870                 875                 880 ctc ttg ctt gac tct ctg ggc gac aga acc agg tat ttc agt atg tgg       19421
Leu Leu Leu Asp Ser Leu Gly Asp Arg Thr Arg Tyr Phe Ser Met Trp
    885                 890                 895 aat cag gcg gtg gac agc tat gac ccc gat gtg cgc att att gaa aat       19469
Asn Gln Ala Val Asp Ser Tyr Asp Pro Asp Val Arg Ile Ile Glu Asn
900                 905                 910                 915 cac ggt gtg gag gat gaa ctc cct aac tat tgc ttc ccc ctg gat gct       19517
His Gly Val Glu Asp Glu Leu Pro Asn Tyr Cys Phe Pro Leu Asp Ala
                920                 925                 930 gtg ggt aga act gat act tac cag gga att aag gcc aat ggt gct gat       19565
Val Gly Arg Thr Asp Thr Tyr Gln Gly Ile Lys Ala Asn Gly Ala Asp
            935                 940                 945 caa acc acc tgg acc aaa gat gat act gtt aat gat gct aat gaa ttg       19613
Gln Thr Thr Trp Thr Lys Asp Asp Thr Val Asn Asp Ala Asn Glu Leu
        950                 955                 960 ggc aag ggc aat cct ttc gcc atg gag atc aac atc cag gcc aac ctg       19661
Gly Lys Gly Asn Pro Phe Ala Met Glu Ile Asn Ile Gln Ala Asn Leu
    965                 970                 975 tgg cgg aac ttc ctc tac gcg aac gtg gcg ctg tac ctg ccc gac tcc       19709
Trp Arg Asn Phe Leu Tyr Ala Asn Val Ala Leu Tyr Leu Pro Asp Ser
980                 985                 990                 995 tac aag tac acg ccg gcc aac atc acg ctg ccg acc aac acc aac           19754
Tyr Lys Tyr Thr Pro Ala Asn Ile Thr Leu Pro Thr Asn Thr Asn
                1000                1005                1010 acc tac gat tac atg  aac ggc cgc gtg gtg  gcg ccc tcg ctg gtg         19799
Thr Tyr Asp Tyr Met  Asn Gly Arg Val Val  Ala Pro Ser Leu Val
            1015                1020                1025 gac gcc tac atc aac  atc ggg gcg cgc tgg  tcg ctg gac ccc atg         19844
Asp Ala Tyr Ile Asn  Ile Gly Ala Arg Trp  Ser Leu Asp Pro Met
        1030                1035                1040
```

```
gac aac gtc aac ccc ttc aac cac cac cgc aac gcg ggc ctg cgc        19889
Asp Asn Val Asn Pro Phe Asn His His Arg Asn Ala Gly Leu Arg
            1045                1050                1055 tac cgc tcc atg ctc ctg ggc aac ggg cgc tac gtg ccc ttc cac        19934
Tyr Arg Ser Met Leu Leu Gly Asn Gly Arg Tyr Val Pro Phe His
            1060                1065                1070 atc cag gtg ccc caa aag ttc ttc gcc atc aag agc ctc ctg ctc        19979
Ile Gln Val Pro Gln Lys Phe Phe Ala Ile Lys Ser Leu Leu Leu
            1075                1080                1085 ctg ccc ggg tcc tac acc tac gag tgg aac ttc cgc aag gac gtc        20024
Leu Pro Gly Ser Tyr Thr Tyr Glu Trp Asn Phe Arg Lys Asp Val
            1090                1095                1100 aac atg atc ctg cag agc tcc ctc ggc aac gac ctg cgc acg gac        20069
Asn Met Ile Leu Gln Ser Ser Leu Gly Asn Asp Leu Arg Thr Asp
            1105                1110                1115 ggg gcc tcc atc gcc ttc acc agc atc aac ctc tac gcc acc ttc        20114
Gly Ala Ser Ile Ala Phe Thr Ser Ile Asn Leu Tyr Ala Thr Phe
            1120                1125                1130 ttc ccc atg gcg cac aac acc gcc tcc acg ctc gag gcc atg ctg        20159
Phe Pro Met Ala His Asn Thr Ala Ser Thr Leu Glu Ala Met Leu
            1135                1140                1145 cgc aac gac acc aac gac cag tcc ttc aac gac tac ctc tcg gcg        20204
Arg Asn Asp Thr Asn Asp Gln Ser Phe Asn Asp Tyr Leu Ser Ala
            1150                1155                1160 gcc aac atg ctc tac ccc atc ccg gcc aac gcc acc aac gtg ccc        20249
Ala Asn Met Leu Tyr Pro Ile Pro Ala Asn Ala Thr Asn Val Pro
            1165                1170                1175 atc tcc atc ccc tcg cgc aac tgg gcc gcc ttc cgc gga tgg tcc        20294
Ile Ser Ile Pro Ser Arg Asn Trp Ala Ala Phe Arg Gly Trp Ser
            1180                1185                1190 ttc acg cgc ctc aag acc cgc gag acg ccc tcg ctc ggc tcc ggg        20339
Phe Thr Arg Leu Lys Thr Arg Glu Thr Pro Ser Leu Gly Ser Gly
            1195                1200                1205 ttc gac ccc tac ttc gtc tac tcg ggc tcc atc ccc tac ctc gac        20384
Phe Asp Pro Tyr Phe Val Tyr Ser Gly Ser Ile Pro Tyr Leu Asp
            1210                1215                1220 ggc acc ttc tac ctc aac cac acc ttc aag aag gtc tcc atc acc        20429
Gly Thr Phe Tyr Leu Asn His Thr Phe Lys Lys Val Ser Ile Thr
            1225                1230                1235 ttc gac tcc tcc gtc agc tgg ccc ggc aac gac cgc ctc ctg acg        20474
Phe Asp Ser Ser Val Ser Trp Pro Gly Asn Asp Arg Leu Leu Thr
            1240                1245                1250 ccc aac gag ttc gaa atc aag cgc acc gtc gac gga gag ggg tac        20519
Pro Asn Glu Phe Glu Ile Lys Arg Thr Val Asp Gly Glu Gly Tyr
            1255                1260                1265 aac gtg gcc cag tgc aac atg acc aag gac tgg ttc ctg gtc cag        20564
Asn Val Ala Gln Cys Asn Met Thr Lys Asp Trp Phe Leu Val Gln
            1270                1275                1280 atg ctg gcc cac tac aac atc ggc tac cag ggc ttc tac gtg ccc        20609
Met Leu Ala His Tyr Asn Ile Gly Tyr Gln Gly Phe Tyr Val Pro
            1285                1290                1295 gag ggc tac aag gac cgc atg tac tcc ttc ttc cgc aac ttc cag        20654
Glu Gly Tyr Lys Asp Arg Met Tyr Ser Phe Phe Arg Asn Phe Gln
            1300                1305                1310 ccc atg agc cgc cag gtc gtg gac gag gtc aac tac aag gac tac        20699
Pro Met Ser Arg Gln Val Val Asp Glu Val Asn Tyr Lys Asp Tyr
            1315                1320                1325 cag gcc gtc acc ctg gcc tac cag cac aac aac tcg ggc ttc gtc        20744
Gln Ala Val Thr Leu Ala Tyr Gln His Asn Asn Ser Gly Phe Val
            1330                1335                1340
```

| | | | | | | | | | | | | |
|---|---|---|---|---|---|---|---|---|---|---|---|---|
| ggc | tac | ctc | gcg | ccc | acc | atg | cgc | cag | gga | cag | ccc | tac | ccc | gcc | 20789 |
| Gly | Tyr | Leu | Ala | Pro | Thr | Met | Arg | Gln | Gly | Gln | Pro | Tyr | Pro | Ala | |
| | | | | 1345 | | | | | 1350 | | | | 1355 | | |

| aac | tac | ccc | tac | ccg | ctc | atc | ggc | aag | agc | gcc | gtc | gcc | agc | gtc | 20834 |
| Asn | Tyr | Pro | Tyr | Pro | Leu | Ile | Gly | Lys | Ser | Ala | Val | Ala | Ser | Val |
| | | | 1360 | | | | | 1365 | | | | | 1370 | | |

| acc | cag | aaa | aag | ttc | ctc | tgc | gac | cgg | gtc | atg | tgg | cgc | atc | ccc | 20879 |
| Thr | Gln | Lys | Lys | Phe | Leu | Cys | Asp | Arg | Val | Met | Trp | Arg | Ile | Pro |
| | | | 1375 | | | | | 1380 | | | | | 1385 | | |

| ttc | tcc | agc | aac | ttc | atg | tcc | atg | ggc | gcg | ctc | acc | gac | ctc | ggc | 20924 |
| Phe | Ser | Ser | Asn | Phe | Met | Ser | Met | Gly | Ala | Leu | Thr | Asp | Leu | Gly |
| | | | 1390 | | | | | 1395 | | | | | 1400 | | |

| cag | aac | atg | ctc | tac | gcc | aac | tcc | gcc | cac | gcg | cta | gac | atg | aat | 20969 |
| Gln | Asn | Met | Leu | Tyr | Ala | Asn | Ser | Ala | His | Ala | Leu | Asp | Met | Asn |
| | | | 1405 | | | | | 1410 | | | | | 1415 | | |

| ttc | gaa | gtc | gac | ccc | atg | gat | gag | tcc | acc | ctt | ctc | tat | gtt | gtc | 21014 |
| Phe | Glu | Val | Asp | Pro | Met | Asp | Glu | Ser | Thr | Leu | Leu | Tyr | Val | Val |
| | | | 1420 | | | | | 1425 | | | | | 1430 | | |

| ttc | gaa | gtc | ttc | gac | gtc | gtc | cga | gtg | cac | cag | ccc | cac | cgc | ggc | 21059 |
| Phe | Glu | Val | Phe | Asp | Val | Val | Arg | Val | His | Gln | Pro | His | Arg | Gly |
| | | | 1435 | | | | | 1440 | | | | | 1445 | | |

| gtc | atc | gag | gcc | gtc | tac | ctg | cgc | acg | ccc | ttc | tcg | gcc | ggc | aac | 21104 |
| Val | Ile | Glu | Ala | Val | Tyr | Leu | Arg | Thr | Pro | Phe | Ser | Ala | Gly | Asn |
| | | | 1450 | | | | | 1455 | | | | | 1460 | | |

| gcc acc acc taa gccccgctct tgcttcttgc aagatgacgg cctgtgcggg | 21156 |
| Ala Thr Thr | |

| ctccggcgag caggagctca gggccatcct ccgcgacctg ggctgcgggc cctgcttcct | 21216 |
| gggcaccttc gacaagcgct ccccgggatt catggccccg cacaagctgg cctgcgccat | 21276 |
| cgtcaacacg gccggccgcg agaccggggg cgagcactgg ctggccttcg cctggaaccc | 21336 |
| gcgctcccac acctgctacc tcttcgaccc cttcgggttc tcggacgagc gcctcaagca | 21396 |
| gatctaccag ttcgagtacg agggcctgct gcgccgcagc gccctggcca ccgaggaccg | 21456 |
| ctgcgtcacc ctggaaaagt ccacccagac cgtgcagggt ccgcgctcgg ccgcctgcgg | 21516 |
| gctcttctgc tgcatgttcc tgcacgcctt cgtgcactgg cccgaccgcc ccatggacaa | 21576 |
| gaaccccacc atgaacttgc tgacgggggt gcccaacggc atgctccagt cgccccaggt | 21636 |
| ggaacccacc ctgcgccgca accaggaggc gctctaccgc ttcctcaacg cccactccgc | 21696 |
| ctactttcgc tcccaccgcg cgcgcatcga aaggccacc gccttcgacc gcatgaatca | 21756 |
| agacatgtaa accgtgtgtg tatgtgaatg ctttattcat aataaacagc acatgtttat | 21816 |
| gccacctttt ctgaggctct gactttattt agaaatcgaa ggggttctgc cggctctcgg | 21876 |
| cgtgccccgc gggcagggat acgttgcgga actggtactt gggcagccac ttgaactcgg | 21936 |
| ggatcagcag cttcggcacg gggaggtcgg ggaacgagtc gctccacagc ttgcgcgtga | 21996 |
| gttgcagggc gcccagcagg tcgggcgcgg agatcttgaa atcgcagttg gacccgcgt | 22056 |
| tctgcgcgcg ggagttgcgg tacacggggt tgcagcactg gaacaccatc agggccggt | 22116 |
| gcttcacgct cgccagcacc gtcgcgtcgg tgatgccctc cacgtccaga tcctcggcgt | 22176 |
| tggccatccc gaaggggtc atcttgcagg tctgccgccc catgctgggc acgcagccgc | 22236 |
| gcttgtggtt gcaatcgcag tgcagggga tcagcatcat ctgggcctgc tcggagctca | 22296 |
| tgcccgggta catggccttc atgaaagcct ccagctggcg gaaggcctgc tgcgccttgc | 22356 |
| cgccctcggt gaagaagacc ccgcaggact tgctagagaa ctggttggtg gcgcagccgg | 22416 |
| cgtcgtgcac gcagcagcgc gcgtcgttgt tggccagctg caccacgctg cgccccagc | 22476 |

```
ggttctgggt gatcttggcc cggtcggggt tctccttcag cgcgcgctgc ccgttctcgc   22536
tcgccacatc catctcgatc gtgtgctcct tctggatcat cacggtcccg tgcaggcatc   22596
gcagcttgcc ctcggcctcg gtgcacccgt gcagccacag cgcgcagccg gtgcactccc   22656
agttcttgtg ggcgatctgg gagtgcgagt gcacgaagcc ctgcaggaag cggcccatca   22716
tcgtggtcag ggtcttgttg ctggtgaagg tcagcgggat gccgcggtgc tcctcgttca   22776
catacaggtg gcagatgcgg cggtacacct cgccctgctc gggcatcagc tggaaggcgg   22836
acttcaggtc gctctccacg cggtaccggt ccatcagcag cgtcatgact tccatgccct   22896
tctcccaggc cgagacgatc ggcaggctca gggggttctt caccgccgtt gtcatcttag   22956
tcgccgccgc tgaggtcagg gggtcgttct cgtccagggt ctcaaacact cgcttgccgt   23016
ccttctcggt gatgcgcacg gggggaaagc tgaagcccac ggccgccagc tcctcctcgg   23076
cctgcctttc gtcctcgctg tcctggctga tgtcttgcaa aggcacatgc ttggtcttgc   23136
ggggtttctt tttgggcggc agaggcgcg gcggagacgt gctgggcgag cgcgagttct   23196
cgctcaccac gactatttct tcttcttggc cgtcgtccga gaccacgcgg cggtaggcat   23256
gcctcttctg gggcagaggc ggaggcgacg ggctctcgcg gttcggcggg cggctggcag   23316
agccccttcc gcgttcgggg gtgcgctcct ggcggcgctg ctctgactga cttcctccgc   23376
ggccggccat tgtgttctcc tagggagcaa caagcatgga gactcagcca tcgtcgccaa   23436
catcgccatc tgcccccgcc gccgccgacg agaaccagca gcagaatgaa agcttaaccg   23496
ccccgccgcc cagccccacc tccgacgccg ccgcggcccc agacatgcaa gagatggagg   23556
aatccatcga gattgacctg ggctacgtga cgcccgcgga gcacgaggag gagctggcag   23616
cgcgcttttc agccccggaa gagaaccacc aagagcagcc agagcaggaa gcagagagcg   23676
agcagcagca ggctgggctc gagcatggcg actacctgag cggggcagag gacgtgctca   23736
tcaagcatct ggcccgccaa tgcatcatcg tcaaggacgc gctgctcgac cgcgccgagg   23796
tgcccctcag cgtggcggag ctcagccgcg cctacgagcg caacctcttc tcgccgcgcg   23856 tgcccccaa gcgccagccc aacggcacct gcgagcccaa cccgcgcctc aacttctacc   23916
cggtcttcgc ggtgcccgag gccctggcca cctaccacct cttttcaag aaccaaagga   23976 tccccgtctc ctgccgcgcc aaccgcaccc gcgccgacgc cctgctcaac ctgggtcccg   24036
gcgcccgcct acctgatatc gcctccttgg aagaggttcc caagatcttc gagggtctgg   24096
gcagcgacga gactcgggcc gcgaacgctc tgcaaggaag cggagaggag catgagcacc   24156
acagcgccct ggtggagttg gaaggcgaca acgcgcgcct ggcggtgctc aagcgcacgg   24216
tcgagctgac ccacttcgcc tacccggcgc tcaacctgcc ccccaaggtc atgagcgccg   24276
tcatggacca ggtgctcatc aagcgcgcct cgccctctc ggatgaggac atgcaggacc   24336
ccgagagctc ggacgagggc aagcccgtgg tcagcgacga gcagctggcg cgctggctgg   24396
gagcgagtag cacccccag agcttggaag agcggcgcaa gctcatgatg gccgtggtcc   24456
tggtgaccgt ggagctggag tgtctgcgcc gcttcttcgc cgacgcagag accctgcgca   24516
aggtcgagga gaacctgcac tacctcttca ggcacgggtt tgtgcgccag gcctgcaaga   24576
tctccaacgt ggagctgacc aacctggtct cctacatggg catcctgcac gagaaccgcc   24636
tggggcagaa cgtgctgcac accaccctgc gcggggaggc ccgccgcgac tacatccgcg   24696
actgcgtcta cctgtacctc tgccacacct ggcagacggg catgggcgtg tggcagcagt   24756
gcctggagga gcagaacctg aaagagctct gcaagctcct gcagaagaac ctgaaggccc   24816
```

```
tgtggaccgg gttcgacgag cgcaccaccg cctcggacct ggccgacctc atcttcccg   24876
agcgcctgcg gctgacgctg cgcaacggac tgcccgactt tatgagtcaa agcatgttgc   24936
aaaactttcg ctctttcatc ctcgaacgct ccgggatcct gcccgccacc tgctccgcgc   24996
tgccctcgga cttcgtgccg ctgaccttcc gcgagtgccc ccgccgctc tggagccact   25056
gctacctgct gcgcctggcc aactacctgg cctaccactc ggacgtgatc gaggacgtca   25116
gcggcgaggg tctgctcgag tgccactgcc gctgcaacct ctgcacgccg caccgctccc   25176
tggcctgcaa cccccagctg ctgagcgaga cccagatcat cggcaccttc gagttgcaag   25236
gccccggcga gggcaagggg ggtctgaaac tcaccccggg gctgtggacc tcggcctact   25296
tgcgcaagtt cgtgcccgag gactaccatc ccttcgagat caggttctac gaggaccaat   25356
cccagccgcc caaggccgaa ctgtcggcct gcgtcatcac ccaggggccc atcctggccc   25416
aattgcaagc catccagaaa tcccgccaag aatttctgct gaaaagggc cacggggtct   25476
acctggaccc ccagaccgga gaggagctca accccagctt cccccaggat gcccgagga   25536
agcagcaaga agctgaaagt ggagctgccg ccgccggagg atttggagga agactgggag   25596
agcagtcagg cagaggagga ggagatggaa gactgggaca gcactcaggc agaggaggac   25656
agcctgcaag acagtctgga agacgaggtg gaggaggagg cagaggaaga agcagccgcc   25716
gccagaccgt cgtcctcggc ggagaaagca agcagcacgg ataccatctc cgctccgggt   25776
cggggtcgcg gcgaccgggc ccacagtagg tgggacgaga ccgggcgctt cccgaaccc   25836
accacccaga ccggtaagaa ggagcggcag ggatacaagt cctggcgggg gcacaaaaac   25896
gccatcgtct cctgcttgca agcctgcggg ggcaacatct ccttcacccg ccgctacctg   25956
ctcttccacc gcggggtgaa cttcccccgc aacatcttgc attactaccg tcacctccac   26016
agccctact actgttttcca agaagaggca gaaacccagc agcagcagaa aaccagcggc   26076
agcagcagct agaaaatcca cagcggcggc aggtggactg aggatcgcag cgaacgagcc   26136
ggcgcagacc cgggagctga ggaaccggat ctttcccacc ctctatgcca tcttccagca   26196
gagtcgggg caggagcagg aactgaaagt caagaaccgt tctctgcgct cgctcacccg   26256
cagttgtctg tatcacaaga gcgaagacca acttcagcgc actctcgagg acgccgaggc   26316
tctcttcaac aagtactgcg cgctcactct taaagagtag cccgcgcccg cccacacacg   26376
gaaaaaggcg ggaattacgt caccacctgc gcccttcgcc cgaccatcat catgagcaaa   26436
gagattccca cgccttacat gtggagctac cagccccaga tgggcctggc cgccggcgcc   26496
gcccaggact actccacccg catgaactgg ctcagcgccg ggcccgcgat gatctcacgg   26556
gtgaatgaca tccgcgcccg ccgaaaccag atactcctag aacagtcagc gatcaccgcc   26616
acgccccgcc atcaccttaa tccgcgtaat tggcccgccg ccctggtgta ccaggaaatt   26676
ccccagccca cgaccgtact acttccgcga gacgcccagg ccgaagtcca gctgactaac   26736
tcaggtgtcc agctggccgg cggcgccgcc ctgtgtcgtc accgcccgc tcagggtata   26796
aagcggctgg tgatccgagg cagaggcaca cagctcaacg acgaggtggt gagctcttcg   26856
ctgggtctgc gacctgacgg agtcttccaa ctcgccggat cggggagatc ttccttcacg   26916
cctcgtcagg ccgtcctgac tttggagagt tcgtcctcgc agccccgctc gggtggcatc   26976
ggcactctcc agttcgtgga ggagttcact ccctcggtct acttcaaccc cttctccggc   27036
tccccccggcc actacccgga cgagttcatc ccgaacttcg acgccatcag cgagtcggtg   27096
gacggctacg attgaatgtc ccatggtggc gcagctgacc tagctcggct tcgacacctg   27156
gaccactgcc gccgcttccg ctgcttcgct cgggatctcg ccgagtttgc ctactttgag   27216
```

```
ctgcccgagg agcaccctca gggcccggcc cacggagtgc ggatcatcgt cgaaggggc    27276
ctcgactccc acctgcttcg gatcttcagc cagcgaccga tcctggtcga gcgcgagcaa   27336
ggacagaccc ttctgaccct gtactgcatc tgcaaccacc ccggcctgca tgaaagtctt   27396
tgttgtctgc tgtgtactga gtataataaa agctgagatc agcgactact ccggactcga   27456
ttgtggtgtt cctgctatca accggtccct gttcttcacc gggaacgaga ccgagctcca   27516
gcttcagtgt aagccccaca agaagtacct cacctggctg ttccagggct ccccgatcgc   27576
cgttgtcaac cactgcgaca acgacggagt cctgctgagc ggccccgcca accttacttt   27636
ttccacccgc agaagcaagc tccagctctt ccaacccttc ctccccggga cctatcagtg   27696
cgtctcggga ccctgccatc acaccttcca cctgatcccg aataccacag cgccgctccc   27756
cgctactaac aaccaaacta cccaccatcg ccaccgtcgc gacctttctg aatctaacac   27816
taccacccac accggaggtg agctccgagg tcgaccaacc tctgggattt actacggccc   27876
ctggaggtg gtgggttaa tagcgctagg cctagttgtg ggtgggcttt tggctctctg    27936
ctacctatac ctcccttgct gttcgtactt agtggtgctg tgttgctggt ttaagaaatg   27996
gggaagatca ccctagtgag ctgcggtgcg ctggtggcgg tggtggtgtt ttcgattgtg   28056
ggactgggcg gcgcggctgt agtgaaggag aaggccgatc cctgcttgca tttcaatccc   28116
gacaattgcc agctgagttt tcagcccgat ggcaatcggt gcgcggtgct gatcaagtgc   28176
ggatgggaat gcgagaacgt gagaatcgag tacaataaca agactcggaa caatactctc   28236
gcgtccgtgt ggcagcccgg ggaccccgag tggtacaccg tctctgtccc cggtgctgac   28296
ggctccccgc gcaccgtgaa caatactttc attttgcgc acatgtgcga cacggtcatg    28356
tggatgagca agcagtacga tatgtggccc cccacgaagg agaacatcgt ggtcttctcc   28416
atcgcttaca gcgcgtgcac ggcgctaatc accgctatcg tgtgcctgag cattcacatg   28476
ctcatcgcta ttcgcccag aaataatgcc gaaaaagaga acagccata acacgttttt    28536
tcacacacct ttttcagacc atggcctctg ttaaatttt gcttttattt gccagtctca    28596
ttactgttat aagtaatgag aaactcacta tttacattgg cactaaccac actttagacg   28656
gaattccaaa atcctcatgg tattgctatt ttgatcaaga tccagactta actatagaac   28716
tgtgtggtaa caagggaaaa aatacaagca ttcatttaat taactttaat tgcggagaca   28776
atttgaaatt aattaatatc actaaagagt atggaggtat gtattactat gttgcagaaa   28836
ataacaacat gcagttttat gaagttactg taactaatcc caccacacct agaacaacaa   28896
caaccaccac cacaaaaact acacctgtta ccactatgca gctcactacc aataacattt   28956
ttgccatgcg tcaaatggtc aacaatagca ctcaacccac cccacccagt gaggaaattc   29016
ccaaatccat gattggcatt attgttgctg tagtggtgtg catgttgatc atcgccttgt   29076
gcatggtgta ctatgccttc tgctacagaa agcacagact gaacgacaag ctggaacact   29136
tactaagtgt tgaattttaa ttttttagaa ccatgaagat cctaggcctt ttaattttt    29196
ctatcattac ctctgctcta tgcaattctg acaatgagga cgttactgtc gttgtcggaa   29256
ccaattatac actgaaaggt ccagcgaagg gtatgctttc gtggtattgc tggtttggaa   29316
ctgacgagca acagacagag ctctgcaatg ctcaaaaagg caaaacctca aattctaaaa   29376
tctctaatta tcaatgcaat ggcactgact tagtactgct caatgtcacg aaagcatatg   29436
ctggcagcta cacctgccct ggagatgata ctgagaacat gattttttac aaagtggaag   29496
tggttgatcc cactactcca cctccaccca ccacaactac tcacaccaca cacacagaac   29556
```

```
aaaccacagc agaggaggca gcaaagttag ccttgcaggt ccaagacagt tcatttgttg    29616
gcattacccc tacacctgat cagcggtgtc cggggctgct cgtcagcggc attgtcggtg    29676
tgctttcggg attagcagtc ataatcatct gcatgttcat ttttgcttgc tgctatagaa    29736
ggctttaccg acaaaaatca gacccactgc tgaacctcta tgtttaattt tttccagagc    29796
catgaaggca gttagcactc tagttttttg ttctttgatt ggcactgttt ttagtgttag    29856
cttttttgaaa caaatcaatg ttactgaggg ggaaaatgtg acactggtag gcgtagaggg    29916
tgctcaaaat accacctgga caaaattcca tctagatggg tggaaagaaa tttgcacctg    29976
gaatgtcagt acttatacat gtgaaggagt taatcttacc attgtcaatg tcagccaaat    30036
tcaaagggt tggattaaag ggcaatctgt tagtgttagc aatagtgggt actatacccca    30096
gcatactctt atctatgaca ttatagttat accactgcct acacctagcc cacctagcac    30156
taccacacag acaacccaca ctacacaaac aaccacatac agtacatcaa atcagcctac    30216
caccactaca acagcagagg ttgccagctc gtctggggtc cgagtggcat ttttgatgtt    30276
ggccccatct agcagtccca ctgctagtac caatgagcag actactgaat ttttgtccac    30336
tgtcgagagc cacaccacag ctacctcgag tgccttctct agcaccgcca atctatcctc    30396
gctttcctct acaccaatca gtcccgctac tactcctacc cccgctattc tccccactcc    30456
cctgaagcaa acagacggcg acatgcaatg gcagatcacc ctgctcattg tgatcgggtt    30516
ggtcatcctg gccgtgttgc tctactacat cttctgccgc cgcattccca acgcgcaccg    30576
caagccggcc tacaagccca tcgttgtcgg gcagccggag ccgcttcagg tggaaggggg    30636
tctaaggaat cttctcttct cttttacagt atggtgattg aattatgatt cctagacaaa    30696
tcttgatcac tattcttatc tgcctcctcc aagtctgtgc caccctcgct ctggtggcca    30756
acgccagtcc agactgtatt gggcccttcg cctcctacgt gctctttgcc ttcatcacct    30816
gcatctgctg ctgtagcata gtctgcctgc ttatcacctt cttccagttc attgactgga    30876
tctttgtgcg catcgcctac ctgcgccacc accccagta ccgcgaccag cgagtggcgc    30936
ggctgctcag gatcctctga taagcatgcg ggctctgcta cttctcgcgc ttctgctgtt    30996
agtgctcccc cgtcccgtcg accccggac ccccacccag tccccgagg aggtccgcaa    31056
atgcaaattc caagaaccct ggaaattcct caaatgctac cgccaaaaat cagacatgca    31116
tcccagctgg atcatgatca ttgggatcgt gaacattctg gcctgcaccc tcatctcctt    31176
tgtgatttac ccctgctttg actttggttg gaactcgcca gaggcgctct atctcccgcc    31236
tgaacctgac acaccaccac agcaacctca ggcacacgca ctaccaccac caccacagcc    31296
taggccacaa tacatgccca tattagacta tgaggccgag ccacagcgac ccatgctccc    31356
cgctattagt tacttcaatc taaccggcgg agatgactga cccactggcc aacaacaacg    31416
tcaacgacct tctcctggac atggacggcc gcgcctcgga gcagcgactc gcccaacttc    31476
gcattcgcca gcagcaggag agagccgtca aggagctgca ggacggcata gccatccacc    31536
agtgcaagaa aggcatcttc tgcctggtga acaggccaa gatctcctac gaggtcaccc    31596
agaccgacca tcgcctctcc tacgagctcc tgcagcagcg ccagaagttc acctgcctgg    31656
tcggagtcaa ccccatcgtc atcacccagc agtcgggcga taccaagggg tgcatccact    31716
gctcctgcga ctcccccgac tgcgtccaca ctctgatcaa gaccctctgc ggcctccgcg    31776
acctcctccc catgaactaa tcaccccctt atccagtgaa ataaagatca tattgatgat    31836
ttgagtttaa taaaataaa gaatcactta cttgaaatct gataccaggt ctctgtccat    31896
gttttctgcc aacaccactt cactcccctc ttcccagctc tggtactgca ggccccggcg    31956
```

```
ggctgcaaac ttcctccaca ccctgaaggg gatgtcaaat tcctcctgtc cctcaatctt    32016
cattttatct tctatcag atg tcc  aaa aag cgc gtc cgg  gtg gat gat gac    32067
                    Met Ser  Lys Lys Arg Val Arg  Val Asp Asp Asp
                        1465                 1470 ttc gac ccc gtc tac ccc  tac gat gca gac aac  gca ccg acc gtg        32112
Phe Asp Pro Val Tyr Pro  Tyr Asp Ala Asp Asn  Ala Pro Thr Val
1475            1480                     1485 ccc ttc atc aac ccc ccc  ttc gtc tct tca gat  gga ttc caa gag        32157
Pro Phe Ile Asn Pro Pro  Phe Val Ser Ser Asp  Gly Phe Gln Glu
1490            1495                     1500 aag ccc ctg ggg gtg ctg  tcc ctg cgt ctg gcc  gat ccc gtc acc        32202
Lys Pro Leu Gly Val Leu  Ser Leu Arg Leu Ala  Asp Pro Val Thr
1505            1510                     1515 acc aag aac ggg gaa atc  acc ctc aag ctg gga  gat ggg gtg gac        32247
Thr Lys Asn Gly Glu Ile  Thr Leu Lys Leu Gly  Asp Gly Val Asp
1520            1525                     1530 ctc gac tcc tcg gga aaa  ctc atc tcc aac acg  gcc acc aag gcc        32292
Leu Asp Ser Ser Gly Lys  Leu Ile Ser Asn Thr  Ala Thr Lys Ala
1535            1540                     1545 gcc gcc cct ctc agt ttt  tcc aac aac acc att  tcc ctt aac atg        32337
Ala Ala Pro Leu Ser Phe  Ser Asn Asn Thr Ile  Ser Leu Asn Met
1550            1555                     1560 gat acc cct ttt tac aac  aac aat gga aag tta  ggc atg aaa gtc        32382
Asp Thr Pro Phe Tyr Asn  Asn Asn Gly Lys Leu  Gly Met Lys Val
1565            1570                     1575 act gct cca ctg aag ata  cta gac aca gac ttg  cta aaa aca ctt        32427
Thr Ala Pro Leu Lys Ile  Leu Asp Thr Asp Leu  Leu Lys Thr Leu
1580            1585                     1590 gtt gta gct tat gga caa  ggt tta gga aca aac  acc act ggt gcc        32472
Val Val Ala Tyr Gly Gln  Gly Leu Gly Thr Asn  Thr Thr Gly Ala
1595            1600                     1605 ctt gtt gcc caa cta gca  tcc cca ctt gct ttt  gat agc aat agc        32517
Leu Val Ala Gln Leu Ala  Ser Pro Leu Ala Phe  Asp Ser Asn Ser
1610            1615                     1620 aaa att gcc ctt aat tta  ggc aat gga cca ttg  aaa gtg gat gca        32562
Lys Ile Ala Leu Asn Leu  Gly Asn Gly Pro Leu  Lys Val Asp Ala
1625            1630                     1635 aat aga ctg aac atc aat  tgc aat aga gga ctc  tat gtt act acc        32607
Asn Arg Leu Asn Ile Asn  Cys Asn Arg Gly Leu  Tyr Val Thr Thr
1640            1645                     1650 aca aaa gat gca ctg gaa  gcc aat ata agt tgg  gct aat gct atg        32652
Thr Lys Asp Ala Leu Glu  Ala Asn Ile Ser Trp  Ala Asn Ala Met
1655            1660                     1665 aca ttt ata gga aat gcc  atg ggt gtc aat att  gat aca caa aaa        32697
Thr Phe Ile Gly Asn Ala  Met Gly Val Asn Ile  Asp Thr Gln Lys
1670            1675                     1680 ggc ttg caa ttt ggc acc  act agt acc gtc gca  gat gtt aaa aac        32742
Gly Leu Gln Phe Gly Thr  Thr Ser Thr Val Ala  Asp Val Lys Asn
1685            1690                     1695 gct tac ccc ata caa atc  aaa ctt gga gct ggt  ctc aca ttt gac        32787
Ala Tyr Pro Ile Gln Ile  Lys Leu Gly Ala Gly  Leu Thr Phe Asp
1700            1705                     1710 agc aca ggt gca att gtt  gca tgg aac aaa gat  gat gac aag ctt        32832
Ser Thr Gly Ala Ile Val  Ala Trp Asn Lys Asp  Asp Asp Lys Leu
1715            1720                     1725 aca cta tgg acc aca gcc  gac ccc tct cca aat  tgt cac ata tat        32877
Thr Leu Trp Thr Thr Ala  Asp Pro Ser Pro Asn  Cys His Ile Tyr
1730            1735                     1740
```

| | | | | | | | | | | | | |
|---|---|---|---|---|---|---|---|---|---|---|---|---|
| tct | gaa | aag | gat | gct | aag | ctt | aca | ctt | tgc | ttg | aca | aag tgt ggc |
| Ser | Glu | Lys | Asp | Ala | Lys | Leu | Thr | Leu | Cys | Leu | Thr | Lys Cys Gly |
| 1745 | | | | | 1750 | | | | | 1755 | | |

32922

| agt | cag | att | ctg | ggc | act | gtt | tcc | ctc | ata | gct | gtt | gat act ggc |
|---|---|---|---|---|---|---|---|---|---|---|---|---|
| Ser | Gln | Ile | Leu | Gly | Thr | Val | Ser | Leu | Ile | Ala | Val | Asp Thr Gly |
| 1760 | | | | | 1765 | | | | | 1770 | | |

32967

| agt | tta | aat | ccc | ata | aca | gga | aca | gta | acc | act | gct | ctt gtc tca |
|---|---|---|---|---|---|---|---|---|---|---|---|---|
| Ser | Leu | Asn | Pro | Ile | Thr | Gly | Thr | Val | Thr | Thr | Ala | Leu Val Ser |
| 1775 | | | | | 1780 | | | | | 1785 | | |

33012

| ctt | aaa | ttc | gat | gca | aat | gga | gtt | ttg | caa | agc | agc | tca aca cta |
|---|---|---|---|---|---|---|---|---|---|---|---|---|
| Leu | Lys | Phe | Asp | Ala | Asn | Gly | Val | Leu | Gln | Ser | Ser | Ser Thr Leu |
| 1790 | | | | | 1795 | | | | | 1800 | | |

33057

| gac | tca | gac | tat | tgg | aat | ttc | aga | cag | gga | gat | gtt | aca cct gct |
|---|---|---|---|---|---|---|---|---|---|---|---|---|
| Asp | Ser | Asp | Tyr | Trp | Asn | Phe | Arg | Gln | Gly | Asp | Val | Thr Pro Ala |
| 1805 | | | | | 1810 | | | | | 1815 | | |

33102

| gaa | gcc | tat | act | aat | gct | ata | ggt | ttc | atg | ccc | aat | cta aaa gca |
|---|---|---|---|---|---|---|---|---|---|---|---|---|
| Glu | Ala | Tyr | Thr | Asn | Ala | Ile | Gly | Phe | Met | Pro | Asn | Leu Lys Ala |
| 1820 | | | | | 1825 | | | | | 1830 | | |

33147

| tac | cct | aaa | aac | aca | agt | gga | gct | gca | aaa | agt | cac | att gtt ggg |
|---|---|---|---|---|---|---|---|---|---|---|---|---|
| Tyr | Pro | Lys | Asn | Thr | Ser | Gly | Ala | Ala | Lys | Ser | His | Ile Val Gly |
| 1835 | | | | | 1840 | | | | | 1845 | | |

33192

| aaa | gtg | tac | cta | cat | ggg | gat | aca | ggc | aaa | cca | ctg | gac ctc att |
|---|---|---|---|---|---|---|---|---|---|---|---|---|
| Lys | Val | Tyr | Leu | His | Gly | Asp | Thr | Gly | Lys | Pro | Leu | Asp Leu Ile |
| 1850 | | | | | 1855 | | | | | 1860 | | |

33237

| att | act | ttc | aat | gaa | aca | agt | gat | gaa | tct | tgc | act | tac tgt att |
|---|---|---|---|---|---|---|---|---|---|---|---|---|
| Ile | Thr | Phe | Asn | Glu | Thr | Ser | Asp | Glu | Ser | Cys | Thr | Tyr Cys Ile |
| 1865 | | | | | 1870 | | | | | 1875 | | |

33282

| aac | ttt | caa | tgg | cag | tgg | ggg | gct | gat | caa | tat | aaa | aat gaa aca |
|---|---|---|---|---|---|---|---|---|---|---|---|---|
| Asn | Phe | Gln | Trp | Gln | Trp | Gly | Ala | Asp | Gln | Tyr | Lys | Asn Glu Thr |
| 1880 | | | | | 1885 | | | | | 1890 | | |

33327

| ctt | gcc | gtc | agt | tca | ttc | acc | ttt | tcc | tat | att | gct | aaa gaa taa |
|---|---|---|---|---|---|---|---|---|---|---|---|---|
| Leu | Ala | Val | Ser | Ser | Phe | Thr | Phe | Ser | Tyr | Ile | Ala | Lys Glu |
| 1895 | | | | | 1900 | | | | | 1905 | | |

33372

| | | |
|---|---|---|
| accccactct gtaccccatc tctgtctatg gaaaaaactc tgaaacacaa aataaaataa | 33432 |
| agttcaagtg ttttattgat tcaacagttt tacaggattc gagcagttat ttttcctcca | 33492 |
| ccctcccagg acatggaata caccaccctc tcccccccgca cagccttgaa catctgaatg | 33552 |
| ccattggtga tggacatgct tttggtctcc acgttccaca cagtttcaga gcgagccagt | 33612 |
| ctcgggtcgg tcaggagat gaaaccctcc gggcactccc gcatctgcac ctcacagctc | 33672 |
| aacagctgag gattgtcctc ggtggtcggg atcacggtta tctggaagaa gcagaagagc | 33732 |
| ggcggtggga atcatagtcc gcgaacggga tcggccggtg gtgtcgcatc aggcccgca | 33792 |
| gcagtcgctg tcgccgccgc tccgtcaagc tgctgctcag ggggtccggg tccagggact | 33852 |
| ccctcagcat gatgcccacg gccctcagca tcagtcgtct ggtgcggcgg gcgcagcagc | 33912 |
| gcatgcggat ctcgctcagg tcgctgcagt acgtgcaaca caggaccacc aggttgttca | 33972 |
| acagtccata gttcaacacg ctccagccga aactcatcgc gggaaggatg ctacccacgt | 34032 |
| ggccgtcgta ccagatcctc aggtaaatca agtggcgccc cctccagaac acgctgccca | 34092 |
| tgtacatgat ctccttgggc atgtggcggt tcaccacctc ccggtaccac atcaccctct | 34152 |
| ggttgaacat gcagccccgg atgatcctgc ggaaccacag ggccagcacc gccccgcccg | 34212 |
| ccatgcagcg aagagacccc gggtcccgac aatggcaatg gaggacccac cgctcgtacc | 34272 |
| cgtggatcat ctgggagctg aacaagtcta tgttggcaca gcacaggcat atgctcatgc | 34332 |
| atctcttcag cactctcagc tcctcggggg tcaaaaccat atcccagggc acggggaact | 34392 |
| cttgcaggac agcgaacccc gcagaacagg gcaatcctcg cacataactt acattgtgca | 34452 |

| | | | | |
|---|---|---|---|---|
| tggacagggt | atcgcaatca | ggcagcaccg | ggtgatcctc | caccagagaa gcgcgggtct | 34512 |
| cggtctcctc | acagcgtggt | aagggggccg | gccgatacgg | gtgatggcgg gacgcggctg | 34572 |
| atcgtgttcg | cgaccgtgtt | atgatgcagt | tgctttcgga | cattttcgta cttgctgtag | 34632 |
| cagaacctgg | tccgggcgct | gcacaccgat | cgccggcggc | ggtcccggcg cttggaacgc | 34692 |
| tcggtgttga | agttgtaaaa | cagccactct | ctcagaccgt | gcagcagatc tagggcctca | 34752 |
| ggagtgatga | agatcccatc | atgcctgatg | gctctaatca | catcgaccac cgtggaatgg | 34812 |
| gccagaccca | gccagatgat | gcaattttgt | tgggtttcgg | tgacggcggg ggagggaaga | 34872 |
| acaggaagaa | ccatgattaa | cttttaatcc | aaacggtctc | ggagcacttc aaaatgaaga | 34932 |
| tcgcggagat | ggcacctctc | gcccccgctg | tgttggtgga | aaataacagc caggtcaaag | 34992 |
| gtgatacggt | tctcgagatg | ttccacggtg | gcttccagca | aagcctccac gcgcacatcc | 35052 |
| agaaacaaga | caatagcgaa | agcgggaggg | ttctctaatt | cctcaatcat catgttacac | 35112 |
| tcctgcacca | tccccagata | attttcattt | ttccagcctt | gaatgattcg aactagttcc | 35172 |
| tgaggtaaat | ccaagccagc | catgataaag | agctcgcgca | gagcgccctc caccggcatt | 35232 |
| cttaagcaca | ccctcataat | tccaagatat | tctgctcctg | gttcacctgc agcagattga | 35292 |
| caagcggaat | atcaaaatct | ctgccgcgat | ccctaagctc | ctccctcagc aataactgta | 35352 |
| agtactcttt | catatcctct | ccgaaatttt | tagccatagg | accaccagga ataagattag | 35412 |
| ggcaagccac | agtacagata | aaccgaagtc | ctccccagtg | agcattgcca aatgcaagac | 35472 |
| tgctataagc | atgctggcta | gacccggtga | tatcttccag | ataactggac agaaaatcgc | 35532 |
| ccaggcaatt | tttaagaaaa | tcaacaaaag | aaaaatcctc | caggtgcacg tttagagcct | 35592 |
| cgggaacaac | gatggagtaa | atgcaagcgg | tgcgttccag | catggttagt tagctgatct | 35652 |
| gtagaaaaaa | acaaaaatga | acattaaacc | atgctagcct | ggcgaacagg tgggtaaatc | 35712 |
| gttctctcca | gcaccaggca | ggccacgggg | tctccggcac | gaccctcgta aaaattgtcg | 35772 |
| ctatgattga | aaaccatcac | agagagacgt | tcccggtggc | cggcgtgaat gattcgacaa | 35832 |
| gatgaataca | ccccccggaac | attggcgtcc | gcgagtgaaa | aaaagcgccc aaggaagcaa | 35892 |
| taaggcacta | caatgctcag | tctcaagtcc | agcaaagcga | tgccatgcgg atgaagcaca | 35952 |
| aaattctcag | gtgcgtacaa | aatgtaatta | ctcccctcct | gcacaggcag caaagccccc | 36012 |
| gatccctcca | ggtacacata | caaagcctca | gcgtccatag | cttaccgagc agcagcacac | 36072 |
| aacaggcgca | agagtcagag | aaaggctgag | ctctaacctg | tccacccgct ctctgctcaa | 36132 |
| tatatagccc | agatctacac | tgacgtaaag | gccaaagtct | aaaaataccc gccaaataat | 36192 |
| cacacacgcc | cagcacacgc | ccagaaaccg | gtgacacact | caaaaaaata cgcgcacttc | 36252 |
| ctcaaacgcc | caaactgccg | tcatttccgg | gttcccacgc | tacgtcatca aaattcgact | 36312 |
| ttcaaattcc | gtcgaccgtt | aaaaacgtcg | cccgccccgc | ccctaacggt cgccgctccc | 36372 |
| gcagccaatc | accgccccgc | atccccaaat | tcaaataccct | catttgcata ttaacgcgca | 36432 |
| ccaaaagttt | gaggtatatt | attgatgatg | | | 36462 |

<210> SEQ ID NO 2
<211> LENGTH: 530
<212> TYPE: PRT
<213> ORGANISM: chimpanzee adenovirus serotype Pan5

<400> SEQUENCE: 2

Met Met Arg Arg Val Tyr Pro Glu Gly Pro Pro Pro Ser Tyr Glu Ser
1               5                   10                  15

```
Val Met Gln Gln Ala Val Ala Ala Met Gln Pro Pro Leu Glu Ala
            20                  25                  30

Pro Tyr Val Pro Pro Arg Tyr Leu Ala Pro Thr Glu Gly Arg Asn Ser
            35                  40                  45

Ile Arg Tyr Ser Glu Leu Ala Pro Leu Tyr Asp Thr Thr Arg Leu Tyr
 50                  55                  60

Leu Val Asp Asn Lys Ser Ala Asp Ile Ala Ser Leu Asn Tyr Gln Asn
 65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Gly Arg Ser Arg
            100                 105                 110

Trp Gly Gly Gln Leu Lys Thr Ile Met His Thr Asn Met Pro Asn Val
            115                 120                 125

Asn Glu Phe Met Tyr Ser Asn Lys Phe Lys Ala Arg Val Met Val Ser
            130                 135                 140

Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
                165                 170                 175

Val Thr Met Thr Ile Asp Leu Met Asn Asn Ala Ile Ile Asp Asn Tyr
                180                 185                 190

Leu Ala Val Gly Arg Gln Asn Gly Val Leu Glu Ser Asp Ile Gly Val
                195                 200                 205

Lys Phe Asp Thr Arg Asn Phe Arg Leu Gly Trp Asp Pro Val Thr Glu
210                 215                 220

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
                260                 265                 270

Ile Leu Tyr Glu Asp Leu Glu Gly Gly Asn Ile Pro Ala Leu Leu Asp
                275                 280                 285

Val Asp Ala Tyr Glu Lys Ser Lys Glu Asp Ser Ala Ala Ala Ala Thr
            290                 295                 300

Ala Ala Val Ala Thr Ala Ser Thr Glu Val Arg Gly Asp Asn Phe Ala
305                 310                 315                 320

Ser Ala Ala Thr Leu Ala Ala Glu Ala Ala Glu Thr Glu Ser Lys
                325                 330                 335

Ile Val Ile Gln Pro Val Glu Lys Asp Ser Lys Glu Arg Ser Tyr Asn
                340                 345                 350

Val Leu Ala Asp Lys Lys Asn Thr Ala Tyr Arg Ser Trp Tyr Leu Ala
                355                 360                 365

Tyr Asn Tyr Gly Asp Pro Glu Lys Gly Val Arg Ser Trp Thr Leu Leu
                370                 375                 380

Thr Thr Ser Asp Val Thr Cys Gly Val Glu Gln Val Tyr Trp Ser Leu
385                 390                 395                 400

Pro Asp Met Met Gln Asp Pro Val Thr Phe Arg Ser Thr Arg Gln Val
                405                 410                 415

Ser Asn Tyr Pro Val Val Gly Ala Glu Leu Leu Pro Val Tyr Ser Lys
                420                 425                 430
```

```
Ser Phe Phe Asn Glu Gln Ala Val Tyr Ser Gln Gln Leu Arg Ala Phe
            435                 440                 445

Thr Ser Leu Thr His Val Phe Asn Arg Phe Pro Glu Asn Gln Ile Leu
450                 455                 460

Val Arg Pro Pro Ala Pro Thr Ile Thr Thr Val Ser Glu Asn Val Pro
465                 470                 475                 480

Ala Leu Thr Asp His Gly Thr Leu Pro Leu Arg Ser Ser Ile Arg Gly
                485                 490                 495

Val Gln Arg Val Thr Val Thr Asp Ala Arg Arg Thr Cys Pro Tyr
                500                 505                 510

Val Tyr Lys Ala Leu Gly Val Val Ala Pro Arg Val Leu Ser Ser Arg
            515                 520                 525

Thr Phe
    530

<210> SEQ ID NO 3
<211> LENGTH: 933
<212> TYPE: PRT
<213> ORGANISM: chimpanzee adenovirus serotype Pan5

<400> SEQUENCE: 3

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
                100                 105                 110

Phe Lys Pro Tyr Ser Gly Thr Ala Tyr Asn Ser Leu Ala Pro Lys Gly
            115                 120                 125

Ala Pro Asn Thr Cys Gln Trp Thr Tyr Lys Ala Asp Gly Asp Thr Gly
130                 135                 140

Thr Glu Lys Thr Tyr Thr Tyr Gly Asn Ala Pro Val Gln Gly Ile Ser
145                 150                 155                 160

Ile Thr Lys Asp Gly Ile Gln Leu Gly Thr Asp Thr Asp Gln Pro
                165                 170                 175

Ile Tyr Ala Asp Lys Thr Tyr Gln Pro Glu Pro Gln Val Gly Asp Ala
                180                 185                 190

Glu Trp His Asp Ile Thr Gly Thr Asp Glu Lys Tyr Gly Gly Arg Ala
                195                 200                 205

Leu Lys Pro Asp Thr Lys Met Lys Pro Cys Tyr Gly Ser Phe Ala Lys
            210                 215                 220

Pro Thr Asn Lys Glu Gly Gly Gln Ala Asn Val Lys Thr Glu Thr Gly
225                 230                 235                 240

Gly Thr Lys Glu Tyr Asp Ile Asp Met Ala Phe Phe Asp Asn Arg Ser
                245                 250                 255

Ala Ala Ala Ala Gly Leu Ala Pro Glu Ile Val Leu Tyr Thr Glu Asn
                260                 265                 270
```

```
Val Asp Leu Glu Thr Pro Asp Thr His Ile Val Tyr Lys Ala Gly Thr
            275                 280                 285

Asp Asp Ser Ser Ser Ile Asn Leu Gly Gln Gln Ser Met Pro Asn
    290                 295                 300

Arg Pro Asn Tyr Ile Gly Phe Arg Asp Asn Phe Ile Gly Leu Met Tyr
305                 310                 315                 320

Tyr Asn Ser Thr Gly Asn Met Gly Val Leu Ala Gly Gln Ala Ser Gln
                325                 330                 335

Leu Asn Ala Val Val Asp Leu Gln Asp Arg Asn Thr Glu Leu Ser Tyr
            340                 345                 350

Gln Leu Leu Asp Ser Leu Gly Asp Arg Thr Arg Tyr Phe Ser Met
        355                 360                 365

Trp Asn Gln Ala Val Asp Ser Tyr Asp Pro Asp Val Arg Ile Ile Glu
    370                 375                 380

Asn His Gly Val Glu Asp Glu Leu Pro Asn Tyr Cys Phe Pro Leu Asp
385                 390                 395                 400

Ala Val Gly Arg Thr Asp Thr Tyr Gln Gly Ile Lys Ala Asn Gly Ala
                405                 410                 415

Asp Gln Thr Thr Trp Thr Lys Asp Asp Thr Val Asn Asp Ala Asn Glu
            420                 425                 430

Leu Gly Lys Gly Asn Pro Phe Ala Met Glu Ile Asn Ile Gln Ala Asn
        435                 440                 445

Leu Trp Arg Asn Phe Leu Tyr Ala Asn Val Ala Leu Tyr Leu Pro Asp
    450                 455                 460

Ser Tyr Lys Tyr Thr Pro Ala Asn Ile Thr Leu Pro Thr Asn Thr Asn
465                 470                 475                 480

Thr Tyr Asp Tyr Met Asn Gly Arg Val Val Ala Pro Ser Leu Val Asp
                485                 490                 495

Ala Tyr Ile Asn Ile Gly Ala Arg Trp Ser Leu Asp Pro Met Asp Asn
            500                 505                 510

Val Asn Pro Phe Asn His His Arg Asn Ala Gly Leu Arg Tyr Arg Ser
        515                 520                 525

Met Leu Leu Gly Asn Gly Arg Tyr Val Pro Phe His Ile Gln Val Pro
    530                 535                 540

Gln Lys Phe Phe Ala Ile Lys Ser Leu Leu Leu Pro Gly Ser Tyr
545                 550                 555                 560

Thr Tyr Glu Trp Asn Phe Arg Lys Asp Val Asn Met Ile Leu Gln Ser
                565                 570                 575

Ser Leu Gly Asn Asp Leu Arg Thr Asp Gly Ala Ser Ile Ala Phe Thr
            580                 585                 590

Ser Ile Asn Leu Tyr Ala Thr Phe Phe Pro Met Ala His Asn Thr Ala
        595                 600                 605

Ser Thr Leu Glu Ala Met Leu Arg Asn Asp Thr Asn Asp Gln Ser Phe
    610                 615                 620

Asn Asp Tyr Leu Ser Ala Ala Asn Met Leu Tyr Pro Ile Pro Ala Asn
625                 630                 635                 640

Ala Thr Asn Val Pro Ile Ser Ile Pro Ser Arg Asn Trp Ala Ala Phe
                645                 650                 655

Arg Gly Trp Ser Phe Thr Arg Leu Lys Thr Arg Glu Thr Pro Ser Leu
            660                 665                 670

Gly Ser Gly Phe Asp Pro Tyr Phe Val Tyr Ser Gly Ser Ile Pro Tyr
        675                 680                 685
```

Leu Asp Gly Thr Phe Tyr Leu Asn His Thr Phe Lys Lys Val Ser Ile
690                 695                 700

Thr Phe Asp Ser Ser Val Ser Trp Pro Gly Asn Asp Arg Leu Leu Thr
705                 710                 715                 720

Pro Asn Glu Phe Glu Ile Lys Arg Thr Val Asp Gly Glu Gly Tyr Asn
                725                 730                 735

Val Ala Gln Cys Asn Met Thr Lys Asp Trp Phe Leu Val Gln Met Leu
            740                 745                 750

Ala His Tyr Asn Ile Gly Tyr Gln Gly Phe Tyr Val Pro Glu Gly Tyr
        755                 760                 765

Lys Asp Arg Met Tyr Ser Phe Phe Arg Asn Phe Gln Pro Met Ser Arg
770                 775                 780

Gln Val Val Asp Glu Val Asn Tyr Lys Asp Tyr Gln Ala Val Thr Leu
785                 790                 795                 800

Ala Tyr Gln His Asn Asn Ser Gly Phe Val Gly Tyr Leu Ala Pro Thr
                805                 810                 815

Met Arg Gln Gly Gln Pro Tyr Pro Ala Asn Tyr Pro Tyr Pro Leu Ile
                820                 825                 830

Gly Lys Ser Ala Val Ala Ser Val Thr Gln Lys Lys Phe Leu Cys Asp
            835                 840                 845

Arg Val Met Trp Arg Ile Pro Phe Ser Ser Asn Phe Met Ser Met Gly
850                 855                 860

Ala Leu Thr Asp Leu Gly Gln Asn Met Leu Tyr Ala Asn Ser Ala His
865                 870                 875                 880

Ala Leu Asp Met Asn Phe Glu Val Asp Pro Met Asp Glu Ser Thr Leu
                885                 890                 895

Leu Tyr Val Val Phe Glu Val Phe Asp Val Val Arg Val His Gln Pro
                900                 905                 910

His Arg Gly Val Ile Glu Ala Val Tyr Leu Arg Thr Pro Phe Ser Ala
            915                 920                 925

Gly Asn Ala Thr Thr
        930

<210> SEQ ID NO 4
<211> LENGTH: 445
<212> TYPE: PRT
<213> ORGANISM: chimpanzee adenovirus serotype Pan5

<400> SEQUENCE: 4

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
        50                  55                  60

Lys Leu Gly Asp Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp Thr Pro Phe Tyr Asn Asn Asn Gly Lys Leu
            100                 105                 110

Gly Met Lys Val Thr Ala Pro Leu Lys Ile Leu Asp Thr Asp Leu Leu
        115                 120                 125

```
Lys Thr Leu Val Val Ala Tyr Gly Gln Gly Leu Gly Thr Asn Thr Thr
            130                 135                 140

Gly Ala Leu Val Ala Gln Leu Ala Ser Pro Leu Ala Phe Asp Ser Asn
145                 150                 155                 160

Ser Lys Ile Ala Leu Asn Leu Gly Asn Gly Pro Leu Lys Val Asp Ala
                165                 170                 175

Asn Arg Leu Asn Ile Asn Cys Asn Arg Gly Leu Tyr Val Thr Thr Thr
            180                 185                 190

Lys Asp Ala Leu Glu Ala Asn Ile Ser Trp Ala Asn Ala Met Thr Phe
        195                 200                 205

Ile Gly Asn Ala Met Gly Val Asn Ile Asp Thr Gln Lys Gly Leu Gln
210                 215                 220

Phe Gly Thr Thr Ser Thr Val Ala Asp Val Lys Asn Ala Tyr Pro Ile
225                 230                 235                 240

Gln Ile Lys Leu Gly Ala Gly Leu Thr Phe Asp Ser Thr Gly Ala Ile
                245                 250                 255

Val Ala Trp Asn Lys Asp Asp Lys Leu Thr Leu Trp Thr Thr Ala
            260                 265                 270

Asp Pro Ser Pro Asn Cys His Ile Tyr Ser Glu Lys Asp Ala Lys Leu
        275                 280                 285

Thr Leu Cys Leu Thr Lys Cys Gly Ser Gln Ile Leu Gly Thr Val Ser
290                 295                 300

Leu Ile Ala Val Asp Thr Gly Ser Leu Asn Pro Ile Thr Gly Thr Val
305                 310                 315                 320

Thr Thr Ala Leu Val Ser Leu Lys Phe Asp Ala Asn Gly Val Leu Gln
                325                 330                 335

Ser Ser Ser Thr Leu Asp Ser Asp Tyr Trp Asn Phe Arg Gln Gly Asp
            340                 345                 350

Val Thr Pro Ala Glu Ala Tyr Thr Asn Ala Ile Gly Phe Met Pro Asn
        355                 360                 365

Leu Lys Ala Tyr Pro Lys Asn Thr Ser Gly Ala Ala Lys Ser His Ile
370                 375                 380

Val Gly Lys Val Tyr Leu His Gly Asp Thr Gly Lys Pro Leu Asp Leu
385                 390                 395                 400

Ile Ile Thr Phe Asn Glu Thr Ser Asp Glu Ser Cys Thr Tyr Cys Ile
                405                 410                 415

Asn Phe Gln Trp Gln Trp Gly Ala Asp Gln Tyr Lys Asn Glu Thr Leu
            420                 425                 430

Ala Val Ser Ser Phe Thr Phe Ser Tyr Ile Ala Lys Glu
        435                 440                 445

<210> SEQ ID NO 5
<211> LENGTH: 36604
<212> TYPE: DNA
<213> ORGANISM: chimpanzee adenovirus serotype Pan6
<220> FEATURE:
<221> NAME/KEY: CDS
<222> LOCATION: (13878)..(15467)
<223> OTHER INFORMATION: L2 Penton
<220> FEATURE:
<221> NAME/KEY: CDS
<222> LOCATION: (18284)..(21112)
<223> OTHER INFORMATION: L3 Hexon
<220> FEATURE:
<221> NAME/KEY: CDS
<222> LOCATION: (32162)..(33493)
<223> OTHER INFORMATION: L5 Fiber
```

```
<400> SEQUENCE: 5
catcatcaat aatatacctc aaacttttgg tgcgcgttaa tatgcaaatg agctgtttga     60
atttggggag ggaggaaggt gattggctgc gggagcggcg accgttaggg gcggggcggg    120
tgacgttttg atgacgtggc tatgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaatttcg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggc gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaatt ggtggtggac gccatgatgg    660
gtgacgaccc tccagagccc cctaccccat ttgaggcgcc ttcgctgtac gatttgtatg    720
atctggaggt ggatgtgccc gagagcgacc ctaacgagga ggcggtgaat gatttgttta    780
gcgatgccgc gctgctggct gccgagcagg ctaatacgga ctctggctca gacagcgatt    840
cctctctcca tacccgagac cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgcg gtgaaccagg gagtgaaaac tgcgggcgag agctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagttgggaa ggcagagggt gactgggtgc tgactggttt   1200
atttatgtat atgttttttt atgtgtaggt cccgtctctg acgtagatga accccccact   1260
tcagagtgca tttcatcacc cccagaaatt ggcgaggaac cgcccgaaga tattattcat   1320
agaccagttg cagtgagagt caccgggcgg agagcagctg tggagagttt ggatgacttg   1380
ctacagggtg gggatgaacc tttggacttg tgtacccgga aacgcccgag cactaagtg    1440 ccacacatgt gtgtttactt aaggtgatgt cagtatttat agggtgtgga gtgcaataaa   1500
atccgtgttg actttaagtg cgtgttttat gactcagggg tggggactgt gggtatataa   1560
gcaggtgcag acctgtgtgg tcagttcaga gcaggactca tggagatctg gactgtcttg   1620
gaagactttc accagactag acagttgcta gagaactcat cggagggagt ctcttacctg   1680
tggagattct gcttcggtgg gcctctagct aagctagtct ataggccaa acaggattat    1740 aaggaacaat ttgaggatat tttgagagag tgtcctggta ttttttgactc tctcaacttg   1800 ggccatcagt ctcactttaa ccagagtatt ctgagagccc ttgactttc tactcctggc    1860 agaactaccg ccgcggtagc cttttttgcc tttattcttg acaaatggag tcaagaaacc   1920
catttcagca gggattaccg tctggactgc ttagcagtag ctttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaccgaga agagaacccg agagccggtc tggaccctcc ggtggcggag   2160
gaggaggagt agctgacttg tttcccgagc tgcgccgggt gctgactagg tcttccagtg   2220
gacgggagag ggggattaag cgggagaggc atgaggagac tagccacaga actgaactga   2280
ctgtcagtct gatgagccgc aggcgcccag aatcggtgtg gtggcatgag gtgcagtcgc   2340
```

```
agggatagga tgaggtctcg gtgatgcatg agaaatattc cctagaacaa gtcaagactt      2400
gttggttgga gcccgaggat gattgggagg tagccatcag gaattatgcc aagctggctc      2460
tgaagccaga caagaagtac aagattacca aactgattaa tatcagaaat tcctgctaca      2520
tttcagggaa tggggccgag gtggagatca gtacccagga gagggtggcc ttcagatgtt      2580
gtatgatgaa tatgtacccg ggggtggtgg gcatggaggg agtcaccttt atgaacacga      2640
ggttcagggg tgatgggtat aatggggtgg tctttatggc caacaccaag ctgacagtgc      2700
acggatgctc cttctttggc ttcaataaca tgtgcatcga ggcctggggc agtgtttcag      2760
tgaggggatg cagcttttca gccaactgga tgggggtcgt gggcagaacc aagagcaagg      2820
tgtcagtgaa gaaatgcctg ttcgagaggt gccacctggg ggtgatgagc gagggcgaag      2880
ccaaagtcaa acactgcgcc tctaccgaga cgggctgctt tgtgctgatc aagggcaatg      2940
cccaagtcaa gcataacatg atctgtgggg cctcggatga gcgcggctac cagatgctga      3000
cctgcgccgg tgggaacagc catatgctgg ccaccgtgca tgtggcctcg caccccgcca      3060
agacatggcc cgagttcgag cacaacgtca tgacccgctg caatgtgcac ctgggctccc      3120
gccgaggcat gttcatgccc taccagtgca acatgcaatt tgtgaaggtg ctgctggagc      3180
ccgatgccat gtccagagtg agcctgacgg gggtgtttga catgaatgtg gagctgtgga      3240
aaattctgag atatgatgaa tccaagacca ggtgccgggc ctgcgaatgc ggaggcaagc      3300
acgccaggct tcagcccgtg tgtgtggagg tgacggagga cctgcgaccc gatcatttgg      3360
tgttgtcctg caacgggacg gagttcggct ccagcgggga agaatctgac tagagtgagt      3420
agtgtttggg gctgggtgtg agcctgcatg aggggcagaa tgactaaaat ctgtggtttt      3480
ctgtgtgttg cagcagcatg agcggaagcg cctcctttga gggaggggta ttcagcccct      3540
atctgacggg gcgtctcccc tcctgggcgg gagtgcgtca gaatgtgatg ggatccacgg      3600
tggacggccg gcccgtgcag cccgcgaact cttcaaccct gacctacgcg accctgagct      3660
cctcgtccgt ggacgcagct gccgccgcag ctgctgcttc cgccgccagc gccgtgcgcg      3720
gaatggccct gggcgccggc tactacagct ctctggtggc caactcgagt tccaccaata      3780
atcccgccag cctgaacgag gagaagctgc tgctgctgat ggcccagctc gaggccctga      3840
cccagcgcct gggcgagctg acccagcagg tggctcagct gcaggcggag acgcgggccg      3900
cggttgccac ggtgaaaacc aaataaaaaa tgaatcaata aataaacgga gacggttgtt      3960
gattttaaca cagagtcttg aatctttatt tgattttttcg cgcgcggtag gccctggacc      4020
accggtctcg atcattgagc acccggtgga tcttttccag gacccggtag aggtgggctt      4080
ggatgttgag gtacatgggc atgagcccgt cccgggggtg gaggtagctc cattgcaggg      4140
cctcgtgctc gggatggtg ttgtaaatca cccagtcata gcagggcgc agggcgtggt      4200 gctgcacgat gtccttgagg aggagactga tggccacggg cagccccttg tgtaggtgt      4260 tgacgaacct gttgagctgg gagggatgca tgcgggggga gatgagatgc atcttggcct      4320
ggatcttgag attggcgatg ttcccgccca gatcccgccg ggggttcatg ttgtgcagga      4380
ccaccagcac ggtgtatccg gtgcacttgg ggaatttgtc atgcaacttg aagggaagg      4440 cgtgaaagaa tttggagacg cccttgtgac cgccaggtt ttccatgcac tcatccatga      4500
tgatggcgat gggcccgtgg gcggcggcct gggcaaagac gtttcggggg tcggacacat      4560
cgtagttgtg gtcctgggtg agctcgtcat aggccatttt aatgaatttg ggcggaggg      4620 tgcccgactg ggggacgaag gtgccctcga tcccgggggc gtagttgccc tcgcagatct      4680
```

```
gcatctccca ggccttgagc tcggaggggg ggatcatgtc cacctgcggg gcgatgaaaa    4740
aaacggtttc cggggcgggg gagatgagct gggccgaaag caggttccgg agcagctggg    4800
acttgccgca accggtgggg ccgtagatga ccccgatgac cggctgcagg tggtagttga    4860
gggagagaca gctgccgtcc tcgcggagga gggggggccac ctcgttcatc atctcgcgca    4920
catgcatgtt ctcgcgcacg agttccgcca ggaggcgctc gcccccagc gagaggagct    4980
cttgcagcga ggcgaagttt ttcagcggct tgagtccgtc ggccatgggc attttggaga    5040
gggtctgttg caagagttcc agacggtccc agagctcggt gatgtgctct agggcatctc    5100
gatccagcag acctcctcgt ttcgcggggtt ggggcgactg cgggagtagg gcaccaggcg    5160
atgggcgtcc agcgaggcca gggtccggtc cttccagggc cgcagggtcc gcgtcagcgt    5220
ggtctccgtc acggtgaagg ggtgcgcgcc gggctgggcg cttgcgaggg tgcgcttcag    5280
gctcatccgg ctggtcgaga accgctcccg gtcggcgccc tgcgcgtcgg ccaggtagca    5340
attgagcatg agttcgtagt tgagcgcctc ggccgcgtgg cccttggcgc ggagcttacc    5400
tttgaagtg tgtccgcaga cgggacagag gagggacttg agggcgtaga gcttgggggc    5460
gaggaagacg gactcggggg cgtaggcgtc cgccgcgcag ctggcgcaga cggtctcgca    5520
ctccacgagc caggtgaggt cggggcggtt ggggtcaaaa acgaggtttc ctccgtgctt    5580
tttgatgcgt ttcttacctc tggtctccat gagctcgtgt ccccgctggg tgacaaagag    5640
gctgtccgtg tccccgtaga ccgactttat gggccggtcc tcgagcgggg tgccgcggtc    5700
ctcgtcgtag aggaacccg cccactccga gacgaaggcc cgggtccagg ccagcacgaa    5760
ggaggccacg tgggagggt agcggtcgtt gtccaccagc gggtccacct tctccagggt    5820
atgcaagcac atgtccccct cgtccacatc caggaaggtg attggcttgt aagtgtaggc    5880
cacgtgaccg ggggtcccgg ccggggggt ataaaagggg gcgggcccct gctcgtcctc    5940
actgtcttcc ggatcgctgt ccaggagcgc cagctgttgg ggtaggtatt ccctctcgaa    6000
ggcgggcatg acctcggcac tcaggttgtc agtttctaga aacgaggagg atttgatatt    6060
gacggtgccg ttggagacgc ctttcatgag cccctcgtcc atttggtcag aaaagacgat    6120
cttttttgttg tcgagcttgg tggcgaagga gcctagagg gcgttggaga gcagcttggc    6180
gatggagcgc atggtctggt tcttttcctt gtcggcgcgc tccttggcgg cgatgttgag    6240
ctgcacgtac tcgcgcgcca cgcacttcca ttcggggaag acggtggtga gctcgtcggg    6300
cacgattctg acccgccagc cgcggttgtg cagggtgatg aggtccacgc tggtggccac    6360
ctcgccgcgc aggggctcgt tggtccagca gaggcgcccg cccttgcgcg agcagaaggg    6420
gggcagcggg tccagcatga gctcgtcggg ggggtcggcg tccacggtga agatgccggg    6480
caggagctcg gggtcgaagt agctgatgca ggtgcccaga ttgtccagcg ccgcttgcca    6540
gtcgcgcacg gccagcgcgc gctcgtaggg gctgaggggc gtgcccagg gcatgggtg    6600
cgtgagcgcg gaggcgtaca tgccgcagat gtcgtagacg tagagggct cctcgaggac    6660
gccgatgtag gtggggtagc agcgccccc gcggatgctg gcgcgcacgt agtcgtacag    6720
ctcgtgcgag ggcgcgagga gccccgtgcc gaggttggag cgttgcggct tttcggcgcg    6780
gtagacgatc tggcggaaga tggcgtggga gttgaggag atggtggcc tttgaagat    6840
gttgaagtgg gcgtggggca ggccgaccga gtccctgatg aagtgggcgt aggagtcctg    6900
cagcttggcg acgagctcgg cggtgacgag gacgtccagg gcgcagtagt cgagggtctc    6960
ttggatgatg tcatacttga gctggccctt ctgcttccac agctcgcggt tgagaaggaa    7020
ctcttcgcgg tccttccagt actcttcgag ggggaacccg tcctgatcgg cacggtaaga    7080
```

```
gcccaccatg tagaactggt tgacggcctt gtaggcgcag cagcccttct ccacggggag    7140
ggcgtaagct tgcgcggcct tgcgcaggga ggtgtgggtg agggcgaagg tgtcgcgcac    7200
catgaccttg aggaactggt gcttgaagtc gaggtcgtcg cagccgccct gctcccagag    7260
ttggaagtcc gtgcgcttct tgtaggcggg gttaggcaaa gcgaaagtaa catcgttgaa    7320
gaggatcttg cccgcgcggg gcatgaagtt gcgagtgatg cggaaaggct ggggcacctc    7380
ggcccggttg ttgatgacct gggcggcgag gacgatctcg tcgaagccgt tgatgttgtg    7440
cccgacgatg tagagttcca cgaatcgcgg gcggcccttg acgtgggggca gcttcttgag   7500 ctcgtcgtag gtgagctcgg cggggtcgct gagcccgtgc tgctcgaggg cccagtcggc    7560
gacgtggggg ttggcgctga ggaaggaagt ccagagatcc acggccaggg cggtctgcaa    7620
gcggtcccgg tactgacgga actgttggcc cacggccatt ttttcggggg tgacgcagta    7680
gaaggtgcgg gggtcgccgt gccagcggtc ccacttgagc tggagggcga ggtcgtgggc    7740
gagctcgacg agcggcgggt ccccggagag tttcatgacc agcatgaagg ggacgagctg    7800
cttgccgaag gaccccatcc aggtgtaggt ttccacatcg taggtgagga agagcctttc    7860
ggtgcgagga tgcgagccga tggggaagaa ctggatctcc tgccaccagt tggaggaatg    7920
gctgttgatg tgatggaagt agaaatgccg acggcgcgcc gagcactcgt gcttgtgttt    7980
atacaagcgt ccgcagtgct cgcaacgctg cacgggatgc acgtgctgca cgagctgtac    8040
ctgggttcct ttggcgagga atttcagtgg gcagtggagc gctggcggct gcatctcgtg    8100
ctgtactacg tcttggccat cggcgtggcc atcgtctgcc tcgatggtgg tcatgctgac    8160
gagcccgcgc gggaggcagg tccagacctc ggctcggacg ggtcggagag cgaggacgag    8220
ggcgcgcagg ccggagctgt ccagggtcct gagacgctgc ggagtcaggt cagtgggcag    8280
cggcggcgcg cggttgactt gcaggagctt ttccagggcg cgcgggaggt ccagatggta    8340
cttgatctcc acggcgccgt tggtggctac gtccacggct tgcagggtgc cgtgcccctg    8400
gggcgccacc accgtgcccc gtttcttctt gggcgctgct tccatgtcgg tcagaagcgg    8460
cggcgaggac gcgcgccggg cggcagggge ggctcggggc ccggaggcag gggcggcagg    8520
ggcacgtcgg cgccgcgcgc gggcaggttc tggtactgcg cccggagaag actggcgtga    8580
gcgacgacgc gacggttgac gtcctggatc tgacgcctct gggtgaaggc cacgggaccc    8640
gtgagtttga acctgaaaga gagttcgaca gaatcaatct cggtatcgtt gacggcggcc    8700
tgccgcagga tctcttgcac gtcgcccgag ttgtcctggt aggcgatctc ggtcatgaac    8760
tgctcgatct cctcctcctg aaggtctccg cggccggcgc gctcgacggt ggccgcgagg    8820
tcgttggaga tgcggcccat gagctgcgag aaggcgttca tgccggcctc gttccagacg    8880
cggctgtaga ccacggctcc gtcggggtcg cgcgcgcgca tgaccacctg ggcgaggttg    8940
agctcgacgt ggcgcgtgaa gaccgcgtag ttgcagaggc gctggtagag gtagttgagc    9000
gtggtggcga tgtgctcggt gacgaagaag tacatgatcc agcggcggag cggcatctcg    9060
ctgacgtcgc ccagggcttc caagcgttcc atggcctcgt agaagtccac ggcgaagttg    9120
aaaaactggg agttgcgcgc cgagacggtc aactcctcct ccagaagacg gatgagctcg    9180
gcgatggtgg cgcgcacctc gcgctcgaag gccccgggggg ctcctcttc catctcctcc    9240 tcttcctcct ccactaacat ctcttctact tcctcctcag gaggcggtgg cggggagggg    9300
gccctgcgtc gccggcggcg cacgggcaga cggtcgatga agcgctcgat ggtctccccg    9360
cgccggcgac gcatggtctc ggtgacggcg cgcccgtcct cgcggggccg cagcatgaag   9420
```

```
acgccgccgc gcatctccag gtggccgccg ggggggtctc cgttgggcag ggagagggcg    9480
ctgacgatgc atcttatcaa ttgacccgta gggactccgc gcaaggacct gagcgtctcg    9540
agatccacgg gatccgaaaa ccgctgaacg aaggcttcga gccagtcgca gtcgcaaggt    9600
aggctgagcc cggtttcttg ttcttcgggt atttggtcgg gaggcgggcg ggcgatgctg    9660
ctggtgatga agttgaagta ggcggtcctg agacggcgga tggtggcgag gagcaccagg    9720
tccttgggcc cggcttgctg gatgcgcaga cggtcggcca tgcccaggcc gtggtcctga    9780
cacctggcga ggtccttgta gtagtcctgc atgagccgct ccacgggcac ctcctcctcg    9840
cccgcgcggc cgtgcatgcg cgtgagcccg aacccgcgct gcggctggac gagcgccagg    9900
tcggcgacga cgcgctcggt gaggatggcc tgctggatct gggtgagggt ggtctggaag    9960
tcgtcgaagt cgacgaagcg gtggtaggct ccggtgttga tggtgtagga gcagttggcc   10020
atgacggacc agttgacggt ctggtggccg ggtcgcacga gctcgtggta cttgaggcgc   10080
gagtaggcgc gcgtgtcgaa gatgtagtcg ttgcaggcgc gcacgaggta ctggtatccg   10140
acgaggaagt gcggcggcgg ctggcggtag agcggccatc gctcggtggc gggggcgccg   10200
ggcgcgaggt cctcgagcat gaggcggtgg tagccgtaga tgtacctgga catccaggtg   10260
atgccggcgc cggtggtgga ggcgcgcggg aactcgcgga cgcggttcca gatgttgcgc   10320
agcggcagga agtagttcat ggtggccgcg gtctggcccg tgaggcgcgc gcagtcgtgg   10380
atgctctaga catacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtactg gcactcccgt ctcgacccaa gcctgctaac gaaacctcca   10560
ggatacggag gcgggtcgtt ttttggcctt ggtcgctggt catgaaaaac tagtaagcgc   10620
ggaaagcggc cgcccgcgat ggctcgctgc cgtagtctgg agaaagaatc gccagggttg   10680
cgttgcggtg tgccccggtt cgagcctcag cgctcggcgc cggccggatt ccgcggctaa   10740
cgtgggcgtg gctgccccgt cgtttccaag acccccttagc cagccgactt ctccagttac   10800
ggagcgagcc cctctttttt tttcttgtgt ttttgccaga tgcatcccgt actgcggcag   10860
atgcgccccc accctccacc acaaccgccc ctaccgcagc agcagcaaca gccggcgctt   10920
ctgccccgc cccagcagca gccagccact accgcggcgg ccgccgtgag cggagccggc   10980
gttcagtatg acctggcctt ggaagagggc gaggggctgg cgcggctggg ggcgtcgtcg   11040
ccggagcggc acccgcgcgt gcagatgaaa agggacgctc gcgaggccta cgtgcccaag   11100
cagaacctgt tcagagacag gagcggcgag gagcccgagg agatgcgcgc ctcccgcttc   11160
cacgcggggc gggagctgcg gcgcggcctg gaccgaaagc gggtgctgag ggacgaggat   11220
ttcgaggcgg acgagctgac ggggatcagc cccgcgcgcg cgcacgtggc cgcggccaac   11280
ctggtcacgg cgtacgagca gaccgtgaag gaggagagca acttccaaaa atccttcaac   11340
aaccacgtgc gcacgctgat cgcgcgcgag gaggtgaccc tgggcctgat gcacctgtgg   11400
gacctgctgg aggccatcgt gcagaacccc acgagcaagc cgctgacggc gcagctgttt   11460
ctggtggtgc agcacagtcg ggacaacgag acgttcaggg aggcgctgct gaatatcacc   11520
gagcccgagg gccgctggct cctggacctg gtgaacattt tgcagagcat cgtggtgcag   11580
gagcgcgggc tgccgctgtc cgagaagctg gcggccatca acttctcggt gctgagtctg   11640
ggcaagtact acgctaggaa gatctacaag acccccgtacg tgcccataga caaggaggtg   11700
aagatcgacg ggttttacat gcgcatgacc ctgaaagtgc tgaccctgag cgacgatctg   11760
ggggtgtacc gcaacgacag gatgcaccgc gcggtgagcg ccagccgccg gcgcgagctg   11820
```

```
agcgaccagg agctgatgca cagcctgcag cgggccctga ccggggccgg gaccgagggg    11880
gagagctact ttgacatggg cgcggacctg cgctggcagc ccagccgccg ggccttggaa    11940
gctgccggcg gttcccccta cgtggaggag gtggacgatg aggaggagga gggcgagtac    12000
ctggaagact gatggcgcga ccgtattttt gctagatgca gcaacagcca ccgccgccgc    12060
ctcctgatcc cgcgatgcgg gcggcgctgc agagccagcc gtccggcatt aactcctcgg    12120
acgattggac ccaggccatg caacgcatca tggcgctgac gacccgcaat cccgaagcct    12180
ttagacagca gcctcaggcc aaccggctct cggccatcct ggaggccgtg gtgccctcgc    12240
gctcgaaccc cacgcacgag aaggtgctgg ccatcgtgaa cgcgctggtg gagaacaagg    12300
ccatccgcgg tgacgaggcc gggctggtgt acaacgcgct gctggagcgc gtggcccgct    12360
acaacagcac caacgtgcag acgaacctgg accgcatggt gaccgacgtg cgcgaggcgg    12420
tgtcgcagcg cgagcggttc caccgcgagt cgaacctggg ctccatggtg gcgctgaacg    12480
ccttcctgag cacgcagccc gccaacgtgc ccgggggcca ggaggactac accaacttca    12540
tcagcgcgct gcggctgatg gtggccgagg tgccccagag cgaggtgtac cagtcggggc    12600
cggactactt cttccagacc agtcgccagg gcttgcagac cgtgaacctg agccaggctt    12660
tcaagaactt gcagggactg tggggcgtgc aggccccggt cggggaccgc gcgacggtgt    12720
cgagcctgct gacgccgaac tcgcgcctgc tgctgctgct ggtggcgccc ttcacggaca    12780
gcggcagcgt gagccgcgac tcgtacctgg gctacctgct taacctgtac cgcgaggcca    12840
tcggacaggc gcacgtggac gagcagacct accaggagat cacccacgtg agccgcgcgc    12900
tgggccagga ggacccgggc aacctggagg ccaccctgaa cttcctgctg accaaccggt    12960
cgcagaagat cccgcgccag tacgcgctga gcaccgagga ggagcgcatc ctgcgctacg    13020
tgcagcagag cgtggggctg ttcctgatgc aggagggggc cacgcccagc gcggcgctcg    13080
acatgaccgc gcgcaacatg gagcccagca tgtacgcccg caaccgcccg ttcatcaata    13140
agctgatgga ctacttgcat cgggcggccg ccatgaactc ggactacttt accaacgcca    13200
tcttgaaccc gcactggctc ccgccgcccg ggttctacac gggcgagtac gacatgcccg    13260
accccaacga cgggttcctg tgggacgacg tggacagcag cgtgttctcg ccgcgtccag    13320
gaaccaatgc cgtgtggaag aaagagggcg gggaccggcg gccgtcctcg gcgctgtccg    13380
gtcgcgcggg tgctgccgcg gcggtgcccg aggccgccag ccccttcccg agcctgccct    13440
tttcgctgaa cagcgtgcgc agcagcgagc tgggtcggct gacgcgaccg cgcctgctgg    13500
gcgaggagga gtacctgaac gactccttgt tgaggcccga gcgcgagaag aacttcccca    13560
ataacgggat agagagcctg gtggacaaga tgagccgctg gaagacgtac gcgcacgagc    13620
acagggacga gccccgagct agcagcgcag gcacccgtag acgccagcgg cacgacaggc    13680
agcggggact ggtgtgggac gatgaggatt ccgccgacga cagcagcgtg ttggacttgg    13740
gtgggagtgg tggtaacccg ttcgctcacc tgccccccg tatcgggcgc ctgatgtaag    13800
aatctgaaaa aataaaagac ggtactcacc aaggccatgg cgaccagcgt gcgttcttct    13860
ctgttgtttg tagtagt atg atg agg cgc gtg tac ccg gag ggt cct cct      13910
                    Met Met Arg Arg Val Tyr Pro Glu Gly Pro Pro
                    1               5                   10 ccc tcg tac gag agc gtg atg cag cag gcg gtg gcg gcg gcg atg cag    13958
Pro Ser Tyr Glu Ser Val Met Gln Gln Ala Val Ala Ala Ala Met Gln
            15                  20                  25 ccc ccg ctg gag gcg cct tac gtg ccc ccg cgg tac ctg gcg cct acg    14006
Pro Pro Leu Glu Ala Pro Tyr Val Pro Pro Arg Tyr Leu Ala Pro Thr
```

```
              30                  35                  40
gag ggg cgg aac agc att cgt tac tcg gag ctg gca ccc ttg tac gat   14054
Glu Gly Arg Asn Ser Ile Arg Tyr Ser Glu Leu Ala Pro Leu Tyr Asp
         45                  50                  55 acc acc cgg ttg tac ctg gtg gac aac aag tcg gca gac atc gcc tcg   14102
Thr Thr Arg Leu Tyr Leu Val Asp Asn Lys Ser Ala Asp Ile Ala Ser
 60                  65                  70                  75 ctg aac tac cag aac gac cac agc aac ttc ctg acc acc gtg gtg cag   14150
Leu Asn Tyr Gln Asn Asp His Ser Asn Phe Leu Thr Thr Val Val Gln
                     80                  85                  90 aac aac gat ttc acc ccc acg gag gcc agc acc cag acc atc aac ttt   14198
Asn Asn Asp Phe Thr Pro Thr Glu Ala Ser Thr Gln Thr Ile Asn Phe
             95                  100                 105 gac gag cgc tcg cgg tgg ggc ggc cag ctg aaa acc atc atg cac acc   14246
Asp Glu Arg Ser Arg Trp Gly Gly Gln Leu Lys Thr Ile Met His Thr
         110                 115                 120 aac atg ccc aac gtg aac gag ttc atg tac agc aac aag ttc aag gcg   14294
Asn Met Pro Asn Val Asn Glu Phe Met Tyr Ser Asn Lys Phe Lys Ala
     125                 130                 135 cgg gtg atg gtc tcg cgc aag acc ccc aac ggg gtg gat gat gat tat   14342
Arg Val Met Val Ser Arg Lys Thr Pro Asn Gly Val Asp Asp Asp Tyr
140                 145                 150                 155 gat ggt agt cag gac gag ctg acc tac gag tgg gtg gag ttt gag ctg   14390
Asp Gly Ser Gln Asp Glu Leu Thr Tyr Glu Trp Val Glu Phe Glu Leu
                 160                 165                 170 ccc gag ggc aac ttc tcg gtg acc atg acc atc gat ctg atg aac aac   14438
Pro Glu Gly Asn Phe Ser Val Thr Met Thr Ile Asp Leu Met Asn Asn
             175                 180                 185 gcc atc atc gac aac tac ttg gcg gtg ggg cgg cag aac ggg gtg ctg   14486
Ala Ile Ile Asp Asn Tyr Leu Ala Val Gly Arg Gln Asn Gly Val Leu
         190                 195                 200 gag agc gac atc ggc gtg aag ttc gac acg cgc aac ttc cgg ctg ggc   14534
Glu Ser Asp Ile Gly Val Lys Phe Asp Thr Arg Asn Phe Arg Leu Gly
     205                 210                 215 tgg gac ccc gtg acc gag ctg gtg atg ccg ggc gtg tac acc aac gag   14582
Trp Asp Pro Val Thr Glu Leu Val Met Pro Gly Val Tyr Thr Asn Glu
220                 225                 230                 235 gcc ttc cac ccc gac atc gtc ctg ctg ccc ggc tgc ggc gtg gac ttc   14630
Ala Phe His Pro Asp Ile Val Leu Leu Pro Gly Cys Gly Val Asp Phe
                 240                 245                 250 acc gag agc cgc ctc agc aac ctg ctg ggc atc cgc aag cgg cag ccc   14678
Thr Glu Ser Arg Leu Ser Asn Leu Leu Gly Ile Arg Lys Arg Gln Pro
             255                 260                 265 ttc cag gag ggc ttc cag atc ctg tac gag gac ctg gag ggg ggc aac   14726
Phe Gln Glu Gly Phe Gln Ile Leu Tyr Glu Asp Leu Glu Gly Gly Asn
         270                 275                 280 atc ccc gcg ctc ttg gat gtc gaa gcc tac gag aaa agc aag gag gat   14774
Ile Pro Ala Leu Leu Asp Val Glu Ala Tyr Glu Lys Ser Lys Glu Asp
     285                 290                 295 agc acc gcc gcg gcg acc gca gcc gtg gcc acc gcc tct acc gag gtg   14822
Ser Thr Ala Ala Ala Thr Ala Ala Val Ala Thr Ala Ser Thr Glu Val
300                 305                 310                 315 cgg ggc gat aat ttt gct agc gct gcg gca gcg gcc gag gcg gct gaa   14870
Arg Gly Asp Asn Phe Ala Ser Ala Ala Ala Ala Glu Ala Ala Glu
                 320                 325                 330 acc gaa agt aag ata gtc atc cag ccg gtg gag aag gac agc aag gac   14918
Thr Glu Ser Lys Ile Val Ile Gln Pro Val Glu Lys Asp Ser Lys Asp
             335                 340                 345 agg agc tac aac gtg ctc gcg gac aag aaa aac acc gcc tac cgc agc   14966
```

```
                 Arg Ser Tyr Asn Val Leu Ala Asp Lys Lys Asn Thr Ala Tyr Arg Ser
                             350                 355                 360 tgg tac ctg gcc tac aac tac ggc gac ccc gag aag ggc gtg cgc tcc          15014
Trp Tyr Leu Ala Tyr Asn Tyr Gly Asp Pro Glu Lys Gly Val Arg Ser
            365                 370                 375 tgg acg ctg ctc acc acc tcg gac gtc acc tgc ggc gtg gag caa gtc          15062
Trp Thr Leu Leu Thr Thr Ser Asp Val Thr Cys Gly Val Glu Gln Val
380                 385                 390                 395 tac tgg tcg ctg ccc gac atg atg caa gac ccg gtc acc ttc cgc tcc          15110
Tyr Trp Ser Leu Pro Asp Met Met Gln Asp Pro Val Thr Phe Arg Ser
                400                 405                 410 acg cgt caa gtt agc aac tac ccg gtg gtg ggc gcc gag ctc ctg ccc          15158
Thr Arg Gln Val Ser Asn Tyr Pro Val Val Gly Ala Glu Leu Leu Pro
            415                 420                 425 gtc tac tcc aag agc ttc ttc aac gag cag gcc gtc tac tcg cag cag          15206
Val Tyr Ser Lys Ser Phe Phe Asn Glu Gln Ala Val Tyr Ser Gln Gln
        430                 435                 440 ctg cgc gcc ttc acc tcg ctc acg cac gtc ttc aac cgc ttc ccc gag          15254
Leu Arg Ala Phe Thr Ser Leu Thr His Val Phe Asn Arg Phe Pro Glu
    445                 450                 455 aac cag atc ctc gtc cgc ccg ccc gcg ccc acc att acc acc gtc agt          15302
Asn Gln Ile Leu Val Arg Pro Pro Ala Pro Thr Ile Thr Thr Val Ser
460                 465                 470                 475 gaa aac gtt cct gct ctc aca gat cac ggg acc ctg ccg ctc cgc agc          15350
Glu Asn Val Pro Ala Leu Thr Asp His Gly Thr Leu Pro Leu Arg Ser
                480                 485                 490 agt atc cgg gga gtc cag cgc gtg acc gtc act gac gcc aga cgc cgc          15398
Ser Ile Arg Gly Val Gln Arg Val Thr Val Thr Asp Ala Arg Arg Arg
            495                 500                 505 acc tgc ccc tac gtc tac aag gcc ctg ggc gta gtc gcg ccg cgc gtc          15446
Thr Cys Pro Tyr Val Tyr Lys Ala Leu Gly Val Val Ala Pro Arg Val
        510                 515                 520 ctc tcg agc cgc acc ttc taa aaaatgtcca ttctcatctc gcccagtaat             15497
Leu Ser Ser Arg Thr Phe
    525 aacaccggtt ggggcctgcg cgcgcccagc aagatgtacg gaggcgctcg ccaacgctcc        15557 acgcaacacc ccgtgcgcgt gcgcgggcac ttccgcgctc cctggggcgc cctcaagggc        15617 cgcgtgcgct cgcgcaccac cgtcgacgac gtgatcgacc aggtggtggc cgacgcgcgc        15677 aactacacgc ccgccgccgc gcccgtctcc accgtggacg ccgtcatcga cagcgtggtg        15737 gccgacgcgc gccggtacgc ccgcaccaag agccggcggc ggcgcatcgc ccggcggcac        15797 cggagcaccc ccgccatgcg cgcggcgcga gccttgctgc gcagggccag cgcacgggga        15857 cgcagggcca tgctcagggc ggccagacgc gcggcctccg gcagcagcag cgccggcagg        15917 acccgcagac gcgcggccac ggcggcggcg cggccatcg ccagcatgtc ccgcccgcgg         15977 cgcggcaacg tgtactgggg gcgcgacgcc ggcaccggtg tgcgcgtgcc cgtgcgcacc        16037 cgcccccctc gcacttgaag atgctgactt cgcgatgttg atgtgtccca gcggcgagga        16097 ggatgtccaa gcgcaaatac aaggaagaga tgctccaggt catcgcgcct gagatctacg        16157 gccccgcggc ggcggtgaag gaggaaagaa agccccgcaa actgaagcgg gtcaaaaagg        16217 acaaaaagga ggaggaagat gacggactgg tggagtttgt gcgcgagttc gcccccggc         16277 ggcgcgtgca gtggcgcggg cggaaagtga aaccggtgct gcggcccggc accacggtgg        16337 tcttcacgcc cggcgagcgt tccggctccg cctccaagcg ctcctacgac gaggtgtacg        16397 gggacgagga catcctcgag caggcggtcg agcgtctggg cgagtttgcg tacggcaagc        16457
```

-continued

```
gcagccgccc cgcgcccttg aaagaggagg cggtgtccat cccgctggac cacggcaacc    16517
ccacgccgag cctgaagccg gtgaccctgc agcaggtgct accgagcgcg cgccgcgcc     16577
ggggcttcaa gcgcgagggc ggcgaggatc tgtacccgac catgcagctg atggtgccca    16637
agcgccagaa gctggaggac gtgctggagc acatgaaggt ggaccccgag gtgcagcccg    16697
aggtcaaggt gcggcccatc aagcaggtgg ccccgggcct gggcgtgcag accgtggaca    16757
tcaagatccc cacggagccc atggaaacgc agaccgagcc cgtgaagccc agcaccagca    16817
ccatggaggt gcagacggat ccctggatgc cagcaccagc ttccaccagc actcgccgaa    16877
gacgcaagta cggcgcggcc agcctgctga tgcccaacta cgcgctgcat ccttccatca    16937
tccccacgcc gggctaccgc ggcacgcgct tctaccgcgg ctacaccagc agccgccgcc    16997
gcaagaccac cacccgccgc cgtcgtcgca gccgccgcag cagcaccgcg acttccgcct    17057
tggtgcggag agtgtatcgc agcgggcgcg agcctctgac cctgccgcgc gcgcgctacc    17117
acccgagcat cgccatttaa ctaccgcctc ctacttgcag atatggccct cacatgccgc    17177
ctccgcgtcc ccattacggg ctaccgagga agaaagccgc gccgtagaag gctgacgggg    17237
aacgggctgc gtcgccatca ccaccggcgg cggcgcgcca tcagcaagcg gttgggggga    17297
ggcttcctgc ccgcgctgat ccccatcatc gccgcggcga tcggggcgat ccccggcata    17357
gcttccgtgg cggtgcaggc ctctcagcgc cactgagaca caaaaaagca tggatttgta    17417
ataaaaaaaa aaatgactg acgctcctgg tcctgtgatg tgtgttttta gatggaagac     17477
atcaattttt cgtccctggc accgcgacac ggcacgcggc cgtttatggg cacctggagc    17537
gacatcggca acagccaact gaacgggggc gccttcaatt ggagcagtct ctggagcggg    17597
cttaagaatt tcgggtccac gctcaaaacc tatggcaaca aggcgtggaa cagcagcaca    17657
gggcaggcgc tgagggaaaa gctgaaagaa cagaacttcc agcagaaggt ggttgatggc    17717
ctggcctcag gcatcaacgg ggtggttgac ctggccaacc aggccgtgca gaaacagatc    17777
aacagccgcc tggacgcggt cccgcccgcg ggtccgtgg agatgcccca ggtggaggag     17837
gagctgcctc ccctggacaa gcgcggcgac aagcgaccgc gtcccgacgc ggaggagacg    17897
ctgctgacgc acacggacga gccgccccg tacgaggagg cggtgaaact gggcctgccc     17957
accacgcggc ccgtggcgcc tctggccacc ggagtgctga aacccagcag cagccagccc    18017
gcgaccctgg acttgcctcc gcctcgcccc tccacagtgg ctaagcccct gccgccggtg    18077
gccgtcgcgt cgcgcgcccc ccgaggccgc ccccaggcga actggcagag cactctgaac    18137
agcatcgtgg gtctgggagt gcagagtgtg aagcgccgcc gctgctatta aaagacactg    18197
tagcgcttaa cttgcttgtc tgtgtgtata tgtatgtccg ccgaccagaa ggaggagtgt    18257
gaagaggcgc gtcgccgagt tgcaag atg gcc acc cca tcg atg ctg ccc cag    18310
                                 Met Ala Thr Pro Ser Met Leu Pro Gln
                                 530                 535
tgg gcg tac atg cac atc gcc gga cag gac gct tcg gag tac ctg agt     18358
Trp Ala Tyr Met His Ile Ala Gly Gln Asp Ala Ser Glu Tyr Leu Ser
    540                 545                 550
ccg ggt ctg gtg cag ttc gcc cgc gcc aca gac acc tac ttc agt ctg     18406
Pro Gly Leu Val Gln Phe Ala Arg Ala Thr Asp Thr Tyr Phe Ser Leu
555                 560                 565                 570
ggg aac aag ttt agg aac ccc acg gtg gcg ccc acg cac gat gtg acc     18454
Gly Asn Lys Phe Arg Asn Pro Thr Val Ala Pro Thr His Asp Val Thr
                575                 580                 585
acc gac cgc agc cag cgg ctg acg ctg cgc ttc gtg ccc gtg gac cgc     18502
Thr Asp Arg Ser Gln Arg Leu Thr Leu Arg Phe Val Pro Val Asp Arg
            590                 595                 600
```

```
gag gac aac acc tac tcg tac aaa gtg cgc tac acg ctg gcc gtg ggc      18550
Glu Asp Asn Thr Tyr Ser Tyr Lys Val Arg Tyr Thr Leu Ala Val Gly
            605                 610                 615 gac aac cgc gtg ctg gac atg gcc agc acc tac ttt gac atc cgc ggc      18598
Asp Asn Arg Val Leu Asp Met Ala Ser Thr Tyr Phe Asp Ile Arg Gly
        620                 625                 630 gtg ctg gac cgg ggc cct agc ttc aaa ccc tac tct ggc acc gcc tac      18646
Val Leu Asp Arg Gly Pro Ser Phe Lys Pro Tyr Ser Gly Thr Ala Tyr
635                 640                 645                 650 aac agc cta gct ccc aag gga gct ccc aat tcc agc cag tgg gag caa      18694
Asn Ser Leu Ala Pro Lys Gly Ala Pro Asn Ser Ser Gln Trp Glu Gln
                655                 660                 665 gca aaa aca ggc aat ggg gga act atg gaa aca cac aca tat ggt gtg      18742
Ala Lys Thr Gly Asn Gly Gly Thr Met Glu Thr His Thr Tyr Gly Val
            670                 675                 680 gcc cca atg ggc gga gag aat att aca aaa gat ggt ctt caa att gga      18790
Ala Pro Met Gly Gly Glu Asn Ile Thr Lys Asp Gly Leu Gln Ile Gly
        685                 690                 695 act gac gtt aca gcg aat cag aat aaa cca att tat gcc gac aaa aca      18838
Thr Asp Val Thr Ala Asn Gln Asn Lys Pro Ile Tyr Ala Asp Lys Thr
700                 705                 710 ttt caa cca gaa ccg caa gta gga gaa gaa aat tgg caa gaa act gaa      18886
Phe Gln Pro Glu Pro Gln Val Gly Glu Glu Asn Trp Gln Glu Thr Glu
715                 720                 725                 730 aac ttt tat ggc ggt aga gct ctt aaa aaa gac aca aac atg aaa cct      18934
Asn Phe Tyr Gly Gly Arg Ala Leu Lys Lys Asp Thr Asn Met Lys Pro
                735                 740                 745 tgc tat ggc tcc tat gct aga ccc acc aat gaa aaa gga ggt caa gct      18982
Cys Tyr Gly Ser Tyr Ala Arg Pro Thr Asn Glu Lys Gly Gly Gln Ala
            750                 755                 760 aaa ctt aaa gtt gga gat gat gga gtt cca acc aaa gaa ttc gac ata      19030
Lys Leu Lys Val Gly Asp Asp Gly Val Pro Thr Lys Glu Phe Asp Ile
        765                 770                 775 gac ctg gct ttc ttt gat act ccc ggt ggc acc gtg aac ggt caa gac      19078
Asp Leu Ala Phe Phe Asp Thr Pro Gly Gly Thr Val Asn Gly Gln Asp
780                 785                 790 gag tat aaa gca gac att gtc atg tat acc gaa aac acg tat ttg gaa      19126
Glu Tyr Lys Ala Asp Ile Val Met Tyr Thr Glu Asn Thr Tyr Leu Glu
795                 800                 805                 810 act cca gac acg cat gtg gta tac aaa cca ggc aag gat gat gca agt      19174
Thr Pro Asp Thr His Val Val Tyr Lys Pro Gly Lys Asp Asp Ala Ser
                815                 820                 825 tct gaa att aac ctg gtt cag cag tct atg ccc aac aga ccc aac tac      19222
Ser Glu Ile Asn Leu Val Gln Gln Ser Met Pro Asn Arg Pro Asn Tyr
            830                 835                 840 att ggg ttc agg gac aac ttt atc ggt ctt atg tac tac aac agc act      19270
Ile Gly Phe Arg Asp Asn Phe Ile Gly Leu Met Tyr Tyr Asn Ser Thr
        845                 850                 855 ggc aat atg ggt gtg ctt gct ggt cag gcc tcc cag ctg aat gct gtg      19318
Gly Asn Met Gly Val Leu Ala Gly Gln Ala Ser Gln Leu Asn Ala Val
860                 865                 870 gtt gat ttg caa gac aga aac acc gag ctg tcc tac cag ctc ttg ctt      19366
Val Asp Leu Gln Asp Arg Asn Thr Glu Leu Ser Tyr Gln Leu Leu Leu
875                 880                 885                 890 gac tct ttg ggt gac aga acc cgg tat ttc agt atg tgg aac cag gcg      19414
Asp Ser Leu Gly Asp Arg Thr Arg Tyr Phe Ser Met Trp Asn Gln Ala
                895                 900                 905 gtg gac agt tat gac ccc gat gtg cgc atc atc gaa aac cat ggt gtg      19462
Val Asp Ser Tyr Asp Pro Asp Val Arg Ile Ile Glu Asn His Gly Val
```

|  |  |  |  |  |  |  |  |  |  |  |  |  |  |  |
|---|---|---|---|---|---|---|---|---|---|---|---|---|---|---|
|  |  | 910 |  |  |  | 915 |  |  |  | 920 |  |  |  |  |
| gag | gat | gaa | ttg | cca | aac | tat | tgc | ttc | ccc | ttg | gac | ggc | tct | ggc act | 19510 |
| Glu | Asp | Glu | Leu | Pro | Asn | Tyr | Cys | Phe | Pro | Leu | Asp | Gly | Ser | Gly Thr |
|  |  | 925 |  |  |  | 930 |  |  |  | 935 |  |  |  |  |
| aac | gcc | gca | tac | caa | ggt | gtg | aaa | gta | aaa | gat | ggt | caa | gat | ggt gat | 19558 |
| Asn | Ala | Ala | Tyr | Gln | Gly | Val | Lys | Val | Lys | Asp | Gly | Gln | Asp | Gly Asp |
|  |  | 940 |  |  |  | 945 |  |  |  | 950 |  |  |  |  |
| gtt | gag | agt | gaa | tgg | gaa | aat | gac | gat | act | gtt | gca | gct | cga | aat caa | 19606 |
| Val | Glu | Ser | Glu | Trp | Glu | Asn | Asp | Asp | Thr | Val | Ala | Ala | Arg | Asn Gln |
| 955 |  |  |  | 960 |  |  |  | 965 |  |  |  | 970 |  |  |
| tta | tgt | aaa | ggt | aac | att | ttc | gcc | atg | gag | att | aat | ctc | cag | gct aac | 19654 |
| Leu | Cys | Lys | Gly | Asn | Ile | Phe | Ala | Met | Glu | Ile | Asn | Leu | Gln | Ala Asn |
|  |  |  | 975 |  |  |  | 980 |  |  |  | 985 |  |  |  |
| ctg | tgg | aga | agt | ttc | ctc | tac | tcg | aac | gtg | gcc | ctg | tac | ctg | ccc gac | 19702 |
| Leu | Trp | Arg | Ser | Phe | Leu | Tyr | Ser | Asn | Val | Ala | Leu | Tyr | Leu | Pro Asp |
|  |  | 990 |  |  |  | 995 |  |  |  | 1000 |  |  |  |  |
| tcc | tac | aag | tac | acg | ccg | acc | aac | gtc | acg | ctg | ccg | acc | aac | acc | 19747 |
| Ser | Tyr | Lys | Tyr | Thr | Pro | Thr | Asn | Val | Thr | Leu | Pro | Thr | Asn | Thr |
|  |  | 1005 |  |  |  | 1010 |  |  |  | 1015 |  |  |  |  |
| aac | acc | tac | gat | tac | atg | aat | ggc | aga | gtg | aca | cct | ccc | tcg | ctg | 19792 |
| Asn | Thr | Tyr | Asp | Tyr | Met | Asn | Gly | Arg | Val | Thr | Pro | Pro | Ser | Leu |
|  |  | 1020 |  |  |  | 1025 |  |  |  | 1030 |  |  |  |  |
| gta | gac | gcc | tac | ctc | aac | atc | ggg | gcg | cgc | tgg | tcg | ctg | gac | ccc | 19837 |
| Val | Asp | Ala | Tyr | Leu | Asn | Ile | Gly | Ala | Arg | Trp | Ser | Leu | Asp | Pro |
|  |  | 1035 |  |  |  | 1040 |  |  |  | 1045 |  |  |  |  |
| atg | gac | aac | gtc | aac | ccc | ttc | aac | cac | cac | cgc | aac | gcg | ggc | ctg | 19882 |
| Met | Asp | Asn | Val | Asn | Pro | Phe | Asn | His | His | Arg | Asn | Ala | Gly | Leu |
|  |  | 1050 |  |  |  | 1055 |  |  |  | 1060 |  |  |  |  |
| cgc | tac | cgc | tcc | atg | ctc | ctg | ggc | aac | ggg | cgc | tac | gtg | ccc | ttc | 19927 |
| Arg | Tyr | Arg | Ser | Met | Leu | Leu | Gly | Asn | Gly | Arg | Tyr | Val | Pro | Phe |
|  |  | 1065 |  |  |  | 1070 |  |  |  | 1075 |  |  |  |  |
| cac | atc | cag | gtg | ccc | caa | aag | ttt | ttc | gcc | atc | aag | agc | ctc | ctg | 19972 |
| His | Ile | Gln | Val | Pro | Gln | Lys | Phe | Phe | Ala | Ile | Lys | Ser | Leu | Leu |
|  |  | 1080 |  |  |  | 1085 |  |  |  | 1090 |  |  |  |  |
| ctc | ctg | ccc | ggg | tcc | tac | acc | tac | gag | tgg | aac | ttc | cgc | aag | gac | 20017 |
| Leu | Leu | Pro | Gly | Ser | Tyr | Thr | Tyr | Glu | Trp | Asn | Phe | Arg | Lys | Asp |
|  |  | 1095 |  |  |  | 1100 |  |  |  | 1105 |  |  |  |  |
| gtc | aac | atg | atc | ctg | cag | agc | tcc | cta | ggc | aac | gac | ctg | cgc | acg | 20062 |
| Val | Asn | Met | Ile | Leu | Gln | Ser | Ser | Leu | Gly | Asn | Asp | Leu | Arg | Thr |
|  |  | 1110 |  |  |  | 1115 |  |  |  | 1120 |  |  |  |  |
| gac | ggg | gcc | tcc | atc | gcc | ttc | acc | agc | atc | aac | ctc | tac | gcc | acc | 20107 |
| Asp | Gly | Ala | Ser | Ile | Ala | Phe | Thr | Ser | Ile | Asn | Leu | Tyr | Ala | Thr |
|  |  | 1125 |  |  |  | 1130 |  |  |  | 1135 |  |  |  |  |
| ttc | ttc | ccc | atg | gcg | cac | aac | acc | gcc | tcc | acg | ctc | gag | gcc | atg | 20152 |
| Phe | Phe | Pro | Met | Ala | His | Asn | Thr | Ala | Ser | Thr | Leu | Glu | Ala | Met |
|  |  | 1140 |  |  |  | 1145 |  |  |  | 1150 |  |  |  |  |
| ctg | cgc | aac | gac | acc | aac | gac | cag | tcc | ttc | aac | gac | tac | ctc | tcg | 20197 |
| Leu | Arg | Asn | Asp | Thr | Asn | Asp | Gln | Ser | Phe | Asn | Asp | Tyr | Leu | Ser |
|  |  | 1155 |  |  |  | 1160 |  |  |  | 1165 |  |  |  |  |
| gcg | gcc | aac | atg | ctc | tac | ccc | atc | ccg | gcc | aac | gcc | acc | aac | gtg | 20242 |
| Ala | Ala | Asn | Met | Leu | Tyr | Pro | Ile | Pro | Ala | Asn | Ala | Thr | Asn | Val |
|  |  | 1170 |  |  |  | 1175 |  |  |  | 1180 |  |  |  |  |
| ccc | atc | tcc | atc | ccc | tcg | cgc | aac | tgg | gcc | gcc | ttc | cgc | gga | tgg | 20287 |
| Pro | Ile | Ser | Ile | Pro | Ser | Arg | Asn | Trp | Ala | Ala | Phe | Arg | Gly | Trp |
|  |  | 1185 |  |  |  | 1190 |  |  |  | 1195 |  |  |  |  |
| tcc | ttc | acg | cgc | ctg | aag | acc | cgc | gag | acg | ccg | tcg | ctc | ggc | tcc | 20332 |
| Ser | Phe | Thr | Arg | Leu | Lys | Thr | Arg | Glu | Thr | Pro | Ser | Leu | Gly | Ser |
|  |  | 1200 |  |  |  | 1205 |  |  |  | 1210 |  |  |  |  |
| ggg | ttc | gac | ccc | tac | ttc | gtc | tac | tcg | ggc | tcc | atc | ccc | tac | cta | 20377 |

|   |   |   |   |   |   |   |   |   |   |   |   |   |
|---|---|---|---|---|---|---|---|---|---|---|---|---|
| Gly | Phe | Asp 1215 | Pro | Tyr | Phe | Val 1220 | Tyr | Ser | Gly | Ser 1225 | Ile | Pro | Tyr | Leu |

```
gac ggc acc ttc tac ctc aac cac acc ttc aag aag gtc tcc atc      20422
Asp Gly Thr Phe Tyr Leu Asn His Thr Phe Lys Lys Val Ser Ile
        1230                1235                1240 acc ttc gac tcc tcc gtc agc tgg ccc ggc aac gac cgc ctc ctg      20467
Thr Phe Asp Ser Ser Val Ser Trp Pro Gly Asn Asp Arg Leu Leu
        1245                1250                1255 acg ccc aac gag ttc gaa atc aag cgc acc gtc gac gga gag gga      20512
Thr Pro Asn Glu Phe Glu Ile Lys Arg Thr Val Asp Gly Glu Gly
        1260                1265                1270 tac aac gtg gcc cag tgc aac atg acc aag gac tgg ttc ctg gtc      20557
Tyr Asn Val Ala Gln Cys Asn Met Thr Lys Asp Trp Phe Leu Val
        1275                1280                1285 cag atg ctg gcc cac tac aac atc ggc tac cag ggc ttc tac gtg      20602
Gln Met Leu Ala His Tyr Asn Ile Gly Tyr Gln Gly Phe Tyr Val
        1290                1295                1300 ccc gag ggc tac aag gac cgc atg tac tcc ttc ttc cgc aac ttc      20647
Pro Glu Gly Tyr Lys Asp Arg Met Tyr Ser Phe Phe Arg Asn Phe
        1305                1310                1315 cag ccc atg agc cgc cag gtc gtg gac gag gtc aac tac aag gac      20692
Gln Pro Met Ser Arg Gln Val Val Asp Glu Val Asn Tyr Lys Asp
        1320                1325                1330 tac cag gcc gtc acc ctg gcc tac cag cac aac aac tcg ggc ttc      20737
Tyr Gln Ala Val Thr Leu Ala Tyr Gln His Asn Asn Ser Gly Phe
        1335                1340                1345 gtc ggc tac ctc gcg ccc acc atg cgc cag ggc cag ccc tac ccc      20782
Val Gly Tyr Leu Ala Pro Thr Met Arg Gln Gly Gln Pro Tyr Pro
        1350                1355                1360 gcc aac tac ccc tac ccg ctc atc ggc aag agc gcc gtc gcc agc      20827
Ala Asn Tyr Pro Tyr Pro Leu Ile Gly Lys Ser Ala Val Ala Ser
        1365                1370                1375 gtc acc cag aaa aag ttc ctc tgc gac cgg gtc atg tgg cgc atc      20872
Val Thr Gln Lys Lys Phe Leu Cys Asp Arg Val Met Trp Arg Ile
        1380                1385                1390 ccc ttc tcc agc aac ttc atg tcc atg ggc gcg ctc acc gac ctc      20917
Pro Phe Ser Ser Asn Phe Met Ser Met Gly Ala Leu Thr Asp Leu
        1395                1400                1405 ggc cag aac atg ctc tac gcc aac tcc gcc cac gcg cta gac atg      20962
Gly Gln Asn Met Leu Tyr Ala Asn Ser Ala His Ala Leu Asp Met
        1410                1415                1420 aat ttc gaa gtc gac ccc atg gat gag tcc acc ctt ctc tat gtt      21007
Asn Phe Glu Val Asp Pro Met Asp Glu Ser Thr Leu Leu Tyr Val
        1425                1430                1435 gtc ttc gaa gtc ttc gac gtc gtc cga gtg cac cag ccc cac cgc      21052
Val Phe Glu Val Phe Asp Val Val Arg Val His Gln Pro His Arg
        1440                1445                1450 ggc gtc atc gaa gcc gtc tac ctg cgc acg ccc ttc tcg gcc ggc      21097
Gly Val Ile Glu Ala Val Tyr Leu Arg Thr Pro Phe Ser Ala Gly
        1455                1460                1465 aac gcc acc acc taa gccgctcttg cttcttgcaa gatgacggcg ggctccggcg   21152
Asn Ala Thr Thr
        1470 agcaggagct cagggccatc ctccgcgacc tgggctgcgg gccctgcttc ctgggcacct  21212 tcgacaagcg cttccctgga ttcatggccc cgcacaagct ggcctgcgcc atcgtgaaca  21272 cggccgccg cgagaccggg ggcgagcact ggctggcctt cgcctggaac ccgcgctccc   21332 acacatgcta cctcttcgac cccttcgggt tctcggacga gcgcctcaag cagatctacc  21392
```

```
agttcgagta cgagggcctg ctgcgtcgca gcgccctggc caccgaggac cgctgcgtca   21452
ccctggaaaa gtccacccag accgtgcagg gtccgcgctc ggccgcctgc gggctcttct   21512
gctgcatgtt cctgcacgcc ttcgtgcact ggcccgaccg ccccatggac aagaacccca   21572
ccatgaactt actgacgggg gtgcccaacg gcatgctcca gtcgcccag gtggaaccca   21632 ccctgcgccg caaccaggaa gcgctctacc gcttcctcaa tgcccactcc gcctactttc   21692
gctcccaccg cgcgcgcatc gagaaggcca ccgccttcga ccgcatgaat caagacatgt   21752
aaaaaaccgg tgtgtgtatg tgaatgcttt attcataata aacagcacat gtttatgcca   21812
ccttctctga ggctctgact ttatttagaa atcgaagggg ttctgccggc tctcggcatg   21872
gcccgcgggc agggatacgt tgcggaactg gtacttgggc agccacttga actcggggat   21932
cagcagcttg ggcacgggga ggtcggggaa cgagtcgctc cacagcttgc gcgtgagttg   21992
cagggcgccc agcaggtcgg gcgcggagat cttgaaatcg cagttgggac ccgcgttctg   22052
cgcgcgagag ttgcggtaca cggggttgca gcactggaac accatcaggg ccgggtgctt   22112
cacgcttgcc agcaccgtcg cgtcggtgat gccctccacg tccagatcct cggcgttggc   22172
catcccgaag ggggtcatct tgcaggtctg ccgccccatg ctgggcacgc agccgggctt   22232
gtggttgcaa tcgcagtgca gggggatcag catcatctgg gcctgctcgg agctcatgcc   22292
cgggtacatg gccttcatga aagcctccag ctggcggaag gcctgctgcg ccttgccgcc   22352
ctcggtgaag aagaccccgc aggacttgct agagaactgg ttggtggcgc agccggcgtc   22412
gtgcacgcag cagcgcgcgt cgttgttggc cagctgcacc acgctgcgcc cccagcggtt   22472
ctgggtgatc ttgcccggt tggggttctc cttcagcgcg cgctgcccgt tctcgctcgc   22532
cacatccatc tcgatagtgt gctccttctg gatcatcacg gtcccgtgca ggcaccgcag   22592
cttgccctcg gcttcggtgc agccgtgcag ccacagcgcg cagccggtgc actcccagtt   22652
cttgtgggcg atctgggagt gcgagtgcac gaagccctgc aggaagcggc ccatcatcgc   22712
ggtcagggtc ttgttgctgg tgaaggtcag cgggatgccg cggtgctcct cgttcacata   22772
caggtggcag atgcggcggt acacctcgcc ctgctcgggc atcagctgga aggcggactt   22832
caggtcgctc tccacgcggt accggtccat cagcagcgtc atcacttcca tgcccttctc   22892
ccaggccgaa acgatcggca ggctcagggg gttcttcacc gccattgtca tcttagtcgc   22952
cgccgccgag gtcagggggt cgttctcgtc cagggtctca aacactcgct tgccgtcctt   23012
ctcgatgatg cgcacggggg gaaagctgaa gcccacggcc gccagctcct cctcggcctg   23072
cctttcgtcc tcgctgtcct ggctgatgtc ttgcaaaggc acatgcttgg tcttgcgggg   23132 tttcttttg ggcggcagag gcggcggcga tgtgctggga gagcgcgagt tctcgttcac   23192
cacgactatt tcttcttctt ggccgtcgtc cgagaccacg cggcggtagg catgcctctt   23252
ctggggcaga ggcggaggcg acgggctctc gcggttcggc gggcggctgg cagagcccct   23312
tccgcgttcg ggggtgcgct cctggcgcg ctgctctgac tgacttcctc cgcggccggc   23372
cattgtgttc tcctagggag caacaacaag catgagact cagccatcgt cgccaacatc   23432
gccatctgcc cccgccgcca ccgccgacga gaaccagcag cagaatgaaa gcttaaccgc   23492
cccgccgccc agccccacct ccgacgccgc ggccccagac atgcaagaga tggaggaatc   23552
catcgagatt gacctgggct acgtgacgcc ccgcgagcac gaggaggagc tggcagcgcg   23612 ctttttcagcc ccggaagaga accaccaaga gcagccagag caggaagcag agaacgagca   23672
gaaccaggct gggcacgagc atggcgacta cctgagcggg gcagaggacg tgctcatcaa   23732
gcatctggcc cgccaatgca tcatcgtcaa ggacgcgctg ctcgaccgcg ccgaggtgcc   23792
```

```
cctcagcgtg gcggagctca gccgcgccta cgagcgcaac ctcttctcgc cgcgcgtgcc  23852
ccccaagcgc cagcccaacg gcacctgtga gcccaacccg cgcctcaact tctacccggt  23912
cttcgcggtg cccgaggccc tggccaccta ccacctcttt ttcaagaacc aaaggatccc  23972
cgtctcctgc cgcgccaacc gcacccgcgc cgacgccctg ctcaacctgg gccccggcgc  24032
ccgcctacct gatatcacct ccttggaaga ggttcccaag atcttcgagg gtctgggcag  24092
cgacgagact cgggccgcga acgctctgca aggaagcgga gaggagcatg agcaccacag  24152
cgccctggtg gagttggaag gcgacaacgc gcgcctggcg gtcctcaagc gcacggtcga  24212
gctgacccac ttcgcctacc cggcgctcaa cctgccccccc aaggtcatga gcgccgtcat  24272
ggaccaggtg ctcatcaagc gcgcctcgcc cctctcggag gaggagatgc aggaccccga  24332
gagttcggac gagggcaagc ccgtggtcag cgacgagcag ctggcgcgct ggctgggagc  24392
gagtagcacc ccccagagcc tggaagagcg gcgcaagctc atgatggccg tggtcctggt  24452
gaccgtggag ctggagtgtc tgcgccgctt ctttgccgac gcggagaccc tgcgcaaggt  24512
cgaggagaac ctgcactacc tcttcaggca cgggttcgtg cgccaggcct gcaagatctc  24572
caacgtggag ctgaccaacc tggtctccta catgggcatc ctgcacgaga accgcctggg  24632
gcaaaacgtg ctgcacacca ccctgcgcgg ggaggcccgc cgcgactaca tccgcgactg  24692
cgtctacctg tacctctgcc acacctggca gacgggcatg ggcgtgtggc agcagtgcct  24752
ggaggagcag aacctgaaag agctctgcaa gctcctgcag aagaacctca aggccctgtg  24812
gaccgggttc gacgagcgta ccaccgcctc ggacctggcc gacctcatct tccccgagcg  24872
cctgcggctg acgctgcgca acgggctgcc cgactttatg agccaaagca tgttgcaaaa  24932 cttcgctct ttcatcctcg aacgctccgg gatcctgccc gccacctgct ccgcgctgcc  24992
ctcggacttc gtgccgctga ccttccgcga gtgcccccg ccgctctgga gccactgcta  25052
cttgctgcgc ctggccaact acctggccta ccactcggac gtgatcgagg acgtcagcgg  25112
cgagggtctg ctggagtgcc actgccgctg caacctctgc acgccgcacc gctccctggc  25172
ctgcaacccc cagctgctga gcagaccca gatcatcggc accttcgagt tgcaaggccc  25232
cggcgacggc gagggcaagg ggggtctgaa actcaccccg gggctgtgga cctcggccta  25292
cttgcgcaag ttcgtgcccg aggactacca tcccttcgag atcaggttct acgaggacca  25352
atcccagccg cccaaggccg agctgtcggc ctgcgtcatc acccagggg ccatcctggc  25412 ccaattgcaa gccatccaga aatcccgcca agaatttctg ctgaaaaagg gccacggggt  25472
ctacttggac ccccagaccg gagaggagct caaccccagc ttcccccagg atgccccgag  25532
gaagcagcaa gaagctgaaa gtggagctgc cgccgccgga ggatttggag aagactggg  25592 agagcagtca ggcagaggag gaggagatgg aagactggga cagcactcag gcagaggagg  25652
acagcctgca agacagtctg gaggaggaag acgaggtgga ggaggcagag gaagaagcag  25712
ccgccgccag accgtcgtcc tcggcggaga aagcaagcag cacggatacc atctccgctc  25772
cgggtcgggg tcgcggcggc cgggcccaca gtaggtggga cgagaccggg cgcttcccga  25832
accccaccac ccagaccggt aagaaggagc ggcagggata caagtcctgg cgggggcaca  25892
aaaacgccat cgtctcctgc ttgcaagcct gcgggggcaa catctccttc acccggcgct  25952
acctgctctt ccaccgcggg gtgaacttcc cccgcaacat cttgcattac taccgtcacc  26012
tccacagccc ctactactgt ttccaagaag aggcagaaac ccagcagcag cagaaaacca  26072
gcggcagcag cagctagaaa atccacagcg gcggcaggtg gactgaggat cgcggcgaac  26132
```

```
gagccggcgc agacccggga gctgaggaac cggatctttc ccaccctcta tgccatcttc   26192
cagcagagtc gggggcagga gcaggaactg aaagtcaaga accgttctct gcgctcgctc   26252
acccgcagtt gtctgtatca aagagcgaa gaccaacttc agcgcactct cgaggacgcc    26312
gaggctctct tcaacaagta ctgcgcgctc actcttaaag agtagcccgc gcccgcccac   26372
acacggaaaa aggcgggaat tacgtcacca cctgcgccct tcgcccgacc atcatgagca   26432
aagagattcc cacgccttac atgtggagct accagcccca gatgggcctg ccgccggcg    26492 ccgcccagga ctactccacc cgcatgaact ggctcagtgc cgggcccgcg atgatctcac   26552
gggtgaatga catccgcgcc caccgaaacc agatactcct agaacagtca gcgatcaccg   26612
ccacgccccg ccatcacctt aatccgcgta attggcccgc cgccctggtg taccaggaaa   26672
ttccccagcc cacgaccgta ctacttccgc gagacgccca ggccgaagtc cagctgacta   26732
actcaggtgt ccagctggcc ggcggcgccg ccctgtgtcg tcaccgcccc gctcagggta   26792
taaagcggct ggtgatccga ggcagaggca cacagctcaa cgacgaggtg gtgagctctt   26852
cgctgggtct gcgacctgac ggagtcttcc aactcgccgg atcggggaga tcttccttca   26912
cgcctcgtca ggccgtcctg actttggaga gttcgtcctc gcagcccgc tcgggcggca    26972 tcggcactct ccagttcgtg gaggagttca ctccctcggt ctacttcaac ccttctccg    27032 gctcccccgg ccactacccg gacgagttca tcccgaactt cgacgccatc agcgagtcgg   27092
tggacggcta cgattgaatg tcccatggtg gcgcagctga cctagctcgg cttcgacacc   27152
tggaccactg ccgccgcttc cgctgcttcg ctcgggatct cgccgagttt gcctactttg   27212
agctgcccga ggagcaccct cagggcccag cccacggagt gcggatcatc gtcgaagggg   27272
gcctcgactc ccacctgctt cggatcttca gccagcgacc gatcctggtc gagcgcgaac   27332
aaggacagac ccttcttact ttgtactgca tctgcaacca ccccggcctg catgaaagtc   27392
tttgttgtct gctgtgtact gagtataata aaagctgaga tcagcgacta ctccggactc   27452
gattgtggtg ttcctgctat caaccggtcc ctgttcttca ccgggaacga gaccgagctc   27512
cagctccagt gtaagcccca caagaagtac ctcacctggc tgttccaggg ctccccgatc   27572
gccgttgtca accactgcga caacgacgga gtcctgctga gcggccctgc caaccttact   27632
ttttccaccc gcagaagcaa gctccagctc ttccaaccct tcctccccgg gacctatcag   27692
tgcgtctcag gaccctgcca tcacaccttc cacctgatcc cgaataccac agcgccgctc   27752
cccgctacta caaccaaac tacccaccaa cgccaccgtc gcgacctttc tctgaatct    27812 aataccacta ccggaggtga gctccgaggt cgaccaacct ctgggattta ctacggcccc   27872
tgggaggtgg tggggttaat agcgctaggc ctagttgcgg gtgggctttt ggttctctgc   27932
tacctatacc tcccttgctg ttcgtactta gtggtgctgt gttgctggtt taagaaatgg   27992
ggaagatcac cctagtgagc tgcggtgcgc tggtggcggt gttgctttcg attgtgggac   28052
tgggcggcgc ggctgtagtg aaggagaagg ccgatccctg cttgcatttc aatcccaaca   28112
aatgccagct gagttttcag cccgatggca atcggtgcgc ggtactgatc aagtgcggat   28172
gggaatgcga gaacgtgaga atcgagtaca ataacaagac tcggaacaat actctcgcgt   28232
ccgtgtggca gccggggac cccgagtggt acaccgtctc tgtccccggt gctgacggct    28292
ccccgcgcac cgtgaataat actttcattt ttgcgcacat gtgcaacacg gtcatgtgga   28352
tgagcaagca gtacgatatg tggcccccca cgaaggagaa catcgtggtc ttctccatcg   28412
cttacagcct gtgcacggcg ctaatcaccg ctatcgtgtg cctgagcatt cacatgctca   28472
tcgctattcg ccccagaaat aatgccgaga aagagaaaca gccataacac gttttttcac   28532
```

```
acaccttgtt tttacagaca atgcgtctgt taaattttt aaacattgtg ctcagtattg    28592
cttatgcctc tggttatgca aacatacaga aaacccttta tgtaggatct gatggtacac    28652
tagagggtac ccaatcacaa gccaaggttg catggtattt ttatagaacc aacactgatc    28712
cagttaaact ttgtaagggt gaattgccgc gtacacataa aactccactt acatttagtt    28772
gcagcaataa taatcttaca cttttttcaa ttacaaaaca atatactggt acttattaca    28832
gtacaaactt tcatacagga caagataaat attatactgt taaggtagaa atcctacca    28892 ctcctagaac taccaccacc accactactg caaagcccac tgtgaaaact caactagga    28952 ccaccacaac tacagaaacc accaccagca caacacttgc tgcaactaca cacacacaca    29012
ctaagctaac cttacagacc actaatgatt tgatcgccct gctgcaaaag ggggataaca    29072
gcaccacttc caatgaggag atacccaaat ccatgattgg cattattgtt gctgtagtgg    29132
tgtgcatgtt gatcatcgcc ttgtgcatgg tgtactatgc cttctgctac agaaagcaca    29192
gactgaacga caagctggaa cacttactaa gtgttgaatt ttaatttttt agaaccatga    29252
agatcctagg cctttttagt ttttctatca ttacctctgc tctttgtgaa tcagtggata    29312
gagatgttac tattaccact ggttctaatt atacactgaa agggccaccc tcaggtatgc    29372
tttcgtggta ttgctatttt ggaactgaca ctgatcaaac tgaattatgc aattttcaaa    29432
aaggcaaaac ctcaaactct aaaatctcta attatcaatg caatggcact gatctgatac    29492
tactcaatgt cacgaaagca tatggtggca gttattattg ccctggacaa aacactgaag    29552
aaatgatttt ttacaaagtg gaagtggttg atcccactac accacccacc accacaacta    29612
ttcataccac acacagaa caaacaccag aggcaacaga agcagagttg gccttccagg    29672
ttcacggaga ttcctttgct gtcaataccc ctacacccga tcagcggtgt ccggggccgc    29732
tagtcagcgg cattgtcggt gtgctttcgg gattagcagt cataatcatc tgcatgttca    29792
tttttgcttg ctgctataga aggctttacc gacaaaaatc agaccactg ctgaacctct    29852 atgtttaatt ttttccagag ccatgaaggc agttagcgct ctagttttt gttctttgat    29912 tggcattgtt tttaatagta aaattaccag agttagcttt attaaacatg ttaatgtaac    29972
tgaaggagat aacatcacac tagcaggtgt agaaggtgct caaaacacca cctggacaaa    30032
ataccatcta ggatggagag atatttgcac ctggaatgta acttattatt gcataggagt    30092
taatcttacc attgttaacg ctaaccaatc tcagaatggg ttaattaaag gacagagtgt    30152
tagtgtgacc agtgatgggt actatacca gcatagtttt aactacaaca ttactgtcat    30212
accactgcct acgcctagcc cacctagcac taccacacag acaaccacat acagtacatc    30272
aaatcagcct accaccacta cagcagcaga ggttgccagc tcgtctgggg tccgagtggc    30332 attttgatg ttggccccat ctagcagtcc cactgctagt accaatgagc agactactga    30392 attttgtcc actgtcgaga gccacaccac agctacctcc agtgccttct ctagcaccgc    30452
caatctctcc tcgcttttcct ctacaccaat cagccccgct actactccta gccccgctcc    30512
tcttcccact cccctgaagc aaacagacgg cggcatgcaa tggcagatca ccctgctcat    30572
tgtgatcggg ttggtcatcc tggccgtgtt gctctactac atcttctgcc gccgcattcc    30632
caacgcgcac cgcaagccgg cctacaagcc catcgttatc gggcagccgg agccgcttca    30692
ggtggaaggg ggtctaagga atcttctctt ctctttaca gtatggtgat tgaactatga    30752
ttcctagaca attcttgatc actattctta tctgcctcct ccaagtctgt gccaccctcg    30812
ctctggtggc caacgccagt ccagactgta ttgggccctt cgcctcctac gtgctctttg    30872
```

```
ccttcgtcac ctgcatctgc tgctgtagca tagtctgcct gcttatcacc ttcttccagt    30932
tcattgactg gatctttgtg cgcatcgcct acctgcgcca ccaccccag taccgcgacc     30992
agcgagtggc gcagctgctc aggctcctct gataagcatg cgggctctgc tacttctcgc    31052
gcttctgctg ttagtgctcc cccgtcccgt cgaccccgg tccccactc agtccccga      31112
ggaggttcgc aaatgcaaat tccaagaacc ctggaaattc tcaaatgct accgccaaaa     31172
atcagacatg catcccagct ggatcatgat cattgggatc gtgaacattc tggcctgcac    31232
cctcatctcc tttgtgattt acccctgctt tgactttggt tggaactcgc cagaggcgct    31292
ctatctcccg cctgaacctg acacaccacc acagcagcaa cctcaggcac acgcactacc    31352
accaccacag cctaggccac aatacatgcc catattagac tatgaggccg agccacagcg    31412
acccatgctc cccgctatta gttacttcaa tctaaccggc ggagatgact gacccactgg    31472
ccaataacaa cgtcaacgac cttctcctgg acatggacgg ccgcgcctcg gagcagcgac    31532
tcgcccaact tcgcattcgt cagcagcagg agagagccgt caaggagctg caggacggca    31592
tagccatcca ccagtgcaag agaggcatct tctgcctggt gaaacaggcc aagatctcct    31652
acgaggtcac ccagaccgac catcgcctct cctacgagct cctgcagcag cgccagaagt    31712
tcacctgcct ggtcggagtc aaccccatcg tcatcaccca gcagtcgggc gataccaagg    31772
ggtgcatcca ctgctcctgc gactcccccg actgcgtcca cactctgatc aagaccctct    31832
gcggcctccg cgacctcctc cccatgaact aatcaccccc ttatccagtg aaataaagat    31892
catattgatg atgatttaaa taaaaaaaat aatcatttga tttgaaataa agatacaatc    31952
atattgatga tttgagttta acaaaaataa agaatcactt acttgaaatc tgataccagg    32012
tctctgtcca tgttttctgc caacaccacc tcactcccct cttcccagct ctggtactgc    32072
aggcccggc gggctgcaaa cttcctccac acgctgaagg ggatgtcaaa ttcctcctgt     32132
ccctcaatct tcattttatc ttctatcag atg tcc aaa aag cgc gtc cgg gtg     32185
                                  Met Ser Lys Lys Arg Val Arg Val
                                                        1475 gat gat gac ttc gac ccc gtc tac ccc tac gat gca gac aac gca          32230
Asp Asp Asp Phe Asp Pro Val Tyr Pro Tyr Asp Ala Asp Asn Ala
1480                1485                1490 ccg acc gtg ccc ttc atc aac ccc ccc ttc gtc tct tca gat gga          32275
Pro Thr Val Pro Phe Ile Asn Pro Pro Phe Val Ser Ser Asp Gly
1495                1500                1505 ttc caa gag aag ccc ctg ggg gtg ttg tcc ctg cga ctg gct gac          32320
Phe Gln Glu Lys Pro Leu Gly Val Leu Ser Leu Arg Leu Ala Asp
1510                1515                1520 ccc gtc acc acc aag aac ggg gaa atc acc ctc aag ctg gga gag          32365
Pro Val Thr Thr Lys Asn Gly Glu Ile Thr Leu Lys Leu Gly Glu
1525                1530                1535 ggg gtg gac ctc gac tcg tcg gga aaa ctc atc tcc aac acg gcc          32410
Gly Val Asp Leu Asp Ser Ser Gly Lys Leu Ile Ser Asn Thr Ala
1540                1545                1550 acc aag gcc gcc gcc cct ctc agt att tca aac aac acc att tcc          32455
Thr Lys Ala Ala Ala Pro Leu Ser Ile Ser Asn Asn Thr Ile Ser
1555                1560                1565 ctt aaa act gct gcc cct ttc tac aac aac aat gga act tta agc          32500
Leu Lys Thr Ala Ala Pro Phe Tyr Asn Asn Asn Gly Thr Leu Ser
1570                1575                1580 ctc aat gtc tcc aca cca tta gca gta ttt ccc aca ttt aac act          32545
Leu Asn Val Ser Thr Pro Leu Ala Val Phe Pro Thr Phe Asn Thr
1585                1590                1595 tta ggc ata agt ctt gga aac ggt ctt cag act tca aat aag ttg          32590
```

```
Leu Gly Ile Ser Leu Gly Asn Gly Leu Gln Thr Ser Asn Lys Leu
1600                1605                1610 ttg act gta caa cta act cat cct ctt aca ttc agc tca aat agc    32635
Leu Thr Val Gln Leu Thr His Pro Leu Thr Phe Ser Ser Asn Ser
1615                1620                1625 atc aca gta aaa aca gac aaa ggg cta tat att aac tcc agt gga    32680
Ile Thr Val Lys Thr Asp Lys Gly Leu Tyr Ile Asn Ser Ser Gly
1630                1635                1640 aac aga gga ctt gag gct aat ata agc cta aaa aga gga cta gtt    32725
Asn Arg Gly Leu Glu Ala Asn Ile Ser Leu Lys Arg Gly Leu Val
1645                1650                1655 ttt gac ggt aat gct att gca aca tat att gga aat ggc tta gac    32770
Phe Asp Gly Asn Ala Ile Ala Thr Tyr Ile Gly Asn Gly Leu Asp
1660                1665                1670 tat gga tct tat gat agt gat gga aaa aca aga ccc gta att acc    32815
Tyr Gly Ser Tyr Asp Ser Asp Gly Lys Thr Arg Pro Val Ile Thr
1675                1680                1685 aaa att gga gca gga tta aat ttt gat gct aac aaa gca ata gct    32860
Lys Ile Gly Ala Gly Leu Asn Phe Asp Ala Asn Lys Ala Ile Ala
1690                1695                1700 gtc aaa cta ggc aca ggt tta agt ttt gac tcc gct ggt gcc ttg    32905
Val Lys Leu Gly Thr Gly Leu Ser Phe Asp Ser Ala Gly Ala Leu
1705                1710                1715 aca gct gga aac aaa cag gat gac aag cta aca ctt tgg act acc    32950
Thr Ala Gly Asn Lys Gln Asp Asp Lys Leu Thr Leu Trp Thr Thr
1720                1725                1730 cct gac cca agc cct aat tgt caa tta ctt tca gac aga gat gcc    32995
Pro Asp Pro Ser Pro Asn Cys Gln Leu Leu Ser Asp Arg Asp Ala
1735                1740                1745 aaa ttt act ctc tgt ctt aca aaa tgc ggt agt caa ata cta ggc    33040
Lys Phe Thr Leu Cys Leu Thr Lys Cys Gly Ser Gln Ile Leu Gly
1750                1755                1760 act gtg gca gtg gcg gct gtt act gta gga tca gca cta aat cca    33085
Thr Val Ala Val Ala Ala Val Thr Val Gly Ser Ala Leu Asn Pro
1765                1770                1775 att aat gac aca gtc aaa agc gcc ata gtt ttc ctt aga ttt gat    33130
Ile Asn Asp Thr Val Lys Ser Ala Ile Val Phe Leu Arg Phe Asp
1780                1785                1790 tcc gat ggt gta ctc atg tca aac tca tca atg gta ggt gat tac    33175
Ser Asp Gly Val Leu Met Ser Asn Ser Ser Met Val Gly Asp Tyr
1795                1800                1805 tgg aac ttt agg gag gga cag acc act caa agt gta gcc tat aca    33220
Trp Asn Phe Arg Glu Gly Gln Thr Thr Gln Ser Val Ala Tyr Thr
1810                1815                1820 aat gct gtg gga ttc atg cca aat ata ggt gca tat cca aaa acc    33265
Asn Ala Val Gly Phe Met Pro Asn Ile Gly Ala Tyr Pro Lys Thr
1825                1830                1835 caa agt aaa aca cct aaa aat agc ata gtc agt cag gta tat tta    33310
Gln Ser Lys Thr Pro Lys Asn Ser Ile Val Ser Gln Val Tyr Leu
1840                1845                1850 act gga gaa act act atg cca atg aca cta acc ata act ttc aat    33355
Thr Gly Glu Thr Thr Met Pro Met Thr Leu Thr Ile Thr Phe Asn
1855                1860                1865 ggc act gat gaa aaa gac aca acc cca gtt agc acc tac tct atg    33400
Gly Thr Asp Glu Lys Asp Thr Thr Pro Val Ser Thr Tyr Ser Met
1870                1875                1880 act ttt aca tgg cag tgg act gga gac tat aag gac aaa aat att    33445
Thr Phe Thr Trp Gln Trp Thr Gly Asp Tyr Lys Asp Lys Asn Ile
1885                1890                1895
```

| | | |
|---|---|---|
| acc ttt gct acc aac tca ttc tct ttt tcc tac atc gcc cag gaa<br>Thr Phe Ala Thr Asn Ser Phe Ser Phe Ser Tyr Ile Ala Gln Glu<br>1900          1905               1910 | 33490 |
| taa tcccacccag caagccaacc cctttttccca ccacctttgt ctatatggaa | 33543 |
| actctgaaac agaaaaataa agttcaagtg ttttattgaa tcaacagttt tacaggactc | 33603 |
| gagcagttat ttttcctcca ccctcccagg acatggaata caccaccctc tcccccccgca | 33663 |
| cagccttgaa catctgaatg ccattggtga tggacatgct tttggtctcc acgttccaca | 33723 |
| cagtttcaga gcgagccagt ctcggatcgg tcagggagat gaaaccctcc gggcactccc | 33783 |
| gcatctgcac ctcacagctc aacagctgag gattgtcctc ggtggtcggg atcacggtta | 33843 |
| tctggaagaa gcagaagagc ggcggtggga atcatagtcc gcgaacggga tcggccggtg | 33903 |
| gtgtcgcatc aggccccgca gcagtcgctg ccgccgccgc tccgtcaagc tgctgctcag | 33963 |
| ggggttcggg tccagggact ccctcagcat gatgcccacg gccctcagca tcagtcgtct | 34023 |
| ggtgcggcgg gcgcagcagc gcatgcgaat ctcgctcagg tcactgcagt acgtgcaaca | 34083 |
| caggaccacc aggttgttca acagtccata gttcaacacg ctccagccga aactcatcgc | 34143 |
| gggaaggatg ctacccacgt ggccgtcgta ccagatcctc aggtaaatca agtggcgctc | 34203 |
| cctccagaag acgctgccca tgtacatgat ctccttgggc atgtggcggt tcaccacctc | 34263 |
| ccggtaccac atcaccctct ggttgaacat gcagccccgg atgatcctgc ggaaccacag | 34323 |
| ggccagcacc gccccgcccg ccatgcagcg aagagacccc ggatcccggc aatgacaatg | 34383 |
| gaggacccac cgctcgtacc cgtggatcat ctgggagctg aacaagtcta tgttggcaca | 34443 |
| gcacaggcat atgctcatgc atctcttcag cactctcagc cctcggggg tcaaaaccat | 34503 |
| atcccagggc acgggaact cttgcaggac agcgaacccc gcagaacagg gcaatcctcg | 34563 |
| cacataactt acattgtgca tggacagggt atcgcaatca ggcagcaccg ggtgatcctc | 34623 |
| caccagagaa gcgcgggtct cggtctcctc acagcgtggt aaggggccg gccgatacgg | 34683 |
| gtgatggcgg gacgcggctg atcgtgttct cgaccgtgtc atgatgcagt tgctttcgga | 34743 |
| cattttcgta cttgctgtag cagaacctgg tccgggcgct gcacaccgat cgccggcggc | 34803 |
| ggtctcggcg cttggaacgc tcggtgttaa agttgtaaaa cagccactct ctcagaccgt | 34863 |
| gcagcagatc tagggcctca ggagtgatga agatcccatc atgcctgata gctctgatca | 34923 |
| catcgaccac cgtggaatgg gccaggccca gccagatgat gcaattttgt tgggtttcgg | 34983 |
| tgacggcggg ggagggaaga acaggaagaa ccatgattaa ctttttaatcc aaacggtctc | 35043 |
| ggagcacttc aaaatgaagg tcacggagat ggcacctctc gccccgctg tgttggtgga | 35103 |
| aaataacagc caggtcaaag gtgatacggt tctcgagatg ttccacggtg gcttccagca | 35163 |
| aagcctccac gcgcacatcc agaaacaaga caatagcgaa agcgggaggg ttctctaatt | 35223 |
| cctcaaccat catgttacac tcctgcacca tccccagata attttcattt ttccagcctt | 35283 |
| gaatgattcg aactagttcc tgaggtaaat ccaagccagc catgataaaa agctcgcgca | 35343 |
| gagcaccctc caccggcatt cttaagcaca ccctcataat tccaagatat tctgctcctg | 35403 |
| gttcacctgc agcagattga caagcggaat atcaaaatct ctgccgcgat ccctgagctc | 35463 |
| ctccctcagc aataactgta agtactcttt catatcgtct ccgaaatttt tagccatagg | 35523 |
| acccccagga ataagagaag ggcaagccac attacagata aaccgaagtc cccccagtg | 35583 |
| agcattgcca aatgtaagat tgaaataagc atgctggcta gacccggtga tatcttccag | 35643 |
| ataactggac agaaaatcgg gtaagcaatt tttaagaaaa tcaacaaaag aaaaatcttc | 35703 |
| caggtgcacg tttagggcct cgggaacaac gatggagtaa gtgcaagggg tgcgttccag | 35763 |

-continued

```
catggttagt tagctgatct gtaaaaaaac aaaaaataaa acattaaacc atgctagcct  35823
ggcgaacagg tgggtaaatc gttctctcca gcaccaggca ggccacgggg tctccggcgc  35883
gaccctcgta aaaattgtcg ctatgattga aaaccatcac agagagacgt tccggtggc   35943
cggcgtgaat gattcgagaa gaagcataca cccccggaac attggagtcc gtgagtgaaa  36003
aaaagcggcc gaggaagcaa tgaggcacta caacgctcac tctcaagtcc agcaaagcga  36063
tgccatgcgg atgaagcaca aaattttcag gtgcgtaaaa aatgtaatta ctcccctcct   36123
gcacaggcag cgaagctccc gatccctcca gatacacata caaagcctca gcgtccatag   36183
cttaccgagc ggcagcagca gcggcacaca acaggcgcaa gagtcagaga aaagactgag   36243
ctctaacctg tccgcccgct ctctgctcaa tatatagccc cagatctaca ctgacgtaaa   36303
ggccaaagtc taaaaatacc cgccaaataa tcacacacgc ccagcacacg cccagaaacc   36363
ggtgacacac tcagaaaaat acgcgcactt cctcaaacgg ccaaactgcc gtcatttccg   36423
ggttcccacg ctacgtcatc aaaacacgac tttcaaattc cgtcgaccgt taaaaacatc   36483
acccgccccg cccctaacgg tcgccgctcc cgcagccaat caccttcctc cctccccaaa   36543
ttcaaacagc tcatttgcat attaacgcgc accaaaagtt tgaggtatat tattgatgat   36603
g                                                                   36604
```

<210> SEQ ID NO 6
<211> LENGTH: 529
<212> TYPE: PRT
<213> ORGANISM: chimpanzee adenovirus serotype Pan6

<400> SEQUENCE: 6

```
Met Met Arg Arg Val Tyr Pro Glu Gly Pro Pro Ser Tyr Glu Ser
1               5                   10                  15

Val Met Gln Gln Ala Val Ala Ala Met Gln Pro Pro Leu Glu Ala
                20                  25                  30

Pro Tyr Val Pro Pro Arg Tyr Leu Ala Pro Thr Glu Gly Arg Asn Ser
            35                  40                  45

Ile Arg Tyr Ser Glu Leu Ala Pro Leu Tyr Asp Thr Thr Arg Leu Tyr
50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
    130                 135                 140

Arg Lys Thr Pro Asn Gly Val Asp Asp Tyr Asp Gly Ser Gln Asp
145                 150                 155                 160

Glu Leu Thr Tyr Glu Trp Val Glu Phe Glu Leu Pro Glu Gly Asn Phe
                165                 170                 175

Ser Val Thr Met Thr Ile Asp Leu Met Asn Asn Ala Ile Ile Asp Asn
            180                 185                 190

Tyr Leu Ala Val Gly Arg Gln Asn Gly Val Leu Glu Ser Asp Ile Gly
        195                 200                 205

Val Lys Phe Asp Thr Arg Asn Phe Arg Leu Gly Trp Asp Pro Val Thr
```

```
            210                 215                 220
Glu Leu Val Met Pro Gly Val Tyr Thr Asn Glu Ala Phe His Pro Asp
225                 230                 235                 240

Ile Val Leu Leu Pro Gly Cys Gly Val Asp Phe Thr Glu Ser Arg Leu
                245                 250                 255

Ser Asn Leu Leu Gly Ile Arg Lys Arg Gln Pro Phe Gln Glu Gly Phe
            260                 265                 270

Gln Ile Leu Tyr Glu Asp Leu Glu Gly Gly Asn Ile Pro Ala Leu Leu
        275                 280                 285

Asp Val Glu Ala Tyr Glu Lys Ser Lys Glu Asp Ser Thr Ala Ala Ala
    290                 295                 300

Thr Ala Ala Val Ala Thr Ala Ser Thr Glu Val Arg Gly Asp Asn Phe
305                 310                 315                 320

Ala Ser Ala Ala Ala Ala Ala Glu Ala Ala Glu Thr Glu Ser Lys Ile
                325                 330                 335

Val Ile Gln Pro Val Glu Lys Asp Ser Lys Asp Arg Ser Tyr Asn Val
            340                 345                 350

Leu Ala Asp Lys Lys Asn Thr Ala Tyr Arg Ser Trp Tyr Leu Ala Tyr
        355                 360                 365

Asn Tyr Gly Asp Pro Glu Lys Gly Val Arg Ser Trp Thr Leu Leu Thr
    370                 375                 380

Thr Ser Asp Val Thr Cys Gly Val Glu Gln Val Tyr Trp Ser Leu Pro
385                 390                 395                 400

Asp Met Met Gln Asp Pro Val Thr Phe Arg Ser Thr Arg Gln Val Ser
                405                 410                 415

Asn Tyr Pro Val Val Gly Ala Glu Leu Leu Pro Val Tyr Ser Lys Ser
            420                 425                 430

Phe Phe Asn Glu Gln Ala Val Tyr Ser Gln Leu Arg Ala Phe Thr
        435                 440                 445

Ser Leu Thr His Val Phe Asn Arg Phe Pro Glu Asn Gln Ile Leu Val
    450                 455                 460

Arg Pro Pro Ala Pro Thr Ile Thr Thr Val Ser Glu Asn Val Pro Ala
465                 470                 475                 480

Leu Thr Asp His Gly Thr Leu Pro Leu Arg Ser Ser Ile Arg Gly Val
                485                 490                 495

Gln Arg Val Thr Val Thr Asp Ala Arg Arg Arg Thr Cys Pro Tyr Val
            500                 505                 510

Tyr Lys Ala Leu Gly Val Val Ala Pro Arg Val Leu Ser Ser Arg Thr
        515                 520                 525

Phe

<210> SEQ ID NO 7
<211> LENGTH: 942
<212> TYPE: PRT
<213> ORGANISM: chimpanzee adenovirus serotype Pan6

<400> SEQUENCE: 7

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
```

```
              50                  55                  60
Thr Leu Arg Phe Val Pro Val Asp Arg Glu Asp Asn Thr Tyr Ser Tyr
 65                      70                  75                  80

Lys Val Arg Tyr Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Ser
                100                 105                 110

Phe Lys Pro Tyr Ser Gly Thr Ala Tyr Asn Ser Leu Ala Pro Lys Gly
            115                 120                 125

Ala Pro Asn Ser Ser Gln Trp Glu Gln Ala Lys Thr Gly Asn Gly Gly
            130                 135                 140

Thr Met Glu Thr His Thr Tyr Gly Val Ala Pro Met Gly Gly Glu Asn
145                 150                 155                 160

Ile Thr Lys Asp Gly Leu Gln Ile Gly Thr Asp Val Thr Ala Asn Gln
                165                 170                 175

Asn Lys Pro Ile Tyr Ala Asp Lys Thr Phe Gln Pro Glu Pro Gln Val
                180                 185                 190

Gly Glu Glu Asn Trp Gln Glu Thr Glu Asn Phe Tyr Gly Gly Arg Ala
                195                 200                 205

Leu Lys Lys Asp Thr Asn Met Lys Pro Cys Tyr Gly Ser Tyr Ala Arg
210                 215                 220

Pro Thr Asn Glu Lys Gly Gly Gln Ala Lys Leu Lys Val Gly Asp Asp
225                 230                 235                 240

Gly Val Pro Thr Lys Glu Phe Asp Ile Asp Leu Ala Phe Phe Asp Thr
                245                 250                 255

Pro Gly Gly Thr Val Asn Gly Gln Asp Glu Tyr Lys Ala Asp Ile Val
                260                 265                 270

Met Tyr Thr Glu Asn Thr Tyr Leu Glu Thr Pro Asp Thr His Val Val
                275                 280                 285

Tyr Lys Pro Gly Lys Asp Asp Ala Ser Ser Glu Ile Asn Leu Val Gln
                290                 295                 300

Gln Ser Met Pro Asn Arg Pro Asn Tyr Ile Gly Phe Arg Asp Asn Phe
305                 310                 315                 320

Ile Gly Leu Met Tyr Tyr Asn Ser Thr Gly Asn Met Gly Val Leu Ala
                325                 330                 335

Gly Gln Ala Ser Gln Leu Asn Ala Val Val Asp Leu Gln Asp Arg Asn
            340                 345                 350

Thr Glu Leu Ser Tyr Gln Leu Leu Asp Ser Leu Gly Asp Arg Thr
            355                 360                 365

Arg Tyr Phe Ser Met Trp Asn Gln Ala Val Asp Ser Tyr Asp Pro Asp
370                 375                 380

Val Arg Ile Ile Glu Asn His Gly Val Glu Asp Leu Pro Asn Tyr
385                 390                 395                 400

Cys Phe Pro Leu Asp Gly Ser Gly Thr Asn Ala Ala Tyr Gln Gly Val
                405                 410                 415

Lys Val Lys Asp Gly Gln Asp Gly Asp Val Glu Ser Glu Trp Glu Asn
                420                 425                 430

Asp Asp Thr Val Ala Ala Arg Asn Gln Leu Cys Lys Gly Asn Ile Phe
            435                 440                 445

Ala Met Glu Ile Asn Leu Gln Ala Asn Leu Trp Arg Ser Phe Leu Tyr
            450                 455                 460

Ser Asn Val Ala Leu Tyr Leu Pro Asp Ser Tyr Lys Tyr Thr Pro Thr
465                 470                 475                 480
```

```
Asn Val Thr Leu Pro Thr Asn Thr Asn Thr Tyr Asp Tyr Met Asn Gly
            485                 490                 495
Arg Val Thr Pro Pro Ser Leu Val Asp Ala Tyr Leu Asn Ile Gly Ala
            500                 505                 510
Arg Trp Ser Leu Asp Pro Met Asp Asn Val Asn Pro Phe Asn His His
            515                 520                 525
Arg Asn Ala Gly Leu Arg Tyr Arg Ser Met Leu Leu Gly Asn Gly Arg
530                 535                 540
Tyr Val Pro Phe His Ile Gln Val Pro Gln Lys Phe Phe Ala Ile Lys
545                 550                 555                 560
Ser Leu Leu Leu Leu Pro Gly Ser Tyr Thr Tyr Glu Trp Asn Phe Arg
                565                 570                 575
Lys Asp Val Asn Met Ile Leu Gln Ser Ser Leu Gly Asn Asp Leu Arg
                580                 585                 590
Thr Asp Gly Ala Ser Ile Ala Phe Thr Ser Ile Asn Leu Tyr Ala Thr
            595                 600                 605
Phe Phe Pro Met Ala His Asn Thr Ala Ser Thr Leu Glu Ala Met Leu
            610                 615                 620
Arg Asn Asp Thr Asn Asp Gln Ser Phe Asn Asp Tyr Leu Ser Ala Ala
625                 630                 635                 640
Asn Met Leu Tyr Pro Ile Pro Ala Asn Ala Thr Asn Val Pro Ile Ser
                645                 650                 655
Ile Pro Ser Arg Asn Trp Ala Ala Phe Arg Gly Trp Ser Phe Thr Arg
                660                 665                 670
Leu Lys Thr Arg Glu Thr Pro Ser Leu Gly Ser Gly Phe Asp Pro Tyr
            675                 680                 685
Phe Val Tyr Ser Gly Ser Ile Pro Tyr Leu Asp Gly Thr Phe Tyr Leu
            690                 695                 700
Asn His Thr Phe Lys Lys Val Ser Ile Thr Phe Asp Ser Ser Val Ser
705                 710                 715                 720
Trp Pro Gly Asn Asp Arg Leu Leu Thr Pro Asn Glu Phe Glu Ile Lys
                725                 730                 735
Arg Thr Val Asp Gly Glu Gly Tyr Asn Val Ala Gln Cys Asn Met Thr
                740                 745                 750
Lys Asp Trp Phe Leu Val Gln Met Leu Ala His Tyr Asn Ile Gly Tyr
            755                 760                 765
Gln Gly Phe Tyr Val Pro Glu Gly Tyr Lys Asp Arg Met Tyr Ser Phe
            770                 775                 780
Phe Arg Asn Phe Gln Pro Met Ser Arg Gln Val Val Asp Glu Val Asn
785                 790                 795                 800
Tyr Lys Asp Tyr Gln Ala Val Thr Leu Ala Tyr Gln His Asn Asn Ser
                805                 810                 815
Gly Phe Val Gly Tyr Leu Ala Pro Thr Met Arg Gln Gly Gln Pro Tyr
            820                 825                 830
Pro Ala Asn Tyr Pro Tyr Pro Leu Ile Gly Lys Ser Ala Val Ala Ser
            835                 840                 845
Val Thr Gln Lys Lys Phe Leu Cys Asp Arg Val Met Trp Arg Ile Pro
850                 855                 860
Phe Ser Ser Asn Phe Met Ser Met Gly Ala Leu Thr Asp Leu Gly Gln
865                 870                 875                 880
Asn Met Leu Tyr Ala Asn Ser Ala His Ala Leu Asp Met Asn Phe Glu
                885                 890                 895
```

```
Val Asp Pro Met Asp Glu Ser Thr Leu Leu Tyr Val Phe Glu Val
            900                 905                 910

Phe Asp Val Val Arg Val His Gln Pro His Arg Gly Val Ile Glu Ala
        915                 920                 925

Val Tyr Leu Arg Thr Pro Phe Ser Ala Gly Asn Ala Thr Thr
        930                 935                 940

<210> SEQ ID NO 8
<211> LENGTH: 443
<212> TYPE: PRT
<213> ORGANISM: chimpanzee adenovirus serotype Pan6

<400> SEQUENCE: 8

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Ile Ser Asn Asn Thr
                85                  90                  95

Ile Ser Leu Lys Thr Ala Ala Pro Phe Tyr Asn Asn Asn Gly Thr Leu
                100                 105                 110

Ser Leu Asn Val Ser Thr Pro Leu Ala Val Phe Pro Thr Phe Asn Thr
            115                 120                 125

Leu Gly Ile Ser Leu Gly Asn Gly Leu Gln Thr Ser Asn Lys Leu Leu
            130                 135                 140

Thr Val Gln Leu Thr His Pro Leu Thr Phe Ser Ser Asn Ser Ile Thr
145                 150                 155                 160

Val Lys Thr Asp Lys Gly Leu Tyr Ile Asn Ser Ser Gly Asn Arg Gly
                165                 170                 175

Leu Glu Ala Asn Ile Ser Leu Lys Arg Gly Leu Val Phe Asp Gly Asn
            180                 185                 190

Ala Ile Ala Thr Tyr Ile Gly Asn Gly Leu Asp Tyr Gly Ser Tyr Asp
            195                 200                 205

Ser Asp Gly Lys Thr Arg Pro Val Ile Thr Lys Ile Gly Ala Gly Leu
        210                 215                 220

Asn Phe Asp Ala Asn Lys Ala Ile Ala Val Lys Leu Gly Thr Gly Leu
225                 230                 235                 240

Ser Phe Asp Ser Ala Gly Ala Leu Thr Ala Gly Asn Lys Gln Asp Asp
                245                 250                 255

Lys Leu Thr Leu Trp Thr Thr Pro Asp Pro Ser Pro Asn Cys Gln Leu
            260                 265                 270

Leu Ser Asp Arg Asp Ala Lys Phe Thr Leu Cys Leu Thr Lys Cys Gly
            275                 280                 285

Ser Gln Ile Leu Gly Thr Val Ala Val Ala Ala Val Thr Val Gly Ser
            290                 295                 300

Ala Leu Asn Pro Ile Asn Asp Thr Val Lys Ser Ala Ile Val Phe Leu
305                 310                 315                 320

Arg Phe Asp Ser Asp Gly Val Leu Met Ser Asn Ser Ser Met Val Gly
                325                 330                 335
```

```
Asp Tyr Trp Asn Phe Arg Glu Gly Gln Thr Thr Gln Ser Val Ala Tyr
                340                 345                 350
Thr Asn Ala Val Gly Phe Met Pro Asn Ile Gly Ala Tyr Pro Lys Thr
            355                 360                 365
Gln Ser Lys Thr Pro Lys Asn Ser Ile Val Ser Gln Val Tyr Leu Thr
        370                 375                 380
Gly Glu Thr Thr Met Pro Met Thr Leu Thr Ile Thr Phe Asn Gly Thr
385                 390                 395                 400
Asp Glu Lys Asp Thr Thr Pro Val Ser Thr Tyr Ser Met Thr Phe Thr
                405                 410                 415
Trp Gln Trp Thr Gly Asp Tyr Lys Asp Lys Asn Ile Thr Phe Ala Thr
            420                 425                 430
Asn Ser Phe Ser Phe Ser Tyr Ile Ala Gln Glu
        435                 440
```

<210> SEQ ID NO 9
<211> LENGTH: 36535
<212> TYPE: DNA
<213> ORGANISM: chimpanzee adenovirus serotype Pan7
<220> FEATURE:
<221> NAME/KEY: CDS
<222> LOCATION: (13874)..(15469)
<223> OTHER INFORMATION: L2 Penton
<220> FEATURE:
<221> NAME/KEY: CDS
<222> LOCATION: (18288)..(21086)
<223> OTHER INFORMATION: L3 Hexon
<220> FEATURE:
<221> NAME/KEY: CDS
<222> LOCATION: (32094)..(33425)
<223> OTHER INFORMATION: L5 Fiber

<400> SEQUENCE: 9

```
catcatcaat aatatacctc aaacttttgg tgcgcgttaa tatgcaaatg agctgtttga      60
atttggggag ggaggaaggt gattggccga gagacgggcg accgttaggg gcggggcggg     120
tgacgttttt aatacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgtaggc gtcagctgat cgccagggta     480
tttaaacctg cgctctctag tcaagaggcc actcttgagt gccagcgagt agagttttct     540
cctccgcgcc gcgagtcaga tctacacttt gaaagatgag gcacctgaga gacctgcccg     600
gtaatgtttt cctggctact gggaacgaga ttctggaatt ggtggtggac gccatgatgg     660
gtggcgaccc tcctgagccc cctacccccat ttgaggcgcc ttcgctgtac gatttgtatg     720
atctggaggt ggatgtgccc gagaacgacc ccaacgagga ggcggtgaat gatttgttta     780
gcgatgccgc gctgctggct gccgagcagg ctaatacgga ctctggctca gacagcgatt     840
cctctctcca tacccgaga cccggcagag gtgagaaaaa gatccccgag cttaaagggg     900
aagagctcga cctgcgctgc tatgaggaat gcttgcctcc gagcgatgat gaggaggacg     960
aggaggcgat tcgagctgca tcgaaccagg gagtgaaagc tgcgggcgaa agctttagcc    1020
tggactgtcc tactctgccc ggacacggct gtaagtcttg tgaatttcat cgcatgaata    1080
ctggagataa gaatgtgatg tgtgccctgt gctatatgag agcttacaac cattgtgttt    1140
```

```
acagtaagtg tgattaactt tagttgggaa ggcagagggt gactgggtgc tgactggttt    1200
atttatgtat atgttttttt atgtgtaggt cccgtctctg acgtagatga gaccccact    1260 tcagagtgca tttcatcacc cccagaaatt ggcgaggaac cgcccgaaga tattattcat    1320
agaccagttg cagtgagagt caccgggcgg agagcagctg tggagagttt ggatgacttg    1380
ctacagggtg gggatgaacc tttggacttg tgtacccgga aacgcccag gcactaagtg     1440 ccacacatgt gtgtttactt aaggtgatgt cagtatttat agggtgtgga gtgcaataaa    1500
atccgtgttg actttaagtg cgtggtttat gactcagggg tggggactgt gggtatataa    1560
gcaggtgcag acctgtgtgg tcagttcaga gcaggactca tggagatctg gacggtcttg    1620
gaagactttc accagactag acagctgcta gagaactcat cggagggggt ctcttacctg    1680
tggagattct gcttcggtgg gcctctagct aagctagtct atagggccaa acaggattat    1740
aaggatcaat ttgaggatat tttgagagag tgtcctggta ttttgactc tctcaacttg     1800 ggccatcagt ctcactttaa ccagagtatt ctgagagccc ttgactttc tactcctggc     1860 agaactaccg ccgcggtagc cttttttgcc tttatccttg acaaatggag tcaagaaacc    1920
catttcagca gggattaccg tctggactgc ttagcagtag cttttgtggag aacatggagg   1980 tgccagcgcc tgaatgcaat ctccggctac ttgccagtac agccggtaga cacgctgagg    2040
atcctgagtc tccagtcacc ccaggaacac caacgccgcc agcagccgca gcaggagcag    2100
cagcaagagg aggaggagga tcgagaagag aacccgagag ccggtctgga ccctccggtg    2160
gcggaggagg aggagtagct gacttgtttc ccgagctgcg ccgggtgctg actaggtctt    2220
ccagtggacg ggagagggggg attaagcggg agaggcatga ggagactagc cacagaactg   2280
aactgactgt cagtctgatg agccgcaggc gcccagaatc ggtgtggtgg catgaggttc    2340
agtcgcaggg gatagatgag gtctcggtga tgcatgagaa atattccctg gaacaagtca    2400
agacttgttg gttggagcct gaggatgatt gggaggtagc catcaggaat tatgccaagc    2460
tggctctgaa gccagacaag aagtacaaga ttaccaaact gattaatatc agaaattcct    2520
gctacatttc agggaatggg gccgaggtgg agatcagtac ccaggagagg gtggccttca    2580
gatgttgtat gatgaatatg tacccggggg tggtgggcat ggagggagtc acctttatga    2640
acgcgaggtt caggggtgat gggtataatg gggtggtctt tatggccaac accaagctga    2700
cagtgcacgg atgctccttc tttgggttca ataacatgtg catcgaggcc tggggcagtg    2760
tttcagtgag gggatgcagc ttttcagcca actggatggg ggtcgtgggc agaaccaaga    2820
gcaaggtgtc agtgaagaaa tgcctgttcg agaggtgcca cctgggggtg atgagcgagg    2880
gcgaagccaa agtcaaacac tgcgcctcta ctgagacggg ctgctttgtg ctgatcaagg    2940
gcaatgccca agtcaagcat aacatgatct gtggggcctc ggatgagcgc ggctaccaga    3000
tgctgacctg cgccggtggg aacagccata tgctggccac cgtgcatgtg acctcgcacc    3060
cccgcaagac atggcccgag ttcgagcaca acgtcatgac ccgatgcaat gtgcacctgg    3120
ggtcccgccg aggcatgttc atgccctacc agtgcaacat gcaatttgtg aaggtgctgc    3180
tggagcccga tgccatgtcc agagtgagcc tgacgggggt gtttgacatg aatgtggagc    3240
tgtggaaaat tctgagatat gatgaatcca agaccaggtg ccgggcctgc gaatgcggag    3300
gcaagcacgc caggcttcag cccgtgtgtg tggaggtgac ggaggacctg cgacccgatc    3360
atttggtgtt gtcctgcaac gggacggagt tcggctccag cggggaagaa tctgactaga    3420
gtgagtagtg tttgggggag gtggagggct tgtatgaggg gcagaatgac taaaatctgt    3480
```

```
gttttttctgt gtgttgcagc agcatgagcg gaagcgcctc ctttgaggga ggggtattca    3540
gcccttatct gacggggcgt ctcccctcct gggcgggagt gcgtcagaat gtgatgggat    3600
ccacggtgga cggccggccc gtgcagcccg cgaactcttc aaccctgacc tacgcgaccc    3660
tgagctcctc gtccgtggac gcagctgccg ccgcagctgc tgcttccgcc gccagcgccg    3720
tgcgcggaat ggccctgggc gccggctact acagctctct ggtggccaac tcgacttcca    3780
ccaataatcc cgccagcctg aacgaggaga agctgctgct gctgatggcc cagctcgagg    3840
ccctgaccca gcgcctgggc gagctgaccc agcaggtggc tcagctgcag gcggagacgc    3900
gggccgcggt tgccacggtg aaaaccaaat aaaaaatgaa tcaataaata aacggagacg    3960
gttgttgatt ttaacacaga gtcttgaatc tttatttgat ttttcgcgcg cggtaggccc    4020
tggaccaccg gtctcgatca ttgagcaccc ggtggatttt ttccaggacc cggtagaggt    4080
gggcttggat gttgaggtac atgggcatga gcccgtcccg ggggtggagg tagctccatt    4140
gcagggcctc gtgctcgggg gtggtgttgt aaatcaccca gtcatagcag ggcgcaggg    4200
cgtggtgctg cacgatgtcc ttgaggagga gactgatggc cacgggcagc cccttggtgt    4260
aggtgttgac gaacctgttg agctgggagg gatgcatgcg gggggagatg agatgcatct    4320
tggcctggat cttgagattg gcgatgttcc cgcccagatc ccgccggggg ttcatgttgt    4380
gcaggaccac cagcacggtg tatccggtgc acttggggaa tttgtcatgc aacttggaag    4440
ggaaggcgtg aaagaatttg gagacgccct tgtgaccgcc caggttttcc atgcactcat    4500
ccatgatgat ggcgatgggc ccgtgggcgg cggcctgggc aaagacgttt cgggggtcgg    4560
acacatcgta gttgtggtcc tgggtgagct cgtcataggc catttaatg aatttggggc    4620
ggagggtgcc cgactggggg acgaaggtgc cctcgatccc ggggggcgtag ttgccctcgc    4680
agatctgcat ctcccaggcc ttgagctcgg aggggggggat catgtccacc tgcggggcga    4740
tgaaaaaaac ggtttccggg gcgggggaga tgagctgggc cgaaagcagg ttccggagca    4800
gctgggactt gccgcagccg gtggggccgt agatgacccc gatgaccggc tgcaggtggt    4860
agttgaggga gagacagctg ccgtcctcgc ggaggagggg ggccacctcg ttcatcatct    4920
cgcgcacatg catgttctcg cgcacgagtt ccgccaggag gcgctcgccc ccagcgaga    4980
ggagctcttg cagcgaggcg aagttttttca gcggcttgag yccgtcggcc atgggcattt    5040
tggagagggt ctgttgcaag agttccagac ggtcccagag ctcggtgatg tgctctaggg    5100
catctcgatc cagcagacct cctcgtttcg cgggttgggg cgactgcggg agtagggcac    5160
caggcgatgg gcgtccagcg aggccagggt ccggtccttc cagggtcgca gggtccgcgt    5220
cagcgtggtc tccgtcacgg tgaagggggtg cgcgccgggc tgggcgcttg cgagggtgcg    5280
cttcaggctc atccggctgg tcgagaaccg ctcccggtcg gcgccctgcg cgtcggccag    5340
gtagcaattg agcatgagtt cgtagttgag cgcctcggcc gcgtggccct tggcgcggag    5400
cttacctttg gaagtgtgtc cgcagacggg acagaggagg gacttgaggg cgtagagctt    5460
gggggcgagg aagacggact cggggcgta ggcgtccgcg ccgcagctgg cgcagacggt    5520
ctcgcactcc acgagccagg tgaggtcggg ccggttgggg tcaaaaacga ggtttcctcc    5580
gtgctttttg atgcgtttct tacctctggt ctccatgagc tcgtgtcccc gctgggtgac    5640
aaagaggctg tccgtgtccc cgtagaccga ctttatgggc cggtcctcga gcggggtgcc    5700
gcggtcctcg tcgtagagga accccgccca ctccgagacg aaggcccggg tccaggccag    5760
cacgaaggag gccacgtggg aggggtagcg gtcgttgtcc accagcgggt ccaccttctc    5820
cagggtatgc aagcacatgt cccctcgtc cacatccagg aaggtgattg gcttgtaagt    5880
```

-continued

```
gtaggccacg tgaccggggg tcccggccgg gggggtataa aagggggcgg gccoctgctc    5940 gtcctcactg tcttccggat cgctgtccag gagcgccagc tgttggggta ggtattccct    6000
ctcgaaggct ggcataacct cggcactcag gttgtcagtt tctagaaacg aggaggattt    6060
gatattgacg gtgccgttgg agacgccttt catgagcccc tcgtccatct ggtcagaaaa    6120
gacgatcttt ttgttgtcga gcttggtggc gaaggagccg tagagggcgt tggagaggag    6180
cttggcgatg gagcgcatgg tctggttctt ttccttgtcg gcgcgctcct tggcggcgat    6240
gttgagctgc acgtactcgc gcgccacgca cttccattcg gggaagacgg tggtgagctc    6300
gtcgggcacg attctgaccc gccagccgcg gttgtgcagg gtgatgaggt ccacgctggt    6360
ggccacctcg ccgcgcaggg gctcgttggt ccagcagagg cgcccgccct gcgcgagca     6420 gaagggggcg agcgggtcca gcatgagctc gtcgggggg tcggcgtcca cggtgaagat     6480
gccgggcaga agctcggggt cgaagtagct gatgcaggtg tccagatcgt ccagcgccgc    6540
ttgccagtcg cgcacggcca gcgcgcgctc gtaggggctg aggggcgtgc cccagggcat    6600
ggggtgcgtg agcgcggagg cgtacatgcc gcagatgtcg tagacgtaga ggggctcctc    6660
gaggacgccg atgtaggtgg ggtagcagcg ccccccgcgg atgctggcgc gcacgtagtc    6720
gtacagctcg tgcgagggcg cgaggagccc cgtgccgagg ttggagcgtt gcggcttttc    6780
ggcgcggtag acgatctggc ggaagatggc gtgggagttg gaggagatgg tgggcctctg    6840
gaagatgttg aagtgggcgt ggggcaggcc gaccgagtcc ctgatgaagt gggcgtagga    6900
gtcctgcagc ttggcgacga gctcggcggt gacgaggacg tccagggcgc agtagtcgag    6960
ggtctcttgg atgatgtcgt acttgagctg gcccttctgc ttccacagct cgcggttgag    7020
aaggaactct tcgcggtcct tccagtactc ttcgaggggg aacccgtcct gatcggcacg    7080
gtaagagccc accatgtaga actggttgac ggccttgtag gcgcagcagc ccttctccac    7140
ggggagggcg taagcttgtg cggccttgcg cagggaggtg tgggtgaggg cgaaggtgtc    7200
gcgcaccatg accttgagga actggtgctt gaagtcgagg tcgtcgcagc cgccctgctc    7260
ccagagctgg aagtccgtgc gcttcttgta ggcggggttg ggcaaagcga agtaacatc     7320 gttgaagagg atcttgcccg cgcggggcat gaagttgcga gtgatgcgga aaggctgggg    7380
cacctcggcc cggttgttga tgacctgggc ggcgaggacg atctcgtcga agccgttgat    7440
gttgtgcccg acgatgtaga gttccacgaa tcgcgggcgg cccttaacgt ggggcagctt    7500
cttgagctcg tcgtaggtga gctcggcggg gtcgctgagc ccgtgctgct cgagggccca    7560
gtcggcgacg tggggggttgg cgctgaggaa ggaagtccag agatccacgg ccagggcggt    7620
ctgcaagcgg tcccggtact gacggaactg ctggcccacg gccatttttt cggggggtgac    7680 gcagtagaag gtgcggggggt cgccgtgcca gcggtcccac ttgagctgga gggcgaggtc    7740
gtgggcgagc tcgacgagcg gcgggtcccc ggagagtttc atgaccagca tgaaggggac    7800
gagctgcttg ccgaaggacc ccatccaggt gtaggtttcc acatcgtagg tgaggaagag    7860
cctttcggtg cgaggatgcg agccgatggg gaagaactgg atctcctgcc accagttgga    7920
ggaatggctg ttgatgtgat ggaagtagaa atgccgacgg cgcgccgagc actcgtgctt    7980
gtgtttatac aagcgtccgc agtgctcgca acgctgcacg ggatgcacgt gctgcacgag    8040
ctgtacctgg gttcctttga cgaggaattt cagtgggcag tggagcgctg gcggctgcat    8100
ctggtgctgt actacgtcct ggccatcggc gtggccatcg tctgcctcga tggtggtcat    8160
gctgacgagc ccgcgcggga ggcaggtcca gacttcggct cggacgggtc ggagagcgag    8220
```

```
gacgagggcg cgcaggccgg agctgtccag ggtcctgaga cgctgcggag tcaggtcagt   8280
gggcagcggc ggcgcgcggt tgacttgcag gagcttttcc agggcgcgcg ggaggtccag   8340
atggtacttg atctccacgg cgccgttggt ggcgacgtcc acggcttgca gggtcccgtg   8400
cccctggggc gccaccaccg tgccccgttt cttcttgggc gctgcttcca tgccggtcag   8460
aagcggcggc gaggacgcgc gccgggcggc aggggcggct cgggacccgg aggcaggggc   8520
ggcaggggca cgtcggcgcc gcgcgcgggc aggttctggt actgcgcccg gagaagactg   8580
gcgtgagcga cgacgcgacg gttgacgtcc tggatctgac gcctctgggt gaaggccacg   8640
ggacccgtga gtttgaacct gaaagagagt tcgacagaat caatctcggt atcgttgacg   8700
gcggcctgcc gcaggatctc ttgcacgtcg cccgagttgt cctggtaggc gatctcggtc   8760
atgaactgct cgatctcctc ctcctgaagg tctccgcggc cggcgcgctc gacggtggcc   8820
gcgaggtcgt tggagatgcg gcccatgagc tgcgagaagg cgttcatgcc ggcctcgttc   8880
cagacgcggc tgtagaccac ggctccgtcg ggtcgcgcg cgcgcatgac cacctgggcg   8940
aggttgagct cgacgtggcg cgtgaagacc gcgtagttgc agaggcgctg gtagaggtag   9000
ttgagcgtgg tggcgatgtg ctcggtgacg aagaagtaca tgatccagcg gcggagcggc   9060
atctcgctga cgtcgcccag ggcttccaag cgctccatgg cctcgtagaa gtccacggcg   9120
aagttgaaaa actgggagtt gcgcgccgag acggtcaact cctcctccag aagacggatg   9180
agctcagcga tggtggcgcg cacctcgcgc tcgaaggccc cgggggggctc ctcttcttcc   9240 atctcttcct cctccactaa catctcttct acttcctcct caggaggcgg cggcggggga   9300
ggggccctgc gtcgccggcg gcgcacgggc agacggtcga tgaagcgctc gatggtctcc   9360
ccgcgccggc gacgcatggt ctcggtgacg gcgcgcccgt cctcgcgggg ccgcagcgtg   9420
aagacgccgc cgcgcatctc caggtggccg ccgggggggt ctccgttggg cagggagagg   9480
gcgctgacga tgcatcttat caattgggcc gtagggactc cgcgcaagga cctgagcgtc   9540
tcgagatcca cggatccga aaccgctga acgaaggctt cgagccagtc gcagtcgcaa   9600
ggtaggctga gcccggtttc ttgttcttcg gggatttcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgccccaggc gtggtcctga   9780
cacctggcga ggtccttgta gtagtcctgc atgagccgct ccacgggcac ctcctcctcg   9840
cccgcgcggc cgtgcatgcg cgtgagcccg aacccgcgct ggggctggac gagcgccagg   9900
tcggcgacga cgcgctcggc gaggatggcc tgctgtatct gggtgagggt ggtctggaag   9960
tcgtcgaagt cgacgaagcg gtggtaggct ccggtgttga tggtatagga gcagttggcc  10020
atgacggacc agttgacggt ctggtggccg ggtcgcacga gctcgtggta cttgaggcgc  10080
gagtaggcgc gcgtgtcgaa gatgtagtcg ttgcaggtgc gcacgaggta ctggtatccg  10140
acgaggaagt gcggcggcgg ctggcggtag agcggccatc gctcggtggc gggggcgccg  10200
ggcgcgaggt cctcgagcat gaggcggtgg tagccgtaga tgtacctgga catccaggtg  10260
atgccggcgg cggtggtgga ggcgcgcggg aactcgcgga cgcggttcca gatgttgcgc  10320
agcggcagga agtagttcat ggtggccgcg gtctggcccg tgaggcgcgc gcagtcgtgg  10380
atgctctaga catacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtactg gcactcccgt ctcgacccaa gcctgctaac gaaacctcca  10560
ggatacggag gcgggtcgtt ttttggcctt ggtcgctggt catgaaaaac tagtaagcgc  10620
```

```
ggaaagcgac cgcccgcgat ggctcgctgc cgtagtctgg agaaagaatc gccagggttg    10680
cgttgcggtg tgccccggtt cgagcctcag cgctcggcgc cggccggatt ccgcggctaa    10740
cgtgggcgtg gctgcccgt cgtttccaag accccttagc cagccgactt ctccagttac     10800
ggagcgagcc cctctttttc ttgtgttttt gccagatgca tcccgtactg cggcagatgc    10860
gcccccaccc tccacctcaa ccgcccctac cgccgcagca gcagcaacag ccggcgcttc    10920 tgccccgcc ccagcagcag ccagccacta ccgcggcggc cgccgtgagc ggagccggcg     10980
ttcagtatga cctggccttg aagagggcg aggggctggc gcggctgggg gcgtcgtcgc     11040
cggagcggca cccgcgcgtg cagatgaaaa gggacgctcg cgaggcctac gtgcccaagc    11100
agaacctgtt cagagacagg agcggcgagg agcccgagga gatgcgcgcc tcccgcttcc    11160
acgcggggcg ggagctgcgg cgcggcctgg accgaaagcg ggtgctgagg gacgaggatt    11220
tcgaggcgga cgagctgacg gggatcagcc ccgcgcgcgc gcacgtggcc gcggccaacc    11280
tggtcacggc gtacgagcag accgtgaagg aggagagcaa cttccaaaaa tccttcaaca    11340
accacgtgcg cacgctgatc gcgcgcgagg aggtgaccct gggcctgatg cacctgtggg    11400
acctgctgga ggccatcgtg cagaacccca cgagcaagcc gctgacggcg cagctgtttc    11460
tggtggtgca gcacagtcgg gacaacgaga cgttcaggga ggcgctgctg aatatcaccg    11520
agcccgaggg ccgctggctc ctggacctgg tgaacattct gcagagcatc gtggtgcagg    11580
agcgcgggct gccgctgtcc gagaagctgg cggctatcaa cttctcggtg ctgagcctgg    11640
gcaagtacta cgctaggaag atctacaaga ccccgtacgt gcccatagac aaggaggtga    11700
agatcgacgg gttttacatg cgcatgaccc tgaaagtgct gaccctgagc gacgatctgg    11760
gggtgtaccg caacgacagg atgcaccgcg cggtgagcgc cagccgccgg cgcgagctga    11820
gcgaccagga gctgatgcac agcctgcagc gggccctgac cggggccggg accgaggggg    11880
agagctactt tgacatgggc gcggacctgc gctggcagcc cagccgccgg gccttggaag    11940
ctgccggcgg ttcccctac gtggaggagg tggacgatga ggaggaggag ggcgagtacc     12000
tggaagactg atggcgcgac cgtattttg ctagatgcag caacagccac cgcctcctga     12060
tcccgcgatg cgggcggcgc tgcagagcca gccgtccggc attaactcct cggacgattg    12120
gacccaggcc atgcaacgca tcatggcgct gacgacccgc aatcccgaag cctttagaca    12180
gcagcctcag gccaaccggc tctcggccat cctggaggcc gtggtgccct cgcgctcgaa    12240
ccccacgcac gagaaggtgc tggccatcgt gaacgcgctg gtggagaaca aggccatccg    12300
cggcgacgag gccgggctgg tgtacaacgc gctgctggag cgcgtggccc gctacaacag    12360
caccaacgtg cagacgaacc tggaccgcat ggtgaccgac gtgcgcgagg cggtgtcgca    12420
gcgcgagcgg ttcaccgcg agtcgaacct gggctccatg gtggcgctga acgccttcct    12480
gagcacgcag cccgccaacg tgccccgggg ccaggaggac tacaccaact tcatcagcgc    12540
gctgcggctg atggtggccg aggtgcccca gagcgaggtg taccagtcgg ggccggacta    12600
cttcttccag accagtcgcc agggcttgca gaccgtgaac ctgagccagg ctttcaagaa    12660
cttgcaggga ctgtggggcg tgcaggcccc ggtcggggac cgcgcgacgg tgtcgagcct    12720
gctgacgcca aactcgcgcc tgctgctgct gctggtggcg cccttcacgg acagcggcag    12780
cgtgagccgc gactcgtacc tgggctacct gcttaacctg taccgcgagg ccatcgggca    12840
ggcgcacgtg gacgagcaga cctaccagga gatcacccac gtgagccgcg cgctgggcca    12900
ggaggacccg ggcaacctgg aggccaccct gaacttcctg ctgaccaacc ggtcgcagaa    12960
```

-continued

```
gatcccgccc cagtacgcgc tgagcaccga ggaggagcgc atcctgcgct acgtgcagca   13020
gagcgtgggg ctgttcctga tgcaggaggg ggccacgccc agcgccgcgc tcgacatgac   13080
cgcgcgcaac atggagccca gcatgtacgc tcgcaaccgc ccgttcatca ataagctgat   13140
ggactacttg catcgggcgg ccgccatgaa ctcggactac tttaccaacg ccatcttgaa   13200
cccgcactgg ctcccgccgc ccgggttcta cacgggcgag tacgacatgc ccgaccccaa   13260
cgacgggttc ctgtgggacg acgtggacag cagcgtgttc tcgccgcgcc ccgccaccac   13320
cgtgtggaag aaagagggcg gggaccggcg gccgtcctcg gcgctgtccg gtcgcgcggg   13380
tgctgccgcg gcggtgcctg aggccgccag ccccttcccg agcctgccct tttcgctgaa   13440
cagcgtgcgc agcagcgagc tgggtcggct gacgcggccg cgcctgctgg gcgaggagga   13500
gtacctgaac gactccttgt tgaggcccga gcgcagaaag aacttcccca ataacgggat   13560
agagagcctg gtggacaaga tgagccgctg gaagacgtac gcgcacgagc acagggacga   13620
gccccgagct agcagcagcg caggcacccg tagacgccag cgacacgaca ggcagcgggg   13680
tctggtgtgg gacgatgagg attccgccga cgacagcagc gtgttggact tgggtgggag   13740
tggtggtggt aacccgttcg ctcacttgcg cccccgtatc gggcgcctga tgtaagaatc   13800
tgaaaaaata aaaacggta ctcaccaagg ccatggcgac cagcgtgcgt tcttctctgt   13860
tgtttgtagt agt atg atg agg cgc gtg tac ccg gag ggt cct cct ccc       13909
            Met Met Arg Arg Val Tyr Pro Glu Gly Pro Pro Pro
            1               5                   10 tcg tac gag agc gtg atg cag cag gcg gtg gcg gcg gcg atg cag ccc       13957
Ser Tyr Glu Ser Val Met Gln Gln Ala Val Ala Ala Ala Met Gln Pro
            15                  20                  25 ccg ctg gag gcg cct tac gtg ccc ccg cgg tac ctg gcg cct acg gag       14005
Pro Leu Glu Ala Pro Tyr Val Pro Pro Arg Tyr Leu Ala Pro Thr Glu
    30                  35                  40 ggg cgg aac agc att cgt tac tcg gag ctg gca ccc ttg tac gat acc       14053
Gly Arg Asn Ser Ile Arg Tyr Ser Glu Leu Ala Pro Leu Tyr Asp Thr
45                  50                  55                  60 acc cgg ttg tac ctg gtg gac aac aag tcg gcg gac atc gcc tcg ctg       14101
Thr Arg Leu Tyr Leu Val Asp Asn Lys Ser Ala Asp Ile Ala Ser Leu
                65                  70                  75 aac tac cag aac gac cac agc aac ttc ctg acc acc gtg gtg cag aac       14149
Asn Tyr Gln Asn Asp His Ser Asn Phe Leu Thr Thr Val Val Gln Asn
        80                  85                  90 aac gat ttc acc ccc acg gag gcc agc acc cag acc atc aac ttt gac       14197
Asn Asp Phe Thr Pro Thr Glu Ala Ser Thr Gln Thr Ile Asn Phe Asp
            95                  100                 105 gag cgc tcg cgg tgg ggc ggc cag ctg aaa acc atc atg cac acc aac       14245
Glu Arg Ser Arg Trp Gly Gly Gln Leu Lys Thr Ile Met His Thr Asn
110                 115                 120 atg ccc aac gtg aac gag ttc atg tac agc aac aag ttc aag gcg cgg       14293
Met Pro Asn Val Asn Glu Phe Met Tyr Ser Asn Lys Phe Lys Ala Arg
125                 130                 135                 140 gtg atg gtc tcg cgc aag acc ccc aat ggg gtc gcg gtg gat gag aat       14341
Val Met Val Ser Arg Lys Thr Pro Asn Gly Val Ala Val Asp Glu Asn
                145                 150                 155 tat gat ggt agt cag gac gag ctg act tac gag tgg gtg gag ttt gag       14389
Tyr Asp Gly Ser Gln Asp Glu Leu Thr Tyr Glu Trp Val Glu Phe Glu
            160                 165                 170 ctg ccc gag ggc aac ttc tcg gtg acc atg acc atc gat ctg atg aac       14437
Leu Pro Glu Gly Asn Phe Ser Val Thr Met Thr Ile Asp Leu Met Asn
        175                 180                 185 aac gcc atc atc gac aac tac ttg gcg gtg ggg cgt cag aac ggg gtg       14485
```

```
                Asn Ala Ile Ile Asp Asn Tyr Leu Ala Val Gly Arg Gln Asn Gly Val
                                190                 195                 200 ctg gag agc gac atc ggc gtg aag ttc gac acg cgc aac ttc cgg ctg             14533
Leu Glu Ser Asp Ile Gly Val Lys Phe Asp Thr Arg Asn Phe Arg Leu
205                 210                 215                 220 ggc tgg gac ccc gtg acc gag ctg gtg atg ccg ggc gtg tac acc aac             14581
Gly Trp Asp Pro Val Thr Glu Leu Val Met Pro Gly Val Tyr Thr Asn
                225                 230                 235 gag gcc ttc cac ccc gac atc gtc ctg ctg ccc ggc tgc ggc gtg gac             14629
Glu Ala Phe His Pro Asp Ile Val Leu Leu Pro Gly Cys Gly Val Asp
    240                 245                 250 ttc acc gag agc cgc ctc agc aac ctg ctg ggc atc cgc aag cgg cag             14677
Phe Thr Glu Ser Arg Leu Ser Asn Leu Leu Gly Ile Arg Lys Arg Gln
                255                 260                 265 ccc ttc cag gag ggc ttc cag atc ctg tac gag gac ctg gag ggg ggc             14725
Pro Phe Gln Glu Gly Phe Gln Ile Leu Tyr Glu Asp Leu Glu Gly Gly
            270                 275                 280 aac atc ccc gcg ctc ttg gat gtc gaa gcc tat gag aaa agc aag gag             14773
Asn Ile Pro Ala Leu Leu Asp Val Glu Ala Tyr Glu Lys Ser Lys Glu
285                 290                 295                 300 gag gcc gcc gca gcg gcg acc gca gcc gtg gcc acc gcc tct acc gag             14821
Glu Ala Ala Ala Ala Thr Ala Ala Val Ala Thr Ala Ser Thr Glu
                305                 310                 315 gtg cgg ggc gat aat ttt gct agc gcc gcg gca gtg gcc gag gcg gct             14869
Val Arg Gly Asp Asn Phe Ala Ser Ala Ala Val Ala Glu Ala Ala
    320                 325                 330 gaa acc gaa agt aag ata gtc atc cag ccg gtg gag aag gac agc aag             14917
Glu Thr Glu Ser Lys Ile Val Ile Gln Pro Val Glu Lys Asp Ser Lys
                335                 340                 345 gac agg agc tac aac gtg ctc gcg gac aag aaa aac acc gcc tac cgc             14965
Asp Arg Ser Tyr Asn Val Leu Ala Asp Lys Lys Asn Thr Ala Tyr Arg
350                 355                 360 agc tgg tac ctg gcc tac aac tac ggc gac ccc gag aag ggc gtg cgc             15013
Ser Trp Tyr Leu Ala Tyr Asn Tyr Gly Asp Pro Glu Lys Gly Val Arg
365                 370                 375                 380 tcc tgg acg ctg ctc acc acc tcg gac gtc acc tgc ggc gtg gag caa             15061
Ser Trp Thr Leu Leu Thr Thr Ser Asp Val Thr Cys Gly Val Glu Gln
                385                 390                 395 gtc tac tgg tcg ctg ccc gac atg atg caa gac ccg gtc acc ttc cgc             15109
Val Tyr Trp Ser Leu Pro Asp Met Met Gln Asp Pro Val Thr Phe Arg
    400                 405                 410 tcc acg cgt caa gtt agc aac tac ccg gtg gtg ggc gcc gag ctc ctg             15157
Ser Thr Arg Gln Val Ser Asn Tyr Pro Val Val Gly Ala Glu Leu Leu
                415                 420                 425 ccc gtc tac tcc aag agc ttc ttc aac gag cag gcc gtc tac tcg cag             15205
Pro Val Tyr Ser Lys Ser Phe Phe Asn Glu Gln Ala Val Tyr Ser Gln
430                 435                 440 cag ctg cgc gcc ttc acc tcg ctc acg cac gtc ttc aac cgc ttc ccc             15253
Gln Leu Arg Ala Phe Thr Ser Leu Thr His Val Phe Asn Arg Phe Pro
445                 450                 455                 460 gag aac cag atc ctc gtc cgc ccg ccc gcg ccc acc att acc acc gtc             15301
Glu Asn Gln Ile Leu Val Arg Pro Pro Ala Pro Thr Ile Thr Thr Val
                465                 470                 475 agt gaa aac gtt cct gct ctc aca gat cac ggg acc ctg ccg ctg cgc             15349
Ser Glu Asn Val Pro Ala Leu Thr Asp His Gly Thr Leu Pro Leu Arg
    480                 485                 490 agc agt atc cgg gga gtc cag cgc gtg acc gtc act gac gcc aga cgc             15397
Ser Ser Ile Arg Gly Val Gln Arg Val Thr Val Thr Asp Ala Arg Arg
                495                 500                 505
```

| | |
|---|---|
| cgc acc tgc ccc tac gtc tac aag gcc ctg ggc gta gtc gcg ccg cgc<br>Arg Thr Cys Pro Tyr Val Tyr Lys Ala Leu Gly Val Val Ala Pro Arg<br>510    515    520 | 15445 |
| gtc ctc tcg agc cgc acc ttc taa aaaatgtcca ttctcatctc gcccagtaat<br>Val Leu Ser Ser Arg Thr Phe<br>525    530 | 15499 |
| aacaccggtt ggggcctgcg cgcgcccagc aagatgtacg gaggcgctcg ccaacgctcc | 15559 |
| acgcaacacc ccgtgcgcgt gcgcgggcac ttccgcgctc cctggggcgc cctcaagggc | 15619 |
| cgcgtgcgct cgcgcaccac cgtcgacgac gtgatcgacc aggtggtggc cgacgcgcgc | 15679 |
| aactacacgc ccgccgccgc gcccgcctcc accgtggacg ccgtcatcga cagcgtggtg | 15739 |
| gccgatgcgc gccggtacgc ccgcgccaag agccggcggc ggcgcatcgc ccggcggcac | 15799 |
| cggagcaccc ccgccatgcg cgcggcgcga gccttgctgc gcagggccag cgcacgggga | 15859 |
| cgcagggcca tgctcagggc ggccagacgc gcggcctccg gcagcagcag cgccggcagg | 15919 |
| acccgcagac gcgcggccac ggcggcggcg gcggccatcg ccagcatgtc ccgcccgcgg | 15979 |
| cgcggcaacg tgtactgggt gcgcgacgcc gccaccggtg tgcgcgtgcc cgtgcgcacc | 16039 |
| cgccccctc gcacttgaag atgctgactt cgcgatgttg atgtgtccca gcggcgagga | 16099 |
| ggatgtccaa gcgcaaatac aaggaagaga tgctccaggt catcgcgcct gagatctacg | 16159 |
| gccccgcggt gaaggaggaa agaaagcccc gcaaactgaa gcgggtcaaa aaggacaaaa | 16219 |
| aggaggagga agatgtggac ggactggtgg agtttgtgcg cgagttcgcc ccccggcggc | 16279 |
| gcgtgcagtg gcgcgggcgg aaagtgaaac cggtgctgcg gcccggcacc acggtggtct | 16339 |
| tcacgcccgg cgagcgttcc ggctccgcct ccaagcgctc ctacgacgag gtgtacgggg | 16399 |
| acgaggacat cctcgagcag gcggtcgagc gtctgggcga gtttgcttac ggcaagcgca | 16459 |
| gccgccccgc gcccttgaaa gaggaggcgg tgtccatccc gctggaccac ggcaacccca | 16519 |
| cgccgagcct gaagccggtg accctgcagc aggtgctgcc gagcgcggcg ccgcgccggg | 16579 |
| gcttcaagcg cgagggcggc gaggatctgt acccgaccat gcagctgatg gtgcccaagc | 16639 |
| gccagaagct ggaggacgtg ctggagcaca tgaaggtgga ccccgaggtg cagcccgagg | 16699 |
| tcaaggtgcg gccatcaag caggtggccc cgggcctggg cgtgcagacc gtggacatca | 16759 |
| agatccccac ggagcccatg gaaacgcaga ccgagcccgt gaagcccagc accagcacca | 16819 |
| tggaggtgca gacggatccc tggatgccgg cgccggcttc caccactcgc cgaagacgcg | 16879 |
| agtacggcgc ggccagcctg ctgatgccca actacgcgct gcatccttcc atcatcccca | 16939 |
| cgccgggcta ccgcggcacg cgcttctacc gcggctacac cagcagccgc cgcaagacca | 16999 |
| ccacccgccg ccgccgtcgt cgcacccgcc gcagcagcac cgcgacttcc gccgccgccc | 17059 |
| tggtgcggag agtgtaccgc agcgggcgcg agcctctgac cctgccgcgc gcgcgctacc | 17119 |
| acccgagcat cgccatttaa ctctgccgtc gcctcctact gcagatatg gccctcacat | 17179 |
| gccgcctccg cgtccccatt acgggctacc gaggaagaaa gccgcgccgt agaaggctga | 17239 |
| cggggaacgg gctgcgtcgc catcaccacc ggcggcggcg cgccatcagc aagcggttgg | 17299 |
| ggggaggctt cctgcccgcg ctgatcccca tcatcgccgc ggcgatcggg gcgatccccg | 17359 |
| gcatagcttc cgtggcggtg caggcctctc agcgccactg agacacagct tggaaaattt | 17419 |
| gtaataaaaa aatggactga cgctcctggt cctgtgatgt gtgttttag atggaagaca | 17479 |
| tcaattttc gtccctggca ccgcgacacg gcacgcggcc gtttatgggc acctggagcg | 17539 |
| acatcggcaa cagccaactg aacggggcg ccttcaattg gagcagtctc tggagcgggc | 17599 |
| ttaagaattt cgggtccacg ctcaaaacct atggcaacaa ggcgtggaac agcagcacag | 17659 |

-continued

```
ggcaggcgct gagggaaaag ctgaaagagc agaacttcca gcagaaggtg gtcgatggcc    17719
tggcctcggg catcaacggg gtggtggacc tggccaacca ggccgtgcag aaacagatca    17779
acagccgcct ggacgcggtc ccgcccgcgg ggtccgtgga gatgccccag gtggaggagg    17839
agctgcctcc cctggacaag cgcggcgaca agcgaccgcg tcccgacgcg gaggagacgc    17899
tgctgacgca cacggacgag ccgcccccgt acgaggaggc ggtgaaactg ggtctgccca    17959
ccacgcggcc cgtggcgcct ctggccaccg gggtgctgaa acccagcagc agcagccagc    18019
ccgcgaccct ggacttgcct ccgcctgctt cccgcccctc cacagtggct aagcccctgc    18079
cgccggtggc cgtcgcgtcg cgcgcccccc gaggccgccc ccaggcgaac tggcagagca    18139
ctctgaacag catcgtgggt ctgggagtgc agagtgtgaa gcgccgccgc tgctattaaa    18199
agacactgta gcgcttaact tgcttgtctg tgtgtatatg tatgtccgcc gaccagaagg    18259
aggaagaggc gcgtcgccga gttgcaag atg gcc acc cca tcg atg ctg ccc      18311
                                Met Ala Thr Pro Ser Met Leu Pro
                                                535 cag tgg gcg tac atg cac atc gcc gga cag gac gct tcg gag tac ctg    18359
Gln Trp Ala Tyr Met His Ile Ala Gly Gln Asp Ala Ser Glu Tyr Leu
540                 545                 550                 555 agt ccg ggt ctg gtg cag ttc gcc cgc gcc aca gac acc tac ttc agt    18407
Ser Pro Gly Leu Val Gln Phe Ala Arg Ala Thr Asp Thr Tyr Phe Ser
                560                 565                 570 ctg ggg aac aag ttt agg aac ccc acg gtg gcg ccc acg cac gat gtg    18455
Leu Gly Asn Lys Phe Arg Asn Pro Thr Val Ala Pro Thr His Asp Val
            575                 580                 585 acc acc gac cgc agc cag cgg ctg acg ctg cgc ttc gtg ccc gtg gac    18503
Thr Thr Asp Arg Ser Gln Arg Leu Thr Leu Arg Phe Val Pro Val Asp
        590                 595                 600 cgc gag gac aac acc tac tcg tac aaa gtg cgc tac acg ctg gcc gtg    18551
Arg Glu Asp Asn Thr Tyr Ser Tyr Lys Val Arg Tyr Thr Leu Ala Val
    605                 610                 615 ggc gac aac cgc gtg ctg gac atg gcc agc acc tac ttt gac atc cgc    18599
Gly Asp Asn Arg Val Leu Asp Met Ala Ser Thr Tyr Phe Asp Ile Arg
620                 625                 630                 635 ggc gtg ctg gat cgg ggg ccc agc ttc aaa ccc tac tcc ggc acc gcc    18647
Gly Val Leu Asp Arg Gly Pro Ser Phe Lys Pro Tyr Ser Gly Thr Ala
                640                 645                 650 tac aac agc ctg gct ccc aag gga gcg ccc aac act tgc cag tgg aca    18695
Tyr Asn Ser Leu Ala Pro Lys Gly Ala Pro Asn Thr Cys Gln Trp Thr
            655                 660                 665 tat aaa gct ggt gat act gat aca gaa aaa acc tat aca tat gga aat    18743
Tyr Lys Ala Gly Asp Thr Asp Thr Glu Lys Thr Tyr Thr Tyr Gly Asn
        670                 675                 680 gca cct gtg caa ggc att agc att aca aag gat ggt att caa ctt gga    18791
Ala Pro Val Gln Gly Ile Ser Ile Thr Lys Asp Gly Ile Gln Leu Gly
    685                 690                 695 act gac agc gat ggt cag gca atc tat gca gac gaa act tat caa cca    18839
Thr Asp Ser Asp Gly Gln Ala Ile Tyr Ala Asp Glu Thr Tyr Gln Pro
700                 705                 710                 715 gag cct caa gtg ggt gat gct gaa tgg cat gac atc act ggt act gat    18887
Glu Pro Gln Val Gly Asp Ala Glu Trp His Asp Ile Thr Gly Thr Asp
                720                 725                 730 gaa aaa tat gga ggc aga gct ctt aag cct gac acc aaa atg aag cct    18935
Glu Lys Tyr Gly Gly Arg Ala Leu Lys Pro Asp Thr Lys Met Lys Pro
            735                 740                 745 tgc tat ggt tct ttt gcc aag cct acc aat aaa gaa gga ggc cag gca    18983
Cys Tyr Gly Ser Phe Ala Lys Pro Thr Asn Lys Glu Gly Gly Gln Ala
```

-continued

```
             750                      755                      760
aat gtg aaa acc gaa aca ggc ggt acc aaa gaa tat gac att gac atg        19031
Asn Val Lys Thr Glu Thr Gly Gly Thr Lys Glu Tyr Asp Ile Asp Met
765                     770                     775 gca ttc ttc gat aat cga agt gca gct gcc gcc gga cta gcc cca gaa        19079
Ala Phe Phe Asp Asn Arg Ser Ala Ala Ala Ala Gly Leu Ala Pro Glu
        780                     785                     790                     795 att gtt ttg tat act gag aat gtg gat ctg gaa act cca gat acc cat        19127
Ile Val Leu Tyr Thr Glu Asn Val Asp Leu Glu Thr Pro Asp Thr His
                        800                     805                     810 att gta tac aag gca ggt aca gat gac agt agc tct tct atc aat ttg        19175
Ile Val Tyr Lys Ala Gly Thr Asp Asp Ser Ser Ser Ser Ile Asn Leu
                815                     820                     825 ggt cag cag tcc atg ccc aac aga ccc aac tac att ggc ttc aga gac        19223
Gly Gln Gln Ser Met Pro Asn Arg Pro Asn Tyr Ile Gly Phe Arg Asp
830                     835                     840 aac ttt atc ggt ctg atg tac tac aac agc act ggc aat atg ggt gta        19271
Asn Phe Ile Gly Leu Met Tyr Tyr Asn Ser Thr Gly Asn Met Gly Val
        845                     850                     855 ctg gct gga cag gcc tcc cag ctg aat gct gtg gtg gac ttg cag gac        19319
Leu Ala Gly Gln Ala Ser Gln Leu Asn Ala Val Val Asp Leu Gln Asp
860                     865                     870                     875 aga aac acc gaa ctg tcc tac cag ctc ttg ctt gac tct ctg ggt gac        19367
Arg Asn Thr Glu Leu Ser Tyr Gln Leu Leu Leu Asp Ser Leu Gly Asp
                        880                     885                     890 aga acc agg tat ttc agt atg tgg aat cag gcg gtg gac agt tat gac        19415
Arg Thr Arg Tyr Phe Ser Met Trp Asn Gln Ala Val Asp Ser Tyr Asp
                895                     900                     905 ccc gat gtg cgc att att gaa aat cac ggt gtg gag gat gaa ctt cct        19463
Pro Asp Val Arg Ile Ile Glu Asn His Gly Val Glu Asp Glu Leu Pro
910                     915                     920 aac tat tgc ttc ccc ctg gat gct gtg ggt aga act gat act tac cag        19511
Asn Tyr Cys Phe Pro Leu Asp Ala Val Gly Arg Thr Asp Thr Tyr Gln
        925                     930                     935 gga att aag gcc aat ggt gat aat caa acc acc tgg acc aaa gat gat        19559
Gly Ile Lys Ala Asn Gly Asp Asn Gln Thr Thr Trp Thr Lys Asp Asp
940                     945                     950                     955 act gtt aat gat gct aat gaa ttg ggc aag ggc aat cct ttc gcc atg        19607
Thr Val Asn Asp Ala Asn Glu Leu Gly Lys Gly Asn Pro Phe Ala Met
                        960                     965                     970 gag atc aac atc cag gcc aac ctg tgg cgg aac ttc ctc tac gcg aac        19655
Glu Ile Asn Ile Gln Ala Asn Leu Trp Arg Asn Phe Leu Tyr Ala Asn
                975                     980                     985 gtg gcg ctg tac ctg ccc gac tcc tac aag tac acg ccg  gcc aac atc      19703
Val Ala Leu Tyr Leu Pro Asp Ser Tyr Lys Tyr Thr Pro  Ala Asn Ile
                        990                     995                     1000 acg ctg  ccc acc aac acc aac  acc tac gat tac atg  aac ggc cgc         19748
Thr Leu Pro Thr Asn Thr Asn  Thr Tyr Asp Tyr Met  Asn Gly Arg
    1005                    1010                    1015 gtg gtg gcg ccc tcg ctg gtg  gac gcc tac atc aac  atc ggg gcg          19793
Val Val Ala Pro Ser Leu Val  Asp Ala Tyr Ile Asn  Ile Gly Ala
1020                    1025                    1030 cgc tgg tcg ctg gac ccc atg  gac aac gtc aac ccc  ttc aac cac          19838
Arg Trp Ser Leu Asp Pro Met  Asp Asn Val Asn Pro  Phe Asn His
    1035                    1040                    1045 cac cgc  aac gcg ggc ctg cga  tac cgc tcc atg ctc  ctg ggc aac         19883
His Arg Asn Ala Gly Leu Arg Tyr Arg Ser Met Leu  Leu Gly Asn
    1050                    1055                    1060 ggg cgc tac gtg ccc ttc cac  atc cag gtg ccc caa  aag ttt ttc          19928
```

```
Gly Arg Tyr Val Pro Phe His Ile Gln Val Pro Gln Lys Phe Phe
1065                    1070                1075 gcc atc aag agc ctc ctg ctc ctg ccc ggg tcc tac acc tac gag    19973
Ala Ile Lys Ser Leu Leu Leu Leu Pro Gly Ser Tyr Thr Tyr Glu
    1080                1085                1090 tgg aac ttc cgc aag gac gtc aac atg atc ctg cag agc tcc ctc    20018
Trp Asn Phe Arg Lys Asp Val Asn Met Ile Leu Gln Ser Ser Leu
1095                    1100                1105 ggc aac gac ctg cgc acg gac ggg gcc tcc atc gcc ttc acc agc    20063
Gly Asn Asp Leu Arg Thr Asp Gly Ala Ser Ile Ala Phe Thr Ser
    1110                1115                1120 atc aac ctc tac gcc acc ttc ttc ccc atg gcg cac aac acc gcc    20108
Ile Asn Leu Tyr Ala Thr Phe Phe Pro Met Ala His Asn Thr Ala
1125                    1130                1135 tcc acg ctc gag gcc atg ctg cgc aac gac acc aac gac cag tcc    20153
Ser Thr Leu Glu Ala Met Leu Arg Asn Asp Thr Asn Asp Gln Ser
    1140                1145                1150 ttc aac gac tac ctc tcg gcg gcc aac atg ctc tac ccc atc ccg    20198
Phe Asn Asp Tyr Leu Ser Ala Ala Asn Met Leu Tyr Pro Ile Pro
1155                    1160                1165 gcc aac gcc acc aac gtg ccc atc tcc atc ccc tcg cgc aac tgg    20243
Ala Asn Ala Thr Asn Val Pro Ile Ser Ile Pro Ser Arg Asn Trp
    1170                1175                1180 gcc gcc ttc cgc ggc tgg tcc ttc acg cgc ctc aag acc cgc gag    20288
Ala Ala Phe Arg Gly Trp Ser Phe Thr Arg Leu Lys Thr Arg Glu
1185                    1190                1195 acg ccc tcg ctc ggc tcc ggg ttc gac ccc tac ttc gtc tac tcg    20333
Thr Pro Ser Leu Gly Ser Gly Phe Asp Pro Tyr Phe Val Tyr Ser
    1200                1205                1210 ggc tcc atc ccc tac ctc gac ggc acc ttc tac ctc aac cac acc    20378
Gly Ser Ile Pro Tyr Leu Asp Gly Thr Phe Tyr Leu Asn His Thr
1215                    1220                1225 ttc aag aag gtc tcc atc acc ttc gac tcc tcc gtc agc tgg ccc    20423
Phe Lys Lys Val Ser Ile Thr Phe Asp Ser Ser Val Ser Trp Pro
    1230                1235                1240 ggc aac gac cgc ctc ctg acg ccc aac gag ttc gaa atc aag cgc    20468
Gly Asn Asp Arg Leu Leu Thr Pro Asn Glu Phe Glu Ile Lys Arg
1245                    1250                1255 acc gtc gac gga gag ggg tac aac gtg gcc cag tgc aac atg acc    20513
Thr Val Asp Gly Glu Gly Tyr Asn Val Ala Gln Cys Asn Met Thr
    1260                1265                1270 aag gac tgg ttc ctg gtc cag atg ctg gcc cac tac aac atc ggc    20558
Lys Asp Trp Phe Leu Val Gln Met Leu Ala His Tyr Asn Ile Gly
1275                    1280                1285 tac cag ggc ttc tac gtg ccc gag ggc tac aag gac cgc atg tac    20603
Tyr Gln Gly Phe Tyr Val Pro Glu Gly Tyr Lys Asp Arg Met Tyr
    1290                1295                1300 tcc ttc ttc cgc aac ttc cag ccc atg agc cgc cag gtc gtg gac    20648
Ser Phe Phe Arg Asn Phe Gln Pro Met Ser Arg Gln Val Val Asp
1305                    1310                1315 gag gtc aac tac aag gac tac cag gcc gtc acc ctg gcc tac cag    20693
Glu Val Asn Tyr Lys Asp Tyr Gln Ala Val Thr Leu Ala Tyr Gln
    1320                1325                1330 cac aac aac tcg ggc ttc gtc ggc tac ctc gcg ccc acc atg cgc    20738
His Asn Asn Ser Gly Phe Val Gly Tyr Leu Ala Pro Thr Met Arg
1335                    1340                1345 cag ggc cag ccc tac ccc gcc aac tac ccc tac ccg ctc atc ggc    20783
Gln Gly Gln Pro Tyr Pro Ala Asn Tyr Pro Tyr Pro Leu Ile Gly
    1350                1355                1360
```

| | |
|---|---:|
| aag agc gcc gtc gcc agc gtc acc cag aaa aag ttc ctc tgc gac<br>Lys Ser Ala Val Ala Ser Val Thr Gln Lys Lys Phe Leu Cys Asp<br>1365                  1370                    1375 | 20828 |
| cgg gtc atg tgg cgc atc ccc ttc tcc agc aac ttc atg tcc atg<br>Arg Val Met Trp Arg Ile Pro Phe Ser Ser Asn Phe Met Ser Met<br>1380                    1385                    1390 | 20873 |
| ggc gcg ctc acc gac ctc ggc cag aac atg ctc tac gcc aac tcc<br>Gly Ala Leu Thr Asp Leu Gly Gln Asn Met Leu Tyr Ala Asn Ser<br>1395                  1400                  1405 | 20918 |
| gcc cac gcg cta gac atg aat ttc gaa gtc gac ccc atg gat gag<br>Ala His Ala Leu Asp Met Asn Phe Glu Val Asp Pro Met Asp Glu<br>1410                  1415                  1420 | 20963 |
| tcc acc ctt ctc tat gtt gtc ttc gaa gtc ttc gac gtc gtc cga<br>Ser Thr Leu Leu Tyr Val Val Phe Glu Val Phe Asp Val Val Arg<br>1425                  1430                  1435 | 21008 |
| gtg cac cag ccc cac cgc ggc gtc atc gag gcc gtc tac ctg cgc<br>Val His Gln Pro His Arg Gly Val Ile Glu Ala Val Tyr Leu Arg<br>1440                  1445                  1450 | 21053 |
| acg ccc ttc tcg gcc ggc aac gcc acc acc taa gcctcttgct<br>Thr Pro Phe Ser Ala Gly Asn Ala Thr Thr<br>1455                  1460 | 21096 |
| tcttgcaaga tgacggcctg cgcgggctcc ggcgagcagg agctcagggc catcctccgc | 21156 |
| gacctgggct gcgggccctg cttcctgggc accttcgaca gcgcttccc gggattcatg | 21216 |
| gccccgcaca gctggcctg cgccatcgtc aacacggccg ccgcgagac cggggggcgag | 21276 |
| cactggctgg ccttcgcctg gaacccgcgc tcccacacct gctacctctt cgacccctcc | 21336 |
| gggttctcgg acgagcgcct caagcagatc taccagttcg agtacgaggg cctgctgcgt | 21396 |
| cgcagcgccc tggccaccga ggaccgctgc gtcaccctgg aaaagtccac ccagaccgtg | 21456 |
| cagggtccgc gctcggccgc ctgcgggctc ttctgctgca tgttcctgca cgccttcgtg | 21516 |
| cactggcccg accgcccat ggacaagaac cccaccatga acttgctgac gggggtgccc | 21576 |
| aacggcatgt ccagtcgcc ccaggtggaa cccaccctgc gccgcaacca ggaggcgctc | 21636 |
| taccgcttcc tcaacgccca ctccgcctac tttcgctccc accgcgcgcg catcgagaag | 21696 |
| gccaccgcct tcgaccgcat gaatcaagac atgtaatccg gtgtgtgtat gtgaatgctt | 21756 |
| tattcatcat aataaacagc acatgtttat gccaccttct ctgaggctct gactttattt | 21816 |
| agaaatcgaa ggggttctgc cggctctcgg catggcccgc gggcagggat acgttgcgga | 21876 |
| actggtactt gggcagccac ttgaactcgg ggatcagcag cttcggcacg gggaggtcgg | 21936 |
| ggaacgagtc gctccacagc ttgcgcgtga gttcagggc gcccagcagg tcggcgcgcg | 21996 |
| agatcttgaa atcgcagttg ggacccgcgt tctgcgcgcg agagttacgg tacacggggt | 22056 |
| tgcagcactg gaacaccatc agggccgggt gcttcacgct cgccagcacc gtcgcgtcgg | 22116 |
| tgatgccctc cacgtccaga tcctcggcgt tggccatccc gaagggggtc atcttgcagg | 22176 |
| tctgccgccc catgctgggc acgcagccgg gcttgtggtt gcaatcgcag tgcaggggga | 22236 |
| tcagcatcat ctgggcctgc tcggagctca tgcccgggta catggccttc atgaaagcct | 22296 |
| ccagctggcg gaaggcctgc tgcgccttgc cgccctcggt gaagaagacc ccgcaggact | 22356 |
| tgctagagaa ctggttggtg gcgcagccag cgtcgtgcac gcagcagcgc gcgtcgttgt | 22416 |
| tggccagctg caccacgctg cgcccccagc ggttctgggt gatcttggcc cggtcggggt | 22476 |
| tctccttcag cgcgcgctgc ccgttctcgc tcgccacatc catctcgatc gtgtgctcct | 22536 |
| tctggatcat cacggtcccg tgcaggcacc gcagcttgcc ctcggcctcg gtgcaccgt | 22596 |
| gcagccacag cgcgcagccg gtgctctccc agttcttgtg ggcgatctgg gagtgcgagt | 22656 |

```
gcacgaagcc ctgcaggaag cggcccatca tcgtggtcag ggtcttgttg ctggtgaagg   22716
tcagcggaat gccgcggtgc tcctcgttca catacaggtg gcagatacgg cggtacacct   22776
cgccctgctc gggcatcagc tggaaggcgg acttcaggtc gctctccacg cggtaccggt   22836
ccatcagcag cgtcatcact tccatgccct tctcccaggc cgaaacgatc ggcaggctca   22896
gggggttctt caccgttgtc atcttagtcg ccgccgccga agtcagggggg tcgttctcgt   22956 ccagggtctc aaacactcgc ttgccgtcct tctcggtgat gcgcacgggg ggaaagctga   23016
agcccacggc cgccagctcc tcctcggcct gcctttcgtc ctcgctgtcc tggctgatgt   23076
cttgcaaagg cacatgcttg gtcttgcggg gttttctttt gggcggcaga ggcggcggcg   23136
gagacgtgct gggcgagcgc gagttctcgc tcaccacgac tatttcttct ccttggccgt   23196
cgtccgagac cacgcggcgg taggcatgcc tcttctgggg cagaggcgga ggcgacgggc   23256
tctcgcggtt cggcgggcgg ctggcagagc cccttccgcg ttcgggggtg cgctcctggc   23316
ggcgctgctc tgactgactt cctccgcggc cggccattgt gttctcctag ggagcaagca   23376
tggagactca gccatcgtcg ccaacatcgc catctgcccc cgccgccgcc gacgagaacc   23436
agcagcagca gaatgaaagc ttaaccgccc cgccgcccag ccccacctcc gacgccgcag   23496
ccccagacat gcaagagatg gaggaatcca tcgagattga cctgggctac gtgacgcccg   23556
cggagcacga ggaggagctg gcagcgcgct tttcagcccc ggaagagaac caccaagagc   23616
agccagagca ggaagcagag agcgagcaga accaggctgg gctcgagcat ggcgactacc   23676
tgagcggggc agaggacgtg ctcatcaagc atctggcccg ccaatgcatc atcgtcaagg   23736
acgcgctgct cgaccgcgcc gaggtgcccc tcagcgtggg ggagctcagc cgcgcctacg   23796
agcgcaacct cttctcgccg cgcgtgcccc caagcgcca gcccaacggc acctgcgagc   23856
ccaacccgcg cctcaacttc taccgggtct tcgcggtgcc cgaggccctg gccacctacc   23916
acctcttttt caagaaccaa aggatccccg tctcctgccg cgccaacgc acccgcgccg   23976 acgccctgct caacctgggc cccggcgccc gcctacctga tatcgcctcc ttggaagagg   24036
ttcccaagat cttcgagggt ctgggcagcg acgagactcg ggccgcgaac gctctgcaag   24096
gaagcggaga ggagcatgag caccacagcg ccctggtgga gttggaaggc gacaacgcgc   24156
gcctggcggt cctcaagcgc acggtcgagc tgacccactt cgcctacccg gcgctcaacc   24216 tgcccccaa ggtcatgagc gccgtcatgg accaggtgct catcaagcgc gcctcgcccc   24276
tctcggagga ggagatgcag gaccccgaga gctcggacga gggcaagccc gtggtcagcg   24336
acgagcagct ggcgcgctgg ctgggagcga gtagcacccc ccagagcctg gaagagcggc   24396
gcaagctcat gatggccgtg gtcctggtga ccgtggagct ggagtgtctg cgccgcttct   24456
tcgccgacgc ggagaccctg cgcaaggtcg aggagaacct gcactacctc ttcagacacg   24516
ggttcgtgcg ccaggcctgc aagatctcca acgtggagct gaccaacctg gtctcctaca   24576
tgggcatcct gcacgagaac cgcctggggc agaacgtgct gcacaccacc ctgcgcgggg   24636
aggcccgccg cgactacatc cgcgactgcg tctacctgta cctctgccac acctggcaga   24696
cgggcatggg cgtgtggcag cagtgcctgg aggagcagaa cctgaaagag ctctgcaagc   24756
tcctgcagaa gaacctcaag gccctgtgga ccgggttcga cgagcgcacc accgccgcgg   24816
acctggccga cctcatcttc cccgagcgcc tgcggctgac gctgcgcaac gggctgcccg   24876
actttatgag ccaaagcatg ttgcaaaact ttcgctcttt catcctcgaa cgctccggga   24936 tcctgccgc cacctgctcc gcgctgccct cggacttcgt gccgctgacc ttccgcgagt   24996
```

```
gcccccccgcc gctctggagc cactgctacc tgctgcgcct ggccaactac ctggcctacc   25056
actcggacgt gatcgaggac gtcagcggcg agggcctgct cgagtgccac tgccgctgca   25116
acctctgcac gccgcaccgc tccctggcct gcaaccccca gctgctgagc gagacccaga   25176
tcatcggcac cttcgagttg caaggccccg gcgagggcaa gggggggtctg aaactcaccc   25236
cggggctgtg gacctcggcc tacttgcgca agttcgtgcc cgaggactac catcccttcg   25296
agatcaggtt ctacgaggac caatcccagc cgcccaaggc cgagctgtcg gcctgcgtca   25356
tcacccaggg ggccatcctg gcccaattgc aagccatcca gaaatcccgc caagaatttc   25416
tgctgaaaaa gggccacggg gtctacttgg accccccagac cggagaggag ctcaacccca   25476
gcttccccca ggatgccccg aggaagcagc aagaagctga aagtggagct gccgccgccg   25536
ccggaggatt tggaggaaga ctgggagagc agtcaggcag aggaggagga gatggaagac   25596
tgggacagca ctcaggcaga ggaggacagc ctgcaagaca gtctggagga ggaagacgag   25656
gtggaggagg cagaggaaga agcagccgcc gccagaccgt cgtcctcggc ggaggaggag   25716
aaagcaagca gcacggatac catctccgct ccgggtcggg gtcgcggcgg ccgggcccac   25776
agtagatggg acgagaccgg gcgcttcccg aaccccacca cccagaccgg taagaaggag   25836
cggcagggat acaagtcctg gcgggggcac aaaaacgcca tcgtctcctg cttgcaagcc   25896
tgcgggggca acatctcctt cacccggcgc tacctgctct ccaccgcgg ggtgaacttc   25956
ccccgcaaca tcttgcatta ctaccgtcac ctccacagcc cctactactg tttccaagaa   26016
gaggcagaaa cccagcagca gcagcagcag cagaaaacca gcggcagcag ctagaaaatc   26076
cacagcggcg gcaggtggac tgaggatcgc ggcgaacgag ccggcgcaga cccgggagct   26136
gaggaaccgg atctttccca ccctctatgc catcttccag cagagtcggg ggcaagagca   26196
ggaactgaaa gtcaagaacc gttctctgcg ctcgctcacc cgcagttgtc tgtatcacaa   26256
gagcgaagac caacttcagc gcactctcga ggacgccgag gctctcttca caagtactg   26316
cgcgctcact cttaaagagt agcccgcgcc cgcccacaca cggaaaaagg cgggaattac   26376
gtcaccacct gcgcccttcg cccgaccatc atcatgagca aagagattcc cacgccttac   26436
atgtggagct accagcccca gatgggcctg gccgccggcg ccgcccagga ctactccacc   26496
cgcatgaact ggctcagtgc cgggcccgcg atgatctcac gggtgaatga catccgcgcc   26556
caccgaaacc agatactcct agaacagtca gcgatcaccg ccacgccccg ccatcacctt   26616
aatccgcgta attggcccgc cgccctggtg taccaggaaa ttccccagcc cacgaccgta   26676
ctacttccgc gagacgccca ggccgaagtc cagctgacta actcaggtgt ccagctggcc   26736
ggcggcgccg ccctgtgtcg tcaccgcccc gctcagggta taaagcggct ggtgatccga   26796
ggcagaggca cacagctcaa cgacgaggtg gtgagctctt cgctgggtct gcgacctgac   26856
ggagtcttcc aactcgccgg atcggggaga tcttccttca cgcctcgtca ggccgtcctg   26916
actttggaga gttcgtcctc gcagcccgc tcggtggca tcggcactct ccagttcgtg   26976
gaggagttca ctccctcggt ctacttcaac cccttctccg gctcccccgg ccactacccg   27036
gacgagttca tccccgaactt cgacgccatc agcgagtcgg tggacggcta cgattgaatg   27096
tcccatggtg gcgcggctga cctagctcgg cttcgacacc tggaccactg ccgccgcttc   27156
cgctgcttcg ctcgggatct cgccgagttt gcctactttg agctgccga ggagcaccct   27216
cagggcccgg cccacggagt gcggatcgtc gtcgaagggg gtctcgactc ccacctgctt   27276
cggatcttca gccagcgtcc gatcctggcc gagcgcgagc aaggacagac ccttctgacc   27336
ctgtactgca tctgcaacca ccccggcctg catgaaagtc tttgttgtct gctgtgtact   27396
```

```
gagtataata aaagctgaga tcagcgacta ctccggactt ccgtgtgttc ctgctatcaa   27456
ccagtccctg ttcttcaccg ggaacgagac cgagctccag ctccagtgta agccccacaa   27516
gaagtacctc acctggctgt tccagggctc tccgatcgcc gttgtcaacc actgcgacaa   27576
cgacggagtc ctgctgagcg gccctgccaa ccttactttt tccacccgca gaagcaagct   27636
ccagctcttc caaccttcc tccccgggac ctatcagtgc gtctcgggac cctgccatca   27696
caccttccac ctgatcccga ataccacagc gtcgctcccc gctactaaca accaaactac   27756
ccaccaacgc caccgtcgcg acctttcctc tgggtctaat accactaccg gaggtgagct   27816
ccgaggtcga ccaacctctg ggatttacta cggcccctgg gaggtggtag ggttaatagc   27876
gctaggccta gttgcgggtg ggcttttggc tctctgctac ctataccctcc cttgctgttc   27936 gtacttagtg gtgctgtgtt gctggtttaa gaaatgggga agatcaccct agtgagctgc   27996
ggtgtgctgg tggcggtggt gctttcgatt gtgggactgg gcggcgcggc tgtagtgaag   28056
gagaaggccg atccctgctt gcatttcaat cccgacaaat gccagctgag ttttcagccc   28116
gatggcaatc ggtgcgcggt gctgatcaag tgcggatggg aatgcgagaa cgtgagaatc   28176
gagtacaata acaagactcg gaacaatact ctcgcgtccg tgtggcagcc cggggacccc   28236
gagtggtaca ccgtctctgt ccccggtgct gacggctccc cgcgcaccgt gaataatact   28296 ttcattttg cgcacatgtg cgacacggtc atgtggatga gcaagcagta cgatatgtgg   28356 cccccacga aggagaacat cgtggtcttc tccatcgctt acagcgtgtg cacggcgcta   28416
atcaccgcta tcgtgtgcct gagcattcac atgctcatcg ctattcgccc cagaaataat   28476
gccgaaaaag aaaacagcc ataacacgtt ttttcacaca ccttttcag accatggcct   28536 ctgttaaatt tttgctttta tttgccagtc tcattgccgt cattcatgga atgagtaatg   28596
agaaaattac tatttacact ggcactaatc acacattgaa aggtccagaa aaagccacag   28656
aagtttcatg gtattgttat tttaatgaat cagatgtatc tactgaactc tgtggaaaca   28716
ataacaaaaa aaatgagagc attactctca tcaagtttca atgtggatct gacttaaccc   28776
taattaacat cactagagac tatgtaggta tgtattatgg aactacagca ggcatttcgg   28836
acatggaatt ttatcaagtt tctgtgtctg aacccaccac gcctagaatg accacaacca   28896
caaaaactac acctgttacc actatacagc tcactaccaa tggctttctt gccatgcttc   28956
aagtggctga aaatagcacc agcattcaac ccacccccacc cagtgaggaa attcccagat   29016
ccatgattgg cattattgtt gctgtagtgg tgtgcatgtt gatcatcgcc ttgtgcatgg   29076
tgtactatgc cttctgctac agaaagcaca gactgaacga caagctggaa cacttactaa   29136
gtgttgaatt ttaatttttt agaaccatga agatcctagg cctttttagtt ttttctatca   29196 ttacctctgc tctatgcaat tctgacaatg aggacgttac tgtcgttgtc ggatcaaatt   29256
atacactaaa aggtccagca aaaggtatgc tttcgtggta ttgttggttc ggaactgacg   29316
agcaacagac agaactttgc aatgctcaaa aaggcaaaac ctcaaattct aaaatctcta   29376
attatcaatg caatggcact gacttagtat tgctcaatgt cacgaaagca tatgctggca   29436
gttacacctg ccctggagat gatgccgaca atatgatttt ttacaaagtg gaagtggttg   29496 atccccactac tccaccgccc accaccacaa ctactcatac cacacacaca gaacaaaac   29556 cagaggcagc agaagcagag ttggccttcc aggttcacgg agattccttt gctgtcaata   29616
cccctacacc cgatcagcgg tgtccgggc tgctccgtcag cggcattgtc ggtgtgcttt   29676
cgggattagc agtcataatc atctgcatgt tcattttgc ttgctgctat agaaggcttt   29736
```

```
accgacaaaa atcagaccca ctgctgaacc tctatgttta attttttcca gagccatgaa   29796
ggcagttagc gctctagttt tttgttcttt gattggcatt gtttttagtg ctgggttttt   29856
gaaaaatctt accatttatg aaggtgagaa tgccactcta gtgggcatca gtggtcaaaa   29916
tgtcagctgg ctaaaatacc atctagatgg gtggaaagac atttgcgatt ggaatgtcac   29976
tgtgtataca tgtaatggag ttaacctcac cattactaat gccacccaag atcagaatgg   30036
taggtttaag ggccagagtt tcactagaaa taatgggtat gaatcccata acatgtttat   30096
ctatgacgtc actgtcatca gaaatgagac tgccaccacc acacagatgc ccactacaca   30156
cagttctacc actactacca tgcaaaccac acagacaacc actacatcaa ctcagcatat   30216
gaccaccact acagcagcaa agccaagtag tgcagcgcct cagccccagg ctttggcttt   30276
gaaagctgca caacctagta caactactag gaccaatgag cagactactg aattttttgtc   30336
cactgtcgag agccacacca cagctacctc cagtgccttc tctagcaccg ccaatctctc   30396
ctcgctttcc tctacaccaa tcagtcccgc tactactccc accccagctc ttctccccac   30456
tccccctgaag caaactgagg acagcggcat gcaatggcag atcaccctgc tcattgtgat   30516
cgggttggtc atcctggccg tgttgctcta ctacatcttc tgccgccgca ttcccaacgc   30576
gcaccgcaaa ccggcctaca agcccatcgt tatcgggcag ccggagccgc ttcaggtgga   30636
agggggtcta aggaatcttc tcttctcttt tacagtatgg tgattgaact atgattccta   30696
gacaattctt gatcactatt cttatctgcc tcctccaagt ctgtgccacc ctcgctctgg   30756
tggccaacgc cagtccagac tgtattgggc ccttcgcctc ctacgtgctc tttgccttca   30816
tcacctgcat ctgctgctgt agcatagtct gcctgcttat caccttcttc cagttcattg   30876
actggatctt tgtgcgcatc gcctacctgc gccaccaccc ccagtaccgc gaccagcgag   30936
tggcgcggct gctcaggctc ctctgataag catgcgggct ctgctacttc tcgcgcttct   30996
gctgttagtg ctcccccgcc ccgtcgaccc ccggtccccc actcagtccc ccgaagaggt   31056
ccgcaaatgc aaattccaag aaccctggaa attcctcaaa tgctaccgcc aaaaatcaga   31116
catgcttccc agctggatca tgatcattgg gatcgtgaac attctggcct gcaccctcat   31176
ctcctttgtg atttaccccct gctttgactt tggttggaac tcgccagagg cgctctatct   31236
cccgcctgaa cctgacacac caccacagca acctcaggca cacgcactac caccaccaca   31296
gcctaggcca caatacatgc ccatattaga ctatgaggcc gagccacagc gacccatgct   31356
ccccgctatt agttacttca atctaaccgg cggagatgac tgacccactg ccaacaaca   31416
acgtcaacga ccttctcctg gacatggacg gccgcgcctc ggagcagcga ctcgcccaac   31476
ttcgcattcg ccagcagcag gagagagccg tcaaggagct gcaggacggc atagccatcc   31536
accagtgcaa gaaaggcatc ttctgcctgg tgaaacaggc caagatctcc tacgaggtca   31596
ccccgaccga ccatcgcctc tcctacgagc tcctgcagca gcgccagaag ttcacctgcc   31656
tggtcggagt caaccccatc gtcatcaccc agcagtcggg cgataccaag gggtgcatcc   31716
actgctcctg cgactccccc gactgcgtcc acactctgat caagaccctc tgcggcctcc   31776
gcgacctcct ccccatgaac taatcacccc cttatccagt gaaataaata tcatattgat   31836
gatgatttaa ataaaaaata atcatttgat ttgaaataaa gatacaatca tattgatgat   31896
ttgagtttta aaaaataaag aatcacttac ttgaaatctg ataccaggtc tctgtccatg   31956
ttttctgcca acaccacctc actcccctct tcccagctct ggtactgcag acccggcgg   32016
gctgcaaact tcctccacac gctgaagggg atgtcaaatt cctcctgtcc ctcaatcttc   32076
attttatctt ctatcag atg tcc  aaa aag cgc gtc cgg  gtg gat gat gac   32126
```

```
                    Met  Ser  Lys  Lys  Arg  Val  Arg   Val  Asp  Asp  Asp
                         1465                     1470 ttc  gac  ccc  gtc  tac  ccc  tac  gat  gca  gac  aac   gca  ccg  acc  gtg    32171
Phe  Asp  Pro  Val  Tyr  Pro  Tyr  Asp  Ala  Asp  Asn   Ala  Pro  Thr  Val
1475                1480                     1485 ccc  ttc  atc  aac  ccc  ccc  ttc  gtc  tct  tca  gat   gga  ttc  caa  gag    32216
Pro  Phe  Ile  Asn  Pro  Pro  Phe  Val  Ser  Ser  Asp   Gly  Phe  Gln  Glu
1490                1495                     1500 aag  ccc  ctg  ggg  gtg  ctg  tcc  ctg  cga  ctg  gct   gac  ccc  gtc  acc    32261
Lys  Pro  Leu  Gly  Val  Leu  Ser  Leu  Arg  Leu  Ala   Asp  Pro  Val  Thr
1505                1510                     1515 acc  aag  aac  ggg  gaa  atc  acc  ctc  aag  ctg  gga   gag  ggg  gtg  gac    32306
Thr  Lys  Asn  Gly  Glu  Ile  Thr  Leu  Lys  Leu  Gly   Glu  Gly  Val  Asp
1520                1525                     1530 ctc  gac  tcc  tcg  gga  aaa  ctc  atc  tcc  aac  acg   gcc  acc  aag  gcc    32351
Leu  Asp  Ser  Ser  Gly  Lys  Leu  Ile  Ser  Asn  Thr   Ala  Thr  Lys  Ala
1535                1540                     1545 gcc  gcc  cct  ctc  agt  ttt  tcc  aac  aac  acc  att   tcc  ctt  aac  atg    32396
Ala  Ala  Pro  Leu  Ser  Phe  Ser  Asn  Asn  Thr  Ile   Ser  Leu  Asn  Met
1550                1555                     1560 gat  acc  cct  ctt  tat  acc  aaa  gat  gga  aaa  tta   tcc  tta  caa  gtt    32441
Asp  Thr  Pro  Leu  Tyr  Thr  Lys  Asp  Gly  Lys  Leu   Ser  Leu  Gln  Val
1565                1570                     1575 tct  cca  ccg  tta  aac  ata  tta  aaa  tca  acc  att   ctg  aac  aca  tta    32486
Ser  Pro  Pro  Leu  Asn  Ile  Leu  Lys  Ser  Thr  Ile   Leu  Asn  Thr  Leu
1580                1585                     1590 gct  gta  gct  tat  gga  tca  ggt  tta  gga  ctg  agt   ggt  ggc  act  gct    32531
Ala  Val  Ala  Tyr  Gly  Ser  Gly  Leu  Gly  Leu  Ser   Gly  Gly  Thr  Ala
1595                1600                     1605 ctt  gca  gta  cag  ttg  gcc  tct  cca  ctc  act  ttt   gat  gaa  aaa  gga    32576
Leu  Ala  Val  Gln  Leu  Ala  Ser  Pro  Leu  Thr  Phe   Asp  Glu  Lys  Gly
1610                1615                     1620 aat  att  aaa  att  aac  cta  gcc  agt  ggt  cca  tta   aca  gtt  gat  gca    32621
Asn  Ile  Lys  Ile  Asn  Leu  Ala  Ser  Gly  Pro  Leu   Thr  Val  Asp  Ala
1625                1630                     1635 agt  cga  ctt  agt  atc  aac  tgc  aaa  aga  ggg  gtc   act  gtc  act  acc    32666
Ser  Arg  Leu  Ser  Ile  Asn  Cys  Lys  Arg  Gly  Val   Thr  Val  Thr  Thr
1640                1645                     1650 tca  gga  gat  gca  att  gaa  agc  aac  ata  agc  tgg   cct  aaa  ggt  ata    32711
Ser  Gly  Asp  Ala  Ile  Glu  Ser  Asn  Ile  Ser  Trp   Pro  Lys  Gly  Ile
1655                1660                     1665 aga  ttt  gaa  ggt  aat  ggc  ata  gct  gca  aac  att   ggc  aga  gga  ttg    32756
Arg  Phe  Glu  Gly  Asn  Gly  Ile  Ala  Ala  Asn  Ile   Gly  Arg  Gly  Leu
1670                1675                     1680 gaa  ttt  gga  acc  act  agt  aca  gag  act  gat  gtc   aca  gat  gca  tac    32801
Glu  Phe  Gly  Thr  Thr  Ser  Thr  Glu  Thr  Asp  Val   Thr  Asp  Ala  Tyr
1685                1690                     1695 cca  att  caa  gtt  aaa  ttg  ggt  act  ggc  ctt  acc   ttt  gac  agt  aca    32846
Pro  Ile  Gln  Val  Lys  Leu  Gly  Thr  Gly  Leu  Thr   Phe  Asp  Ser  Thr
1700                1705                     1710 ggc  gcc  att  gtt  gct  tgg  aac  aaa  gag  gat  gat   aaa  ctt  aca  tta    32891
Gly  Ala  Ile  Val  Ala  Trp  Asn  Lys  Glu  Asp  Asp   Lys  Leu  Thr  Leu
1715                1720                     1725 tgg  acc  aca  gcc  gac  ccc  tcg  cca  aat  tgc  aaa   ata  tac  tct  gaa    32936
Trp  Thr  Thr  Ala  Asp  Pro  Ser  Pro  Asn  Cys  Lys   Ile  Tyr  Ser  Glu
1730                1735                     1740 aaa  gat  gcc  aaa  ctc  aca  ctt  tgc  ttg  aca  aag   tgt  gga  agt  caa    32981
Lys  Asp  Ala  Lys  Leu  Thr  Leu  Cys  Leu  Thr  Lys   Cys  Gly  Ser  Gln
1745                1750                     1755
```

-continued

| att Ile 1760 | ctg Leu | ggt Gly | act Thr | gtg Val | act Thr 1765 | gta Val | ttg Leu | gca Ala | gtg Val | aat Asn 1770 | aat Asn | gga Gly | agt Ser | ctc Leu | 33026 |

| aac Asn 1775 | cca Pro | atc Ile | aca Thr | aac Asn | aca Thr 1780 | gta Val | agc Ser | act Thr | gca Ala | ctc Leu 1785 | gtc Val | tcc Ser | ctc Leu | aag Lys | 33071 |

| ttt Phe 1790 | gat Asp | gca Ala | agt Ser | gga Gly | gtt Val 1795 | ttg Leu | cta Leu | agc Ser | agc Ser | tcc Ser 1800 | aca Thr | tta Leu | gac Asp | aaa Lys | 33116 |

| gaa Glu 1805 | tat Tyr | tgg Trp | aac Asn | ttc Phe | aga Arg 1810 | aag Lys | gga Gly | gat Asp | gtt Val | aca Thr 1815 | cct Pro | gct Ala | gag Glu | ccc Pro | 33161 |

| tat Tyr 1820 | act Thr | aat Asn | gct Ala | ata Ile | ggt Gly 1825 | ttt Phe | atg Met | cct Pro | aac Asn | ata Ile 1830 | aag Lys | gcc Ala | tat Tyr | cct Pro | 33206 |

| aaa Lys 1835 | aac Asn | aca Thr | tct Ser | gca Ala | gct Ala 1840 | tca Ser | aaa Lys | agc Ser | cat His | att Ile 1845 | gtc Val | agt Ser | caa Gln | gtt Val | 33251 |

| tat Tyr 1850 | ctc Leu | aat Asn | ggg Gly | gat Asp | gag Glu 1855 | gcc Ala | aaa Lys | cca Pro | ctg Leu | atg Met 1860 | ctg Leu | att Ile | att Ile | act Thr | 33296 |

| ttt Phe 1865 | aat Asn | gaa Glu | act Thr | gag Glu | gat Asp 1870 | gca Ala | act Thr | tgc Cys | acc Thr | tac Tyr 1875 | agt Ser | atc Ile | act Thr | ttt Phe | 33341 |

| caa Gln 1880 | tgg Trp | aaa Lys | tgg Trp | gat Asp | agt Ser 1885 | act Thr | aag Lys | tac Tyr | aca Thr | ggt Gly 1890 | gaa Glu | aca Thr | ctt Leu | gct Ala | 33386 |

| acc Thr 1895 | agc Ser | tcc Ser | ttc Phe | acc Thr | ttc Phe 1900 | tcc Ser | tac Tyr | atc Ile | gcc Ala | caa Gln 1905 | gaa Glu | tga | | | 33435 |

| ccaccctgca | tgccaaccct | tcccaccccca | ctctgtctat | ggaaaaaact | ctgaagcaca | 33495 |
| aaataaaata | aagttcaagt | gttttattga | ttcaacagtt | ttacaggatt | cgagcagtta | 33555 |
| ttttcctcc | accctcccag | gacatggaat | acaccaccct | ctccccccgc | acagccttga | 33615 |
| acatctgaat | gccattggtg | atggacatgc | ttttggtctc | cacgttccac | acagtttcag | 33675 |
| agcgagccag | tctcgggtcg | gtcagggaga | tgaaaccctc | cgggcactcc | cgcatctgca | 33735 |
| cctcacagct | caacagctga | ggattgtcct | cggtggtcgg | gatcacggtt | atctggaaga | 33795 |
| agcagaagag | cggcggtggg | aatcatagtc | cgcgaacggg | atcggccggt | ggtgtcgcat | 33855 |
| caggccccgc | agcagtcgct | gccgccgccg | ctccgtcaag | ctgctgctca | ggggtccgg | 33915 |
| gtccagggac | tccctcagca | tgatgcccac | ggccctcagc | atcagtcgtc | tggtgcggcg | 33975 |
| ggcgcagcag | cgcatgcgga | tctcgctcag | gtcgctgcag | tacgtgcaac | acaggaccac | 34035 |
| caggttgttc | aacagtccat | agttcaacac | gctccagccg | aaactcatcg | cgggaaggat | 34095 |
| gctacccacg | tggccgtcgt | accagatcct | caggtaaatc | aagtggcgct | ccctccagaa | 34155 |
| cacgctgccc | acgtacatga | tctccttggg | catgtggcgg | ttcaccacct | cccgqtacca | 34215 |
| catcaccctc | tggttgaaca | tgcagccccg | gatgatcctg | cggaaccaca | gggccagcac | 34275 |
| cgccccgccc | gccatgcagc | gaagagaccc | cgggtcccgg | caatggcaat | ggaggaccca | 34335 |
| ccgctcgtac | ccgtggatca | tctgggagct | gaacaagtct | atgttggcac | agcacaggca | 34395 |
| tatgctcatg | catctcttca | gcactctcag | ctcctcgggg | gtcaaaacca | tatcccaggg | 34455 |
| cacggggaac | tcttgcagga | cagcgaaccc | cgcagaacag | ggcaatcctc | gcacataact | 34515 |
| tacattgtgc | atggacaggg | tatcgcaatc | aggcagcacc | gggtgatcct | ccaccagaga | 34575 |
| agcgcgggtc | tcggtctcct | cacagcgtgg | taagggggcc | ggccgatacg | ggtgatggcg | 34635 |

```
ggacgcggct gatcgtgttc gcgaccgtgt catgatgcag ttgctttcgg acatttcgt    34695
acttgctgta gcagaacctg gtccgggcgc tgcacaccga tcgccggcgg cggtcccggc    34755
gcttggaacg ctcggtgttg aaattgtaaa acagccactc tctcagaccg tgcagcagat    34815
ctagggcctc aggagtgatg aagatcccat catgcctgat agctctgatc acatcgacca    34875
ccgtggaatg ggccagaccc agccagatga tgcaattttg ttgggtttcg gtgacggcgg    34935
gggagggaag aacaggaaga accatgatta acttttaatc aaacggtct cggagcactt    34995
caaaatgaag gtcgcggaga tggcacctct cgccccgct gtgttggtgg aaaataacag    35055
ccaggtcaaa ggtgatacgg ttctcgagat gttccacggt ggcttccagc aaagcctcca    35115
cgcgcacatc cagaaacaag acaatagcga agcgggagg gttctctaat cctcaatca    35175
tcatgttaca ctcctgcacc atccccagat aattttcatt tttccagcct tgaatgattc    35235
gaactagttc ctgaggtaaa tccaagccag ccatgataaa gagctcgcgc agagcgccct    35295
ccaccggcat tcttaagcac accctcataa ttccaagata ttctgctcct ggttcacctg    35355
cagcagattg acaagcggaa tatcaaaatc tctgccgcga tccctaagct cctccctcag    35415
caataactgt aagtactctt tcatatcctc tccgaaattt ttagccatag gaccaccagg    35475
aataagatta gggcaagcca cagtacagat aaaccgaagt cctccccagt gagcattgcc    35535
aaatgcaaga ctgctataag catgctggct agacccggtg atatcttcca gataactgga    35595
cagaaaatca cccaggcaat ttttaagaaa atcaacaaaa gaaaaatcct ccaggtgcac    35655
gtttagagcc tcgggaacaa cgatgaagta aatgcaagcg gtgcgttcca gcatggttag    35715
ttagctgatc tgtaaaaaac aaaaaataaa acattaaacc atgctagcct ggcgaacagg    35775
tgggtaaatc gttctctcca gcaccaggca ggccacgggg tctccggcgc gaccctcgta    35835
aaaattgtcg ctatgattga aaaccatcac agagagacgt tcccggtggc cggcgtgaat    35895
gattcgacaa gatgaataca cccccggaac attggcgtcc gcgagtgaaa aaaagcgccc    35955
gaggaagcaa taaggcacta caatgctcag tctcaagtcc agcaaagcga tgccatgcgg    36015
atgaagcaca aaatcctcag gtgcgtacaa aatgtaatta ctcccctcct gcacaggcag    36075
cgaagccccc gatccctcca gatacacata caaagcctca gcgtccatag cttaccgagc    36135
agcagcacac aacaggcgca agagtcagag aaaggctgag ctctaacctg tccaccccgct    36195
ctctgctcaa tatatagccc agatctacac tgacgtaaag gccaaagtct aaaaatacccc    36255
gccaaataat cacacacgcc cagcacacgc ccagaaaccg tgacacact caaaaaaata    36315
cgcgcacttc ctcaaacgcc caaactgccg tcatttccgg gttcccacgc tacgtcatcg    36375
gaattcgact ttcaaattcc gtcgaccgtt aaaaacgtca cccgccccgc cctaacggt    36435
cgcccgtctc tcggccaatc accttcctcc ctccccaaat tcaaacagct catttgcata    36495
ttaacgcgca ccaaaagttt gaggtatatt attgatgatg                          36535
```

<210> SEQ ID NO 10
<211> LENGTH: 531
<212> TYPE: PRT
<213> ORGANISM: chimpanzee adenovirus serotype Pan7

<400> SEQUENCE: 10

```
Met Met Arg Arg Val Tyr Pro Glu Gly Pro Pro Ser Tyr Glu Ser
1               5                   10                  15

Val Met Gln Gln Ala Val Ala Ala Met Gln Pro Pro Leu Glu Ala
            20                  25                  30
```

```
Pro Tyr Val Pro Pro Arg Tyr Leu Ala Pro Thr Glu Gly Arg Asn Ser
         35                  40                  45

Ile Arg Tyr Ser Glu Leu Ala Pro Leu Tyr Asp Thr Thr Arg Leu Tyr
 50                  55                  60

Leu Val Asp Asn Lys Ser Ala Asp Ile Ala Ser Leu Asn Tyr Gln Asn
 65                  70                  75                  80

Asp His Ser Asn Phe Leu Thr Val Val Gln Asn Asn Asp Phe Thr
                 85                  90                  95

Pro Thr Glu Ala Ser Thr Gln Thr Ile Asn Phe Asp Glu Arg Ser Arg
                100                 105                 110

Trp Gly Gly Gln Leu Lys Thr Ile Met His Thr Asn Met Pro Asn Val
                115                 120                 125

Asn Glu Phe Met Tyr Ser Asn Lys Phe Lys Ala Arg Val Met Val Ser
                130                 135                 140

Arg Lys Thr Pro Asn Gly Val Ala Val Asp Glu Asn Tyr Asp Gly Ser
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
                180                 185                 190

Asp Asn Tyr Leu Ala Val Gly Arg Gln Asn Gly Val Leu Glu Ser Asp
                195                 200                 205

Ile Gly Val Lys Phe Asp Thr Arg Asn Phe Arg Leu Gly Trp Asp Pro
                210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
                260                 265                 270

Gly Phe Gln Ile Leu Tyr Glu Asp Leu Glu Gly Gly Asn Ile Pro Ala
                275                 280                 285

Leu Leu Asp Val Glu Ala Tyr Glu Lys Ser Lys Glu Glu Ala Ala Ala
                290                 295                 300

Ala Ala Thr Ala Ala Val Ala Thr Ala Ser Thr Glu Val Arg Gly Asp
305                 310                 315                 320

Asn Phe Ala Ser Ala Ala Val Ala Glu Ala Glu Thr Glu Ser
                325                 330                 335

Lys Ile Val Ile Gln Pro Val Glu Lys Asp Ser Lys Arg Ser Tyr
                340                 345                 350

Asn Val Leu Ala Asp Lys Lys Asn Thr Ala Tyr Arg Ser Trp Tyr Leu
                355                 360                 365

Ala Tyr Asn Tyr Gly Asp Pro Glu Lys Gly Val Arg Ser Trp Thr Leu
                370                 375                 380

Leu Thr Thr Ser Asp Val Thr Cys Gly Val Glu Gln Val Tyr Trp Ser
385                 390                 395                 400

Leu Pro Asp Met Met Gln Asp Pro Val Thr Phe Arg Ser Thr Arg Gln
                405                 410                 415

Val Ser Asn Tyr Pro Val Val Gly Ala Glu Leu Leu Pro Val Tyr Ser
                420                 425                 430

Lys Ser Phe Phe Asn Glu Gln Ala Val Tyr Ser Gln Gln Leu Arg Ala
                435                 440                 445

Phe Thr Ser Leu Thr His Val Phe Asn Arg Phe Pro Glu Asn Gln Ile
```

```
                        450              455              460
Leu Val Arg Pro Pro Ala Pro Thr Ile Thr Thr Val Ser Glu Asn Val
465                     470              475                 480

Pro Ala Leu Thr Asp His Gly Thr Leu Pro Leu Arg Ser Ser Ile Arg
                    485              490                 495

Gly Val Gln Arg Val Thr Val Thr Asp Ala Arg Arg Thr Cys Pro
                500              505                 510

Tyr Val Tyr Lys Ala Leu Gly Val Val Ala Pro Arg Val Leu Ser Ser
                515              520                 525

Arg Thr Phe
    530

<210> SEQ ID NO 11
<211> LENGTH: 932
<212> TYPE: PRT
<213> ORGANISM: chimpanzee adenovirus serotype Pan7

<400> SEQUENCE: 11

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Cys Gln Trp Thr Tyr Lys Ala Gly Asp Thr Asp Thr
    130                 135                 140

Glu Lys Thr Tyr Thr Tyr Gly Asn Ala Pro Val Gln Gly Ile Ser Ile
145                 150                 155                 160

Thr Lys Asp Gly Ile Gln Leu Gly Thr Asp Ser Asp Gly Gln Ala Ile
                165                 170                 175

Tyr Ala Asp Glu Thr Tyr Gln Pro Glu Pro Gln Val Gly Asp Ala Glu
            180                 185                 190

Trp His Asp Ile Thr Gly Thr Asp Glu Lys Tyr Gly Gly Arg Ala Leu
        195                 200                 205

Lys Pro Asp Thr Lys Met Lys Pro Cys Tyr Gly Ser Phe Ala Lys Pro
    210                 215                 220

Thr Asn Lys Glu Gly Gly Gln Ala Asn Val Lys Thr Glu Thr Gly Gly
225                 230                 235                 240

Thr Lys Glu Tyr Asp Ile Asp Met Ala Phe Phe Asp Asn Arg Ser Ala
                245                 250                 255

Ala Ala Ala Gly Leu Ala Pro Glu Ile Val Leu Tyr Thr Glu Asn Val
            260                 265                 270

Asp Leu Glu Thr Pro Asp Thr His Ile Val Tyr Lys Ala Gly Thr Asp
        275                 280                 285
```

```
Asp Ser Ser Ser Ser Ile Asn Leu Gly Gln Gln Ser Met Pro Asn Arg
    290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365

Asn Gln Ala Val Asp Ser Tyr Asp Pro Asp Val Arg Ile Ile Glu Asn
370                 375                 380

His Gly Val Glu Asp Glu Leu Pro Asn Tyr Cys Phe Pro Leu Asp Ala
385                 390                 395                 400

Val Gly Arg Thr Asp Thr Tyr Gln Gly Ile Lys Ala Asn Gly Asp Asn
                405                 410                 415

Gln Thr Thr Trp Thr Lys Asp Asp Thr Val Asn Asp Ala Asn Glu Leu
            420                 425                 430

Gly Lys Gly Asn Pro Phe Ala Met Glu Ile Asn Ile Gln Ala Asn Leu
        435                 440                 445

Trp Arg Asn Phe Leu Tyr Ala Asn Val Ala Leu Tyr Leu Pro Asp Ser
450                 455                 460

Tyr Lys Tyr Thr Pro Ala Asn Ile Thr Leu Pro Thr Asn Thr Asn Thr
465                 470                 475                 480

Tyr Asp Tyr Met Asn Gly Arg Val Val Ala Pro Ser Leu Val Asp Ala
                485                 490                 495

Tyr Ile Asn Ile Gly Ala Arg Trp Ser Leu Asp Pro Met Asp Asn Val
            500                 505                 510

Asn Pro Phe Asn His His Arg Asn Ala Gly Leu Arg Tyr Arg Ser Met
        515                 520                 525

Leu Leu Gly Asn Gly Arg Tyr Val Pro Phe His Ile Gln Val Pro Gln
530                 535                 540

Lys Phe Ala Ile Lys Ser Leu Leu Leu Leu Pro Gly Ser Tyr Thr
545                 550                 555                 560

Tyr Glu Trp Asn Phe Arg Lys Asp Val Asn Met Ile Leu Gln Ser Ser
                565                 570                 575

Leu Gly Asn Asp Leu Arg Thr Asp Gly Ala Ser Ile Ala Phe Thr Ser
            580                 585                 590

Ile Asn Leu Tyr Ala Thr Phe Phe Pro Met Ala His Asn Thr Ala Ser
        595                 600                 605

Thr Leu Glu Ala Met Leu Arg Asn Asp Thr Asn Asp Gln Ser Phe Asn
610                 615                 620

Asp Tyr Leu Ser Ala Ala Asn Met Leu Tyr Pro Ile Pro Ala Asn Ala
625                 630                 635                 640

Thr Asn Val Pro Ile Ser Ile Pro Ser Arg Asn Trp Ala Ala Phe Arg
                645                 650                 655

Gly Trp Ser Phe Thr Arg Leu Lys Thr Arg Glu Thr Pro Ser Leu Gly
            660                 665                 670

Ser Gly Phe Asp Pro Tyr Phe Tyr Ser Gly Ser Ile Pro Tyr Leu
        675                 680                 685

Asp Gly Thr Phe Tyr Leu Asn His Thr Phe Lys Lys Val Ser Ile Thr
690                 695                 700

Phe Asp Ser Ser Val Ser Trp Pro Gly Asn Asp Arg Leu Leu Thr Pro
```

```
                705                 710                 715                 720
Asn Glu Phe Glu Ile Lys Arg Thr Val Asp Gly Glu Gly Tyr Asn Val
                    725                 730                 735
Ala Gln Cys Asn Met Thr Lys Asp Trp Phe Leu Val Gln Met Leu Ala
                    740                 745                 750
His Tyr Asn Ile Gly Tyr Gln Gly Phe Tyr Val Pro Glu Gly Tyr Lys
                    755                 760                 765
Asp Arg Met Tyr Ser Phe Phe Arg Asn Phe Gln Pro Met Ser Arg Gln
                    770                 775                 780
Val Val Asp Glu Val Asn Tyr Lys Asp Tyr Gln Ala Val Thr Leu Ala
785                 790                 795                 800
Tyr Gln His Asn Asn Ser Gly Phe Val Gly Tyr Leu Ala Pro Thr Met
                    805                 810                 815
Arg Gln Gly Gln Pro Tyr Pro Ala Asn Tyr Pro Tyr Pro Leu Ile Gly
                    820                 825                 830
Lys Ser Ala Val Ala Ser Val Thr Gln Lys Lys Phe Leu Cys Asp Arg
                    835                 840                 845
Val Met Trp Arg Ile Pro Phe Ser Ser Asn Phe Met Ser Met Gly Ala
                    850                 855                 860
Leu Thr Asp Leu Gly Gln Asn Met Leu Tyr Ala Asn Ser Ala His Ala
865                 870                 875                 880
Leu Asp Met Asn Phe Glu Val Asp Pro Met Asp Glu Ser Thr Leu Leu
                    885                 890                 895
Tyr Val Val Phe Glu Val Phe Asp Val Val Arg Val His Gln Pro His
                    900                 905                 910
Arg Gly Val Ile Glu Ala Val Tyr Leu Arg Thr Pro Phe Ser Ala Gly
                    915                 920                 925
Asn Ala Thr Thr
        930

<210> SEQ ID NO 12
<211> LENGTH: 443
<212> TYPE: PRT
<213> ORGANISM: chimpanzee adenovirus serotype Pan7

<400> SEQUENCE: 12

Met Ser Lys Lys Arg Val Arg Val Asp Asp Asp Phe Asp Pro Val Tyr
1               5                   10                  15
Pro Tyr Asp Ala Asp Asn Ala Pro Thr Val Pro Phe Ile Asn Pro Pro
                    20                  25                  30
Phe Val Ser Ser Asp Gly Phe Gln Glu Lys Pro Leu Gly Val Leu Ser
                35                  40                  45
Leu Arg Leu Ala Asp Pro Val Thr Thr Lys Asn Gly Glu Ile Thr Leu
        50                  55                  60
Lys Leu Gly Glu Gly Val Asp Leu Asp Ser Ser Gly Lys Leu Ile Ser
65                  70                  75                  80
Asn Thr Ala Thr Lys Ala Ala Pro Leu Ser Phe Ser Asn Asn Thr
                    85                  90                  95
Ile Ser Leu Asn Met Asp Thr Pro Leu Tyr Thr Lys Asp Gly Lys Leu
                    100                 105                 110
Ser Leu Gln Val Ser Pro Pro Leu Asn Ile Leu Lys Ser Thr Ile Leu
                115                 120                 125
Asn Thr Leu Ala Val Ala Tyr Gly Ser Gly Leu Gly Leu Ser Gly Gly
        130                 135                 140
```

```
Thr Ala Leu Ala Val Gln Leu Ala Ser Pro Leu Thr Phe Asp Glu Lys
145                 150                 155                 160

Gly Asn Ile Lys Ile Asn Leu Ala Ser Gly Pro Leu Thr Val Asp Ala
                165                 170                 175

Ser Arg Leu Ser Ile Asn Cys Lys Arg Gly Val Thr Val Thr Thr Ser
            180                 185                 190

Gly Asp Ala Ile Glu Ser Asn Ile Ser Trp Pro Lys Gly Ile Arg Phe
            195                 200                 205

Glu Gly Asn Gly Ile Ala Ala Asn Ile Gly Arg Gly Leu Glu Phe Gly
        210                 215                 220

Thr Thr Ser Thr Glu Thr Asp Val Thr Asp Ala Tyr Pro Ile Gln Val
225                 230                 235                 240

Lys Leu Gly Thr Gly Leu Thr Phe Asp Ser Thr Gly Ala Ile Val Ala
                245                 250                 255

Trp Asn Lys Glu Asp Asp Lys Leu Thr Leu Trp Thr Thr Ala Asp Pro
            260                 265                 270

Ser Pro Asn Cys Lys Ile Tyr Ser Glu Lys Asp Ala Lys Leu Thr Leu
            275                 280                 285

Cys Leu Thr Lys Cys Gly Ser Gln Ile Leu Gly Thr Val Thr Val Leu
        290                 295                 300

Ala Val Asn Asn Gly Ser Leu Asn Pro Ile Thr Asn Thr Val Ser Thr
305                 310                 315                 320

Ala Leu Val Ser Leu Lys Phe Asp Ala Ser Gly Val Leu Leu Ser Ser
                325                 330                 335

Ser Thr Leu Asp Lys Glu Tyr Trp Asn Phe Arg Lys Gly Asp Val Thr
            340                 345                 350

Pro Ala Glu Pro Tyr Thr Asn Ala Ile Gly Phe Met Pro Asn Ile Lys
        355                 360                 365

Ala Tyr Pro Lys Asn Thr Ser Ala Ala Ser Lys Ser His Ile Val Ser
    370                 375                 380

Gln Val Tyr Leu Asn Gly Asp Glu Ala Lys Pro Leu Met Leu Ile Ile
385                 390                 395                 400

Thr Phe Asn Glu Thr Glu Asp Ala Thr Cys Thr Tyr Ser Ile Thr Phe
                405                 410                 415

Gln Trp Lys Trp Asp Ser Thr Lys Tyr Thr Gly Glu Thr Leu Ala Thr
            420                 425                 430

Ser Ser Phe Thr Phe Ser Tyr Ile Ala Gln Glu
            435                 440

<210> SEQ ID NO 13
<211> LENGTH: 338
<212> TYPE: PRT
<213> ORGANISM: simian serotype C1

<400> SEQUENCE: 13

Ala Pro Lys Gly Ala Pro Asn Thr Ser Gln Trp Leu Asp Lys Gly Val
1               5                   10                  15

Thr Thr Thr Asp Asn Asn Thr Glu Asn Gly Asp Glu Glu Asp Glu Val
                20                  25                  30

Ala Glu Glu Gly Glu Glu Lys Gln Ala Thr Tyr Thr Phe Gly Asn
            35                  40                  45

Ala Pro Val Lys Ala Glu Ala Glu Ile Thr Lys Glu Gly Leu Pro Ile
    50                  55                  60

Gly Leu Glu Val Pro Ser Glu Gly Asp Pro Lys Pro Ile Tyr Ala Asp
65                  70                  75                  80
```

-continued

```
Lys Leu Tyr Gln Pro Glu Pro Gln Val Gly Glu Ser Trp Thr Asp
                85                  90                  95

Thr Asp Gly Thr Asp Glu Lys Tyr Gly Arg Ala Leu Lys Pro Glu
            100                 105                 110

Thr Lys Met Lys Pro Cys Tyr Gly Ser Phe Ala Lys Pro Thr Asn Val
        115                 120                 125

Lys Gly Gly Gln Ala Lys Val Lys Lys Val Glu Glu Gly Lys Val Glu
130                 135                 140

Tyr Asp Ile Asp Met Asn Phe Phe Asp Leu Arg Ser Gln Lys Thr Gly
145                 150                 155                 160

Leu Lys Pro Lys Ile Val Met Tyr Ala Glu Asn Val Asp Leu Glu Thr
                165                 170                 175

Pro Asp Thr His Val Val Tyr Lys Pro Gly Ala Ser Asp Ala Ser Ser
            180                 185                 190

His Ala Asn Leu Gly Gln Gln Ser Met Pro Asn Arg Pro Asn Tyr Ile
        195                 200                 205

Gly Phe Arg Asp Asn Phe Ile Gly Leu Met Tyr Tyr Asn Ser Thr Gly
    210                 215                 220

Asn Met Gly Val Leu Ala Gly Gln Ala Ser Gln Leu Asn Ala Val Val
225                 230                 235                 240

Asp Leu Gln Asp Arg Asn Thr Glu Leu Ser Tyr Gln Leu Leu Leu Asp
                245                 250                 255

Ser Leu Gly Asp Arg Thr Arg Tyr Phe Ser Met Trp Asn Gln Ala Val
            260                 265                 270

Asp Ser Tyr Asp Pro Asp Val Arg Val Ile Glu Asn His Gly Val Glu
        275                 280                 285

Asp Glu Leu Pro Asn Tyr Cys Phe Pro Leu Asp Gly Val Gly Pro Arg
    290                 295                 300

Thr Asp Ser Tyr Lys Gly Ile Glu Thr Asn Gly Asp Glu Asn Thr Thr
305                 310                 315                 320

Trp Lys Asp Leu Asp Pro Asn Gly Ile Ser Glu Leu Ala Lys Gly Asn
                325                 330                 335

Pro Phe

<210> SEQ ID NO 14
<211> LENGTH: 315
<212> TYPE: PRT
<213> ORGANISM: chimpanzee adenovirus Pan-9

<400> SEQUENCE: 14

Ala Pro Lys Gly Ala Pro Asn Thr Cys Gln Trp Thr Tyr Lys Ala Asp
1               5                   10                  15

Gly Glu Thr Ala Thr Glu Lys Thr Tyr Thr Tyr Gly Asn Ala Pro Val
            20                  25                  30

Gln Gly Ile Asn Ile Thr Lys Asp Gly Ile Gln Leu Gly Thr Asp Thr
        35                  40                  45

Asp Asp Gln Pro Ile Tyr Ala Asp Lys Thr Tyr Gln Pro Glu Pro Gln
    50                  55                  60

Val Gly Asp Ala Glu Trp His Asp Ile Thr Gly Thr Asp Glu Lys Tyr
65                  70                  75                  80

Gly Gly Arg Ala Leu Lys Pro Asp Thr Lys Met Lys Pro Cys Tyr Gly
                85                  90                  95

Ser Phe Ala Lys Pro Thr Asn Lys Glu Gly Gly Gln Ala Asn Val Lys
            100                 105                 110
```

-continued

```
Thr Gly Thr Gly Thr Thr Lys Glu Tyr Asp Ile Asp Met Ala Phe Phe
            115                 120                 125

Asp Asn Arg Ser Ala Ala Ala Gly Leu Ala Pro Glu Ile Val Leu
130                 135                 140

Tyr Thr Glu Asn Val Asp Leu Glu Thr Pro Asp Thr His Ile Val Tyr
145                 150                 155                 160

Lys Ala Gly Thr Asp Asp Ser Ser Ser Ile Asn Leu Gly Gln Gln
                165                 170                 175

Ala Met Pro Asn Arg Pro Asn Tyr Ile Gly Phe Arg Asp Asn Phe Ile
            180                 185                 190

Gly Leu Met Tyr Tyr Asn Ser Thr Gly Asn Met Gly Val Leu Ala Gly
            195                 200                 205

Gln Ala Ser Gln Leu Asn Ala Val Val Asp Leu Gln Asp Arg Asn Thr
            210                 215                 220

Glu Leu Ser Tyr Gln Leu Leu Asp Ser Leu Gly Asp Arg Thr Arg
225                 230                 235                 240

Tyr Phe Ser Met Trp Asn Gln Ala Val Asp Ser Tyr Asp Pro Asp Val
                245                 250                 255

Arg Ile Ile Glu Asn His Gly Val Glu Asp Glu Leu Pro Asn Tyr Cys
                260                 265                 270

Phe Pro Leu Asp Ala Val Gly Arg Thr Asp Thr Tyr Gln Gly Ile Lys
            275                 280                 285

Ala Asn Gly Thr Asp Gln Thr Thr Trp Thr Lys Asp Asp Ser Val Asn
            290                 295                 300

Asp Ala Asn Glu Ile Gly Lys Gly Asn Pro Phe
305                 310                 315
```

```
<210> SEQ ID NO 15
<211> LENGTH: 315
<212> TYPE: PRT
<213> ORGANISM: chimpanzee adenovirus Pan-5

<400> SEQUENCE: 15
```

```
Ala Pro Lys Gly Ala Pro Asn Thr Cys Gln Trp Thr Tyr Lys Ala Asp
1               5                   10                  15

Gly Asp Thr Gly Thr Glu Lys Thr Tyr Thr Tyr Gly Asn Ala Pro Val
                20                  25                  30

Gln Gly Ile Ser Ile Thr Lys Asp Gly Ile Gln Leu Gly Thr Asp Thr
            35                  40                  45

Asp Asp Gln Pro Ile Tyr Ala Asp Lys Thr Tyr Gln Pro Glu Pro Gln
50                  55                  60

Val Gly Asp Ala Glu Trp His Asp Ile Thr Gly Thr Asp Glu Lys Tyr
65                  70                  75                  80

Gly Gly Arg Ala Leu Lys Pro Asp Thr Lys Met Lys Pro Cys Tyr Gly
                85                  90                  95

Ser Phe Ala Lys Pro Thr Asn Lys Glu Gly Gly Gln Ala Asn Val Lys
            100                 105                 110

Thr Glu Thr Gly Gly Thr Lys Glu Tyr Asp Ile Asp Met Ala Phe Phe
            115                 120                 125

Asp Asn Arg Ser Ala Ala Ala Gly Leu Ala Pro Glu Ile Val Leu
130                 135                 140

Tyr Thr Glu Asn Val Asp Leu Glu Thr Pro Asp Thr His Ile Val Tyr
145                 150                 155                 160

Lys Ala Gly Thr Asp Asp Ser Ser Ser Ile Asn Leu Gly Gln Gln
```

```
                    165                 170                 175
Ser Met Pro Asn Arg Pro Asn Tyr Ile Gly Phe Arg Asp Asn Phe Ile
                180                 185                 190

Gly Leu Met Tyr Tyr Asn Ser Thr Gly Asn Met Gly Val Leu Ala Gly
            195                 200                 205

Gln Ala Ser Gln Leu Asn Ala Val Val Asp Leu Gln Asp Arg Asn Thr
        210                 215                 220

Glu Leu Ser Tyr Gln Leu Leu Asp Ser Leu Gly Asp Arg Thr Arg
225                 230                 235                 240

Tyr Phe Ser Met Trp Asn Gln Ala Val Asp Ser Tyr Asp Pro Asp Val
                245                 250                 255

Arg Ile Ile Glu Asn His Gly Val Glu Asp Glu Leu Pro Asn Tyr Cys
            260                 265                 270

Phe Pro Leu Asp Ala Val Gly Arg Thr Asp Thr Tyr Gln Gly Ile Lys
        275                 280                 285

Ala Asn Gly Ala Asp Gln Thr Thr Trp Thr Lys Asp Asp Thr Val Asn
    290                 295                 300

Asp Ala Asn Glu Leu Gly Lys Gly Asn Pro Phe
305                 310                 315

<210> SEQ ID NO 16
<211> LENGTH: 324
<212> TYPE: PRT
<213> ORGANISM: chimpanzee adenovirus Pan-6

<400> SEQUENCE: 16

Ala Pro Lys Gly Ala Pro Asn Ser Ser Gln Trp Glu Gln Ala Lys Thr
1               5                   10                  15

Gly Asn Gly Gly Thr Met Glu Thr His Thr Tyr Gly Val Ala Pro Met
            20                  25                  30

Gly Gly Glu Asn Ile Thr Lys Asp Gly Leu Gln Ile Gly Thr Asp Val
        35                  40                  45

Thr Ala Asn Gln Asn Lys Pro Ile Tyr Ala Asp Lys Thr Phe Gln Pro
    50                  55                  60

Glu Pro Gln Val Gly Glu Asn Trp Gln Glu Thr Glu Asn Phe Tyr
65                  70                  75                  80

Gly Gly Arg Ala Leu Lys Lys Asp Thr Lys Met Lys Pro Cys Tyr Gly
                85                  90                  95

Ser Tyr Ala Arg Pro Thr Asn Glu Lys Gly Gly Gln Ala Lys Leu Lys
            100                 105                 110

Val Gly Asp Asp Gly Val Pro Thr Lys Glu Phe Asp Ile Asp Leu Ala
        115                 120                 125

Phe Phe Asp Thr Pro Gly Gly Thr Val Asn Gly Gln Asp Glu Tyr Lys
    130                 135                 140

Ala Asp Ile Val Met Tyr Thr Glu Asn Thr Tyr Leu Glu Thr Pro Asp
145                 150                 155                 160

Thr His Val Val Tyr Lys Pro Gly Lys Asp Asp Ala Ser Ser Glu Ile
                165                 170                 175

Asn Leu Val Gln Gln Ser Met Pro Asn Arg Pro Asn Tyr Ile Gly Phe
            180                 185                 190

Arg Asp Asn Phe Ile Gly Leu Met Tyr Tyr Asn Ser Thr Gly Asn Met
        195                 200                 205

Gly Val Leu Ala Gly Gln Ala Ser Gln Leu Asn Ala Val Val Asp Leu
    210                 215                 220
```

-continued

Gln Asp Arg Asn Thr Glu Leu Ser Tyr Gln Leu Leu Asp Ser Leu
225                 230                 235                 240

Gly Asp Arg Thr Arg Tyr Phe Ser Met Trp Asn Gln Ala Val Asp Ser
            245                 250                 255

Tyr Asp Pro Asp Val Arg Ile Ile Glu Asn His Gly Val Glu Asp Glu
        260                 265                 270

Leu Pro Asn Tyr Cys Phe Pro Leu Asp Gly Ser Gly Thr Asn Ala Ala
    275                 280                 285

Tyr Gln Gly Val Lys Val Lys Asp Gly Gln Asp Gly Val Glu Ser
290                 295                 300

Glu Trp Glu Asn Asp Asp Thr Val Ala Ala Arg Asn Gln Leu Cys Lys
305                 310                 315                 320

Gly Asn Ile Phe

<210> SEQ ID NO 17
<211> LENGTH: 314
<212> TYPE: PRT
<213> ORGANISM: chimpanzee adenovirus Pan-7

<400> SEQUENCE: 17

Ala Pro Lys Gly Ala Pro Asn Thr Cys Gln Trp Thr Tyr Lys Ala Gly
1               5                   10                  15

Asp Thr Asp Thr Glu Lys Thr Tyr Thr Tyr Gly Asn Ala Pro Val Gln
            20                  25                  30

Gly Ile Ser Ile Thr Lys Asp Gly Ile Gln Leu Gly Thr Asp Ser Asp
        35                  40                  45

Gly Gln Ala Ile Tyr Ala Asp Glu Thr Tyr Gln Pro Glu Pro Gln Val
    50                  55                  60

Gly Asp Ala Glu Trp His Asp Ile Thr Gly Thr Asp Glu Lys Tyr Gly
65                  70                  75                  80

Gly Arg Ala Leu Lys Pro Asp Thr Lys Met Lys Pro Cys Tyr Gly Ser
                85                  90                  95

Phe Ala Lys Pro Thr Asn Lys Glu Gly Gly Gln Ala Asn Val Lys Thr
            100                 105                 110

Glu Thr Gly Gly Thr Lys Glu Tyr Asp Ile Asp Met Ala Phe Phe Asp
        115                 120                 125

Asn Arg Ser Ala Ala Ala Ala Gly Leu Ala Pro Glu Ile Val Leu Tyr
    130                 135                 140

Thr Glu Asn Val Asp Leu Glu Thr Pro Asp Thr His Ile Val Tyr Lys
145                 150                 155                 160

Ala Gly Thr Asp Asp Ser Ser Ser Ser Ile Asn Leu Gly Gln Gln Ser
                165                 170                 175

Met Pro Asn Arg Pro Asn Tyr Ile Gly Phe Arg Asp Asn Phe Ile Gly
            180                 185                 190

Leu Met Tyr Tyr Asn Ser Thr Gly Asn Met Gly Val Leu Ala Gly Gln
        195                 200                 205

Ala Ser Gln Leu Asn Ala Val Val Asp Leu Gln Asp Arg Asn Thr Glu
    210                 215                 220

Leu Ser Tyr Gln Leu Leu Leu Asp Ser Leu Gly Asp Arg Thr Arg Tyr
225                 230                 235                 240

Phe Ser Met Trp Asn Gln Ala Val Asp Ser Tyr Asp Pro Asp Val Arg
                245                 250                 255

Ile Ile Glu Asn His Gly Val Glu Asp Glu Leu Pro Asn Tyr Cys Phe
            260                 265                 270

```
Pro Leu Asp Ala Val Gly Arg Thr Asp Thr Tyr Gln Gly Ile Lys Ala
            275                 280                 285

Asn Gly Asp Asn Gln Thr Thr Trp Thr Lys Asp Thr Val Asn Asp
290                 295                 300

Ala Asn Glu Leu Gly Lys Gly Asn Pro Phe
305                 310

<210> SEQ ID NO 18
<211> LENGTH: 179
<212> TYPE: PRT
<213> ORGANISM: chimpanzee adenovirus Pan9

<400> SEQUENCE: 18

Thr Leu Trp Thr Thr Pro Asp Pro Ser Pro Asn Cys Gln Ile Leu Ala
1               5                   10                  15

Glu Asn Asp Ala Lys Leu Thr Leu Cys Leu Thr Lys Cys Gly Ser Gln
            20                  25                  30

Ile Leu Ala Thr Val Ser Val Leu Val Val Gly Ser Gly Asn Leu Asn
        35                  40                  45

Pro Ile Thr Gly Thr Val Ser Ser Ala Gln Val Phe Leu Arg Phe Asp
50                  55                  60

Ala Asn Gly Val Leu Leu Thr Glu His Ser Thr Leu Lys Lys Tyr Trp
65                  70                  75                  80

Gly Tyr Arg Gln Gly Asp Ser Ile Asp Gly Thr Pro Tyr Thr Asn Ala
                85                  90                  95

Val Gly Phe Met Pro Asn Leu Lys Ala Tyr Pro Lys Ser Gln Ser Ser
            100                 105                 110

Thr Thr Lys Asn Asn Ile Val Gly Gln Val Tyr Met Asn Gly Asp Val
        115                 120                 125

Ser Lys Pro Met Leu Leu Thr Ile Thr Leu Asn Gly Thr Asp Asp Ser
130                 135                 140

Asn Ser Thr Tyr Ser Met Ser Phe Ser Tyr Thr Trp Thr Asn Gly Ser
145                 150                 155                 160

Tyr Val Gly Ala Thr Phe Gly Ala Asn Ser Tyr Thr Phe Ser Tyr Ile
                165                 170                 175

Ala Gln Glu

<210> SEQ ID NO 19
<211> LENGTH: 185
<212> TYPE: PRT
<213> ORGANISM: chimpanzee adenovirus Pan6

<400> SEQUENCE: 19

Thr Leu Trp Thr Thr Pro Asp Pro Ser Pro Asn Cys Gln Leu Leu Ser
1               5                   10                  15

Asp Arg Asp Ala Lys Phe Thr Leu Cys Leu Thr Lys Cys Gly Ser Gln
            20                  25                  30

Ile Leu Gly Thr Val Ala Val Ala Ala Val Thr Val Gly Ser Ala Leu
        35                  40                  45

Asn Pro Ile Asn Asp Thr Val Lys Ser Ala Ile Val Phe Leu Arg Phe
50                  55                  60

Asp Ser Asp Gly Val Leu Met Ser Asn Ser Ser Met Val Gly Asp Tyr
65                  70                  75                  80

Trp Asn Phe Arg Glu Gly Gln Thr Thr Gln Ser Val Ala Tyr Thr Asn
                85                  90                  95

Ala Val Gly Phe Met Pro Asn Ile Gly Ala Tyr Pro Lys Thr Gln Ser
```

```
            100                 105                 110
Lys Thr Pro Lys Asn Ser Ile Val Ser Gln Val Tyr Leu Thr Gly Glu
        115                 120                 125

Thr Thr Met Pro Met Thr Leu Thr Ile Thr Phe Asn Gly Thr Asp Glu
    130                 135                 140

Lys Asp Thr Thr Pro Val Ser Thr Tyr Ser Met Thr Phe Thr Trp Gln
145                 150                 155                 160

Trp Thr Gly Asp Tyr Lys Asp Lys Asn Ile Thr Phe Ala Thr Asn Ser
                165                 170                 175

Phe Ser Phe Ser Tyr Ile Ala Gln Glu
                180                 185

<210> SEQ ID NO 20
<211> LENGTH: 179
<212> TYPE: PRT
<213> ORGANISM: chimpanzee adenovirus Pan7

<400> SEQUENCE: 20

Thr Leu Trp Thr Thr Ala Asp Pro Ser Pro Asn Cys Lys Ile Tyr Ser
1               5                   10                  15

Glu Lys Asp Ala Lys Leu Thr Leu Cys Leu Thr Lys Cys Gly Ser Gln
            20                  25                  30

Ile Leu Gly Thr Val Thr Val Leu Ala Val Asn Asn Gly Ser Leu Asn
        35                  40                  45

Pro Ile Thr Asn Thr Val Ser Thr Ala Leu Val Ser Leu Lys Phe Asp
    50                  55                  60

Ala Ser Gly Val Leu Leu Ser Ser Ser Thr Leu Asp Lys Glu Tyr Trp
65                  70                  75                  80

Asn Phe Arg Lys Gly Asp Val Thr Pro Ala Glu Pro Tyr Thr Asn Ala
                85                  90                  95

Ile Gly Phe Met Pro Asn Ile Lys Ala Tyr Pro Lys Asn Thr Ser Ala
            100                 105                 110

Ala Ser Lys Ser His Ile Val Ser Gln Val Tyr Leu Asn Gly Asp Glu
        115                 120                 125

Ala Lys Pro Leu Met Leu Ile Ile Thr Phe Asn Glu Thr Glu Asp Ala
    130                 135                 140

Thr Cys Thr Tyr Ser Ile Thr Phe Gln Trp Lys Trp Asp Ser Thr Lys
145                 150                 155                 160

Tyr Thr Gly Glu Thr Leu Ala Thr Ser Ser Phe Thr Phe Ser Tyr Ile
                165                 170                 175

Ala Gln Glu

<210> SEQ ID NO 21
<211> LENGTH: 179
<212> TYPE: PRT
<213> ORGANISM: chimpanzee adenovirus Pan5

<400> SEQUENCE: 21

Thr Leu Trp Thr Thr Ala Asp Pro Ser Pro Asn Cys His Ile Tyr Ser
1               5                   10                  15

Glu Lys Asp Ala Lys Leu Thr Leu Cys Leu Thr Lys Cys Gly Ser Gln
            20                  25                  30

Ile Leu Gly Thr Val Ser Leu Ile Ala Val Asp Thr Gly Ser Leu Asn
        35                  40                  45

Pro Ile Thr Gly Thr Val Thr Ala Leu Val Ser Leu Lys Phe Asp
    50                  55                  60
```

```
Ala Asn Gly Val Leu Gln Ser Ser Thr Leu Asp Ser Asp Tyr Trp
 65                  70                  75                  80

Asn Phe Arg Gln Gly Asp Val Thr Pro Ala Glu Ala Tyr Thr Asn Ala
                 85                  90                  95

Ile Gly Phe Met Pro Asn Leu Lys Ala Tyr Pro Lys Asn Thr Ser Gly
                100                 105                 110

Ala Ala Lys Ser His Ile Val Gly Lys Val Tyr Leu His Gly Asp Thr
            115                 120                 125

Gly Lys Pro Leu Asp Leu Ile Ile Thr Phe Asn Glu Thr Ser Asp Glu
        130                 135                 140

Ser Cys Thr Tyr Cys Ile Asn Phe Gln Trp Gln Trp Gly Ala Asp Gln
145                 150                 155                 160

Tyr Lys Asn Glu Thr Leu Ala Val Ser Ser Phe Thr Phe Ser Tyr Ile
                165                 170                 175

Ala Lys Glu

<210> SEQ ID NO 22
<211> LENGTH: 183
<212> TYPE: PRT
<213> ORGANISM: human adenovirus Ad 2

<400> SEQUENCE: 22

Thr Leu Trp Thr Thr Pro Asp Pro Ser Pro Asn Cys Arg Ile His Ser
 1               5                  10                  15

Asp Asn Asp Cys Lys Phe Thr Leu Val Leu Thr Lys Cys Gly Ser Gln
                 20                  25                  30

Val Leu Ala Thr Val Ala Ala Leu Ala Val Ser Gly Asp Leu Ser Ser
             35                  40                  45

Met Thr Gly Thr Val Ala Ser Val Ser Ile Phe Leu Arg Phe Asp Gln
         50                  55                  60

Asn Gly Val Leu Met Glu Asn Ser Ser Leu Lys Lys His Tyr Trp Asn
 65                  70                  75                  80

Phe Arg Asn Gly Asn Ser Thr Asn Ala Asn Pro Tyr Thr Asn Ala Val
                 85                  90                  95

Gly Phe Met Pro Asn Leu Leu Ala Tyr Pro Lys Thr Gln Ser Gln Thr
                100                 105                 110

Ala Lys Asn Asn Ile Val Ser Gln Val Tyr Leu His Gly Asp Lys Thr
            115                 120                 125

Lys Pro Met Ile Leu Thr Ile Thr Leu Asn Gly Thr Ser Glu Ser Thr
        130                 135                 140

Glu Thr Ser Glu Val Ser Thr Tyr Ser Met Ser Phe Thr Trp Ser Trp
145                 150                 155                 160

Glu Ser Gly Lys Tyr Thr Thr Glu Thr Phe Ala Thr Asn Ser Tyr Thr
                165                 170                 175

Phe Ser Tyr Ile Ala Gln Glu
            180

<210> SEQ ID NO 23
<211> LENGTH: 182
<212> TYPE: PRT
<213> ORGANISM: human adenovirus Ad 5

<400> SEQUENCE: 23

Thr Leu Trp Thr Thr Pro Ala Pro Ser Pro Asn Cys Arg Leu Asn Ala
 1               5                  10                  15
```

```
Glu Lys Asp Ala Lys Leu Thr Leu Val Leu Thr Lys Cys Gly Ser Gln
             20                  25                  30

Ile Leu Ala Thr Val Ser Val Leu Ala Val Lys Gly Ser Leu Ala Pro
         35                  40                  45

Ile Ser Gly Thr Val Gln Ser Ala His Leu Ile Ile Arg Phe Asp Glu
     50                  55                  60

Asn Gly Val Leu Ile Asn Asn Ser Phe Leu Asp Pro Glu Tyr Trp Asn
65                  70                  75                  80

Phe Arg Asn Gly Asp Leu Thr Glu Gly Thr Ala Tyr Thr Asn Ala Val
                 85                  90                  95

Gly Phe Met Pro Asn Leu Ser Ala Tyr Pro Lys Ser His Gly Lys Thr
             100                 105                 110

Ala Lys Ser Asn Ile Val Ser Gln Val Tyr Leu Asn Gly Asp Lys Thr
         115                 120                 125

Lys Pro Val Thr Leu Thr Ile Thr Leu Asn Gly Thr Gln Glu Thr Gly
     130                 135                 140

Asp Thr Thr Pro Ser Ala Tyr Ser Met Ser Phe Ser Trp Asp Trp Ser
145                 150                 155                 160

Gly His Asn Tyr Ile Asn Glu Ile Phe Ala Thr Ser Ser Tyr Thr Glu
                 165                 170                 175

Ser Tyr Ile Ala Gln Glu
             180

<210> SEQ ID NO 24
<211> LENGTH: 34264
<212> TYPE: DNA
<213> ORGANISM: simian adenovirus SV-1
<220> FEATURE:
<221> NAME/KEY: CDS
<222> LOCATION: (12454)..(13965)
<223> OTHER INFORMATION: L2 Penton
<220> FEATURE:
<221> NAME/KEY: CDS
<222> LOCATION: (16841)..(19636)
<223> OTHER INFORMATION: L3 Hexon
<220> FEATURE:
<221> NAME/KEY: CDS
<222> LOCATION: (28059)..(29150)
<223> OTHER INFORMATION: L5 Fiber #2
<220> FEATURE:
<221> NAME/KEY: CDS
<222> LOCATION: (29183)..(30865)
<223> OTHER INFORMATION: L5 Fiber #1

<400> SEQUENCE: 24
tccttattct ggaaacgtgc caatatgata atgagcgggg aggagcgagg cggggccggg     60
gtgacgtgcg gtgacgtggg gtgacgcggg gtggcgcgag ggcggggcgg gagtggggag    120
gcgcttagtt tttacgtatg cggaaggagg ttttataccg gaagttgggt aatttgggcg    180
tatacttgta agtttttgtgt aatttggcgc gaaaaccggg taatgaggaa gttgaggtta    240
atatgtactt tttatgactg gccggaattt ctgctgatca gcagtgaact ttgggcgctg    300
acggggaggt ttcgctacgt ggcagtacca cgagaaggct caaaggtccc atttattgta    360
ctcctcagcg tttcgctgg gtatttaaac gctgtcagat catcaagagg ccactcttga    420
gtgccggcga gtagagtttt ctcctccgcg ctgccgcgat gaggctggtt cccgagatgt    480
acggtgtttt ctgcagcgag acggcccgga actcagatga gctgcttaat acagatctgc    540
tggatgttcc caactcgcct gtggcttcgc ctccgtcgct tcatgatctt ttcgatgtgg    600
aagtggatcc accgcaagat cccaacgagg acgcggtaaa cagtatgttc cctgaatgtc    660
```

```
tgtttgaggc ggctgaggag ggttctcaca gcagtgaaga gagcagacgg ggagaggaac    720
tggacttgaa atgctacgag gaatgtctgc cttctagcga ttctgaaacg gaacagacag    780
ggggagacgg ctgtgagtcg gcaatgaaaa atgaacttgt attagactgt ccagaacatc    840
ctggtcatgg ctgccgtgcc tgtgcttttc atagaaatgc cagcggaaat cctgagactc    900
tatgtgctct gtgttatctg cgccttacca gcgattttgt atacagtaag taaagtgttt    960
tcattggcgt acggtagggg attcgttgaa gtgctttgtg acttattatg tgtcattatt   1020
tctaggtgac gtgtccgacg tggaagggga aggagataga tcaggggctg ctaattctcc   1080
ttgcactttg ggggctgtgg ttccagttgg cattttaaa ccgagtggtg gaggagaacg    1140
agccggagga gaccgagaat ctgagagccg gcctggaccc tccagtggaa gactaggtgc   1200
tgaggatgat cctgaagagg ggactagtgg gggtgctagg aaaaagcaaa aaactgagcc   1260
tgaacctaga aacttttga atgagttgac tgtaagccta atgaatcggc agcgtcctga    1320
gacggtgttt tggactgagt tggaggatga gttcaagaag ggggaattaa acctcttgta   1380
caagtatggg tttgagcagt tgaaaactca ctggttggag ccgtggggagg atatggaaat  1440
ggctctagac acctttgcta aagtggctct gcggccggat aaagtttaca ctattcgccg   1500
cactgttaat ataaaaaaga gtgtttatgt tatcggccat ggagctctgg tgcaggtgca   1560
gaccccagac cgggtggctt tcaattgcgg catgcagagt ttgggccccg gggtgatagg   1620
tttgaatgga gttacatttc aaaatgtcag gtttactggt gatgatttta atggctctgt   1680
gtttgtgact agcacccagc taaccctcca cggtgtttac tttttttaact ttaacaatac   1740
atgtgtggag tcatgggggta gggtgtctct gagggggctgc agttttcatg gttgctggaa  1800
ggcggtggtg ggaagaatta aaagtgtcat gtctgtgaag aaatgcatat ttgaacgctg   1860
tgtgatagct ctagcagtag aggggtacgg acgatcagg aataacgccg catctgagaa    1920
tggatgtttt cttttgctga aaggtacggc cagcgttaag cataatatga tttgcggcag   1980
cggcctgtgc ccctcgcagc tcttaacttg cgcagatgga aactgtcaca ccttgcgcac   2040
cgtgcacata gtgtcccact cgcgccgcac ctggccaaca tttgagcaca atatgctcat   2100
gcgttgcgcc gttcacctag gtgctagacg cggcgtgttt atgccttatc aatgtaactt   2160
tagtcatact aagattttgc tggaaactga ttccttccct cgagtatgtt tcaatggggt   2220
gtttgacatg tcaatggaac tttttaaagt gataagatat gatgaaacca agtctcgttg   2280
tcgctcatgt gaatgcggag ctaatcattt gaggttgtat cctgtaaccc tgaacgttac   2340
cgaggagctg aggacggacc accacatgct gtcttgcctg cgtaccgact atgaatccag   2400
cgatgaggag tgaggtgagg ggcggagcca caaagggtat aaaggggcat gaggggtggg   2460
cgcggtgttt caaaatgagc gggacgacgg acggcaatgc gtttgagggg ggagtgttca   2520
gcccatatct gacatctcgt cttccttcct gggcaggagt tcgtcagaat gtagtgggct   2580
ccaccgtgga cggacggccg gtcgcccctg caaattccgc caccctcacc tatgccaccg   2640
tgggatcatc gttggacact gccgcggcag ctgccgcttc tgctgccgct tctactgctc   2700
gcggcatggc ggctgatttt ggactatata accaactggc cactgcagct gtggcgtctc   2760
ggtctctggt tcaagaagat gccctgaatg tgatcttgac tcgcctggag atcatgtcac   2820
gtcgcctgga cgaactggct gcgcagatat cccaagctaa ccccgatacc gcttcagaat   2880
cttaaaataa agacaaacaa atttgttgaa aagtaaaatg gctttatttg ttttttttgg   2940
ctcggtaggc tcgggtccac ctgtctcggt cgttaaggac tttgtgtatg ttttccaaaa   3000
cacggtacag atgggcttgg atgttcaagt acatgggcat gaggccatct ttggggtgga   3060
```

```
gataggacca ctgaagagcg tcatgttccg gggtggtatt gtaaatcacc cagtcgtagc    3120 agggttttg agcgtggaac tggaatatgt ccttcaggag caggctaatg ccaagggta     3180 gacccttagt gtaggtgttt acaaagcggt tgagctggga gggatgcatg cgggggggaga  3240 tgatatgcat cttggcttgg attttgaggt tagctatgtt accacccagg tctctgcggg   3300
ggttcatgtt atgaaggacc accagcacgg tatagccagt gcatttgggg aacttgtcat   3360
gcagtttgga gggaaggcg tggaagaatt tagataccccc cttgtgcccc ctaggtttt    3420 ccatgcactc atccataata atggcaatgg gaccccctggc ggccgcttta gcaaacacgt  3480
tttgggggtt ggaaacatca tagttttgct ctagagtgag ctcatcatag gccatcttta   3540
caaagcgggg taggagggtg cccgactggg ggatgatagt tccatctggg cctggagcgt   3600
agttgccctc acagatctgc atctcccagg ccttaatttc cgaggggggg atcatgtcca   3660 cctgggggc gataaaaaac acggtttctg gcgggggggtt aatgagctgg gtggaaagca   3720
agttacgcaa cagctgggat ttgccgcaac cggtgggacc gtagatgacc ccgatgacgg   3780
gttgcagctg gtagttcaga gaggaacagc tgccgtcggg gcgcaggagg ggagctacct   3840
cattcatcat gcttctgaca tgtttatttt cactcactaa gttttgcaag agcctctccc   3900
cacccaggga taagagttct tccaggctgt tgaagtgttt cagcggtttc aggccgtcgg   3960
ccatgggcat cttttcaagc gactgacgaa gcaagtacag tcggtcccag agctcggtga   4020
cgtgctctat ggaatctcga tccagcagac ttcttggttt cggggggttgg gccgactttc   4080 gctgtagggc accagccggt gggcgtccag ggccgcgagg gttctgtcct tccagggtct   4140
cagcgttcgg gtgagggtgg tctcggtgac ggtgaaggga tgagccccgg gctgggcgct   4200
tgcgagggtg cgcttcaggc tcatcctgct ggtgctgaag cgggcgtcgt ctccctgtga   4260
gtcggccaga tagcaacgaa gcatgaggtc gtagctgagg gactcggccg cgtgtcccctt  4320 ggcgcgcagc tttcccttgg aaacgtgctg acatttggtg cagtgcagac acttgagggc   4380
gtagagtttt ggggccagga agaccgactc gggcgagtag gcgtcggctc cgcactgagc   4440
gcagacggtc tcgcactcca ccagccacgt gagctcgggt ttagcgggat caaaaaccaa   4500
gttgcctcca tttttttga tgcgtttctt accttgcgtc tccatgagtc tgtgtcccgc    4560
ttccgtgaca aaaaggctgt cggtatcccc gtagaccgac ttgaggggc gatcttccaa    4620 aggtgttccg aggtcttccg cgtacaggaa ctgggaccac tccagacaa aggctcgggt   4680 ccaggctaac acgaaggagg cgatctgcga ggggtatctg tcgttttcaa tgaggggtc    4740 cacctttttcc agggtgtgca gacacaggtc gtcctcctcc gcgtccacga aggtgattgg   4800
cttgtaagtg taggtcacgt gacccgcacc cccccaaggg gtataaaagg gggcgtgccc   4860
actctccccg tcactttctt ccgcatcgct gtggaccaga gccagctgtt cggtgagta    4920 ggccctctca aaagccggca tgatttcggc gctcaagttg tcagtttcta caaacgaggt   4980
ggatttgata ttcacgtgcc ccgcggcgat gcttttgatg gtggagggt ccatctgatc    5040 agaaaacacg atcttttat tgtcaagttt ggtggcgaaa gacccgtaga gggcgttgga    5100
aagcaacttg gcgatggagc gcagggtctg attttttctcc cgatcggccc tctccttggc  5160
ggcgatgttg agttgcacgt actcgcgggc cacgcaccgc cactcgggga acacggcggt   5220
gcgctcgtcg ggcaggatgc gcacgcgcca gccgcggttg tgcagggtga tgaggtccac   5280
gctggtggcc acctccccgc ggaggggctc gttggtccaa cacaatcgcc ccccttttct   5340
ggagcagaac ggaggcaggg gatctagcaa gttggcgggc ggggggtcgg cgtcgatggt   5400
```

```
aaatatgccg ggtagcagaa ttttattaaa ataatcgatt tcggtgtccg tgtcttgcaa   5460
cgcgtcttcc cacttcttca ccgccagggc cctttcgtag ggattcaggg gcggtcccca   5520
gggcatgggg tgggtcaggg ccgaggcgta catgccgcag atgtcgtaca cgtacagggg   5580
ctccctcaac accccgatgt aagtgggta acagcgcccc ccgcggatgc tggctcgcac    5640
gtagtcgtac atctcgtgag agggagccat gagcccgtct cccaagtggg tcttgtgggg   5700
tttttcggcc cggtagagga tctgcctgaa gatggcgtgg gagttggaag agatagtggg   5760
gcgttggaag acgttaaagt tggctccggg cagtcccacg gagtcttgga tgaactgggc   5820
gtaggattcc cggagcttgt ccaccagggc tgcggttacc agcacgtcga gagcgcagta   5880
gtccaacgtc tcgcggacca ggttgtaggc cgtctcttgt tttttctccc acagttcgcg   5940
attgaggagg tattcctcgc ggtctttcca gtactcttcg gcgggaaatc ctttttcgtc   6000
cgctcggtaa gaacctaaca tgtaaaattc gttcacggct ttgtatggac aacagccttt   6060
ttctaccggc agggcgtacg cttgagcggc ctttctgaga gaggtgtggg tgagggcgaa   6120
ggtgtcccgc accatcactt tcaggtactg atgtttgaag tccgtgtcgt cgcaggcgcc   6180
ctgttcccac agcgtgaagt cggtgcgctt tttctgcctg ggattgggga gggcgaatgt   6240
gacgtcgtta agaggatt tccccggcgcg gggcatgaag ttgcgagaga tcctgaaggg   6300
tccgggcacg tccgagcggt tgttgatgac ttgcgccgcc aggacgatct cgtcgaagcc   6360
gttgatgttg tggcccacga tgtaaagttc gataaagcgc ggctgtccct tgagggccgg   6420
cgctttttc aactcctcgt aggtgagaca gtccggcgag gagagaccca gctccgcccg   6480
ggcccagtcg gagagctgag ggttagccgc gaggaaagag ctccacaggt caagggctag   6540
cagagtttgc aagcggtcgc ggaactcgcg aaactttttc cccacggcca ttttctccgg   6600
cgtcaccacg tagaaagtgc aggggcggtc gttccagacg tcccatcgga gctctagggc   6660
cagctcgcag gcttgacgaa cgagggtctc ctcgcccgag acgtgcatga ccagcatgaa   6720
gggtaccaac tgtttcccga acgagcccat ccatgtgtag gttctacgt cgtaggtgac    6780
aaagagccgc tgggtgcgcg cgtgggagcc gatcgggaag aagctgatct cctgccacca   6840
gttggaggaa tgggtgttga tgtggtgaaa gtagaagtcc cgccggcgca cagagcattc   6900
gtgctgatgt ttgtaaaagc gaccgcagta gtcgcagcgc tgcacgctct gtatctcctg   6960
aatgagatgc gcttttcgcc cgcgcaccag aaaccggagg gggaagttga acgggggct    7020
tggtggggcg gcatcccctt cgccttggcg gtgggagtct gcgtctgcgc cctccttctc   7080
tgggtggacg acggtgggga cgacgacgcc ccgggtgccg caagtccaga tctccgccac   7140
ggaggggcgc aggcgttgca ggaggggacg cagctgcccg ctgtccaggg agtcgagggc   7200
ggccgcgctg aggtcggcgg gaagcgtttg caagttcact ttcagaagac cggtaagagc   7260
gtgagccagg tgcacatggt acttgatttc caggggggtg ttggaagagg cgtccacggc   7320
gtagaggagg ccgtgtccgc gcggggccac caccgtgccc cgaggaggtt ttatctcact   7380
cgtcgagggc gagcgccggg gggtagaggc ggctctgcgc cggggggcag cggaggcagt   7440
ggcacgtttt cgtgaggatt cggcagcggt tgatgacgag cccggagact gctggcgtgg   7500
gcgacgacgc ggcggttgag gtcctggatg tgccgtctct gcgtgaagac caccggcccc   7560
cgggtcctga acctgaaaga gagttccaca gaatcaatgt ctgcatcgtt aacggcggcc   7620
tgcctgagga tctcctgtac gtcgcccgag ttgtcttgat aggcgatctc ggccatgaac   7680
tgctccactt cttcctcgcg gaggtcgccg tggcccgctc gctccacggt ggcggccagg   7740
tcgttggaga tgcgacgcat gagttgagag aaggcgttga ggccgttctc gttccacacg   7800
```

```
cggctgtaca ccacgtttcc gaaggagtcg cgcgctcgca tgaccacctg ggccacgttg   7860
agttccacgt ggcgggcgaa gacggcgtag tttctgaggc gctggaagag gtagttgagc   7920
gtggtggcga tgtgctcgca gacgaagaag tacatgatcc agcgccgcag ggtcatctcg   7980
ttgatgtctc cgatggcttc gagacgctcc atggcctcgt agaagtcgac ggcgaagttg   8040
aaaaattggg agttgcgggc ggccaccgtg agttcttctt gcaggaggcg gatgagatcg   8100
gcgaccgtgt cgcgcacctc ctgctcgaaa gcgccccgag gcgcctctgc ttcttcctcc   8160
ggctcctcct cttccagggg cacgggttcc tccggcagct ctgcgacggg gacggggcgg   8220
cgacgtcgtc gtctgaccgg caggcggtcc acgaagcgct cgatcatttc gccgcgccgg   8280
cgacgcatgg tctcggtgac ggcgcgtccg ttttcgcgag gtcgcagttc gaagacgccg   8340
ccgcgcagag cgccccgtg cagggagggt aagtggttag ggccgtcggg cagggacacg   8400
gcgctgacga tgcattttat caattgctgc gtaggcactc cgtgcaggga tctgagaacg   8460
tcgaggtcga cgggatccga gaacttctct aggaaagcgt ctatccaatc gcagtcgcaa   8520
ggtaagctga ggacggtggg ccgctggggg gcgtccgcgg gcagttggga ggtgatgctg   8580
ctgatgatgt aattaaagta ggcggtcttc aggcggcgga tggtggcgag gaggaccacg   8640
tctttgggcc cggcctgttg aatgcgcagg cgctcggcca tgcccaggc ctcgctctga   8700
cagcgacgca ggtctttgta gtagtcttgc atcagtctct ccaccggaac ctctgcttct   8760
cccctgtctg ccatgcgagt cgagccgaac ccccgcaggg gctgcagcaa cgctaggtcg   8820
gccacgaccc tctcggccag cacggcctgt tggatctgcg tgagggtggt ctggaagtcg   8880
tccaggtcca cgaagcggtg ataggccccc gtgttgatgg tgtaggtgca gttggccatg   8940
acggaccagt tgacgacttg catgccgggt tgggtgatct ccgtgtactt gaggcgcgag   9000
taggcgcggg actcgaacac gtagtcgttg catgtgcgta ccagatactg gtagccaacc   9060
aggaagtggg gaggcggttc tcggtacagg ggccagccga ctgtggcggg ggcgccgggg   9120
gacaggtcgt ccagcatgag gcgatggtag tggtagatgt agcgggagag ccaggtgatg   9180
ccggccgagg tggtcgcggc cctggtgaat tcgcggacgc ggttccagat gttgcgcagg   9240
gggcgaaagc gctccatggt gggcacgctc tgccccgtga ggcgggcgca atcttgtacg   9300
ctctagatgg aaaaaagaca gggcggtcat cgactccctt ccgtagctcg ggggtaaag   9360
tcgcaagggt gcggcggcgg ggaaccccgg ttcgagaccg gccggatccg ccgctcccga   9420
tgcgcctggc cccgcatcca cgacgtccgc gtcgagaccc agccgcgacg ctccgcccca   9480
atacggaggg gagtcttttg gtgttttttc gtagatgcat ccggtgctgc ggcagatgcg   9540
acctcagacg cccaccacca ccgccgcggc ggcagtaaac ctgagcggag gcggtgacag   9600
ggaggaggag gagctggctt tagacctgga agagggagag gggctggccc ggctgggagc   9660
gccgtcccca gagagacacc ctagggttca gctcgtgagg gacgccaggc aggcttttgt   9720
gccgaagcag aacctgttta gggaccgcag cggtcaggag gcgaggaga tgcgcgattg   9780
caggtttcgg gcgggtagag agctgagggc gggcttcgat cgggagcggc tcctgagggc   9840
ggaggatttc gagcccgacg agcgttctgg ggtgagcccg gccgcgctc acgtctcggc   9900
ggccaacctg gtgagcgcgt acgagcagac ggtgaacgag gagcgcaact tccaaaagag   9960
ctttaacaat cacgtgagga ccctgatcgc gagggaggag gtgaccatcg ggctgatgca  10020
tctgtggac ttcgtggagg cctacgtgca gaacccggcc agcaaacctc tgacggccca  10080
gctgttcctg atcgtgcagc acagccgcga caacgagacg ttccgcgacg ccatgttgaa  10140
```

```
catcgcggag cccgagggtc gctggctctt ggatctgatt aacatcctgc agagcatcgt    10200
ggtgcaggag aggggcctca gcttagcgga caaggtggcg gccattaact attcgatgca    10260
gagcctgggg aagttctacg ctcgcaagat ctacaagagc ccttacgtgc ccatagacaa    10320
ggaggtgaag atagacagct tttacatgcg catggcgctg aaggtgctga cgctgagcga    10380
cgacctcggc gtgtaccgta acgacaagat ccacaaggcg gtgagcgcca gccgccggcg    10440
ggagctgagc gacagggagc tgatgcacag cctgcagagg gcgctggcgg gcgccgggga    10500
cgaggagcgc gaggcttact tcgacatggg agccgatctg cagtggcgtc ccagcgcgcg    10560
cgccttggag gcggcgggct accccgacga ggaggatcgg gacgatttgg aggaggcagg    10620
cgagtacgag gacgaagcct gaccgggcag gtgttgtttt agatgcagcg gccggcggac    10680
ggggccaccg cggatcccgc acttttggca tccatgcaga gtcaaccttc gggcgtgacc    10740
gcctccgatg actgggcggc ggccatggac cgcattatgg cgctgactac ccgcaacccc    10800
gaggctttta gacagcaacc ccaggccaac cgttttttcgg ccatcttgga agcggtggtg    10860
ccctcccgca ccaaccccac acacgagaaa gtcctgacta tcgtgaacgc cctggtagac    10920
agcaaggcca tccgccgcga cgaggcgggc ttgatttaca acgctctgct ggaacgggtg    10980
gcgcgctaca acagcactaa cgttcagacc aatctggatc gcctcaccac cgacgtgaag    11040
gaggcgctgg ctcagaagga gcggtttctg agggacagca atctgggctc tctggtggca    11100
ctcaacgcct tcctgagcac gcagccgcc aacgtgcccc gcgggcagga ggactacgtg    11160
agcttcatca gcgctctgag gctgctggtg tccgaggtgc cccagagcga ggtgtatcag    11220
tctgggccgg attacttctt ccagacgtcc cgacagggct tgcaaacggt gaacctgact    11280
caggccttta aaaacttgca aggcatgtgg ggcgttaagg ccccggtggg cgatcgagcc    11340
accatctcca gtctgctgac ccccaacact cgcctgctgc tgctcttgat cgcgccgttc    11400
accaacagta gcactatcag ccgtgactcg tacctgggtc atctcatcac tttgtaccgc    11460
gaggccatcg tcaggctca gatcgacgag cacacatatc aggagatcac taacgtgagc    11520
cgggccctgg gtcaggaaga taccggcagc ctggaagcca cgttgaactt tttgctaacc    11580
aaccggaggc aaaaaatacc ctcccagttt acgttaagcg ccgaggagga gaggattctg    11640
cgatacgtgc agcagtccgt gagtctgtac ttgatgcggg agggcgccac cgcttccacg    11700
gctttagaca tgacggctcg gaacatgaaa ccgtcctttt actccgccca ccggccgttc    11760
attaaccgtc tgatggacta cttccatcgc gcggccgcca tgaacgggga gtacttcacc    11820
aatgccatcc tgaatccgca ttggatgccc ccgtccggct tctacaccgg cgagtttgac    11880
ctgcccgaag ccgacgacgg cttttctttgg gacgacgtgt ccgacagcat tttcacgccg    11940
ggcaatcgcc gattccagaa gaaggagggc ggagacgagc tccccctctc cagcgtggag    12000
gcggcctcta ggggagagag tccctttccc agtctgtctt ccgccagcag tggtcgggta    12060
acgcgcccgc ggttgccggg ggagagcgac tacctgaacg accccttgct gcggccggct    12120
aggaagaaaa atttccccaa caacggggtg gaaagcttgg tggataaaat gaatcgttgg    12180
aagacctacg cccaggagca gcgggagtgg gaggacagtc agccgcgacc gctggttccg    12240
ccgcactggc gtcgtcagag agaagacccg gacgactccg cagacgatag tagcgtgttg    12300
gacctgggag ggagcggagc caaccccttt gctcacttgc aacccaaggg gcgttccagt    12360
cgcctctact aataaaaaag acgcggaaac ttaccagagc catggccaca gcgtgtgtcc    12420
tttcttcctc tctttcttcc tcggcgcggc aga atg aga aga gcg gtg aga gtc   12474
                                   Met Arg Arg Ala Val Arg Val
                                    1               5
```

```
acg ccg gcg gcg tat gag ggt ccg ccc cct tct tac gaa agc gtg atg      12522
Thr Pro Ala Ala Tyr Glu Gly Pro Pro Pro Ser Tyr Glu Ser Val Met
         10                  15                  20 gga tca gcg aac gtg ccg gcc acg ctg gag gcg cct tac gtt cct ccc      12570
Gly Ser Ala Asn Val Pro Ala Thr Leu Glu Ala Pro Tyr Val Pro Pro
 25                  30                  35 aga tac ctg gga cct acg gag ggc aga aac agc atc gtt tac tcc gag      12618
Arg Tyr Leu Gly Pro Thr Glu Gly Arg Asn Ser Ile Arg Tyr Ser Glu
40                  45                  50                  55 ctg gca ccc ctg tac gat acc acc aag gtg tac ctg gtg gac aac aag      12666
Leu Ala Pro Leu Tyr Asp Thr Thr Lys Val Tyr Leu Val Asp Asn Lys
                 60                  65                  70 tcg gcg gac atc gcc tcc ctg aat tat caa aac gat cac agc aat ttt      12714
Ser Ala Asp Ile Ala Ser Leu Asn Tyr Gln Asn Asp His Ser Asn Phe
 75                  80                  85 ctg act acc gtg gtg cag aac aat gac ttc acc ccg acg gag gcg ggc      12762
Leu Thr Thr Val Val Gln Asn Asn Asp Phe Thr Pro Thr Glu Ala Gly
         90                  95                 100 acg cag acc att aac ttt gac gag cgt tcc cgc tgg ggc ggt cag ctg      12810
Thr Gln Thr Ile Asn Phe Asp Glu Arg Ser Arg Trp Gly Gly Gln Leu
105                 110                 115 aaa acc atc ctg cac acc aac atg ccc aac atc aac gag ttc atg tcc      12858
Lys Thr Ile Leu His Thr Asn Met Pro Asn Ile Asn Glu Phe Met Ser
120                 125                 130                 135 acc aac aag ttc agg gcc agg ctg atg gtt aaa aag gct gaa aac cag      12906
Thr Asn Lys Phe Arg Ala Arg Leu Met Val Lys Lys Ala Glu Asn Gln
                140                 145                 150 cct ccc gag tac gaa tgg ttt gag ttc acc att ccc gag ggc aac tat      12954
Pro Pro Glu Tyr Glu Trp Phe Glu Phe Thr Ile Pro Glu Gly Asn Tyr
                155                 160                 165 tcc gag acc atg act atc gat ctg atg aac aat gcg atc gtg gac aat      13002
Ser Glu Thr Met Thr Ile Asp Leu Met Asn Asn Ala Ile Val Asp Asn
        170                 175                 180 tac ctg caa gtg ggg agg cag aac ggg gta ttg gaa agc gat atc ggc      13050
Tyr Leu Gln Val Gly Arg Gln Asn Gly Val Leu Glu Ser Asp Ile Gly
185                 190                 195 gta aaa ttt gat acc aga aac ttc cga ctg ggg tgg gat ccc gtg acc      13098
Val Lys Phe Asp Thr Arg Asn Phe Arg Leu Gly Trp Asp Pro Val Thr
200                 205                 210                 215 aag ctg gtg atg cca ggc gtg tac acc aac gag gct ttt cac ccc gac      13146
Lys Leu Val Met Pro Gly Val Tyr Thr Asn Glu Ala Phe His Pro Asp
                220                 225                 230 atc gtg ctg ctg ccg ggg tgc ggt gtg gac ttc act cag agc cgt ttg      13194
Ile Val Leu Leu Pro Gly Cys Gly Val Asp Phe Thr Gln Ser Arg Leu
                235                 240                 245 agt aac ctg tta ggg atc aga aag cgc cgc ccc ttc caa gag ggc ttt      13242
Ser Asn Leu Leu Gly Ile Arg Lys Arg Arg Pro Phe Gln Glu Gly Phe
        250                 255                 260 cag atc atg tat gag gac ctg gaa gga ggt aac att cca ggt ttg cta      13290
Gln Ile Met Tyr Glu Asp Leu Glu Gly Gly Asn Ile Pro Gly Leu Leu
265                 270                 275 gac gtg ccg gcg tat gaa gag agt gtt aaa cag gcg gag gcg cag gga      13338
Asp Val Pro Ala Tyr Glu Glu Ser Val Lys Gln Ala Glu Ala Gln Gly
280                 285                 290                 295 cga gag att cga ggc gac acc ttt gcc acg gaa cct cac gaa ctg gta      13386
Arg Glu Ile Arg Gly Asp Thr Phe Ala Thr Glu Pro His Glu Leu Val
                300                 305                 310 ata aaa cct ctg gaa caa gac agt aaa aaa cgg agt tac aac att ata      13434
Ile Lys Pro Leu Glu Gln Asp Ser Lys Lys Arg Ser Tyr Asn Ile Ile
```

```
              315                 320                 325
tcc ggc act atg aat acc ttg tac cgg agc tgg ttt ctg gct tac aac    13482
Ser Gly Thr Met Asn Thr Leu Tyr Arg Ser Trp Phe Leu Ala Tyr Asn
        330                 335                 340 tac ggg gat ccc gaa aag gga gtg aga tca tgg acc ata ctc acc acc    13530
Tyr Gly Asp Pro Glu Lys Gly Val Arg Ser Trp Thr Ile Leu Thr Thr
345                 350                 355 acg gac gtg acc tgc ggc tcg cag caa gtg tac tgg tcc ctg ccg gat    13578
Thr Asp Val Thr Cys Gly Ser Gln Gln Val Tyr Trp Ser Leu Pro Asp
360                 365                 370                 375 atg atg caa gac ccg gtc acc ttc cgc ccc tcc acc caa gtc agc aac    13626
Met Met Gln Asp Pro Val Thr Phe Arg Pro Ser Thr Gln Val Ser Asn
                380                 385                 390 ttc ccg gtg gtg ggc acc gag ctg ctg ccc gtc cat gcc aag agc ttc    13674
Phe Pro Val Val Gly Thr Glu Leu Leu Pro Val His Ala Lys Ser Phe
            395                 400                 405 tac aac gaa cag gcc gtc tac tcg caa ctc att cgc cag tcc acc gcg    13722
Tyr Asn Glu Gln Ala Val Tyr Ser Gln Leu Ile Arg Gln Ser Thr Ala
        410                 415                 420 ctt acc cac gtg ttc aat cgc ttt ccc gag aac cag att ctg gtg cgc    13770
Leu Thr His Val Phe Asn Arg Phe Pro Glu Asn Gln Ile Leu Val Arg
    425                 430                 435 cct ccc gct cct acc att acc acc gtc agt gaa aac gtt ccc gcc ctc    13818
Pro Pro Ala Pro Thr Ile Thr Thr Val Ser Glu Asn Val Pro Ala Leu
440                 445                 450                 455 aca gat cac gga acc ctg ccg ctg cgc agc agt atc agt gga gtt cag    13866
Thr Asp His Gly Thr Leu Pro Leu Arg Ser Ser Ile Ser Gly Val Gln
                460                 465                 470 cgc gtg acc atc acc gac gcc aga cgt cga acc tgt ccc tac gtt tac    13914
Arg Val Thr Ile Thr Asp Ala Arg Arg Arg Thr Cys Pro Tyr Val Tyr
            475                 480                 485 aaa gct ctt ggc gta gtg gct cct aaa gtg ctc tct agt cgc acc ttc    13962
Lys Ala Leu Gly Val Val Ala Pro Lys Val Leu Ser Ser Arg Thr Phe
        490                 495                 500 taa acatgtccat cctcatctct cccgataaca acaccggctg ggactgggc          14015 tccggcaaga tgtacggcgg agccaaaagg cgctccagtc agcacccagt tcgagttcgg  14075
ggccacttcc gtgctccctg gggagcttac aagcgaggac tctcgggccg aacggcggta  14135
gacgatacca tagatgccgt gattgccgac gcccgccggt acaaccccgg accggtcgct  14195
agcgccgcct ccaccgtgga ttccgtgatc gacagcgtgg tagctggcgc tcgggcctat  14255
gctcgccgca agaggcggct gcatcggaga cgtcgcccca ccgccgccat gctggcagcc  14315
agggccgtgc tgaggcgggc ccggagggta ggcagaaggg ctatgcgccg cgctgccgcc  14375
aacgccgccg ccgggagggc ccgccgacag gctgccgcc aggctgctgc cgccatcgct   14435
agcatggcca gacccaggag agggaacgtg tactgggtgc gcgattctgt gacgggagtc  14495
cgagtgccgg tgcgcagccg acctccccga agttagaaga tccaagctgc gaagacggcg  14555
gtactgagtc tccctgttgt tatcagccca acatgagcaa gcgcaagttt aaagaagaac  14615
tgctgcagac gctggtgcct gagatctatg gccctccgga cgtgaagcct gacattaagc  14675
cccgcgatat caagcgtgtt aaaaagcggg aaaagaaaga ggaactcgcg gtggtagacg  14735
atggcggagt ggaatttatt aggagtttcg ccccgcgacg cagggttcaa tggaaagggc  14795
ggcgggtaca acgcgttttg aggccgggca ccgcggtagt ttttacccg ggagagcggt   14855 cggccgttag gggtttcaaa aggcagtacg acgaggtgta cggcgacgag gacatattgg  14915
aacaggcggc tcaacagatc ggagaatttg cctacggaaa gcgttcgcgt cgcgaagacc  14975
```

```
tggccatcgc tttagacagc ggcaacccca cgcccagcct caaacctgtg acgctgcagc    15035
aggtgctccc cgtgagcgcc agcacggaca gcaagagggg aataaaaaga gaaatggaag    15095
atctgcagcc caccatccag ctcatggtcc ctaaacggca gaggctggaa gaggtcctgg    15155
agaaaatgaa agtggaccca agcatagagc cggacgtcaa agtcaggccg atcaaagaag    15215
tggcccctgg tctcggggtg cagacggtgg atatccagat ccccgtcacg tcagcttcga    15275
ccgccgtgga agccatggaa acgcaaacgg aaaccctgc cgcgatcggt accagggaag    15335
tggcgttgca aaccgacccc tggtacgaat acgccgcccc tcggcgtcag aggcgacccg    15395
ctcgttacgg ccccgccaac gccatcatgc cagaatatgc gctgcatccg tctatcctgc    15455 ccaccccgg ctaccgggga gtgacgtatc gcccgtcagg aacccgccgc cgaacccgtc    15515
gccgccgccg ctcccgtcgt gctctggccc ccgtgtcggt gcgccgcgta acacgccggg    15575
gaaagacagt taccattccc aacccgcgct accaccctag catcctttaa tgactctgcc    15635
gttttgcaga tggctctgac ttgccgcgtg cgccttcccg ttccgcacta tcgaggaaga    15695
tctcgtcgta ggagaggcat ggcgggtagt ggtcgccggc gggctttgcg caggcgcatg    15755
aaaggcggaa ttttacccgc tctgataccc ataatcgccg ccgccatcgg tgccataccc    15815
ggcgtcgctt cagtggcctt gcaagcagct cgtaataaat aaacgaaggc ttttgcactt    15875
atgtcctggt cctgactatt ttatgcagaa agagcatgga agacatcaat tttacgtcgc    15935
tggctccgcg gcacggctcg cggccgctca tgggcacctg gaacgacatc ggcaccagtc    15995
agctcaacgg gggcgctttc aattggggga gcctttggag cggcattaaa aactttggct    16055
ccacgattaa atcctacggc agcaaagcct ggaacagtag tgctggtcag atgctccgag    16115
ataaactgaa ggcaccaac ttccaagaaa aagtggtcaa tggggtggtg accggcatcc    16175
acggcgcggt agatctcgcc aaccaagcgg tgcagaaaga gattgacagg cgtttggaaa    16235
gctcgcgggt gccgccgcag agaggggatg aggtggaggt cgaggaagta gaagtagagg    16295
aaaagctgcc cccgctggag aaagttcccg gtgcgcctcc gagaccgcag aagcgaccca    16355
ggccagaact agaagaaact ctggtgacgg agagcaagga gcctcctcg tacgagcaag    16415 ccttgaaaga gggcgcctct ccaccctacc caatgacaaa accgatcgcg cctatggctc    16475
ggccggtgta cgggaaggac tacaagcctg tcacgctaga gctccccccg ccgccaccgc    16535 cgcccccac gcgcccgacc gttcccccc cctgccggc tccgtcggcg ggacccgtgt    16595
ccgcacccgt cgccgtgcct ctgccagccg cccgcccagt ggccgtggcc actgccagaa    16655
accccagagg ccagagagga gccaactggc aaagcacgct gaacagcatc gtgggcctgg    16715
gagtgaaaag cctgaaacgc cgccgttgct attattaaaa gtgtagctaa aaaatttccc    16775
gttgtatacg cctcctatgt taccgccaga gacgcgtgac tgtcgccgcg agcgccgctt    16835 tcaag atg gcc acc cca tcg atg atg ccg cag tgg tct tac atg cac atc    16885
      Met Ala Thr Pro Ser Met Met Pro Gln Trp Ser Tyr Met His Ile
          505                 510                 515 gcc ggg cag gac gcc tcg gag tac ctg agc ccc ggt ctc gtg cag ttc       16933
Ala Gly Gln Asp Ala Ser Glu Tyr Leu Ser Pro Gly Leu Val Gln Phe
    520                 525                 530 gcc cgc gcc acc gac acc tac ttc agc ttg gga aac aag ttt aga aac       16981
Ala Arg Ala Thr Asp Thr Tyr Phe Ser Leu Gly Asn Lys Phe Arg Asn
535                 540                 545                 550 ccc acc gtg gcc ccc acc cac gat gta acc acg gac cgc tcg caa agg       17029
Pro Thr Val Ala Pro Thr His Asp Val Thr Thr Asp Arg Ser Gln Arg
                555                 560                 565
```

```
ctg acc ctg cgt ttt gtg ccc gta gac cgg gag gac acc gcg tac tct    17077
Leu Thr Leu Arg Phe Val Pro Val Asp Arg Glu Asp Thr Ala Tyr Ser
        570                 575                 580 tac aaa gtg cgc tac acg ctg gcc gta ggg gac aac cga gtg ctg gac    17125
Tyr Lys Val Arg Tyr Thr Leu Ala Val Gly Asp Asn Arg Val Leu Asp
            585                 590                 595 atg gcc agc acc tac ttt gac atc cgg gga gtg ctg gat cgc ggt ccc    17173
Met Ala Ser Thr Tyr Phe Asp Ile Arg Gly Val Leu Asp Arg Gly Pro
600                 605                 610 agt ttt aag ccc tac tcg ggt acc gcg tac aat tcc ctg gct ccc aag    17221
Ser Phe Lys Pro Tyr Ser Gly Thr Ala Tyr Asn Ser Leu Ala Pro Lys
615                 620                 625                 630 ggc gct ccc aac cct gca gaa tgg acg aat tca gac agc aaa gtt aaa    17269
Gly Ala Pro Asn Pro Ala Glu Trp Thr Asn Ser Asp Ser Lys Val Lys
            635                 640                 645 gtg agg gca cag gcg cct ttt gtt agc tcg tat ggt gct aca gcg att    17317
Val Arg Ala Gln Ala Pro Phe Val Ser Ser Tyr Gly Ala Thr Ala Ile
        650                 655                 660 aca aaa gag ggt att cag gtg gga gta acc tta aca gac tcc gga tca    17365
Thr Lys Glu Gly Ile Gln Val Gly Val Thr Leu Thr Asp Ser Gly Ser
        665                 670                 675 aca cca cag tat gca gat aaa acg tat cag cct gag ccg caa att gga    17413
Thr Pro Gln Tyr Ala Asp Lys Thr Tyr Gln Pro Glu Pro Gln Ile Gly
680                 685                 690 gaa cta cag tgg aac agc gat gtt gga acc gat gac aaa ata gca gga    17461
Glu Leu Gln Trp Asn Ser Asp Val Gly Thr Asp Asp Lys Ile Ala Gly
695                 700                 705                 710 aga gtg cta aag aaa aca acg ccc atg ttc cct tgt tac ggc tca tat    17509
Arg Val Leu Lys Lys Thr Thr Pro Met Phe Pro Cys Tyr Gly Ser Tyr
            715                 720                 725 gcc agg ccc act aat gaa aaa gga gga cag gca aca ccg tcc gct agt    17557
Ala Arg Pro Thr Asn Glu Lys Gly Gly Gln Ala Thr Pro Ser Ala Ser
        730                 735                 740 caa gac gtg caa aat ccc gaa tta caa ttt ttt gcc tct act aat gtc    17605
Gln Asp Val Gln Asn Pro Glu Leu Gln Phe Phe Ala Ser Thr Asn Val
        745                 750                 755 gcc aat aca cca aaa gca gtt cta tat gcg gag gac gtg tca att gaa    17653
Ala Asn Thr Pro Lys Ala Val Leu Tyr Ala Glu Asp Val Ser Ile Glu
760                 765                 770 gcg cca gac act cac ttg gtg ttc aaa cca aca gtc act gaa ggc att    17701
Ala Pro Asp Thr His Leu Val Phe Lys Pro Thr Val Thr Glu Gly Ile
775                 780                 785                 790 aca agt tca gag gct cta ctg acc caa caa gct gct ccc aac cgt cca    17749
Thr Ser Ser Glu Ala Leu Leu Thr Gln Gln Ala Ala Pro Asn Arg Pro
            795                 800                 805 aac tac ata gcc ttt aga gat aat ttt att ggt ctc atg tac tac aat    17797
Asn Tyr Ile Ala Phe Arg Asp Asn Phe Ile Gly Leu Met Tyr Tyr Asn
        810                 815                 820 agc aca ggt aac atg gga gta ctg gca ggc cag gct tct cag cta aat    17845
Ser Thr Gly Asn Met Gly Val Leu Ala Gly Gln Ala Ser Gln Leu Asn
        825                 830                 835 gca gtt gtt gac ctg caa gac aga aat act gag ctg tcc tac caa ctc    17893
Ala Val Val Asp Leu Gln Asp Arg Asn Thr Glu Leu Ser Tyr Gln Leu
840                 845                 850 atg ttg gac gcc ctc gga gac cgc agt cgg tac ttt tct atg tgg aac    17941
Met Leu Asp Ala Leu Gly Asp Arg Ser Arg Tyr Phe Ser Met Trp Asn
855                 860                 865                 870 caa gct gtg gat agt tac gat cct gat gta aga atc ata gaa aac cat    17989
Gln Ala Val Asp Ser Tyr Asp Pro Asp Val Arg Ile Ile Glu Asn His
            875                 880                 885
```

```
ggc gta gaa gat gaa ttg cct aat tat tgc ttt cct ttg gga ggc atg    18037
Gly Val Glu Asp Glu Leu Pro Asn Tyr Cys Phe Pro Leu Gly Gly Met
        890                 895                 900 gca gta acc gac acc tac tcg cct ata aag gtt aat gga gga ggc aat    18085
Ala Val Thr Asp Thr Tyr Ser Pro Ile Lys Val Asn Gly Gly Gly Asn
        905                 910                 915 gga tgg gaa gcc aat aac ggc gtt ttc acc gaa aga gga gtg gaa ata    18133
Gly Trp Glu Ala Asn Asn Gly Val Phe Thr Glu Arg Gly Val Glu Ile
        920                 925                 930 ggt tca ggg aac atg ttt gcc atg gag att aac ctg caa gcc aac cta    18181
Gly Ser Gly Asn Met Phe Ala Met Glu Ile Asn Leu Gln Ala Asn Leu
935                 940                 945                 950 tgg cgt agc ttt ctg tac tcc aat att ggg ctg tac ctg cca gac tct    18229
Trp Arg Ser Phe Leu Tyr Ser Asn Ile Gly Leu Tyr Leu Pro Asp Ser
            955                 960                 965 ctc aaa atc act cct gac aac atc aca ctc cca gag aac aaa aac acc    18277
Leu Lys Ile Thr Pro Asp Asn Ile Thr Leu Pro Glu Asn Lys Asn Thr
        970                 975                 980 tat cag tat atg aac ggt cgc gtg acg cca ccc ggg ctg gtt gac acc    18325
Tyr Gln Tyr Met Asn Gly Arg Val Thr Pro Pro Gly Leu Val Asp Thr
            985                 990                 995 tac gtt aac gtg ggc gcg cgc tgg tcc ccc gat gtc atg gac agt        18370
Tyr Val Asn Val Gly Ala Arg Trp Ser Pro Asp Val Met Asp Ser
       1000                1005                1010 att aac cct ttt aat cac cac cgc aac gcc gga ctc cgc tac cgt        18415
Ile Asn Pro Phe Asn His His Arg Asn Ala Gly Leu Arg Tyr Arg
       1015                1020                1025 tcc atg ctc ctg gga aac gga cgc tac gtg ccc ttc cac atc cag        18460
Ser Met Leu Leu Gly Asn Gly Arg Tyr Val Pro Phe His Ile Gln
       1030                1035                1040 gtg ccc cag aaa ttc ttt gca att aaa aac ctg ctg ctc ctc ccc        18505
Val Pro Gln Lys Phe Phe Ala Ile Lys Asn Leu Leu Leu Leu Pro
       1045                1050                1055 ggt tcc tac acc tac gag tgg aac ttc cgc aag gac gtg aac atg        18550
Gly Ser Tyr Thr Tyr Glu Trp Asn Phe Arg Lys Asp Val Asn Met
       1060                1065                1070 atc ttg cag agc tcg ctg ggc aat gac ctg cga gtg gac ggg gcc        18595
Ile Leu Gln Ser Ser Leu Gly Asn Asp Leu Arg Val Asp Gly Ala
       1075                1080                1085 agc atc cgc ttc gac agc atc aac ctg tac gcc aac ttt ttc ccc        18640
Ser Ile Arg Phe Asp Ser Ile Asn Leu Tyr Ala Asn Phe Phe Pro
       1090                1095                1100 atg gcc cac aac acg gcc tcc acc ctg gaa gcc atg ctg cgc aac        18685
Met Ala His Asn Thr Ala Ser Thr Leu Glu Ala Met Leu Arg Asn
       1105                1110                1115 gac acc aac gac caa tct ttc aac gac tac ctg tgc gcg gcc aac        18730
Asp Thr Asn Asp Gln Ser Phe Asn Asp Tyr Leu Cys Ala Ala Asn
       1120                1125                1130 atg ctg tac ccc atc ccc gcc aac gcc acc agc gtg ccc atc tcc        18775
Met Leu Tyr Pro Ile Pro Ala Asn Ala Thr Ser Val Pro Ile Ser
       1135                1140                1145 att ccc tct cgc aac tgg gca gcc ttc agg ggc tgg agt ttc acc        18820
Ile Pro Ser Arg Asn Trp Ala Ala Phe Arg Gly Trp Ser Phe Thr
       1150                1155                1160 cgc ctc aaa acc aag gag acc ccc tcg ctg ggc tcc ggg ttc gac        18865
Arg Leu Lys Thr Lys Glu Thr Pro Ser Leu Gly Ser Gly Phe Asp
       1165                1170                1175 ccc tac ttc gtc tac tcc ggc tcc atc ccc tac ctg gac ggc acc        18910
Pro Tyr Phe Val Tyr Ser Gly Ser Ile Pro Tyr Leu Asp Gly Thr
```

-continued

```
          1180                1185                1190
ttc tac ctc aac cat act ttc aaa aag gtg tca atc atg ttc gac      18955
Phe Tyr Leu Asn His Thr Phe Lys Lys Val Ser Ile Met Phe Asp
         1195                1200                1205 tcc tcc gtc agc tgg ccc ggc aac gac cgt ctg ctg acg ccc aac      19000
Ser Ser Val Ser Trp Pro Gly Asn Asp Arg Leu Leu Thr Pro Asn
         1210                1215                1220 gag ttc gaa atc aag cgt tcg gtg gac ggt gaa ggg tac aac gtg      19045
Glu Phe Glu Ile Lys Arg Ser Val Asp Gly Glu Gly Tyr Asn Val
         1225                1230                1235 gct cag agc aac atg acc aag gac tgg ttc ctg att cag atg ctc      19090
Ala Gln Ser Asn Met Thr Lys Asp Trp Phe Leu Ile Gln Met Leu
         1240                1245                1250 agc cac tac aac atc ggc tac cag ggc ttc tac gtg ccc gaa aat      19135
Ser His Tyr Asn Ile Gly Tyr Gln Gly Phe Tyr Val Pro Glu Asn
         1255                1260                1265 tac aag gac cgc atg tac tct ttc ttc aga aac ttc caa ccc atg      19180
Tyr Lys Asp Arg Met Tyr Ser Phe Phe Arg Asn Phe Gln Pro Met
         1270                1275                1280 agc cgc caa att gta gat tca acg gct tac act aat tat cag gat      19225
Ser Arg Gln Ile Val Asp Ser Thr Ala Tyr Thr Asn Tyr Gln Asp
         1285                1290                1295 gtg aaa ctg cca tac cag cat aac aac tca ggg ttc gtg ggc tac      19270
Val Lys Leu Pro Tyr Gln His Asn Asn Ser Gly Phe Val Gly Tyr
         1300                1305                1310 atg gga ccc acc atg cga gag ggg cag gcc tac ccg gcc aac tat      19315
Met Gly Pro Thr Met Arg Glu Gly Gln Ala Tyr Pro Ala Asn Tyr
         1315                1320                1325 ccc tat ccc ctg att ggg gcc acc gcc gtg ccc agc ctc acg cag      19360
Pro Tyr Pro Leu Ile Gly Ala Thr Ala Val Pro Ser Leu Thr Gln
         1330                1335                1340 aaa aag ttc ctc tgc gac cgg gtg atg tgg agg atc ccc ttc tct      19405
Lys Lys Phe Leu Cys Asp Arg Val Met Trp Arg Ile Pro Phe Ser
         1345                1350                1355 agc aac ttc atg tct atg ggc tcc ctc acc gac ctg ggg cag aac      19450
Ser Asn Phe Met Ser Met Gly Ser Leu Thr Asp Leu Gly Gln Asn
         1360                1365                1370 atg ctg tac gcc aac tcc gct cac gcc ttg gat atg acc ttt gag      19495
Met Leu Tyr Ala Asn Ser Ala His Ala Leu Asp Met Thr Phe Glu
         1375                1380                1385 gtg gat ccc atg gat gag ccc acg ctt ctc tat gtt ctg ttt gaa      19540
Val Asp Pro Met Asp Glu Pro Thr Leu Leu Tyr Val Leu Phe Glu
         1390                1395                1400 gtc ttc gac gtg gtg cgc atc cac cag ccg cac cgc ggc gtc atc      19585
Val Phe Asp Val Val Arg Ile His Gln Pro His Arg Gly Val Ile
         1405                1410                1415 gag gcc gtc tac ctg cgc aca cct ttc tct gcc ggt aac gcc acc      19630
Glu Ala Val Tyr Leu Arg Thr Pro Phe Ser Ala Gly Asn Ala Thr
         1420                1425                1430 acc taa agaagccgat gggctccagc gaacaggagc tgcaggccat tgttcgcgac   19686
Thr ctgggctgcg ggccctactt tttgggcacc ttcgacaagc gttttcccgg cttcatgtcc 19746 ccccacaagc cggcctgtgc catcgttaac acggccggac gggagaccgg ggggtccac  19806 tggctcgcct tcgcctggaa cccgcgtaac cgcacctgct acctgttcga ccctttggt  19866 ttctccgacg aaaggctgaa gcagatctac cagttcgagt acgaggggct cctcaagcgc 19926 agcgctctgg cctccacgcc cgaccactgc gtcaccctgg aaaagtccac ccaaacggtc 19986
```

```
caggggcccc tctcggccgc ctgcgggctc ttctgttgca tgttttttgca cgccttcgtg    20046
cactggcctc acaccccat  ggatcacaac cccaccatgg atctgctcac cggagtgccc    20106
aacagcatgc ttcacagccc ccaggtcgcc cccaccctgc gccgtaacca ggaacacctg    20166
tatcgctttc tggggaaaca ctctgcctat tttcgccgcc accggcagcg catcgaacgg    20226
gccacggcct tcgaaagcat gagccaaaga gtgtaatcaa taaaaaacat ttttatttga    20286
catgatacgc gcttctggcg ttttattaaa aatcgaaggg ttcgagggag ggtcctcgt    20346
gcccgctggg gagggacacg ttgcgatact ggaaacgggc gctccaacga aactcgggga    20406
tcaccagccg cggcaggggc acgtcttcta ggttctgctt ccaaaactgc cgcaccagct    20466
gcagggctcc catgacgtcg gcgccgata  tcttgaagtc gcagttaggg ccggagctcc    20526
cgcggctgtt gcggaacacg gggttggcac actggaacac cagcacgccg gggttgtgga    20586
tactggccag ggccgtcggg tcggtcacct ccgacgcatc cagatcctcg gcgttgctca    20646
gggcaaacgg ggtcagcttg cacatctgcc gcccaatctg gggtactagg tcgcgcttgt    20706
tgaggcagtc gcagcgcaga gggatcagga tgcgtcgctg cccgcgttgc atgataggg    20766
aactcgccgc caggaactcc tccatttgac ggaaggccat ctgggctttg ccgccctcgg    20826
tgtagaatag cccgcaggac ttgctagaga atacgttatg accgcagttg acgtcctccg    20886
cgcagcagcg ggcgtcttcg ttcttcagct gaaccacgtt gcggcccaa  cggttctgga    20946
ccaccttggc tctagtgggg tgctccttca gcgcccgctg tccgttctcg ctggttacat    21006
ccatttccaa cacgtgctcc ttgcagacca tctccactcc gtggaagcaa aacaggacgc    21066
cctcctgctg ggtactgcga tgctcccata cggcgcatcc ggtgggctcc cagctcttgt    21126
gttttacccc cgcgtaggct tccatgtaag ccataaggaa tctgcccatc agctcggtga    21186
aggtcttctg gttggtgaag gttagcggca ggccgcggtg ctcctcgttc aaccaagttt    21246
gacagatctt gcggtacacc gctccctggt cgggcagaaa cttaaaagcc gctctgctgt    21306
cgttgtctac gtggaacttc tccattaaca tcatcatggt ttccataccc ttctcccacg    21366
ctgtcaccag tggtttgctg tcggggttct tcaccaacac ggcggtagag gggccctcgc    21426
cggccccgac gtccttcatg gtcattcttt gaaactccac ggagccgtcc gcgcgacgta    21486
ctctgcgcac cggagggtag ctgaagccca cctccaccac ggtgccttcg ccctcgctgt    21546
cggagacaat ctccggggat ggcggcggcg cgggtgtcgc cttgcgagcc ttcttcttgg    21606
gagggagctg aggcgcctcc tgctcgcgct cggggctcat ctcccgcaag tagggggtaa    21666
tggagctgcc tgcttggttc tgacggttgg ccattgtatc ctaggcagaa agacatggag    21726
cttatgcgcg aggaaacttt aaccgccccg tccccgtca  gcgacgaaga tgtcatcgtc    21786
gaacaggacc cgggctacgt tacgccgccc gaggatctgg aggggcctga ccggcgcgac    21846
gctagtgagc ggcaggaaaa tgagaaagag gaggcctgct acctcctgga aggcgacgtt    21906
ttgctaaagc atttcgccag gcagagcacc atagttaagg aggccttgca agaccgctcc    21966
gaggtgccct tggacgtcgc cgcgctctcc caggcctacg aggcgaacct tttctcgcct    22026
cgagtgcctc cgaagagaca gcccaacggc acctgcgagc caacccgcg  actcaacttc    22086
taccccgtgt tcgccgtacc agaggcgctg gccaccatc  acattttttt caaaaaccaa    22146
cgcatccccc tatcgtgccg ggccaaccgc accgcggccg ataggaatct caggcttaaa    22206
aacggagcca acatacctga tatcacgtcg ctgcaggaag tgcccaagat tttcgagggt    22266
ctgggtcgag atgagaagcg ggcggcgaac gctctgcaga aagaacagaa agagagtcag    22326
aacgtgctgg tggagctgga gggggacaac gcgcgtctgg ccgtcctcaa acgctgcata    22386
```

```
gaagtctccc acttcgccta ccccgccctc aacttgccac ccaaagttat gaaatcggtc   22446
atggatcagc tgctcatcaa gagagctgag cccctggatc cgaccaccc cgaggcggaa   22506
aactcagagg acggaaagcc cgtcgtcagc gacgaggagc tcgagcggtg gctggaaacc   22566
agggacccc aacagttgca agagaggcgc aagatgatga tggcggccgt gctggtcacc   22626
gtggagctgg aatgcctgca acggttttc agcgacgtgg agacgctacg caaaatcggg   22686
gaatccctgc actacacctt ccgccagggc tacgtccgcc aggcctgcaa gatctccaac   22746
gtggagctca gcaacctggt ctcctacatg ggcatcctcc acgagaaccg gctggggcag   22806
agcgtgctgc actgcacctt gcaaggcgag gcgcggcggg actacgtgcg agactgcatc   22866
tacctcttcc tcaccctcac ctggcagacc gccatgggcg tctggcagca gtgcttggaa   22926
gagagaaacc tcaaagagct agacaaactc ctctgccgcc agcggcgcgc cctgtggtcc   22986
ggtttcagcg agcgcacggt cgccagcgct ctggcggaca tcatcttccc ggagcgcctg   23046
atgaaaacct tgcaaaacgg cctgccggat ttcatcagtc aaagcatttt gcaaaacttc   23106
cgctcttttg tcctggaacg ctccgggatc ttgcccgcca tgagctgcgc gctaccttct   23166
gactttgtcc ccctctccta ccgcgagtgc cctccccac tgtggagcca ctgctacctc   23226
ttccaactgg ccaactttct ggcctaccac tccgacctca tggaagacgt aagcggagag   23286
ggttactgg agtgccactg ccgctgcaac ctgtgcaccc cccacagatc gctggcctgc   23346
aacaccgagc tactcagcga aacccaggtc ataggtacct tcgagatcca ggggcccag   23406
cagcaagagg gtgcttccgg cttgaagctc actccggcgc tgtggacctc ggcttactta   23466
cgcaaatttg tagccgagga ctaccacgcc cacaaaattc agttttacga agaccaatct   23526
cgaccaccga aagccccct cacggcctgc gtcatcaccc agagcaagat cctggcccaa   23586
ttgcaatcca tcaaccaagc gcgccgcgat ttccttttga aaaagggtcg ggggtgtac   23646
ctggaccccc agaccggcga ggaactcaac ccgtccacac tctccgtcga agcagccccc   23706
ccgagacatg ccgcccaagg gaaccgccaa gcagctgatc gctcggcaga gagcgaagaa   23766
gcaagagctg ctccagcagc aggtggagga cgaggaagag atgtgggaca gccaggcaga   23826
ggaggtgtca gaggacgagg aggagatgga aagctgggac agcctagacg aggaggagga   23886
cgagctttca gaggaagagg cgaccgaaga aaaaccacct gcatccagcg cgccttctct   23946
gagccgacag ccgaagcccc ggcccccgac gccccggcc ggctcactca aagccagccg   24006
taggtgggac gccaccgaat ctccagcggc agcggcaacg gcagcgggta aggccaaacg   24066
cgagcggcg gggtattgct cctggcgggc ccacaaaagc agtattgtga actgcttgca   24126
acactgcggg ggaaacatct cctttgcccg acgctacctc ctcttccatc acggtgtggc   24186
cttccctcgc aacgttctct attattaccg tcatctctac agccctacg aaacgctcgg   24246
agaaaaagc taaggcctcc tccgccgcga ggaaaaactc cgccgccgct ccgccgcca   24306
aggatccacc ggccaccgaa gagctgagaa agcgcatctt tcccactctg tatgctatct   24366
ttcagcaaag ccgcgggcag caccctcagc gcgaactgaa aataaaaaac cgctccttcc   24426
gctcgctcac ccgcagctgt ctgtaccaca agagagaaga ccagctgcag cgcaccctgg   24486
acgacgccga agcactgttc agcaaatact gctcagcgtc tcttaaagac taaaagaccc   24546
gcgcttttc cccctcggcc gccaaaaccc acgtcatcgc cagcatgagc aaggagattc   24606
ccaccccta catgtggagc tatcagcccc agatgggcct ggccgcgggg gccgcccagg   24666
actactccag caagatgaac tggctcagcg ccggccccca catgatctca cgagttaacg   24726
```

```
gcatccgagc ccaccgaaac cagattctct tagaacaggc ggcaatcacc gccacacccc   24786
ggcgccaact caacccgcct agttggcccg ccgcccaggt gtatcaggaa aatccccgcc   24846
cgaccacagt cctcctgcca cgcgacgcgg aggccgaagt cctcatgact aactctgggg   24906
tacaattagc gggcgggtcc aggtacgcca ggtacagagg tcgggccgct ccttactctc   24966
ccgggagtat aaagagggtg atcattcgag gccgaggtat ccagctcaac gacgagacgg   25026
tgagctcctc aaccggtctc agacctgacg gagtcttcca gctcggagga gcggccgct   25086 cttccttcac cactcgccag gcctacctga ccctgcagag ctcttcctcg cagccgcgct   25146 ccggggaat cggcactctc cagttcgtgg aagagttcgt tccctccgtc tacttcaacc   25206
ccttctccgg ctcgcctgga cgctacccgg acgccttcat tcccaacttt gacgcagtga   25266
gtgaatccgt ggacggctac gactgatgac agatggtgcg gccgtgagag ctcggctgcg   25326
acatctgcat cactgccgtc agcctcgctg ctacgctcgg gaggcgatcg tcttcagcta   25386 cttgagctg ccggacgagc accctcaggg tccggctcac gggttgaaac tcgagatcga   25446
gaacgcgctc gagtctcgcc tcatcgacac cttcaccgcc cgacctctcc tggtagaaat   25506
ccaacggggg atcactacca tcaccctgtt ctgcatctgc cccacgcccg gattacatga   25566
agatctgtgt tgtcatcttt gcgctcagtt taataaaaac tgaactttt gccgcacctt   25626 caacgccatc tgtgatttct acaacaaaaa gttcttctgg caaaggtaca caaactgtat   25686
tttattctaa ttctacctca tctatcgtgc tgaactgcgc ctgcactaac gaacttatcc   25746
agtggattgc aaacggtagt gtgtgcaagt acttttgggg gaacgatata gttagtagaa   25806
ataacagcct ttgcgagcac tgcaactcct ccacactaat cctttatccc ccatttgtta   25866
ctggatggta tatgtgcgtt ggctccggtt taaatcctag ttgctttcat aagtggtttc   25926
tacaaaaaga gacccttccc aacaattctg tttctttttt cgccctatcc tactgctgtt   25986
ctccctctgg ttactctttc aaacctctaa ttggtatttt agctttgata ctcataatct   26046
ttattaactt tataataatt aacaacttac agtaaacatg cttgttctac tgctcgccac   26106
atctttcgct ctctctcacg ccagaacaag tattgttggc gcaggttaca atgcaactct   26166
tcaatctgct tacatgccag attccgacca gataccccat attacgtggt acttacaaac   26226
ctccaaacct aattcttcat tttatgaagg aaacaaactc tgcgatgact ccgacaacag   26286
aacgcacaca tttccccacc cttcactaca attcgaatgc gtaaacaaaa gcttgaagct   26346
ttacaactta aagccttcag attctggctt gtaccatgct gtagttgaaa aaagtaatt   26406 agaagtccac agtgattaca ttgaattgac ggttgtggac ctgccacctc caaaatgtga   26466
ggtttcctcc tcttaccttg aagttcaagg cgtggatgcc tactgcctca tacacattaa   26526
ctgcagcaac tctaaatatc cagctagaat ttactataat ggacaggaaa gtaatctttt   26586
ttattattta acaacaagcg ctggtaacgg taaacagtta cctgactatt ttactgctgt   26646
tgttgaattt tccacctaca gagaaacgta tgccaagcgg ccttacaatt tctcatacccc  26706 gtttaacgac ctttgcaatg aaatacaagc gctcgaaact ggaactgatt ttactccaat   26766
tttcattgct gccattgttg taagcttaat taccattatt gtcagcctag catttactg   26826 cttttacaag cccaaaaacc ctaagtttga aaaacttaaa ctaaaacctg tcattcaaca   26886
agtgtgattt tgttttccag catggtagct gcatttctac ttctcctctg tctacccatc   26946
attttcgtct cttcaacttt cgccgcagtt tcccacctgg aaccagagtg cctaccgcct   27006
tttgacgtgt atctgattct cacctttgtt tgttgtatat ccatttgcag tatagcctgc   27066 tttttataa caatctttca agccgccgac tatttttacg tgcgaattgc ttactttaga   27126
```

```
caccatcctg aatacagaaa tcaaaacgtt gcctccttac tttgtttggc atgattaagt   27186
tattgctgat acttaattat ttaccoctaa tcaactgtaa ttgtccattc accaaaccct   27246
ggtcattcta cacctgttat gataaaatcc ccgacactcc tgttgcttgg ctttacgcag   27306
ccaccgccgc tttggtattt atatctactt gccttggagt aaaattgtat tttatttac    27366 acactgggtg gctacatccc agagaagatt tacctagata tcctcttgta aacgcttttc   27426
aattacagcc tctgcctcct cctgatcttc ttcctcgagc tccctctatt gtgagctact   27486
ttcaactcac cggtggagat gactgactct caggacatta atattagtgt ggaaagaata   27546
gctgctcagc gtcagcgaga aacgcgagtg ttggaatacc tggaactaca gcaacttaaa   27606
gagtcccact ggtgtgagaa aggagtgctg tgccatgtta agcaggcagc cctttcctac   27666
gatgtcagcg ttcagggaca tgaactgtct tacactttgc ctttgcagaa acaaaccttc   27726
tgcaccatga tgggctctac ctccatcaca atcacccaac aagccgggcc tgtagagggg   27786
gctatcctct gtcactgtca cgcacctgat tgcatgtcca aactaatcaa aactctctgt   27846
gctttaggtg atattttaa ggtgtaaatc aataataaac ttaccttaaa tttgacaaca    27906
aatttctggt gacatcattc agcagcacca ctttaccctc ttcccagctc tcgtatggga   27966
tgcgatagtg ggtggcaaac ttcctccaaa ccctaaaaga aatattggta tccacttcct   28026
tgtcctcacc cacaatttc atctttcat ag atg aaa aga acc aga gtt gat        28079
                                    Met Lys Arg Thr Arg Val Asp
                                       1435              1440 gaa gac ttc aac ccc gtc tac ccc tat gac acc aca acc act cct          28124
Glu Asp Phe Asn Pro Val Tyr Pro Tyr Asp Thr Thr Thr Thr Pro
        1445                1450                1455 gca gtt ccc ttt ata tca ccc cct ttt gta aac agc gat ggt ctt          28169
Ala Val Pro Phe Ile Ser Pro Pro Phe Val Asn Ser Asp Gly Leu
    1460                1465                1470 cag gaa aac ccc cca ggt gtt tta agt ctg cga ata gct aaa ccc          28214
Gln Glu Asn Pro Pro Gly Val Leu Ser Leu Arg Ile Ala Lys Pro
    1475                1480                1485 cta tat ttc gac atg gag aga aaa cta gcc ctt tca ctt gga aga          28259
Leu Tyr Phe Asp Met Glu Arg Lys Leu Ala Leu Ser Leu Gly Arg
    1490                1495                1500 ggg ttg aca att acc gcc gcc gga caa tta gaa agt acg cag agc          28304
Gly Leu Thr Ile Thr Ala Ala Gly Gln Leu Glu Ser Thr Gln Ser
    1505                1510                1515 gta caa acc aac cca ccg ttg ata att acc aac aac aac aca ctg          28349
Val Gln Thr Asn Pro Pro Leu Ile Ile Thr Asn Asn Asn Thr Leu
    1520                1525                1530 acc cta cgt cat tct ccc cct tta aac cta act gac aat agc tta          28394
Thr Leu Arg His Ser Pro Pro Leu Asn Leu Thr Asp Asn Ser Leu
    1535                1540                1545 gtg cta ggc tac tcg agt cct ctc cgc gtc aca gac aac aaa ctt          28439
Val Leu Gly Tyr Ser Ser Pro Leu Arg Val Thr Asp Asn Lys Leu
    1550                1555                1560 aca ttt aac ttc aca tca cca ctc cgt tat gaa aat gaa aac ctt          28484
Thr Phe Asn Phe Thr Ser Pro Leu Arg Tyr Glu Asn Glu Asn Leu
    1565                1570                1575 act ttt aac tat aca gag cct ctt aaa ctt ata aat aac agc ctt          28529
Thr Phe Asn Tyr Thr Glu Pro Leu Lys Leu Ile Asn Asn Ser Leu
    1580                1585                1590 gcc att gac atc aat tcc tca aaa ggc ctt agt agc gtc gga ggc          28574
Ala Ile Asp Ile Asn Ser Ser Lys Gly Leu Ser Ser Val Gly Gly
    1595                1600                1605
```

```
                                                      -continued tca cta gct gta aac ctg agt tca gac tta aag ttt gac agc aac        28619
Ser Leu Ala Val Asn Leu Ser Ser Asp Leu Lys Phe Asp Ser Asn
        1610                1615                1620 gga tcc ata gct ttt ggc ata caa acc ctg tgg acc gct ccg acc        28664
Gly Ser Ile Ala Phe Gly Ile Gln Thr Leu Trp Thr Ala Pro Thr
    1625                1630                1635 tcg act ggc aac tgc acc gtc tac agc gag ggc gat tcc cta ctt        28709
Ser Thr Gly Asn Cys Thr Val Tyr Ser Glu Gly Asp Ser Leu Leu
            1640                1645                1650 agt ctc tgt tta acc aaa tgc gga gct cac gtc tta gga agt gta        28754
Ser Leu Cys Leu Thr Lys Cys Gly Ala His Val Leu Gly Ser Val
                1655                1660                1665 agt tta acc ggt tta aca gga acc ata acc caa atg act gat att        28799
Ser Leu Thr Gly Leu Thr Gly Thr Ile Thr Gln Met Thr Asp Ile
        1670                1675                1680 tct gtc acc att caa ttt aca ttt gac aac aat ggt aag cta cta        28844
Ser Val Thr Ile Gln Phe Thr Phe Asp Asn Asn Gly Lys Leu Leu
    1685                1690                1695 agc tct cca ctt ata aac aac gcc ttt agt att cga cag aat gac        28889
Ser Ser Pro Leu Ile Asn Asn Ala Phe Ser Ile Arg Gln Asn Asp
            1700                1705                1710 agt acg gcc tca aac cct acc tac aac gcc ctg gcg ttt atg cct        28934
Ser Thr Ala Ser Asn Pro Thr Tyr Asn Ala Leu Ala Phe Met Pro
                1715                1720                1725 aac agt acc ata tat gca aga ggg gga ggt ggt gaa cca cga aac        28979
Asn Ser Thr Ile Tyr Ala Arg Gly Gly Gly Gly Glu Pro Arg Asn
        1730                1735                1740 aac tac tac gtc caa acg tat ctt agg gga aat gtt caa aaa cca        29024
Asn Tyr Tyr Val Gln Thr Tyr Leu Arg Gly Asn Val Gln Lys Pro
    1745                1750                1755 atc att ctt act gta acc tac aac tca gtc gcc aca gga tat tcc        29069
Ile Ile Leu Thr Val Thr Tyr Asn Ser Val Ala Thr Gly Tyr Ser
            1760                1765                1770 tta tct ttt aag tgg act gct ctt gca cgt gaa aag ttt gca acc        29114
Leu Ser Phe Lys Trp Thr Ala Leu Ala Arg Glu Lys Phe Ala Thr
                1775                1780                1785 cca aca acc tcg ttt tgc tac att aca gaa caa taa aaccgtgtac        29160
Pro Thr Thr Ser Phe Cys Tyr Ile Thr Glu Gln
        1790                1795 cccaccgttt cgttttttc ag atg aaa cgg gcg aga gtt gat gaa gac        29209
                       Met Lys Arg Ala Arg Val Asp Glu Asp
                                1800                1805 ttc aac cca gtg tac cct tat gac ccc cca cat gct cct gtt atg        29254
Phe Asn Pro Val Tyr Pro Tyr Asp Pro Pro His Ala Pro Val Met
        1810                1815                1820 ccc ttc att act cca cct ttt acc tcc tcg gat ggg ttg cag gaa        29299
Pro Phe Ile Thr Pro Pro Phe Thr Ser Ser Asp Gly Leu Gln Glu
    1825                1830                1835 aaa cca ctt gga gtg tta agt tta aac tac aga gat ccc att act        29344
Lys Pro Leu Gly Val Leu Ser Leu Asn Tyr Arg Asp Pro Ile Thr
            1840                1845                1850 acg caa aat gag tct ctt aca att aaa cta gga aac ggc ctc act        29389
Thr Gln Asn Glu Ser Leu Thr Ile Lys Leu Gly Asn Gly Leu Thr
                1855                1860                1865 cta gac aac cag gga caa cta aca tca acc gct ggc gaa gta gaa        29434
Leu Asp Asn Gln Gly Gln Leu Thr Ser Thr Ala Gly Glu Val Glu
        1870                1875                1880 cct cca ctc act aac gct aac aac aaa ctt gca ctg gtc tat agc        29479
Pro Pro Leu Thr Asn Ala Asn Asn Lys Leu Ala Leu Val Tyr Ser
    1885                1890                1895
```

```
gat cct tta gca gta aag cgc aac agc cta acc tta tcg cac acc      29524
Asp Pro Leu Ala Val Lys Arg Asn Ser Leu Thr Leu Ser His Thr
            1900                1905                1910 gct ccc ctt gtt att gct gat aac tct tta gca ttg caa gtt tca      29569
Ala Pro Leu Val Ile Ala Asp Asn Ser Leu Ala Leu Gln Val Ser
            1915                1920                1925 gag cct att ttt ata aat gac aag gac aaa cta gcc ctg caa aca      29614
Glu Pro Ile Phe Ile Asn Asp Lys Asp Lys Leu Ala Leu Gln Thr
            1930                1935                1940 gcc gcg ccc ctt gta act aac gct ggc acc ctt cgc tta caa agc      29659
Ala Ala Pro Leu Val Thr Asn Ala Gly Thr Leu Arg Leu Gln Ser
            1945                1950                1955 gcc gcc cct tta ggc att gca gac caa acc cta aaa ctc ctg ttt      29704
Ala Ala Pro Leu Gly Ile Ala Asp Gln Thr Leu Lys Leu Leu Phe
            1960                1965                1970 acc aac cct ttg tac ttg cag aat aac ttt ctc acg tta gcc att      29749
Thr Asn Pro Leu Tyr Leu Gln Asn Asn Phe Leu Thr Leu Ala Ile
            1975                1980                1985 gaa cga ccc ctt gcc att acc aat act gga aag ctg gct cta cag      29794
Glu Arg Pro Leu Ala Ile Thr Asn Thr Gly Lys Leu Ala Leu Gln
            1990                1995                2000 ctc tcc cca ccg cta caa aca gca gac aca ggc ttg act ttg caa      29839
Leu Ser Pro Pro Leu Gln Thr Ala Asp Thr Gly Leu Thr Leu Gln
            2005                2010                2015 acc aac gtg cca tta act gta agc aac ggg acc cta ggc tta gcc      29884
Thr Asn Val Pro Leu Thr Val Ser Asn Gly Thr Leu Gly Leu Ala
            2020                2025                2030 ata aag cgc cca ctt att att cag gac aac aac ttg ttt ttg gac      29929
Ile Lys Arg Pro Leu Ile Ile Gln Asp Asn Asn Leu Phe Leu Asp
            2035                2040                2045 ttc aga gct ccc ctg cgt ctt ttc aac agc gac cca gta cta ggg      29974
Phe Arg Ala Pro Leu Arg Leu Phe Asn Ser Asp Pro Val Leu Gly
            2050                2055                2060 ctt aac ttt tac acc cct ctt gcg gta cgc gat gag gcg ctc act      30019
Leu Asn Phe Tyr Thr Pro Leu Ala Val Arg Asp Glu Ala Leu Thr
            2065                2070                2075 gtt aac aca ggc cgc ggc ctc aca gtg agt tac gat ggt tta att      30064
Val Asn Thr Gly Arg Gly Leu Thr Val Ser Tyr Asp Gly Leu Ile
            2080                2085                2090 tta aat ctt ggt aag gat ctt cgc ttt gac aac aac acc gtt tct      30109
Leu Asn Leu Gly Lys Asp Leu Arg Phe Asp Asn Asn Thr Val Ser
            2095                2100                2105 gtc gct ctt agt gct gct ttg cct tta caa tac act gat cag ctt      30154
Val Ala Leu Ser Ala Ala Leu Pro Leu Gln Tyr Thr Asp Gln Leu
            2110                2115                2120 cgc ctt aac gtg ggc gct ggg ctg cgt tac aat cca gtg agt aag      30199
Arg Leu Asn Val Gly Ala Gly Leu Arg Tyr Asn Pro Val Ser Lys
            2125                2130                2135 aaa ttg gac gtg aac ccc aat caa aac aag ggt tta acc tgg gaa      30244
Lys Leu Asp Val Asn Pro Asn Gln Asn Lys Gly Leu Thr Trp Glu
            2140                2145                2150 aat gac tac ctc att gta aag cta gga aat gga tta ggt ttt gat      30289
Asn Asp Tyr Leu Ile Val Lys Leu Gly Asn Gly Leu Gly Phe Asp
            2155                2160                2165 ggc gat gga aac ata gct gtt tct cct caa gtt aca tcg cct gac      30334
Gly Asp Gly Asn Ile Ala Val Ser Pro Gln Val Thr Ser Pro Asp
            2170                2175                2180 acc tta tgg acc act gcc gac cca tcc ccc aat tgt tcc atc tac      30379
Thr Leu Trp Thr Thr Ala Asp Pro Ser Pro Asn Cys Ser Ile Tyr
```

|  |  |  |  |  |  |  |  |  |  |  |
|--|--|--|--|--|--|--|--|--|--|--|
| act | gat | tta | gat | gcc | aaa | atg | tgg | ctc | tcg | ttg | gta | aaa | caa | ggg | 30424 |
| Thr | Asp | Leu | Asp | Ala | Lys | Met | Trp | Leu | Ser | Leu | Val | Lys | Gln | Gly |
|  |  |  | 2200 |  |  |  | 2205 |  |  |  | 2210 |  |  |  |

```
        2185                2190                  2195 act gat tta gat gcc aaa atg tgg ctc tcg ttg gta aaa caa ggg       30424
Thr Asp Leu Asp Ala Lys Met Trp Leu Ser Leu Val Lys Gln Gly
            2200                2205                2210 ggt gtg gtt cac ggt tct gtt gct tta aaa gca ttg aaa gga acc       30469
Gly Val Val His Gly Ser Val Ala Leu Lys Ala Leu Lys Gly Thr
            2215                2220                2225 cta ttg agt cct acg gaa agc gcc att gtt ata cta cat ttt           30514
Leu Leu Ser Pro Thr Glu Ser Ala Ile Val Ile Leu His Phe
            2230                2235                2240 gac aat tat gga gtg cga att ctc aat tat ccc act ttg ggc act       30559
Asp Asn Tyr Gly Val Arg Ile Leu Asn Tyr Pro Thr Leu Gly Thr
            2245                2250                2255 caa ggc acg ttg gga aat aat gca act tgg ggt tat agg cag gga       30604
Gln Gly Thr Leu Gly Asn Asn Ala Thr Trp Gly Tyr Arg Gln Gly
            2260                2265                2270 gaa tct gca gac act aat gta ctc aat gca cta gca ttt atg ccc       30649
Glu Ser Ala Asp Thr Asn Val Leu Asn Ala Leu Ala Phe Met Pro
            2275                2280                2285 agt tca aaa agg tac cca aga ggg cgt gga agc gaa gtt cag aat       30694
Ser Ser Lys Arg Tyr Pro Arg Gly Arg Gly Ser Glu Val Gln Asn
            2290                2295                2300 caa act gtg ggc tac act tgt ata cag ggt gac ttt tct atg ccc       30739
Gln Thr Val Gly Tyr Thr Cys Ile Gln Gly Asp Phe Ser Met Pro
            2305                2310                2315 gta ccg tac caa ata cag tac aac tat gga cca act ggc tac tcc       30784
Val Pro Tyr Gln Ile Gln Tyr Asn Tyr Gly Pro Thr Gly Tyr Ser
            2320                2325                2330 ttt aaa ttt att tgg aga act gtt tca aga caa cca ttt gac atc       30829
Phe Lys Phe Ile Trp Arg Thr Val Ser Arg Gln Pro Phe Asp Ile
            2335                2340                2345 cca tgc tgt ttt ttc tct tac att acg gaa gaa taa acaacttt          30875
Pro Cys Cys Phe Phe Ser Tyr Ile Thr Glu Glu
            2350                2355 tcttttatt ttcttttat tttacacgca cagtaaggct tcctccaccc ttccatctca   30935
cagcatacac cagcctctcc cccttcatgg cagtaaactg ttgtgagtca gtccggtatt 30995 tgggagttaa gatccaaaca gtctctttgg tgatgaaaca tggatccgtg atggacacaa 31055 atccctggga caggttctcc aacgtttcgg taaaaaactg catgccgccc tacaaaacaa 31115 acaggttcag gctctccacg ggttatctcc ccgatcaaac tcagacagag taaaggtgcg 31175 atgatgttcc actaaaccac gcaggtggcg ctgtctgaac ctctcggtgc gactcctgtg 31235 aggctggtaa gaagttagat tgtccagcag cctcacagca tggatcatca gtctacgagt 31295 gcgtctggcg cagcagcgca tctgaatctc actgagattc cggcaagaat cgcacaccat 31355 cacaatcagg ttgttcatga tcccatagct gaacacgctc cagccaaagc tcattcgctc 31415 caacagcgcc accgcgtgtc cgtccaacct tactttaaca taaatcaggt gtctgccgcg 31475 tacaaacatg ctacccgcat acagaacctc ccggggcaaa cccctgttca ccacctgcct 31535 gtaccaggga aacctcacat ttatcaggga gccatagata gccattttaa accaattagc 31595 taacaccgcc ccaccagctc tacactgaag agaaccggga gagttacaat gacagtgaat 31655 aatccatctc tcataacccc taatggtctg atggaaatcc agatctaacg tggcacagca 31715 gatacacact ttcatataca ttttcatcac atgtttttcc caggccgtta aaatacaatc 31775 ccaatacacg ggccactcct gcagtacaat aaagctaata caagatggta tactcctcac 31835 ctcactaaca ttgtgcatgt tcatattttc acattctaag taccgagagt tctcctctac 31895
```

```
aacagcactg ccgcggtcct cacaaggtgg tagctggtga cgattgtaag gagccagtct   31955
gcagcgatac cgtctgtcgc gttgcatcgt agaccaggga ccgacgcact tcctcgtact   32015
tgtagtagca gaaccacgtc cgctgccagc acgtctccaa gtaacgccgg tccctgcgtc   32075
gctcacgctc cctcctcaac gcaaagtgca accactcttg taatccacac agatccctct   32135
cggcctccgg ggcgatgcac acctcaaacc tacagatgtc tcggtacagt tccaaacacg   32195
tagtgagggc gagttccaac caagacagac agcctgatct atcccgacac actggaggtg   32255
gaggaagaca cggaagaggc atgttattcc aagcgattca ccaacgggtc gaaatgaaga   32315
tcccgaagat gacaacggtc gcctccggag ccctgatgaa atttaacagc cagatcaaac   32375
attatgcgat tttccaggct atcaatcgcg gcctccaaaa gagcctggac ccgcacttcc   32435
acaaacacca gcaaagcaaa agcgttatta tcaaactctt cgatcatcaa gctgcaggac   32495
tgtacaatgc ccaagtaatt ttcatttctc cactcgcgaa tgatgtcgcg gcaaatagtc   32555
tgaaggttca tgccgtgcat attaaaaagc tccgaaaggg cgccctctat agccatgcgt   32615
agacacacca tcatgactgc aagatatcgg gctcctgaga cacctgcagc agatttaaca   32675
gacccaggtc aggttgctct ccgcgatcgc gaatctccat ccgcaaagtc atttgcaaat   32735
aattaaatag atctgcgccg actaaatctg ttaactccgc gctaggaact aaatcaggtg   32795
tggctacgca gcacaaaagt tccagggatg gcgccaaact cactagaacc gctcccgagt   32855
agcaaaactg atgaatggga gtaacacagt gtaaaatgtt cagccaaaaa tcactaagct   32915
gctcctttaa aaagtccagt acttctatat tcagttcgtg caagtactga agcaactgtg   32975
cgggaatatg cacagcaaaa aaaatagggc ggctcagata catgttgacc taaaataaaa   33035
agaatcatta aactaaagaa gcctggcgaa cggtgggata tatgacacgc tccagcagca   33095
ggcaagcaac cggctgtccc cgggaaccgc ggtaaaattc atccgaatga ttaaaaagaa   33155
caacagagac ttcccaccat gtactcggtt ggatctcctg agcacagagc aatacccccc   33215
tcacattcat atccgctaca gaaaaaaaac gtcccagata cccagcggga atatccaacg   33275
acagctgcaa agacagcaaa acaatccctc tgggagcaat cacaaaatcc tccggtgaaa   33335
aaagcacata catattagaa taaccctgtt gctggggcaa aaaggcccgt cgtcccagca   33395
aatgcacata aatatgttca tcagccattg ccccgtctta ccgcgtaaac agccacgaaa   33455 aaaatcgagct aaaatccacc caacagccta tagctctata tacactccac ccaatgcgc   33515 taataccgca ccacccacga ccaaagttca cccacaccca caaaacccgc gaaaatccag   33575
cgccgtcagc acttccgcaa tttcagtctc acaacgtcac ttccgcgcgc cttttcactt   33635
tcccacacac gcccttcgcc cgcccgccct cgcgccaccc gcgtcaccc cacgtcaccg   33695 cacgtcaccc cggccccgcc tcgctcctcc ccgctcatta tcatattggc acgtttccag   33755
aataaggtat attattgatg cagcaaaaca atccctctgg gagcaatcac aaaatcctcc   33815
ggtgaaaaaa gcatacat attagaataa ccctgttgct ggggcaaaaa ggcccgtcgt   33875
cccagcaaat gcacataaat atgttcatca gccattgccc cgtcttaccg cgtaaacagc   33935
cacgaaaaaa tcgagctaaa atccacccaa cagcctatag ctatatatac actccaccca   33995
atgacgctaa taccgcacca cccacgacca aagttcaccc acacccacaa aacccgcgaa   34055
aatccagcgc cgtcagcact tccgcaattt cagtctcaca acgtcacttc cgcgcgcctt   34115
ttcactttcc cacacacgcc cttcgcccgc ccgcccctcg ccacccccgc gtcacccac   34175 gtcaccgcac gtcaccccgg cccgcctcg ctcctcccg ctcattatca tattggcacg   34235
```

```
tttccagaat aaggtatatt attgatgca                                            34264
```

<210> SEQ ID NO 25
<211> LENGTH: 503
<212> TYPE: PRT
<213> ORGANISM: simian adenovirus SV-1

<400> SEQUENCE: 25

| Met | Arg | Arg | Ala | Val | Arg | Val | Thr | Pro | Ala | Ala | Tyr | Glu | Gly | Pro | Pro |
|---|---|---|---|---|---|---|---|---|---|---|---|---|---|---|---|
| 1 | | | | 5 | | | | | 10 | | | | | 15 | |

| Pro | Ser | Tyr | Glu | Ser | Val | Met | Gly | Ser | Ala | Asn | Val | Pro | Ala | Thr | Leu |
|---|---|---|---|---|---|---|---|---|---|---|---|---|---|---|---|
| | | | 20 | | | | | 25 | | | | | 30 | | |

| Glu | Ala | Pro | Tyr | Val | Pro | Pro | Arg | Tyr | Leu | Gly | Pro | Thr | Glu | Gly | Arg |
| | | 35 | | | | | 40 | | | | | 45 | | | |

| Asn | Ser | Ile | Arg | Tyr | Ser | Glu | Leu | Ala | Pro | Leu | Tyr | Asp | Thr | Thr | Lys |
| 50 | | | | | 55 | | | | | 60 | | | | | |

| Val | Tyr | Leu | Val | Asp | Asn | Lys | Ser | Ala | Asp | Ile | Ala | Ser | Leu | Asn | Tyr |
| 65 | | | | | 70 | | | | | 75 | | | | | 80 |

| Gln | Asn | Asp | His | Ser | Asn | Phe | Leu | Thr | Thr | Val | Val | Gln | Asn | Asn | Asp |
| | | | | 85 | | | | | 90 | | | | | 95 | |

| Phe | Thr | Pro | Thr | Glu | Ala | Gly | Thr | Gln | Thr | Ile | Asn | Phe | Asp | Glu | Arg |
| | | | 100 | | | | | 105 | | | | | 110 | | |

| Ser | Arg | Trp | Gly | Gly | Gln | Leu | Lys | Thr | Ile | Leu | His | Thr | Asn | Met | Pro |
| | | 115 | | | | | 120 | | | | | 125 | | | |

| Asn | Ile | Asn | Glu | Phe | Met | Ser | Thr | Asn | Lys | Phe | Arg | Ala | Arg | Leu | Met |
| 130 | | | | | 135 | | | | | 140 | | | | | |

| Val | Lys | Lys | Ala | Glu | Asn | Gln | Pro | Pro | Glu | Tyr | Glu | Trp | Phe | Glu | Phe |
| 145 | | | | | 150 | | | | | 155 | | | | | 160 |

| Thr | Ile | Pro | Glu | Gly | Asn | Tyr | Ser | Glu | Thr | Met | Thr | Ile | Asp | Leu | Met |
| | | | | 165 | | | | | 170 | | | | | 175 | |

| Asn | Asn | Ala | Ile | Val | Asp | Asn | Tyr | Leu | Gln | Val | Gly | Arg | Gln | Asn | Gly |
| | | | 180 | | | | | 185 | | | | | 190 | | |

| Val | Leu | Glu | Ser | Asp | Ile | Gly | Val | Lys | Phe | Asp | Thr | Arg | Asn | Phe | Arg |
| | | 195 | | | | | 200 | | | | | 205 | | | |

| Leu | Gly | Trp | Asp | Pro | Val | Thr | Lys | Leu | Val | Met | Pro | Gly | Val | Tyr | Thr |
| 210 | | | | | 215 | | | | | 220 | | | | | |

| Asn | Glu | Ala | Phe | His | Pro | Asp | Ile | Val | Leu | Leu | Pro | Gly | Cys | Gly | Val |
| 225 | | | | | 230 | | | | | 235 | | | | | 240 |

| Asp | Phe | Thr | Gln | Ser | Arg | Leu | Ser | Asn | Leu | Leu | Gly | Ile | Arg | Lys | Arg |
| | | | | 245 | | | | | 250 | | | | | 255 | |

| Arg | Pro | Phe | Gln | Glu | Gly | Phe | Gln | Ile | Met | Tyr | Glu | Asp | Leu | Glu | Gly |
| | | | 260 | | | | | 265 | | | | | 270 | | |

| Gly | Asn | Ile | Pro | Gly | Leu | Leu | Asp | Val | Pro | Ala | Tyr | Glu | Glu | Ser | Val |
| | | 275 | | | | | 280 | | | | | 285 | | | |

| Lys | Gln | Ala | Glu | Ala | Gln | Gly | Arg | Glu | Ile | Arg | Gly | Asp | Thr | Phe | Ala |
| 290 | | | | | 295 | | | | | 300 | | | | | |

| Thr | Glu | Pro | His | Glu | Leu | Val | Ile | Lys | Pro | Leu | Glu | Gln | Asp | Ser | Lys |
| 305 | | | | | 310 | | | | | 315 | | | | | 320 |

| Lys | Arg | Ser | Tyr | Asn | Ile | Ile | Ser | Gly | Thr | Met | Asn | Thr | Leu | Tyr | Arg |
| | | | | 325 | | | | | 330 | | | | | 335 | |

| Ser | Trp | Phe | Leu | Ala | Tyr | Asn | Tyr | Gly | Asp | Pro | Glu | Lys | Gly | Val | Arg |
| | | | 340 | | | | | 345 | | | | | 350 | | |

| Ser | Trp | Thr | Ile | Leu | Thr | Thr | Thr | Asp | Val | Thr | Cys | Gly | Ser | Gln | Gln |
| | | 355 | | | | | 360 | | | | | 365 | | | |

```
Val Tyr Trp Ser Leu Pro Asp Met Met Gln Asp Pro Val Thr Phe Arg
    370                 375                 380

Pro Ser Thr Gln Val Ser Asn Phe Pro Val Val Gly Thr Glu Leu Leu
385                 390                 395                 400

Pro Val His Ala Lys Ser Phe Tyr Asn Glu Gln Ala Val Tyr Ser Gln
                405                 410                 415

Leu Ile Arg Gln Ser Thr Ala Leu Thr His Val Phe Asn Arg Phe Pro
            420                 425                 430

Glu Asn Gln Ile Leu Val Arg Pro Ala Pro Thr Ile Thr Thr Val
        435                 440                 445

Ser Glu Asn Val Pro Ala Leu Thr Asp His Gly Thr Leu Pro Leu Arg
450                 455                 460

Ser Ser Ile Ser Gly Val Gln Arg Val Thr Ile Thr Asp Ala Arg Arg
465                 470                 475                 480

Arg Thr Cys Pro Tyr Val Tyr Lys Ala Leu Gly Val Val Ala Pro Lys
                485                 490                 495

Val Leu Ser Ser Arg Thr Phe
            500
```

<210> SEQ ID NO 26
<211> LENGTH: 931
<212> TYPE: PRT
<213> ORGANISM: simian adenovirus SV-1

<400> SEQUENCE: 26

```
Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ala Glu Trp Thr Asn Ser Asp Ser Lys Val Lys Val
    130                 135                 140

Arg Ala Gln Ala Pro Phe Val Ser Ser Tyr Gly Ala Thr Ala Ile Thr
145                 150                 155                 160

Lys Glu Gly Ile Gln Val Gly Val Thr Leu Thr Asp Ser Gly Ser Thr
                165                 170                 175

Pro Gln Tyr Ala Asp Lys Thr Tyr Gln Pro Glu Pro Gln Ile Gly Glu
            180                 185                 190

Leu Gln Trp Asn Ser Asp Val Gly Thr Asp Asp Lys Ile Ala Gly Arg
        195                 200                 205

Val Leu Lys Lys Thr Thr Pro Met Phe Pro Cys Tyr Gly Ser Tyr Ala
    210                 215                 220

Arg Pro Thr Asn Glu Lys Gly Gly Gln Ala Thr Pro Ser Ala Ser Gln
225                 230                 235                 240
```

-continued

Asp Val Gln Asn Pro Glu Leu Gln Phe Phe Ala Ser Thr Asn Val Ala
             245                 250                 255

Asn Thr Pro Lys Ala Val Leu Tyr Ala Glu Asp Val Ser Ile Glu Ala
             260                 265                 270

Pro Asp Thr His Leu Val Phe Lys Pro Thr Val Thr Glu Gly Ile Thr
             275                 280                 285

Ser Ser Glu Ala Leu Leu Thr Gln Gln Ala Ala Pro Asn Arg Pro Asn
             290                 295                 300

Tyr Ile Ala Phe Arg Asp Asn Phe Ile Gly Leu Met Tyr Tyr Asn Ser
305                 310                 315                 320

Thr Gly Asn Met Gly Val Leu Ala Gly Gln Ala Ser Gln Leu Asn Ala
                 325                 330                 335

Val Val Asp Leu Gln Asp Arg Asn Thr Glu Leu Ser Tyr Gln Leu Met
                 340                 345                 350

Leu Asp Ala Leu Gly Asp Arg Ser Arg Tyr Phe Ser Met Trp Asn Gln
                 355                 360                 365

Ala Val Asp Ser Tyr Asp Pro Asp Val Arg Ile Ile Glu Asn His Gly
                 370                 375                 380

Val Glu Asp Glu Leu Pro Asn Tyr Cys Phe Pro Leu Gly Gly Met Ala
385                 390                 395                 400

Val Thr Asp Thr Tyr Ser Pro Ile Lys Val Asn Gly Gly Asn Gly
                 405                 410                 415

Trp Glu Ala Asn Asn Gly Val Phe Thr Glu Arg Gly Val Glu Ile Gly
                 420                 425                 430

Ser Gly Asn Met Phe Ala Met Glu Ile Asn Leu Gln Ala Asn Leu Trp
                 435                 440                 445

Arg Ser Phe Leu Tyr Ser Asn Ile Gly Leu Tyr Leu Pro Asp Ser Leu
             450                 455                 460

Lys Ile Thr Pro Asp Asn Ile Thr Leu Pro Glu Asn Lys Asn Thr Tyr
465                 470                 475                 480

Gln Tyr Met Asn Gly Arg Val Thr Pro Pro Gly Leu Val Asp Thr Tyr
                 485                 490                 495

Val Asn Val Gly Ala Arg Trp Ser Pro Asp Val Met Asp Ser Ile Asn
                 500                 505                 510

Pro Phe Asn His His Arg Asn Ala Gly Leu Arg Tyr Arg Ser Met Leu
             515                 520                 525

Leu Gly Asn Gly Arg Tyr Val Pro Phe His Ile Gln Val Pro Gln Lys
530                 535                 540

Phe Phe Ala Ile Lys Asn Leu Leu Leu Pro Gly Ser Tyr Thr Tyr
545                 550                 555                 560

Glu Trp Asn Phe Arg Lys Asp Val Asn Met Ile Leu Gln Ser Ser Leu
                 565                 570                 575

Gly Asn Asp Leu Arg Val Asp Gly Ala Ser Ile Arg Phe Asp Ser Ile
                 580                 585                 590

Asn Leu Tyr Ala Asn Phe Phe Pro Met Ala His Asn Thr Ala Ser Thr
             595                 600                 605

Leu Glu Ala Met Leu Arg Asn Asp Thr Asn Asp Gln Ser Phe Asn Asp
610                 615                 620

Tyr Leu Cys Ala Ala Asn Met Leu Tyr Pro Ile Pro Ala Asn Ala Thr
625                 630                 635                 640

Ser Val Pro Ile Ser Ile Pro Ser Arg Asn Trp Ala Ala Phe Arg Gly
                 645                 650                 655

```
Trp Ser Phe Thr Arg Leu Lys Thr Lys Glu Thr Pro Ser Leu Gly Ser
                660                 665                 670

Gly Phe Asp Pro Tyr Phe Val Tyr Ser Gly Ser Ile Pro Tyr Leu Asp
            675                 680                 685

Gly Thr Phe Tyr Leu Asn His Thr Phe Lys Lys Val Ser Ile Met Phe
        690                 695                 700

Asp Ser Ser Val Ser Trp Pro Gly Asn Asp Arg Leu Leu Thr Pro Asn
705                 710                 715                 720

Glu Phe Glu Ile Lys Arg Ser Val Asp Gly Gly Tyr Asn Val Ala
                725                 730                 735

Gln Ser Asn Met Thr Lys Asp Trp Phe Leu Ile Gln Met Leu Ser His
                740                 745                 750

Tyr Asn Ile Gly Tyr Gln Gly Phe Tyr Val Pro Glu Asn Tyr Lys Asp
                755                 760                 765

Arg Met Tyr Ser Phe Phe Arg Asn Phe Gln Pro Met Ser Arg Gln Ile
                770                 775                 780

Val Asp Ser Thr Ala Tyr Thr Asn Tyr Gln Asp Val Lys Leu Pro Tyr
785                 790                 795                 800

Gln His Asn Asn Ser Gly Phe Val Gly Tyr Met Gly Pro Thr Met Arg
                805                 810                 815

Glu Gly Gln Ala Tyr Pro Ala Asn Tyr Pro Tyr Pro Leu Ile Gly Ala
                820                 825                 830

Thr Ala Val Pro Ser Leu Thr Gln Lys Lys Phe Leu Cys Asp Arg Val
                835                 840                 845

Met Trp Arg Ile Pro Phe Ser Ser Asn Phe Met Ser Met Gly Ser Leu
850                 855                 860

Thr Asp Leu Gly Gln Asn Met Leu Tyr Ala Asn Ser Ala His Ala Leu
865                 870                 875                 880

Asp Met Thr Phe Glu Val Asp Pro Met Asp Glu Pro Thr Leu Leu Tyr
                885                 890                 895

Val Leu Phe Glu Val Phe Asp Val Val Arg Ile His Gln Pro His Arg
                900                 905                 910

Gly Val Ile Glu Ala Val Tyr Leu Arg Thr Pro Phe Ser Ala Gly Asn
            915                 920                 925

Ala Thr Thr
    930

<210> SEQ ID NO 27
<211> LENGTH: 363
<212> TYPE: PRT
<213> ORGANISM: simian adenovirus SV-1

<400> SEQUENCE: 27

Met Lys Arg Thr Arg Val Asp Glu Asp Phe Asn Pro Val Tyr Pro Tyr
1               5                   10                  15

Asp Thr Thr Thr Pro Ala Val Pro Phe Ile Ser Pro Pro Phe Val
            20                  25                  30

Asn Ser Asp Gly Leu Gln Glu Asn Pro Pro Gly Val Leu Ser Leu Arg
            35                  40                  45

Ile Ala Lys Pro Leu Tyr Phe Asp Met Glu Arg Lys Leu Ala Leu Ser
        50                  55                  60

Leu Gly Arg Gly Leu Thr Ile Thr Ala Ala Gly Gln Leu Glu Ser Thr
65                  70                  75                  80

Gln Ser Val Gln Thr Asn Pro Pro Leu Ile Ile Thr Asn Asn Asn Thr
                85                  90                  95
```

```
Leu Thr Leu Arg His Ser Pro Pro Leu Asn Leu Thr Asp Asn Ser Leu
            100                 105                 110

Val Leu Gly Tyr Ser Ser Pro Leu Arg Val Thr Asp Asn Lys Leu Thr
            115                 120                 125

Phe Asn Phe Thr Ser Pro Leu Arg Tyr Glu Asn Glu Asn Leu Thr Phe
            130                 135                 140

Asn Tyr Thr Glu Pro Leu Lys Leu Ile Asn Asn Ser Leu Ala Ile Asp
145                 150                 155                 160

Ile Asn Ser Ser Lys Gly Leu Ser Ser Val Gly Ser Leu Ala Val
                165                 170                 175

Asn Leu Ser Ser Asp Leu Lys Phe Asp Ser Asn Gly Ser Ile Ala Phe
            180                 185                 190

Gly Ile Gln Thr Leu Trp Thr Ala Pro Thr Ser Thr Gly Asn Cys Thr
            195                 200                 205

Val Tyr Ser Glu Gly Asp Ser Leu Leu Ser Leu Cys Leu Thr Lys Cys
            210                 215                 220

Gly Ala His Val Leu Gly Ser Val Ser Leu Thr Gly Leu Thr Gly Thr
225                 230                 235                 240

Ile Thr Gln Met Thr Asp Ile Ser Val Thr Ile Gln Phe Thr Phe Asp
            245                 250                 255

Asn Asn Gly Lys Leu Leu Ser Ser Pro Leu Ile Asn Asn Ala Phe Ser
            260                 265                 270

Ile Arg Gln Asn Asp Ser Thr Ala Ser Asn Pro Thr Tyr Asn Ala Leu
            275                 280                 285

Ala Phe Met Pro Asn Ser Thr Ile Tyr Ala Arg Gly Gly Gly Gly Glu
            290                 295                 300

Pro Arg Asn Asn Tyr Tyr Val Gln Thr Tyr Leu Arg Gly Asn Val Gln
305                 310                 315                 320

Lys Pro Ile Ile Leu Thr Val Thr Tyr Asn Ser Val Ala Thr Gly Tyr
            325                 330                 335

Ser Leu Ser Phe Lys Trp Thr Ala Leu Ala Arg Glu Lys Phe Ala Thr
            340                 345                 350

Pro Thr Thr Ser Phe Cys Tyr Ile Thr Glu Gln
            355                 360

<210> SEQ ID NO 28
<211> LENGTH: 560
<212> TYPE: PRT
<213> ORGANISM: simian adenovirus SV-1

<400> SEQUENCE: 28

Met Lys Arg Ala Arg Val Asp Glu Asp Phe Asn Pro Val Tyr Pro Tyr
1               5                   10                  15

Asp Pro Pro His Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Arg Asp Pro Ile Thr Thr Gln Asn Glu Ser Leu Thr Ile Lys Leu
    50                  55                  60

Gly Asn Gly Leu Thr Leu Asp Asn Gln Gly Gln Leu Ser Thr Ala
65                  70                  75                  80

Gly Glu Val Glu Pro Pro Leu Thr Asn Ala Asn Asn Lys Leu Ala Leu
            85                  90                  95

Val Tyr Ser Asp Pro Leu Ala Val Lys Arg Asn Ser Leu Thr Leu Ser
```

```
                100             105             110
His Thr Ala Pro Leu Val Ile Ala Asp Asn Ser Leu Ala Leu Gln Val
            115             120             125
Ser Glu Pro Ile Phe Ile Asn Asp Lys Asp Lys Leu Ala Leu Gln Thr
            130             135             140
Ala Ala Pro Leu Val Thr Asn Ala Gly Thr Leu Arg Leu Gln Ser Ala
            145             150             155             160
Ala Pro Leu Gly Ile Ala Asp Gln Thr Leu Lys Leu Leu Phe Thr Asn
                            165             170             175
Pro Leu Tyr Leu Gln Asn Asn Phe Leu Thr Leu Ala Ile Glu Arg Pro
                180             185             190
Leu Ala Ile Thr Asn Thr Gly Lys Leu Ala Leu Gln Leu Ser Pro Pro
                195             200             205
Leu Gln Thr Ala Asp Thr Gly Leu Thr Leu Gln Thr Asn Val Pro Leu
            210             215             220
Thr Val Ser Asn Gly Thr Leu Gly Leu Ala Ile Lys Arg Pro Leu Ile
225             230             235             240
Ile Gln Asp Asn Asn Leu Phe Leu Asp Phe Arg Ala Pro Leu Arg Leu
                            245             250             255
Phe Asn Ser Asp Pro Val Leu Gly Leu Asn Phe Tyr Thr Pro Leu Ala
                260             265             270
Val Arg Asp Glu Ala Leu Thr Val Asn Thr Gly Arg Gly Leu Thr Val
                275             280             285
Ser Tyr Asp Gly Leu Ile Leu Asn Leu Gly Lys Asp Leu Arg Phe Asp
                290             295             300
Asn Asn Thr Val Ser Val Ala Leu Ser Ala Ala Leu Pro Leu Gln Tyr
305             310             315             320
Thr Asp Gln Leu Arg Leu Asn Val Gly Ala Gly Leu Arg Tyr Asn Pro
                            325             330             335
Val Ser Lys Lys Leu Asp Val Asn Pro Asn Gln Asn Lys Gly Leu Thr
                            340             345             350
Trp Glu Asn Asp Tyr Leu Ile Val Lys Leu Gly Asn Gly Leu Gly Phe
                            355             360             365
Asp Gly Asp Gly Asn Ile Ala Val Ser Pro Gln Val Thr Ser Pro Asp
                            370             375             380
Thr Leu Trp Thr Thr Ala Asp Pro Ser Pro Asn Cys Ser Ile Tyr Thr
385             390             395             400
Asp Leu Asp Ala Lys Met Trp Leu Ser Leu Val Lys Gln Gly Gly Val
                            405             410             415
Val His Gly Ser Val Ala Leu Lys Ala Leu Lys Gly Thr Leu Leu Ser
                            420             425             430
Pro Thr Glu Ser Ala Ile Val Ile Leu His Phe Asp Asn Tyr Gly
                            435             440             445
Val Arg Ile Leu Asn Tyr Pro Thr Leu Gly Thr Gln Gly Thr Leu Gly
                            450             455             460
Asn Asn Ala Thr Trp Gly Tyr Arg Gln Gly Glu Ser Ala Asp Thr Asn
465                         470             475             480
Val Leu Asn Ala Leu Ala Phe Met Pro Ser Ser Lys Arg Tyr Pro Arg
                            485             490             495
Gly Arg Gly Ser Glu Val Gln Asn Gln Thr Val Gly Tyr Thr Cys Ile
                            500             505             510
Gln Gly Asp Phe Ser Met Pro Val Pro Tyr Gln Ile Gly Tyr Asn Tyr
                            515             520             525
```

```
Gly Pro Thr Gly Tyr Ser Phe Lys Phe Ile Trp Arg Thr Val Ser Arg
            530                 535                 540

Gln Pro Phe Asp Ile Pro Cys Cys Phe Phe Ser Tyr Ile Thr Glu Glu
545                 550                 555                 560

<210> SEQ ID NO 29
<211> LENGTH: 931
<212> TYPE: PRT
<213> ORGANISM: simian adenovirus SV-1

<400> SEQUENCE: 29

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ala Glu Trp Thr Asn Ser Asp Ser Lys Val Lys Val
    130                 135                 140

Arg Ala Gln Ala Pro Phe Val Ser Ser Tyr Gly Ala Thr Ala Ile Thr
145                 150                 155                 160

Lys Glu Gly Ile Gln Val Gly Val Thr Leu Thr Asp Ser Gly Ser Thr
                165                 170                 175

Pro Gln Tyr Ala Asp Lys Thr Tyr Gln Pro Glu Pro Gln Ile Gly Glu
            180                 185                 190

Leu Gln Trp Asn Ser Asp Val Gly Thr Asp Asp Lys Ile Ala Gly Arg
        195                 200                 205

Val Leu Lys Lys Thr Thr Pro Met Phe Pro Cys Tyr Gly Ser Tyr Ala
    210                 215                 220

Arg Pro Thr Asn Glu Lys Gly Gly Gln Ala Thr Pro Ser Ala Ser Gln
225                 230                 235                 240

Asp Val Gln Asn Pro Glu Leu Gln Phe Phe Ala Ser Thr Asn Val Ala
                245                 250                 255

Asn Thr Pro Lys Ala Val Leu Tyr Ala Glu Asp Val Ser Ile Glu Ala
            260                 265                 270

Pro Asp Thr His Leu Val Phe Lys Pro Thr Val Thr Glu Gly Ile Thr
        275                 280                 285

Ser Ser Glu Ala Leu Leu Thr Gln Gln Ala Ala Pro Asn Arg Pro Asn
    290                 295                 300

Tyr Ile Ala Phe Arg Asp Asn Phe Ile Gly Leu Met Tyr Tyr Asn Ser
305                 310                 315                 320

Thr Gly Asn Met Gly Val Leu Ala Gly Gln Ala Ser Gln Leu Asn Ala
                325                 330                 335

Val Val Asp Leu Gln Asp Arg Asn Thr Glu Leu Ser Tyr Gln Leu Met
```

```
                  340                 345                 350
Leu Asp Ala Leu Gly Asp Arg Ser Arg Tyr Phe Ser Met Trp Asn Gln
            355                 360                 365
Ala Val Asp Ser Tyr Asp Pro Asp Val Arg Ile Ile Glu Asn His Gly
        370                 375                 380
Val Glu Asp Glu Leu Pro Asn Tyr Cys Phe Pro Leu Gly Gly Met Ala
385                 390                 395                 400
Val Thr Asp Thr Tyr Ser Pro Ile Lys Val Asn Gly Gly Asn Gly
                405                 410                 415
Trp Glu Ala Asn Asn Gly Val Phe Thr Glu Arg Gly Val Glu Ile Gly
            420                 425                 430
Ser Gly Asn Met Phe Ala Met Glu Ile Asn Leu Gln Ala Asn Leu Trp
        435                 440                 445
Arg Ser Phe Leu Tyr Ser Asn Ile Gly Leu Tyr Leu Pro Asp Ser Leu
    450                 455                 460
Lys Ile Thr Pro Asp Asn Ile Thr Leu Pro Glu Asn Lys Asn Thr Tyr
465                 470                 475                 480
Gln Tyr Met Asn Gly Arg Val Thr Pro Pro Gly Leu Val Asp Thr Tyr
                485                 490                 495
Val Asn Val Gly Ala Arg Trp Ser Pro Asp Val Met Asp Ser Ile Asn
            500                 505                 510
Pro Phe Asn His His Arg Asn Ala Gly Leu Arg Tyr Arg Ser Met Leu
        515                 520                 525
Leu Gly Asn Gly Arg Tyr Val Pro Phe His Ile Gln Val Pro Gln Lys
    530                 535                 540
Phe Phe Ala Ile Lys Asn Leu Leu Leu Pro Gly Ser Tyr Thr Tyr
545                 550                 555                 560
Glu Trp Asn Phe Arg Lys Asp Val Asn Met Ile Leu Gln Ser Ser Leu
                565                 570                 575
Gly Asn Asp Leu Arg Val Asp Gly Ala Ser Ile Arg Phe Asp Ser Ile
            580                 585                 590
Asn Leu Tyr Ala Asn Phe Phe Pro Met Ala His Asn Thr Ala Ser Thr
        595                 600                 605
Leu Glu Ala Met Leu Arg Asn Asp Thr Asn Asp Gln Ser Phe Asn Asp
    610                 615                 620
Tyr Leu Cys Ala Ala Asn Met Leu Tyr Pro Ile Pro Ala Asn Ala Thr
625                 630                 635                 640
Ser Val Pro Ile Ser Ile Pro Ser Arg Asn Trp Ala Ala Phe Arg Gly
                645                 650                 655
Trp Ser Phe Thr Arg Leu Lys Thr Lys Glu Thr Pro Ser Leu Gly Ser
            660                 665                 670
Gly Phe Asp Pro Tyr Phe Val Tyr Ser Gly Ser Ile Pro Tyr Leu Asp
        675                 680                 685
Gly Thr Phe Tyr Leu Asn His Thr Phe Lys Lys Val Ser Ile Met Phe
    690                 695                 700
Asp Ser Ser Val Ser Trp Pro Gly Asn Asp Arg Leu Leu Thr Pro Asn
705                 710                 715                 720
Glu Phe Glu Ile Lys Arg Ser Val Asp Gly Glu Gly Tyr Asn Val Ala
                725                 730                 735
Gln Ser Asn Met Thr Lys Asp Trp Phe Leu Ile Gln Met Leu Ser His
            740                 745                 750
Tyr Asn Ile Gly Tyr Gln Gly Phe Tyr Val Pro Glu Asn Tyr Lys Asp
        755                 760                 765
```

```
Arg Met Tyr Ser Phe Phe Arg Asn Phe Gln Pro Met Ser Arg Gln Ile
        770                 775                 780

Val Asp Ser Thr Ala Tyr Thr Asn Tyr Gln Asp Val Lys Leu Pro Tyr
785                 790                 795                 800

Gln His Asn Asn Ser Gly Phe Val Gly Tyr Met Gly Pro Thr Met Arg
                805                 810                 815

Glu Gly Gln Ala Tyr Pro Ala Asn Tyr Pro Tyr Pro Leu Ile Gly Ala
            820                 825                 830

Thr Ala Val Pro Ser Leu Thr Gln Lys Lys Phe Leu Cys Asp Arg Val
                835                 840                 845

Met Trp Arg Ile Pro Phe Ser Ser Asn Phe Met Ser Met Gly Ser Leu
850                 855                 860

Thr Asp Leu Gly Gln Asn Met Leu Tyr Ala Asn Ser Ala His Ala Leu
865                 870                 875                 880

Asp Met Thr Phe Glu Val Asp Pro Met Asp Glu Pro Thr Leu Leu Tyr
                885                 890                 895

Val Leu Phe Glu Val Phe Asp Val Val Arg Ile His Gln Pro His Arg
                900                 905                 910

Gly Val Ile Glu Ala Val Tyr Leu Arg Thr Pro Phe Ser Ala Gly Asn
            915                 920                 925

Ala Thr Thr
        930

<210> SEQ ID NO 30
<211> LENGTH: 363
<212> TYPE: PRT
<213> ORGANISM: simian adenovirus SV-1

<400> SEQUENCE: 30

Met Lys Arg Thr Arg Val Asp Glu Asp Phe Asn Pro Val Tyr Pro Tyr
1               5                   10                  15

Asp Thr Thr Thr Thr Pro Ala Val Pro Phe Ile Ser Pro Pro Phe Val
                20                  25                  30

Asn Ser Asp Gly Leu Gln Glu Asn Pro Pro Gly Val Leu Ser Leu Arg
            35                  40                  45

Ile Ala Lys Pro Leu Tyr Phe Asp Met Glu Arg Lys Leu Ala Leu Ser
50                  55                  60

Leu Gly Arg Gly Leu Thr Ile Thr Ala Ala Gly Gln Leu Glu Ser Thr
65                  70                  75                  80

Gln Ser Val Gln Thr Asn Pro Pro Leu Ile Ile Thr Asn Asn Asn Thr
                85                  90                  95

Leu Thr Leu Arg His Ser Pro Pro Leu Asn Leu Thr Asp Asn Ser Leu
                100                 105                 110

Val Leu Gly Tyr Ser Ser Pro Leu Arg Val Thr Asp Asn Lys Leu Thr
            115                 120                 125

Phe Asn Phe Thr Ser Pro Leu Arg Tyr Glu Asn Glu Asn Leu Thr Phe
130                 135                 140

Asn Tyr Thr Glu Pro Leu Lys Leu Ile Asn Asn Ser Leu Ala Ile Asp
145                 150                 155                 160

Ile Asn Ser Ser Lys Gly Leu Ser Val Gly Gly Ser Leu Ala Val
                165                 170                 175

Asn Leu Ser Ser Asp Leu Lys Phe Asp Ser Asn Gly Ser Ile Ala Phe
                180                 185                 190

Gly Ile Gln Thr Leu Trp Thr Ala Pro Thr Ser Thr Gly Asn Cys Thr
```

```
                195                 200                 205
Val Tyr Ser Glu Gly Asp Ser Leu Ser Leu Cys Leu Thr Lys Cys
210                 215                 220

Gly Ala His Val Leu Gly Ser Val Ser Leu Thr Gly Leu Thr Gly Thr
225                 230                 235                 240

Ile Thr Gln Met Thr Asp Ile Ser Val Thr Ile Gln Phe Thr Phe Asp
                245                 250                 255

Asn Asn Gly Lys Leu Leu Ser Ser Pro Leu Ile Asn Asn Ala Phe Ser
            260                 265                 270

Ile Arg Gln Asn Asp Ser Thr Ala Ser Asn Pro Thr Tyr Asn Ala Leu
        275                 280                 285

Ala Phe Met Pro Asn Ser Thr Ile Tyr Ala Arg Gly Gly Gly Glu
    290                 295                 300

Pro Arg Asn Asn Tyr Tyr Val Gln Thr Tyr Leu Arg Gly Asn Val Gln
305                 310                 315                 320

Lys Pro Ile Ile Leu Thr Val Thr Tyr Asn Ser Val Ala Thr Gly Tyr
                325                 330                 335

Ser Leu Ser Phe Lys Trp Thr Ala Leu Ala Arg Glu Lys Phe Ala Thr
            340                 345                 350

Pro Thr Thr Ser Phe Cys Tyr Ile Thr Glu Gln
        355                 360

<210> SEQ ID NO 31
<211> LENGTH: 560
<212> TYPE: PRT
<213> ORGANISM: simian adenovirus SV-1

<400> SEQUENCE: 31

Met Lys Arg Ala Arg Val Asp Glu Asp Phe Asn Pro Val Tyr Pro Tyr
1               5                   10                  15

Asp Pro Pro His Ala Pro Val Met Pro Phe Ile Thr Pro Pro Phe Thr
                20                  25                  30

Ser Ser Asp Gly Leu Gln Glu Lys Pro Leu Gly Val Leu Ser Leu Asn
            35                  40                  45

Tyr Arg Asp Pro Ile Thr Thr Gln Asn Glu Ser Leu Thr Ile Lys Leu
        50                  55                  60

Gly Asn Gly Leu Thr Leu Asp Asn Gln Gly Gln Leu Thr Ser Thr Ala
65                  70                  75                  80

Gly Glu Val Glu Pro Pro Leu Thr Asn Ala Asn Asn Lys Leu Ala Leu
                85                  90                  95

Val Tyr Ser Asp Pro Leu Ala Val Lys Arg Asn Ser Leu Thr Leu Ser
                100                 105                 110

His Thr Ala Pro Leu Val Ile Ala Asp Asn Ser Leu Ala Leu Gln Val
            115                 120                 125

Ser Glu Pro Ile Phe Ile Asn Asp Lys Asp Lys Leu Ala Leu Gln Thr
        130                 135                 140

Ala Ala Pro Leu Val Thr Asn Ala Gly Thr Leu Arg Leu Gln Ser Ala
145                 150                 155                 160

Ala Pro Leu Gly Ile Ala Asp Gln Thr Leu Lys Leu Leu Phe Thr Asn
                165                 170                 175

Pro Leu Tyr Leu Gln Asn Asn Phe Leu Thr Leu Ala Ile Glu Arg Pro
            180                 185                 190

Leu Ala Ile Thr Asn Thr Gly Lys Leu Ala Leu Gln Leu Ser Pro Pro
        195                 200                 205
```

```
Leu Gln Thr Ala Asp Thr Gly Leu Thr Leu Gln Thr Asn Val Pro Leu
210                 215                 220
Thr Val Ser Asn Gly Thr Leu Gly Leu Ala Ile Lys Arg Pro Leu Ile
225                 230                 235                 240
Ile Gln Asp Asn Leu Phe Leu Asp Phe Arg Ala Pro Leu Arg Leu
    245                 250                 255
Phe Asn Ser Asp Pro Val Leu Gly Leu Asn Phe Tyr Thr Pro Leu Ala
        260                 265                 270
Val Arg Asp Glu Ala Leu Thr Val Asn Thr Gly Arg Gly Leu Thr Val
            275                 280                 285
Ser Tyr Asp Gly Leu Ile Leu Asn Leu Gly Lys Asp Leu Arg Phe Asp
290                 295                 300
Asn Asn Thr Val Ser Val Ala Leu Ser Ala Ala Leu Pro Leu Gln Tyr
305                 310                 315                 320
Thr Asp Gln Leu Arg Leu Asn Val Gly Ala Gly Leu Arg Tyr Asn Pro
                325                 330                 335
Val Ser Lys Lys Leu Asp Val Asn Pro Asn Gln Asn Lys Gly Leu Thr
                340                 345                 350
Trp Glu Asn Asp Tyr Leu Ile Val Lys Leu Gly Asn Gly Leu Gly Phe
                355                 360                 365
Asp Gly Asp Gly Asn Ile Ala Val Ser Pro Gln Val Thr Ser Pro Asp
370                 375                 380
Thr Leu Trp Thr Thr Ala Asp Pro Ser Pro Asn Cys Ser Ile Tyr Thr
385                 390                 395                 400
Asp Leu Asp Ala Lys Met Trp Leu Ser Leu Val Lys Gln Gly Gly Val
                405                 410                 415
Val His Gly Ser Val Ala Leu Lys Ala Leu Lys Gly Thr Leu Leu Ser
                420                 425                 430
Pro Thr Glu Ser Ala Ile Val Ile Leu His Phe Asp Asn Tyr Gly
                435                 440                 445
Val Arg Ile Leu Asn Tyr Pro Thr Leu Gly Thr Gln Gly Thr Leu Gly
                450                 455                 460
Asn Asn Ala Thr Trp Gly Tyr Arg Gln Gly Glu Ser Ala Asp Thr Asn
465                 470                 475                 480
Val Leu Asn Ala Leu Ala Phe Met Pro Ser Ser Lys Arg Tyr Pro Arg
                485                 490                 495
Gly Arg Gly Ser Glu Val Gln Asn Gln Thr Val Gly Tyr Thr Cys Ile
                500                 505                 510
Gln Gly Asp Phe Ser Met Pro Val Pro Tyr Gln Ile Gln Tyr Asn Tyr
                515                 520                 525
Gly Pro Thr Gly Tyr Ser Phe Lys Phe Ile Trp Arg Thr Val Ser Arg
530                 535                 540
Gln Pro Phe Asp Ile Pro Cys Cys Phe Phe Ser Tyr Ile Thr Glu Glu
545                 550                 555                 560

<210> SEQ ID NO 32
<211> LENGTH: 31044
<212> TYPE: DNA
<213> ORGANISM: simian adenovirus SV-25
<220> FEATURE:
<221> NAME/KEY: CDS
<222> LOCATION: (12284)..(13801)
<223> OTHER INFORMATION: Penton
<220> FEATURE:
<221> NAME/KEY: CDS
<222> LOCATION: (16681)..(19446)
<223> OTHER INFORMATION: Hexon
```

```
<220> FEATURE:
<221> NAME/KEY: CDS
<222> LOCATION: (25380)..(26423)
<223> OTHER INFORMATION: Fiber #2
<220> FEATURE:
<221> NAME/KEY: CDS
<222> LOCATION: (26457)..(28136)
<223> OTHER INFORMATION: Fiber #1

<400> SEQUENCE: 32
```

| | | | | | |
|---|---|---|---|---|---|
| catcatcaat | aatatacctt | attctggaaa | cgtgccaata | tgataatgag | cggggaggag | 60 |
| cgaggcgggg | ccggggtgac | gtgcggtgac | gcggggtggc | gcgagggcgg | ggcgaagggc | 120 |
| gcgggtgtgt | gtgtgggagg | cgcttagttt | ttacgtatgc | ggaaggaggt | tttataccgg | 180 |
| aagatgggta | atttggcgt | atacttgtaa | gttttgtgta | atttggcgcg | aaaactgggt | 240 |
| aatgaggaag | ttgaggttaa | tatgtacttt | ttatgactgg | gcggaatttc | tgctgatcag | 300 |
| cagtgaactt | tgggcgctga | cggggaggtt | tcgctacgtg | acagtaccac | gagaaggctc | 360 |
| aaaggtccca | tttattgtac | tcttcagcgt | tttcgctggg | tatttaaacg | ctgtcagatc | 420 |
| atcaagaggc | cactcttgag | tgctggcgag | aagagttttc | tcctccgtgc | tgccacgatg | 480 |
| aggctggtcc | ccgagatgta | cggtgttttt | agcgacgaga | cggtgcgtaa | ctcagatgac | 540 |
| ctgctgaatt | cagacgcgct | ggaaatttcc | aattcgcctg | tgctttcgcc | gccgtcactt | 600 |
| cacgacctgt | ttgtgttttg | gctcaacgct | tagcaacgtg | ttatataggg | tcaagaagga | 660 |
| gcaggagacg | cagtttgcta | ggctgttggc | cgatactcct | ggagttttg | tggctctgga | 720 |
| tctaggccat | cactctcttt | tccaagagaa | aattatcaaa | aacttaactt | ttacgtctcc | 780 |
| tggtcgcacg | gttgcttccg | ctgcctttat | tacctatatt | ttggatcaat | ggagcaacag | 840 |
| cgacagccac | ctgtcgtggg | agtacatgct | ggattacatg | tcgatggcgc | tgtggagggc | 900 |
| catgctgcgg | aggagggttt | gcatttactt | gcgggcgcag | cctccgcggc | tggaccgagt | 960 |
| ggaggaggag | gacgagccgg | gggagaccga | gaacctgagg | gccgggctgg | accctccaac | 1020 |
| ggaggactag | gtgctgagga | tgatcccgaa | gaggggacta | gtggggctag | gaagaagcaa | 1080 |
| aagactgagt | ctgaacctcg | aaactttttg | aatgagttga | ctgtgagttt | gatgaatcgt | 1140 |
| cagcgtccgg | agacaatttt | ctggtctgaa | ttggaggagg | aattcaggag | ggggaactg | 1200 |
| aacctgctat | acaagtatgg | gtttgaacag | ttaaaaactc | actggttgga | gccgtgggag | 1260 |
| gattttgaaa | ccgccttgga | cacttttgct | aaagtggctc | tgcggccgga | taaggtttac | 1320 |
| actatccgcc | gcactgttaa | cataaagaag | agtgtttatg | ttataggcca | tggagctctg | 1380 |
| gtgcaggtgc | aaaccgtcga | ccgggtggcc | tttagttgcg | gtatgcaaaa | tctgggcccc | 1440 |
| ggggtgatag | gcttaaatgg | tgtaacattt | cacaatgtaa | ggtttactgg | tgaaagtttt | 1500 |
| aacggctctg | tgtttgcaaa | taacacacag | ctgacgctcc | acggcgttta | ctttttaac | 1560 |
| tttaataaca | catgtgtgga | gtcgtggggc | agggtgtctt | tgagggctg | ctgttttcac | 1620 |
| ggctgctgga | aggcggtggt | gggaagactt | aaaagtgtaa | catctgtaaa | aaaatgcgtg | 1680 |
| tttgagcggt | gtgtgttggc | tttaactgtg | gagggctgtg | gacgcattag | gaataatgcg | 1740 |
| gcgtctgaga | atggatgttt | tcttttgcta | aaaggcacgg | ctagtattaa | gcataacatg | 1800 |
| atatgcggca | gcggtctgta | cccttcacag | ctgttaactt | gcgcggatgg | aaactgtcag | 1860 |
| accttgcgca | ccgtgcacat | agcgtcccac | cagcgccgcg | cctggccaac | attcgagcac | 1920 |
| aatatgctta | tgcgttgtgc | cgtccacttg | ggcctaggc | gaggcgtgtt | tgtgccttac | 1980 |
| cagtgtaact | ttagccatac | caagatttta | ctagaacctg | ataccttctc | tcgagtgtgt | 2040 |

```
ttcaatgggg tgtttgacat gtcaatggaa ctgtttaaag tgataagata tgatgaatcc    2100
aagtctcgtt gtcgcccatg tgaatgcgga gctaatcatc tgaggttgta tcctgtaacc    2160
ctaaacgtta ccgaggagct gaggacggat caccacatgt tgtcctgcct gcgcaccgac    2220
tatgaatcca gcgacgagga gtgaggtgag gggcggagcc acaaagggta taaaggggcg    2280
tgaggggtgg gtgtgatgat tcaaaatgag cgggacgacg gacggcaacg cgtttgaggg    2340
tggagtgttc agcccttatc tgacatctcg tcttccttcc tgggcaggag tgcgtcagaa    2400
tgtagtgggc tccaccgtgg acggacgacc ggtcgcccct gcaaattccg ccaccctcac    2460
ctatgccacc gtgggatcat cgttggacac tgccgcggca gctgccgctt ctgctgccgc    2520
ttctactgct cgcggcatgg cggctgattt tggactgtat aaccaactgg ccactgcagc    2580
tgtggcgtct cggtctctgg ttcaagaaga tgccctgaat gtgatcctga ctcgcctgga    2640
gatcatgtca cgtcgcttgg acgaactggc tgcgcagata tcccaagcta accccgatac    2700
cacttcagaa tcctaaaata aagacaaaca aatatgttga aaagtaaaat ggctttattt    2760
gttttttttg gctcggtagg ctcgggtcca cctgtctcgg tcgttaagaa ctttgtgtat    2820
gttttccaaa acacggtaca gatgggcttg gatgttcaag tacatgggca tgaggccatc    2880
tttggggtga agataggacc attgaagagc gtcatgctcc ggggtggtgt tgtaaattac    2940
ccagtcgtag cagggtttct gggcgtggaa ctggaagatg tcctttagga gtaggctgat    3000
ggccaagggc aggcccttag tgtaggtgtt tacaaagcgg ttaagctggg agggatgcat    3060 gcgggggag atgatatgca tcttggcttg gatcttgagg ttagctatgt taccacccag    3120
gtctctgcgg gggttcatgt tatgaaggac caccagcacg tgtagccggg tgcatttggg    3180
gaacttgtca tgcagtttgg aggggaaggc gtggaagaat ttagagaccc ccttgtggcc    3240
ccctaggttt tccatgcact catccataat gatggcaatg ggacccctgg cggccgcttt    3300
ggcaaacacg ttttgggggt tggaaacatc atagttttgc tctagagtga gctcatcata    3360
ggccatctta acaaagcggg gtaggagggt gcccgactgg gggatgatag ttccatctgg    3420
gcctggggcg tagttaccct cacagatctg catctcccag gccttaattt ccgagggggg    3480
tatcatgtcc acctggggggg caataaagaa cacggttttct ggcgggggat tgatgagctg    3540
ggtggaaagc aagttacgca gcagttgaga tttgccacag ccggtggggc cgtagatgac    3600
cccgatgacg ggttgcagct ggtagttgag agaggaacag ctgccgtcgg ggcgcaggag    3660
gggggctacc tcattcatca tgcttctaac atgtttattt tcactcacta agttttgcaa    3720
gagcctctcc ccacccaggg ataagagttc ttccaggctg ttgaagtgtt tcagcggttt    3780
taggccgtcg gccatgggca tcttttcgag cgactgacga agcaagtaca gtcggtccca    3840
gagctcggtg acgtgctcta tggaatctcg atccagcaga cttcttggtt gcggggttg    3900 ggtcgacttt cgctgtaggg caccagccgg tgggcgtcca gggccgcgag ggttctgtcc    3960
ttccagggtc tcagcgtccg ggtgagggtg gtctcggtga cggtgaaggg atgagcccg    4020 ggctgggcgc ttgcgagggt gcgcttcagg ctcatcctgc tggtgctgaa gcggacgtcg    4080
tctccctgtg agtcggccag atagcaacga agcatgaggt cgtagctgag ggactcggcc    4140
gcgtgtccct ggcgcgcag ctttcccttg gaaacgtgct gacatttggt gcagtgcaga    4200
cattggaggg cgtagagttt gggggccagg aagaccgact cgggcgagta ggcgtcggct    4260
ccgcactgag cgcagacggt ctcgcactcc actagccacg tgagctcggg tttagcggga    4320
tcaaaaacca agttgcctcc atttttttg atgcgtttct taccttgcgt ttccatgagt    4380
ttgtggcccg cttccgtgac aaaaaggctg tcggtgtctc cgtagacaga cttgaggggg    4440
```

```
cgatcttcca aaggtgttcc gaggtcttcc gcgtacagga actgggacca ctccgagacg    4500
aaggctctgg tccaggctaa cacgaaggag gcaatctgcg aggggtatct gtcgttttca    4560
atgagggggt ccacctttc cagggtgtgc agacacaggt cgtcctcctc cgcgtccacg     4620
aaggtgattg gcttgtaagt gtaggtcacg tgatctgcac cccccaaagg ggtataaaag    4680
ggggcgtgcc caccctctcc gtcactttct tccgcatcgc tgtggaccag agccagctgt    4740
tcgggtgagt aggccctctc aaaagccggc atgatctcgg cgctcaagtt gtcagtttct    4800
acaaacgagg tggatttgat attcacgtgc cccgcggcga tgcttttgat ggtggagggg    4860
tccatctgat cagaaaacac gatcttttg ttgtcaagtt tggtggcgaa agacccgtag     4920
agggcgttgg aaagcaactt ggcgatggag cgcagggtct gatttttctc ccgatcggcc    4980
ctctccttgg cggcgatgtt gagttgcacg tactcccggg ccgcgcaccg ccactcgggg    5040
aacacggcgg tgcgctcgtc gggcaggatg cgcacgcgcc agccgcgatt gtgcagggtg    5100
atgaggtcca cgctggtagc cacctccccg cggaggggc cgttggtcca acacaatcgc     5160 ccccctttc tggagcagaa cggaggcagg ggatctagca agttggcggg cgggggtcg      5220 gcgtcgatgt tgaagatacc gggtagcagg atcttattaa aataatcgat ttcggtgtcc    5280
gtgtcttgca acgcgtcttc ccacttcttc accgccaggg ccctttcgta gggattcagg    5340
ggcggtcccc agggcatggg gtgggtcagg gccgaggcgt acatgccgca gatgtcatac    5400
acgtacaggg gttccctcaa cacccccgatg taagtggggt aacagcgccc ccgcggatg    5460 ctggctcgca cgtagtcgta catctcgcgc gaggagccca tgaggccgtc tcccaagtgg    5520
gtcttgtggg gtttttcggc ccggtagagg atctgtctga agatggcgtg ggagttggaa    5580
gagatggtgg ggcgttggaa gacgttaaag ttggccccgg gtagtcccac ggagtcttgg    5640
atgaactggg cgtaggattc ccggagtttg tccaccaggg cggcggtcac cagcacgtcg    5700
agagcgcagt agtccaacgt ctcgcggacc aggttgtagg ccgtctcttg tttttctcc     5760 cacagttcgc ggttgaggag gtattcctcg cggtctttcc agtactcttc ggcgggaaat    5820 ccttttcgt ccgctcggta agaacctaac atgtaaaatt cgttaccgc tttgtatgga     5880 caacagcctt tttctaccgg cagggcgtac gcttgagcgg cctttctgag agaggtgtgg    5940
gtgagggcga aggtgtcccg caccatcact ttcaggtact gatgttgaa gtccgtgtcg     6000 tcgcaggcgc cctgttccca cagcgtgaag tcggtgcgct tttctgcct gggattgggg     6060 agggcgaagg tgacatcgtt aaagagtatt ttcccggcgc ggggcatgaa gttgcgagag    6120
atcctgaagg gcccgggcac gtccgagcgg ttgttgatga cctgcgccgc caggacgatc    6180
tcgtcgaagc cgttgatgtt gtgacccacg atgtaaagtt cgatgaagcg cggctgtccc    6240
ttgagggccg gcgcttttt caactcctcg taggtgagac agtccggcga ggagagaccc     6300
agctcagccc gggcccagtc ggagagttga ggattagccg caaggaagga gctccataga    6360
tccaaggcca ggagagtttg caagcggtcg cggaactcgc ggaactttt ccccacggcc     6420 attttctccg gtgtcactac gtaaaaggtg ttggggcggt tgttccacac gtcccatcgg    6480
agctctaggg ccagctcgca ggcttggcga acgagggtct cctcgccaga gacgtgcatg    6540
accagcataa agggtaccaa ctgtttccg aacgagccca tccatgtgta ggtttctacg     6600
tcgtaggtga caaagagccg ctgggtgcgc gcgtgggagc cgatcggaaa gaagctgatc    6660
tcctgccacc agctggagga atgggtgtta atgtggtgga agtagaagtc ccgcggcgc     6720 acagagcatt cgtgctgatg tttgtaaaag cgaccgcagt agtcgcagcg ctgcacgctc    6780
```

```
tgtatctcct gaacgagatg cgcttttcgc ccgcgcacca gaaaccggag ggggaagttg    6840
agacgggggg ctggtggggc gacatccect tegcettggc ggtgggagte tgcgtctgcg    6900
tcctccttct ctgggtggac gacggtgggg acgacgacgc cccgggtgcc gcaagtccag    6960
atctccgcca cggaggggtg caggcgctgc aggaggggac gcagctgccc gctgtccagg    7020
gagtcgaggg aagtcgcgct gaggtcggcg ggaagcgttt gcaagttcac tttcagaaga    7080
ccggtaagag cgtgagccag gtgcagatgg tacttgattt ccaggggggt gttggatgaa    7140
gcgtccacgg cgtagaggag tccgtgtccg cgcggggcca ccaccgtgcc ccgaggaggt    7200
tttatctcac tcgtcgaggg cgagcgccgg ggggtagagg cggctctgcg ccgggggggca   7260
gcggaggcag aggcacgttt tcgtgaggat tcggcagcgg ttgatgacga gcccggagac    7320
tgctggcgtg ggcgacgacg cggcggttga ggtcctggat gtgccgtctc tgcgtgaaga    7380
ccaccggccc ccgggtcctg aacctaaaga gagttccaca gaatcaatgt ctgcatcgtt    7440
aacggcggcc tgcctgagga tctcctgcac gtcgcccgag ttgtcctgat aggcgatctc    7500
ggccatgaac tgttccactt cttcctcgcg gaggtcaccg tggcccgctc gctccacggt    7560
ggcggccagg tcgttggaga tgcggcgcat gagttgagag aaggcgttga ggccgttctc    7620
gttccacacg cggctgtaca ccacgtttcc gaaggagtcg cgcgctcgca tgaccacctg    7680
ggccacgttg agttccacgt ggcgggcgaa gacggcgtag tttctgaggc gctggaagag    7740
gtagttgagc gtggtggcga tgtgctcgca gacgaagaag tacataatcc agcgccgcag    7800
ggtcatctcg ttgatgtctc cgatggcttc gagacgctcc atggcctcgt agaagtcgac    7860
ggcgaagttg aaaaattggg agttgcgggc ggccaccgtg agttcttctt gcaggaggcg    7920
gatgagatcg gcgaccgtgt cgcgcacctc ctgttcgaaa gcgccccgag gcgcctctgc    7980
ttcttcctcc ggctcctcct cttccagggg ctcgggttcc tccggcagct ctgcgacggg    8040
gacggggcgg cgacgtcgtc gtctgaccgg caggcggtcc acgaagcgct cgatcatttc    8100
gccgcgccgg cgacgcatgg tctcggtgac ggcgcgtccg ttttcgcgag gtcgcagttc    8160
gaagacgccg ccgcgcagag cgccccegtg cagggagggt aagtggttag ggccgtcggg    8220
cagggacacg cgcctgacga tgcatttttat caattgctgc gtaggcactc cgtgcaggga    8280
tctgagaacg tcgaggtcga cgggatccga gaacttctct aggaaagcgt ctatccaatc    8340
gcaatcgcaa ggtaagctga gaacggtggg tcgctgggggg cgttcgcgg gcagttggga    8400
ggtgatgctg ctgatgatgt aattaaagta ggcggtcttc aggcggcgga tggtggcgag    8460
gaggaccacg tctttgggcc cggcctgttg aatgcgcagg cgctcggcca tgccccaggc    8520
ctcgctctga cagcgacgca ggtctttgta gaagtcttgc atcagtctct ccaccggaac    8580
ctctgcttct cccctgtctg ccatgcgagt cgagccgaac ccccgcaggg gctgcagcaa    8640
cgctaggtcg gccacgaccc tttcggccag cacggcctgt tgaatctgcg tgagggtggc    8700
ctggaagtcg tccaggtcca cgaagcggta ataggccccc gtgttgatgg tgtaggtgca    8760
gttggccatg acggaccagt tgacgacttg catgccgggt tgggtgatct ccgtgtactt    8820
gaggcgcgag taggccctgg actcgaacac gtagtcgttg catgtgcgca ccagatactg    8880
gtagccgacc aggaagtgag gaggcggctc tcggtacagg ggccagccaa cggtggcggg    8940
ggcgccgggg gacaggtcgt ccagcatgag gcggtggtag tggtagatgt agcgggagag    9000
ccaggtgatg ccggccgagg tggttgcggc cctggtgaat tcgcggacgc ggttccagat    9060
gttgcgcagg gaccaaaagc gctccatggt gggcacgctc tgccccgtga ggcgggcgca    9120
atcttgtacg ctctagatgg aaaaaagaca gggcggtcat cgactccttt ccgtagcttg    9180
```

```
gggggtaaag tcgcaagggt gcggcggcgg ggaaccccgg ttcgagaccg gccggatccg   9240
ccgctcccga tgcgcctggc cccgcatcca cgacgtccgc gccgagaccc agccgcgacg   9300
ctccgcccca atacggaggg gagtctttg gtgttttttc gtagatgcat ccggtgctgc   9360
ggcagatgcg accccagacg cccactacca ccgccgtggc ggcagtaaac ctgagcggag   9420
gcggtgacag ggaggaggaa gagctggctt tagacctgga agagggagag gggctggccc   9480
ggctgggagc gccatcccca gagagacacc ctagggttca gctcgtgagg gacgccaggc   9540
aggcttttgt gccgaagcag aacctgttta gggaccgcag cggtcaggag cggaggagaa   9600
tgcgcgattg caggtttcgg gcgggcagag agctcagggc gggcttcgat cgggagcggc   9660
tcctgagggc ggaggatttc gagcccgacg agcgttctgg ggtgagcccg gcccgcgctc   9720
acgtatcggc ggccaacctg gtgagcgcgt acgagcagac ggtgaacgag gagcgcaact   9780
tccaaaagag ctttaacaat cacgtgagga ccctgatcgc gagggaggag gtgaccatcg   9840
ggctgatgca tctgtgggac ttcgtggagg cctacgtgca gaacccggct agcaaacccc   9900
tgacggccca gctgttcctg atcgtgcagc acagccgcga caacgagacg ttccgcgacg   9960
ccatgttgaa catcgcggag cccgagggtc gctggctctt ggatctgatt aacatcctgc  10020
agagcatcgt ggtgcaggag aggggcctga gtttagcgga caaggtggcg gccattaact  10080
attcgatgca gagcctgggg aagttctacg ctcgcaagat ctacaagagc ccttacgtgc  10140
ccatagacaa ggaggtgaag atagacagct tttacatgcg catggcgctg aaggtgctga  10200
cgctgagcga cgacctcggc gtgtaccgta acgacaagat ccacaaggcg gtgagcgcca  10260
gccgccggcg ggagctgagc gacagggagc tgatgcacag cctgcagagg gcgctggcgg  10320
gcgccgggga cgaggagcgc gaggcttact tcgacatggg agccgatctg cagtggcgtc  10380
ccagcgcgcg cgccttggag gcggcgggtt atcccgacga ggaggatcgg gacgatttgg  10440
aggaggcagg cgagtacgag gacgaagcct gaccgggcag gtgttgtttt agatgcagcg  10500
gccggcggac gggaccaccg cggatcccgc acttttggca tccatgcaga gtcaaccttc  10560
gggcgtgacc gcctccgatg actgggcggc ggccatggac cgcatcatgg cgctgaccac  10620
ccgcaacccc gaggctttta ggcagcaacc ccaggccaac cgttttcgg ccatcttgga  10680 agcggtggtg ccgtcgcgca ccaacccgac gcacgagaaa gtcctgacta tcgtgaacgc  10740
cctggtagac agcaaggcca tccgccgtga cgaggcgggc ttgatttaca acgtctcttt  10800
ggaacgcgtg gcgcgctaca acagcactaa cgtgcagacc aatctggacc gcctcaccac  10860
cgacgtgaag gaggcgctgg cgcagaagga gcggttctg agggacagta atctgggctc  10920
tctggtggca ctgaacgcct tcctgagctc acagccggcc aacgtgcccc gcgggcagga  10980
ggattacgtg agcttcatca gcgctctgag actgctggtg tccgaggtgc cccagagcga  11040
ggtgtaccag tctgggccgg attacttttt ccagacgtcc cgacagggct tgcaaacggt  11100
gaacctgact caggccttta aaaacttgca aggcatgtgg ggggtcaagg ccccggtggg  11160
cgatcgcgcc actatctcca gtctgctgac ccccaacact cgcctgctgc tgctcttgat  11220
cgcaccgttt accaacagta gcactatcag ccgtgactcg tacctgggtc atctcatcac  11280
tctgtaccgc gaggccatcg gccaggctca gatcgacgag catacgtatc aggagattac  11340
taacgtgagc cgtgcctgg gtcaggaaga taccggcagc ctggaagcca cgttgaactt  11400
tttgctaacc aaccggaggc aaaaaatacc ctcccagttc acgttaagcg ccgaggagga  11460
gaggattctg cgatacgtgc agcagtccgt gagcctgtac ttgatgcgcg agggcgccac  11520
```

```
                                                        -continued
cgcttccacg gctttagaca tgacggctcg gaacatggaa ccgtcctttt actccgccca   11580
ccggccgttc attaaccgtc tgatggacta cttccatcgc gcggccgcca tgaacgggga   11640
gtacttcacc aatgccatcc tgaatccgca ttggatgccc ccgtccggct tctacaccgg   11700
ggagtttgac ctgcccgaag ccgacgacgg ctttctgtgg gacgacgtgt ccgatagcat   11760
tttcacgccg gctaatcgcc gattccagaa gaaggagggc ggagacgagc tccccctctc   11820
cagcgtggaa gcggcctcaa ggggagagag tcccttttcca agtctgtctt ccgccagtag   11880
cggtcgggta acgcgtccac ggttgccggg ggagagcgac tacctgaacg acccccttgct   11940 gcgaccggct agaaagaaaa atttcccaa taacggggtg gaaagcttgg tggataaaat     12000
gaatcgttgg aagacgtacg cccaggagca gcgggagtgg gaggacagtc agccgcggcc   12060
gctggtaccg ccgcattggc gtcgccagag agaagacccg gacgactccg cagacgatag   12120
tagcgtgttg gacctgggag ggagcggagc caaccccttt gctcacttgc aacccaaggg   12180
gcgctcgagt cgcctgtatt aataaaaaag acgcggaaac ttaccagagc catggccaca   12240
gcgtgtgtgc tttcttcctc tctttcttcc tcggcgcggc aga atg aga aga gcg     12295
                                                    Met Arg Arg Ala
                                                      1 gtg aga gtc acg ccg gcg gcg tat gag ggc ccg ccc cct tct tac gaa     12343
Val Arg Val Thr Pro Ala Ala Tyr Glu Gly Pro Pro Pro Ser Tyr Glu
  5              10                  15                  20 agc gtg atg gga tca gcg aac gtg ccg gcc acg ctg gag gcg cct tac     12391
Ser Val Met Gly Ser Ala Asn Val Pro Ala Thr Leu Glu Ala Pro Tyr
             25                  30                  35 gtt cct ccc aga tac ctg gga cct acg gag ggc aga aac agc atc cgt     12439
Val Pro Pro Arg Tyr Leu Gly Pro Thr Glu Gly Arg Asn Ser Ile Arg
         40                  45                  50 tac tcc gag ctg gcg ccc ctg tac gat acc acc aag gtg tac ctg gtg     12487
Tyr Ser Glu Leu Ala Pro Leu Tyr Asp Thr Thr Lys Val Tyr Leu Val
             55                  60                  65 gac aac aag tcg gcg gac atc gcc tcc ctg aat tac caa aac gat cac     12535
Asp Asn Lys Ser Ala Asp Ile Ala Ser Leu Asn Tyr Gln Asn Asp His
 70                  75                  80 agt aac ttt ctg act acc gtg gtg cag aac aat gac ttc acc ccg acg     12583
Ser Asn Phe Leu Thr Thr Val Val Gln Asn Asn Asp Phe Thr Pro Thr
 85                  90                  95                 100 gag gcg ggc acg cag acc att aac ttt gac gag cgt tcc cgc tgg ggc     12631
Glu Ala Gly Thr Gln Thr Ile Asn Phe Asp Glu Arg Ser Arg Trp Gly
             105                 110                 115 ggt cag ctg aaa acc atc ctg cac acc aac atg ccc aac atc aac gag     12679
Gly Gln Leu Lys Thr Ile Leu His Thr Asn Met Pro Asn Ile Asn Glu
         120                 125                 130 ttc atg tcc acc aac aag ttc agg gct aag ctg atg gta gaa aaa agt     12727
Phe Met Ser Thr Asn Lys Phe Arg Ala Lys Leu Met Val Glu Lys Ser
     135                 140                 145 aat gcg gaa act cgg cag ccc cga tac gag tgg ttc gag ttt acc att     12775
Asn Ala Glu Thr Arg Gln Pro Arg Tyr Glu Trp Phe Glu Phe Thr Ile
 150                 155                 160 cca gag ggc aac tat tcc gaa act atg act atc gat ctc atg aat aac     12823
Pro Glu Gly Asn Tyr Ser Glu Thr Met Thr Ile Asp Leu Met Asn Asn
165                 170                 175                 180 gcg atc gtg gac aat tac ctg caa gtg ggg aga cag aac ggg gtg ctg     12871
Ala Ile Val Asp Asn Tyr Leu Gln Val Gly Arg Gln Asn Gly Val Leu
             185                 190                 195 gaa agc gat atc ggc gtg aaa ttc gat acc aga aac ttc cga ctg ggg     12919
Glu Ser Asp Ile Gly Val Lys Phe Asp Thr Arg Asn Phe Arg Leu Gly
         200                 205                 210
```

| | | |
|---|---|---|
| tgg gat ccc gtg acc aag ctg gtg atg cca ggc gtg tac acc aac gag<br>Trp Asp Pro Val Thr Lys Leu Val Met Pro Gly Val Tyr Thr Asn Glu<br>    215                    220                    225 | | 12967 |
| gct ttt cac ccg gac atc gtg ctg ctg ccg ggg tgc ggt gtg gac ttc<br>Ala Phe His Pro Asp Ile Val Leu Leu Pro Gly Cys Gly Val Asp Phe<br>230                    235                    240 | | 13015 |
| act cag agc cgt ttg agt aac ctg tta gga att aga aag cgc cgc ccc<br>Thr Gln Ser Arg Leu Ser Asn Leu Leu Gly Ile Arg Lys Arg Arg Pro<br>245                    250                    255                    260 | | 13063 |
| ttc caa gag ggc ttt caa atc atg tat gag gac ctg gag gga ggt aat<br>Phe Gln Glu Gly Phe Gln Ile Met Tyr Glu Asp Leu Glu Gly Gly Asn<br>                  265                    270                    275 | | 13111 |
| ata ccc gcc tta ctg gac gtg tcg aag tac gaa gct agc ata caa cgc<br>Ile Pro Ala Leu Leu Asp Val Ser Lys Tyr Glu Ala Ser Ile Gln Arg<br>280                    285                    290 | | 13159 |
| gcc aaa gcg gag ggt aga gag att cgg gga gac acc ttt gcg gta gct<br>Ala Lys Ala Glu Gly Arg Glu Ile Arg Gly Asp Thr Phe Ala Val Ala<br>                  295                    300                    305 | | 13207 |
| ccc cag gac ctg gaa ata gtg cct tta act aaa gac agc aaa gac aga<br>Pro Gln Asp Leu Glu Ile Val Pro Leu Thr Lys Asp Ser Lys Asp Arg<br>310                    315                    320 | | 13255 |
| agc tac aat att ata aac aac acg acg gac acc ctg tat cgg agc tgg<br>Ser Tyr Asn Ile Ile Asn Asn Thr Thr Asp Thr Leu Tyr Arg Ser Trp<br>325                    330                    335                    340 | | 13303 |
| ttt ctg gct tac aac tac gga gac ccc gag aaa gga gtg aga tca tgg<br>Phe Leu Ala Tyr Asn Tyr Gly Asp Pro Glu Lys Gly Val Arg Ser Trp<br>                  345                    350                    355 | | 13351 |
| acc ata ctc acc acc acg gac gtg acc tgt ggc tcg cag caa gtg tac<br>Thr Ile Leu Thr Thr Thr Asp Val Thr Cys Gly Ser Gln Gln Val Tyr<br>                    360                    365                    370 | | 13399 |
| tgg tcc ctg ccg gat atg atg caa gac ccg gtc acc ttc cgc ccc tcc<br>Trp Ser Leu Pro Asp Met Met Gln Asp Pro Val Thr Phe Arg Pro Ser<br>                  375                    380                    385 | | 13447 |
| acc caa gtc agc aac ttc ccg gtg gtg ggc acc gag ctg ctg ccc gtc<br>Thr Gln Val Ser Asn Phe Pro Val Val Gly Thr Glu Leu Leu Pro Val<br>390                    395                    400 | | 13495 |
| cat gcc aag agc ttc tac aac gag cag gcc gtc tac tcg caa ctt att<br>His Ala Lys Ser Phe Tyr Asn Glu Gln Ala Val Tyr Ser Gln Leu Ile<br>405                    410                    415                    420 | | 13543 |
| cgc cag tcc acc gcg ctt acc cac gtg ttc aat cgc ttt ccc gag aac<br>Arg Gln Ser Thr Ala Leu Thr His Val Phe Asn Arg Phe Pro Glu Asn<br>                  425                    430                    435 | | 13591 |
| cag att ctg gtg cgc cct ccc gct cct acc att acc acc gtc agt gaa<br>Gln Ile Leu Val Arg Pro Pro Ala Pro Thr Ile Thr Thr Val Ser Glu<br>                    440                    445                    450 | | 13639 |
| aac gtt ccc gcc ctc aca gat cac gga acc ctg ccg ctg cgc agc agt<br>Asn Val Pro Ala Leu Thr Asp His Gly Thr Leu Pro Leu Arg Ser Ser<br>                  455                    460                    465 | | 13687 |
| atc agt gga gtt cag cgc gtg acc atc acc gac gcc aga cgt cga acc<br>Ile Ser Gly Val Gln Arg Val Thr Ile Thr Asp Ala Arg Arg Arg Thr<br>470                    475                    480 | | 13735 |
| tgc ccc tac gtt tac aaa gcg ctt ggc gtg gtg gct cct aaa gtt ctt<br>Cys Pro Tyr Val Tyr Lys Ala Leu Gly Val Val Ala Pro Lys Val Leu<br>485                    490                    495                    500 | | 13783 |
| tct agt cgc acc ttc taa aaacatgtcc atcctcatct ctcccgataa<br>Ser Ser Arg Thr Phe<br>                  505 | | 13831 |
| caacaccggc tggggactgg gctccggcaa gatgtacggc ggagccaaaa ggcgctccag | | 13891 |

```
tcagcaccca gttcgagttc ggggccactt ccgcgctcct tggggagctt acaagcgagg   13951
actctcgggt cgaacggctg tagacgatac catagatgcc gtgattgccg acgcccgccg   14011
gtacaacccc ggaccggtcg ctagcgccgc ctccaccgtg gattccgtga tcgacagcgt   14071
ggtagccggc gctcgggcct atgctcgccg caagaggcgg ctgcatcgga gacgtcgccc   14131
caccgccgcc atgctggcag ccagggccgt gctgaggcgg gcccggaggg caggcagaag   14191
ggctatgcgc cgcgctgccg ccaacgccgc cgccggaggg cccgccgac aggctgcccg    14251 ccaggctgcc gctgccatcg ctagcatggc cagacccagg agagggaacg tgtactgggt   14311
gcgtgattct gtgacgggag tccgagtgcc ggtgcgcagc cgacctcccc gaagttagaa   14371
gatccaagct gcgaagacgg cggtactgag tctccctgtt gttatcagcc caacatgagc   14431
aagcgcaagt ttaaagaaga actgctgcag acgctggtgc ctgagatcta tggccctccg   14491
gacgtgaagc cagacattaa gccccgcgat atcaagcgtg ttaaaaagcg ggaaaagaaa   14551
gaggaactcg cggtggtaga cgatggcgga gtggaattta ttaggagttt cgccccgcga   14611
cgcagggttc aatggaaagg gcggcgggta caacgcgttt tgaggccggg caccgcggta   14671
gtttttaccc cgggagagcg gtcggccgtt aggggtttca aaaggcagta cgacgaggtg   14731 tacgcgacg aggacatatt ggaacaggcg gctcaacaga tcgagaatt tgcctacgga     14791 aagcgttcgc gtcgcgaaga cctggccatc gccttagaca gcggcaaccc cacgcccagc   14851
ctcaaacccg tgacgctgca gcaggtgctt cccgtgagcg ccagcacgga cagcaagagg   14911
gggattaaga gagaaatgga agatctgcat cccaccatcc aactcatggt ccctaaacgg   14971
cagaggctgg aagaggtcct ggagaagatg aaagtggacc ccagcataga gccggatgta   15031
aaagtcagac ctattaagga agtggccccc ggtcttgggg tgcaaacggt ggacattcaa   15091
atccccgtca ccaccgcttc aaccgccgtg gaagctatgg aaacgcaaac ggagacccct   15151
gccgcgatcg gtaccaggga agtggcgttg caaacggagc cttggtacga atacgcagcc   15211
cctcggcgtc agaggcgttc cgctcgttac ggccccgcca acgccatcat gccagaatat   15271
gcgctgcatc cgtctattct gcccactccc ggataccggg gtgtgacgta tcgcccgtct   15331
ggaacccgcc gccgaacccg tcgccgccgc cgctcccgtc gcgctctggc ccccgtgtcg   15391
gtgcggcgtg tgacccgccg gggaaagaca gtcgtcattc ccaacccgcg ttaccaccct   15451
agcatccttt aataactctg ccgttttgca gatggctctg acttgccgcg tgcgccttcc   15511
cgttccgcac tatcgaggaa gatctcgtcg taggagaggc atgacgggca gtggtcgccg   15571
gcgggctttg cgcaggcgca tgaaaggcgg aattttaccc gccctgatac ccataattgc   15631
cgccgccatc ggtgccatac ccggcgttgc ttcagtggcg ttgcaagcag ctcgtaataa   15691
ataaacaaag gcttttgcac ttatgacctg gtcctgacta ttttatgcag aaagagcatg   15751
gaagacatca attttacgtc gctggctccg cggcacggct cgcggccgct catgggcacc   15811
tggaacgaca tcggcaccag tcagctcaac gggggcgctt tcaattgggg gagcctttgg   15871
agcggcatta aaaactttgg ctccacgatt aaatcctacg gcagcaaagc ctggaacagt   15931
agtgctggtc agatgctccg agataaactg aaggacacca acttccaaga aaaagtggtc   15991 aatgggtgg tgaccggcat ccacggcgcg gtagatctcg ccaaccaagc ggtgcagaaa   16051
gagattgaca ggcgtttgga aagctcgcgg gtgccgccgc agagagggga tgaggtggag   16111
gtcgaggaag tagaagtaga ggaaaagctg ccccgctgg agaaagttcc cggtgcgcct   16171 ccgagaccg agaagcggcc caggccagaa ctagaagaga ctctggtgac ggagagcaag   16231
gagcctccct cgtacgagca agccttgaaa gagggcgcct ctccacccte ctacccgatg   16291
```

```
actaagccga tcgcacccat ggctcgaccg gtgtacggca aggattacaa gcccgtcacg    16351
ctagagctgc ccccaccgcc ccccacgcgc ccgaccgtcc cccccctgcc gactccgtcg    16411
gcggccgcgg cgggacccgt gtccgcacca tccgctgtgc ctctgccagc cgcccgtcca    16471
gtggccgtgg ccactgccag aaaccccaga ggccagagag gagccaactg gcaaagcacg    16531
ctgaacagca tcgtgggcct gggagtgaaa agcctgaaac gccgccgttg ctattattaa    16591
aaaagtgtag ctaaaaagtc tcccgttgta tacgcctcct atgttaccgc cagagacgag    16651
```

| | | | | | | | | | | | | | | | |
|---|---|---|---|---|---|---|---|---|---|---|---|---|---|---|---|
| tgactgtcgc cgcgagcgcc gctttcaag | atg | gcc | acc | cca | tcg | atg | atg | ccg | | | | | | | 16704 |
| | Met | Ala | Thr | Pro | Ser | Met | Met | Pro | | | | | | | |
| | | | | 510 | | | | | | | | | | | |

| cag | tgg | tct | tac | atg | cac | atc | gcc | ggc | cag | gac | gcc | tcg | gag | tac | ctg | 16752 |
|---|---|---|---|---|---|---|---|---|---|---|---|---|---|---|---|---|
| Gln | Trp | Ser | Tyr | Met | His | Ile | Ala | Gly | Gln | Asp | Ala | Ser | Glu | Tyr | Leu | |
| | 515 | | | | 520 | | | | | 525 | | | | | | |

| agt | ccc | ggc | ctc | gtg | cag | ttt | gcc | cgc | gcc | acc | gac | acc | tac | ttc | agc | 16800 |
|---|---|---|---|---|---|---|---|---|---|---|---|---|---|---|---|---|
| Ser | Pro | Gly | Leu | Val | Gln | Phe | Ala | Arg | Ala | Thr | Asp | Thr | Tyr | Phe | Ser | |
| 530 | | | | | 535 | | | | | 540 | | | | | 545 | |

| ttg | gga | aac | aag | ttt | aga | aac | ccc | acc | gtg | gcc | ccc | acc | cac | gat | gtg | 16848 |
|---|---|---|---|---|---|---|---|---|---|---|---|---|---|---|---|---|
| Leu | Gly | Asn | Lys | Phe | Arg | Asn | Pro | Thr | Val | Ala | Pro | Thr | His | Asp | Val | |
| | | | 550 | | | | | 555 | | | | | 560 | | | |

| acc | acg | gac | cgc | tcg | cag | agg | ctg | acc | ctg | cgc | ttt | gtg | ccc | gta | gac | 16896 |
|---|---|---|---|---|---|---|---|---|---|---|---|---|---|---|---|---|
| Thr | Thr | Asp | Arg | Ser | Gln | Arg | Leu | Thr | Leu | Arg | Phe | Val | Pro | Val | Asp | |
| | | | 565 | | | | | 570 | | | | | 575 | | | |

| cgg | gag | gac | acc | gcg | tac | tct | tac | aaa | gtg | cgc | tac | acg | ttg | gcc | gta | 16944 |
|---|---|---|---|---|---|---|---|---|---|---|---|---|---|---|---|---|
| Arg | Glu | Asp | Thr | Ala | Tyr | Ser | Tyr | Lys | Val | Arg | Tyr | Thr | Leu | Ala | Val | |
| | | | 580 | | | | | 585 | | | | | 590 | | | |

| ggg | gac | aac | cga | gtg | ctg | gac | atg | gcc | agc | acc | tac | ttt | gac | atc | cgg | 16992 |
|---|---|---|---|---|---|---|---|---|---|---|---|---|---|---|---|---|
| Gly | Asp | Asn | Arg | Val | Leu | Asp | Met | Ala | Ser | Thr | Tyr | Phe | Asp | Ile | Arg | |
| | 595 | | | | | 600 | | | | | 605 | | | | | |

| ggg | gtg | ctg | gat | cgg | ggt | ccc | agc | ttc | aag | ccc | tat | tcc | ggc | acc | gct | 17040 |
|---|---|---|---|---|---|---|---|---|---|---|---|---|---|---|---|---|
| Gly | Val | Leu | Asp | Arg | Gly | Pro | Ser | Phe | Lys | Pro | Tyr | Ser | Gly | Thr | Ala | |
| 610 | | | | | 615 | | | | | 620 | | | | | 625 | |

| tac | aac | tcc | ctg | gcc | ccc | aag | gga | gct | ccc | aac | ccc | tcg | gaa | tgg | acg | 17088 |
|---|---|---|---|---|---|---|---|---|---|---|---|---|---|---|---|---|
| Tyr | Asn | Ser | Leu | Ala | Pro | Lys | Gly | Ala | Pro | Asn | Pro | Ser | Glu | Trp | Thr | |
| | | | 630 | | | | | 635 | | | | | 640 | | | |

| gac | act | tcc | gac | aac | aaa | ctt | aaa | gca | tat | gct | cag | gct | ccc | tac | cag | 17136 |
|---|---|---|---|---|---|---|---|---|---|---|---|---|---|---|---|---|
| Asp | Thr | Ser | Asp | Asn | Lys | Leu | Lys | Ala | Tyr | Ala | Gln | Ala | Pro | Tyr | Gln | |
| | | 645 | | | | | 650 | | | | | 655 | | | | |

| agt | caa | gga | ctt | aca | aag | gat | ggt | att | cag | gtt | ggg | cta | gtt | gtg | aca | 17184 |
|---|---|---|---|---|---|---|---|---|---|---|---|---|---|---|---|---|
| Ser | Gln | Gly | Leu | Thr | Lys | Asp | Gly | Ile | Gln | Val | Gly | Leu | Val | Val | Thr | |
| | | | 660 | | | | | 665 | | | | | 670 | | | |

| gag | tca | gga | caa | aca | ccc | caa | tat | gca | aac | aaa | gtg | tac | caa | ccc | gag | 17232 |
|---|---|---|---|---|---|---|---|---|---|---|---|---|---|---|---|---|
| Glu | Ser | Gly | Gln | Thr | Pro | Gln | Tyr | Ala | Asn | Lys | Val | Tyr | Gln | Pro | Glu | |
| | 675 | | | | | 680 | | | | | 685 | | | | | |

| cca | caa | att | ggg | gaa | aac | caa | tgg | aat | tta | gaa | caa | gaa | gat | aaa | gcg | 17280 |
|---|---|---|---|---|---|---|---|---|---|---|---|---|---|---|---|---|
| Pro | Gln | Ile | Gly | Glu | Asn | Gln | Trp | Asn | Leu | Glu | Gln | Glu | Asp | Lys | Ala | |
| 690 | | | | | 695 | | | | | 700 | | | | | 705 | |

| gcg | gga | aga | gtc | cta | aag | aaa | gat | acc | cct | atg | ttt | ccc | tgc | tat | ggg | 17328 |
|---|---|---|---|---|---|---|---|---|---|---|---|---|---|---|---|---|
| Ala | Gly | Arg | Val | Leu | Lys | Lys | Asp | Thr | Pro | Met | Phe | Pro | Cys | Tyr | Gly | |
| | | | 710 | | | | | 715 | | | | | 720 | | | |

| tca | tat | gcc | agg | ccc | aca | aac | gaa | caa | gga | ggg | cag | gca | aaa | aac | caa | 17376 |
|---|---|---|---|---|---|---|---|---|---|---|---|---|---|---|---|---|
| Ser | Tyr | Ala | Arg | Pro | Thr | Asn | Glu | Gln | Gly | Gly | Gln | Ala | Lys | Asn | Gln | |
| | | 725 | | | | | 730 | | | | | 735 | | | | |

| gaa | gta | gat | tta | cag | ttt | ttt | gcc | act | ccg | ggc | gac | acc | cag | aac | acg | 17424 |
|---|---|---|---|---|---|---|---|---|---|---|---|---|---|---|---|---|
| Glu | Val | Asp | Leu | Gln | Phe | Phe | Ala | Thr | Pro | Gly | Asp | Thr | Gln | Asn | Thr | |
| | | | 740 | | | | | 745 | | | | | 750 | | | |

| gct | aaa | gtg | gta | ctt | tat | gct | gaa | aat | gtc | aac | ctg | gaa | act | cca | gat | 17472 |
|---|---|---|---|---|---|---|---|---|---|---|---|---|---|---|---|---|
| Ala | Lys | Val | Val | Leu | Tyr | Ala | Glu | Asn | Val | Asn | Leu | Glu | Thr | Pro | Asp | |

```
                755                 760                 765
act cac tta gtg ttt aaa ccc gat gac gac agc acc agt tca aaa ctt    17520
Thr His Leu Val Phe Lys Pro Asp Asp Asp Ser Thr Ser Ser Lys Leu
770             775                 780                 785 ctt ctt ggg cag cag gct gca cct aac aga ccc aac tac ata ggt ttt    17568
Leu Leu Gly Gln Gln Ala Ala Pro Asn Arg Pro Asn Tyr Ile Gly Phe
            790                 795                 800 aga gat aat ttt att ggt tta atg tac tac aat agc act gga aac atg    17616
Arg Asp Asn Phe Ile Gly Leu Met Tyr Tyr Asn Ser Thr Gly Asn Met
                805                 810                 815 ggc gtg ctg gcc gga cag gct tct caa ttg aat gcc gta gtc gac ttg    17664
Gly Val Leu Ala Gly Gln Ala Ser Gln Leu Asn Ala Val Val Asp Leu
        820                 825                 830 cag gac aga aac acc gag ttg tcc tac cag ctg atg ctg gac gca ctg    17712
Gln Asp Arg Asn Thr Glu Leu Ser Tyr Gln Leu Met Leu Asp Ala Leu
835                 840                 845 ggg gat cgc agc cga tat ttt tca atg tgg aat cag gca gta gac agc    17760
Gly Asp Arg Ser Arg Tyr Phe Ser Met Trp Asn Gln Ala Val Asp Ser
850                 855                 860                 865 tat gac cca gac gtt aga att ata gaa aac cac gga gtg gaa gac gaa    17808
Tyr Asp Pro Asp Val Arg Ile Ile Glu Asn His Gly Val Glu Asp Glu
                870                 875                 880 ctg cca aac tat tgt ttt cct ctg gga gga atg gtg gtg act gac aat    17856
Leu Pro Asn Tyr Cys Phe Pro Leu Gly Gly Met Val Val Thr Asp Asn
            885                 890                 895 tac aac tct gtg acg cct caa aat gga ggc agt gga aat aca tgg cag    17904
Tyr Asn Ser Val Thr Pro Gln Asn Gly Gly Ser Gly Asn Thr Trp Gln
        900                 905                 910 gca gac aat act aca ttt agt caa aga gga gcg cag att ggc tcc gga    17952
Ala Asp Asn Thr Thr Phe Ser Gln Arg Gly Ala Gln Ile Gly Ser Gly
915                 920                 925 aac atg ttt gcc ctg gaa att aac cta cag gcc aac ctc tgg cgc ggc    18000
Asn Met Phe Ala Leu Glu Ile Asn Leu Gln Ala Asn Leu Trp Arg Gly
930                 935                 940                 945 ttc ttg tat tcc aat att ggg ttg tat ctt cca gac tct ctg aaa atc    18048
Phe Leu Tyr Ser Asn Ile Gly Leu Tyr Leu Pro Asp Ser Leu Lys Ile
                950                 955                 960 acc ccc gac aac atc acg ctg cca gaa aac aaa aac act tat cag tac    18096
Thr Pro Asp Asn Ile Thr Leu Pro Glu Asn Lys Asn Thr Tyr Gln Tyr
            965                 970                 975 atg aac ggt cgc gta acg cca ccc ggg ctc ata gac acc tat gta aac    18144
Met Asn Gly Arg Val Thr Pro Pro Gly Leu Ile Asp Thr Tyr Val Asn
        980                 985                 990 gtg ggc gcg cgc tgg tcc ccc gat gtc atg gac agc att aac ccc ttc    18192
Val Gly Ala Arg Trp Ser Pro Asp Val Met Asp Ser Ile Asn Pro Phe
995                 1000                1005 aac cac cac cgt aac gcg ggc ttg cgc tac cgc tcc atg ctc ttg        18237
Asn His His Arg Asn Ala Gly Leu Arg Tyr Arg Ser Met Leu Leu
1010                1015                1020 ggc aac ggc cgt tat gtg cct ttt cac att cag gtg ccc caa aaa        18282
Gly Asn Gly Arg Tyr Val Pro Phe His Ile Gln Val Pro Gln Lys
1025                1030                1035 ttc ttt gcc att aaa aac ctg ctg ctt ctc ccc ggt tcc tat acc        18327
Phe Phe Ala Ile Lys Asn Leu Leu Leu Leu Pro Gly Ser Tyr Thr
1040                1045                1050 tat gag tgg aac ttc cgc aag gat gtc aac atg atc ctg cag agc        18372
Tyr Glu Trp Asn Phe Arg Lys Asp Val Asn Met Ile Leu Gln Ser
1055                1060                1065 tcg ctg ggt aat gac ctg cga gtg gac ggg gcc agc ata cgc ttt        18417
```

```
Ser Leu Gly Asn Asp Leu Arg Val Asp Gly Ala Ser Ile Arg Phe
1070            1075                1080 gac agc att aac ctg tat gcc aac ttt ttt ccc atg gcc cac aac       18462
Asp Ser Ile Asn Leu Tyr Ala Asn Phe Phe Pro Met Ala His Asn
1085            1090                1095 acg gcc tct acc ctg gaa gcc atg ctg cgc aac gac acc aat gac       18507
Thr Ala Ser Thr Leu Glu Ala Met Leu Arg Asn Asp Thr Asn Asp
1100            1105                1110 cag tcc ttc aac gac tac ctg tgc gcg gct aac atg ctg tac ccc       18552
Gln Ser Phe Asn Asp Tyr Leu Cys Ala Ala Asn Met Leu Tyr Pro
1115            1120                1125 atc ccc gcc aac gcc acc agc gtg ccc att tct att cct tct cgg       18597
Ile Pro Ala Asn Ala Thr Ser Val Pro Ile Ser Ile Pro Ser Arg
1130            1135                1140 aac tgg gct gcc ttc agg ggc tgg agt ttt act cgc ctc aaa acc       18642
Asn Trp Ala Ala Phe Arg Gly Trp Ser Phe Thr Arg Leu Lys Thr
1145            1150                1155 aag gag act ccc tcg ctg ggc tcc ggt ttt gac ccc tac ttt gtt       18687
Lys Glu Thr Pro Ser Leu Gly Ser Gly Phe Asp Pro Tyr Phe Val
1160            1165                1170 tac tcc ggc tcc att ccc tac cta gat ggc acc ttt tac ctc aac       18732
Tyr Ser Gly Ser Ile Pro Tyr Leu Asp Gly Thr Phe Tyr Leu Asn
1175            1180                1185 cac act ttc aaa aag gtg tct att atg ttt gac tcc tcg gtt agc       18777
His Thr Phe Lys Lys Val Ser Ile Met Phe Asp Ser Ser Val Ser
1190            1195                1200 tgg ccc ggc aac gac cgc ctg cta acg ccc aac gag ttc gaa att       18822
Trp Pro Gly Asn Asp Arg Leu Leu Thr Pro Asn Glu Phe Glu Ile
1205            1210                1215 aag cgt tcc gtg gac ggt gaa ggg tac aac gtg gcc cag agc aac       18867
Lys Arg Ser Val Asp Gly Glu Gly Tyr Asn Val Ala Gln Ser Asn
1220            1225                1230 atg acc aag gac tgg ttt cta att caa atg ctc agt cac tat aat       18912
Met Thr Lys Asp Trp Phe Leu Ile Gln Met Leu Ser His Tyr Asn
1235            1240                1245 ata ggt tac cag ggc ttc tat gtg ccc gag aac tac aag gac cgc       18957
Ile Gly Tyr Gln Gly Phe Tyr Val Pro Glu Asn Tyr Lys Asp Arg
1250            1255                1260 atg tac tcc ttc ttc cgc aac ttc caa cca atg agc cgg cag gtg       19002
Met Tyr Ser Phe Phe Arg Asn Phe Gln Pro Met Ser Arg Gln Val
1265            1270                1275 gta gat acc gtg act tat aca gac tac aaa gat gtc aag ctc ccc       19047
Val Asp Thr Val Thr Tyr Thr Asp Tyr Lys Asp Val Lys Leu Pro
1280            1285                1290 tac caa cac aac aac tca ggg ttc gtg ggc tac atg gga ccc acc       19092
Tyr Gln His Asn Asn Ser Gly Phe Val Gly Tyr Met Gly Pro Thr
1295            1300                1305 atg cga gag gga cag gcc tac ccg gcc aac tat ccc tac ccc ctg       19137
Met Arg Glu Gly Gln Ala Tyr Pro Ala Asn Tyr Pro Tyr Pro Leu
1310            1315                1320 atc gga gag act gcc gta ccc agc ctc acg cag aaa aag ttc ctc       19182
Ile Gly Glu Thr Ala Val Pro Ser Leu Thr Gln Lys Lys Phe Leu
1325            1330                1335 tgc gac cgg gtg atg tgg agg ata ccc ttc tct agc aac ttt atg       19227
Cys Asp Arg Val Met Trp Arg Ile Pro Phe Ser Ser Asn Phe Met
1340            1345                1350 tcg atg ggc tcc ctc acc gac ctg ggg cag aac atg ctg tac gcc       19272
Ser Met Gly Ser Leu Thr Asp Leu Gly Gln Asn Met Leu Tyr Ala
1355            1360                1365
```

```
aac tcc gct cac gcc ttg gac atg act ttt gag gtg gat ccc atg      19317
Asn Ser Ala His Ala Leu Asp Met Thr Phe Glu Val Asp Pro Met
1370                1375                1380 gat gag ccc acg ctt ctc tat gtt ctg ttt gaa gtc ttc gac gtg      19362
Asp Glu Pro Thr Leu Leu Tyr Val Leu Phe Glu Val Phe Asp Val
1385                1390                1395 gtg cgc atc cac cag ccg cac cgc ggc gtc atc gag gcc gtc tac      19407
Val Arg Ile His Gln Pro His Arg Gly Val Ile Glu Ala Val Tyr
1400                1405                1410 ctg cgc aca cct ttc tct gcc ggt aac gcc acc acc taa agaagctgat   19456
Leu Arg Thr Pro Phe Ser Ala Gly Asn Ala Thr Thr
1415                1420            1425 gggttccagc gaacaggagt tgcaggccat tgttcgcgac ctgggctgcg ggccctgctt 19516
tttgggcacc ttcgacaagc gttttcccgg attcatgtcc ccccacaagc cggcctgcgc 19576
catcgttaac acggccggac gggagacagg ggggtgcac tggctcgcct tcgcctggaa  19636
cccgcgcaac cgcacctgct acctgttcga ccctttttggt ttctccgacg aaaggctgaa 19696
gcagatctac caattcgagt acgaggggct cctcaagcgc agcgctctgg cctccacgcc  19756
cgaccactgc gtcaccctgg aaaagtccac ccagacggtc caggggcccc tctcggccgc  19816
ctgcgggctt ttctgttgca tgttttttgca cgccttcgtg cactggcctc acccccccat  19876
ggagcgcaac cccaccatgg atctgctcac cggagtgccc aacagcatgc ttcacagtcc  19936
ccaggtcgcc cccaccctgc gtcgcaatca ggaccacctg tatcgctttc tggggaaaca  19996
ctctgcctat ttccgccgcc accggcagcg catcgaacag ccacggcct tcgaaagcat   20056
gagccaaaga gtgtaatcaa taaaaaccgt ttttatttga catgatacgc gcttctggcg  20116
tttttattaa aaatcgaagg gttcgaggga ggggtcctcg tgcccgctgg ggagggacac  20176
gttgcggtac tggaatcggg cgctccaacg aaactcgggg atcaccagcc gcggcagggc  20236
cacgtcttcc atgttctgct tccaaaactg tcgcaccagc tgcagggctc ccatcacgtc  20296
gggcgctgag atcttgaagt cgcagttagg gccggagccc ccgcggctgt tgcggaacac  20356
ggggttggca cactggaaca ccaacacgct ggggttgtgg atactagcca gggccgtcgg  20416
gtcggtcacc tccgatgcat ccagatcctc ggcattgctc agggcgaacg gggtcagctt  20476
gcacatctgc cgcccgatct ggggtaccag gtcgcgcttg ttgaggcagt cgcagcgcag  20536
agggatgagg atgcgacgct gcccgcgttg catgatgggg taactcgccg ccaggaactc  20596
ctctatctga cggaaggcca tctgggcctt gacgccctcg gtgaaaaata gcccacagga  20656
cttgctggaa aacacgttat tgccacagtt gatgtcttcc gcgcagcagc gcgcatcttc  20716
gttcttcagc tgaaccacgt tgcgaccca gcggttctga accaccttgg ctttcgtggg  20776
atgctccttc agcgcccgct gtccgttctc gctggtcaca tccatttcca ccacgtgctc  20836
cttgcagacc atctccactc cgtggaaaca gaacagaatg ccctcctgtt gggtattgcg  20896
atgctcccac acggcgcacc cggtggactc ccagctcttg tgtttcaccc ccgcgtaggc  20956
ttccatgtaa gccattagaa atctgcccat cagctcagtg aaggtcttct ggttggtgaa  21016
ggttagcggc aggccgcggt gttcctcgtt caaccaagtt tgacagatct gcggtacac   21076
ggctccctgg tcgggcagaa acttaaaagt cgttctgctc tcgttgtcca cgtgaactt   21136
ctccatcaac atcgtcatga cttccatgcc cttctcccag gcagtcacca gcggcgcgct  21196
ctcggggttc ttcaccaaca cggcggtgga ggggcccctcg ccggccccga cgtccttcat 21256
ggacattttt tgaaactcca cggtgccgtc cgcgcggcgt actctgcgca tcggagggta  21316
gctgaagccc acctccatga cggtgctttc gccctcgctg tcggagacga tctccgggga  21376
```

```
gggcggcgga acgggggcag acttgcgagc cttcttcttg ggagggagcg gaggcacctc    21436
ctgctcgcgc tcgggactca tctcccgcaa gtaggggtg atggagcttc ctggttggtt     21496
ctgacggttg gccattgtat cctaggcaga aagacatgga gcttatgcgc gaggaaactt    21556
taaccgcccc gtcccccgtc agcgacgaag aggtcatcgt cgaacaggac ccgggctacg    21616
ttacgccgcc cgaggatctg aggggccct tagacgaccg gcgcgacgct agtgagcggc     21676
aggaaaatga gaaagaggag gaggagggct gctacctcct ggaaggcgac gttttgctaa    21736
agcatttcgc caggcagagc accatactca aggaggcctt gcaagaccgc tccgaggtgc    21796
ccttggacgt cgccgcgctc tcccaggcct acgaggcgaa ccttttctcg ccccgagtgc    21856
ctccgaagag acagcccaac ggcacctgcg agcccaaccc gcgactcaac ttctaccccg    21916
tgttcgccgt gcccgaggcg ctggccacct accacatctt tttcaaaaac cagcgcattc    21976
cccttttcctg ccgggccaac cgcaccgcgg ccgataggaa gctaacactc agaaacggag   22036
tcagcatacc tgatatcacg tcactggagg aagtgcctaa gatcttcgag ggtctgggtc    22096
gagatgagaa gcgggcggcg aacgctctgc agaaagaaca gaaagagagt cagaacgtgc    22156
tggtggagct ggaggggac aacgcgcgtc tgaccgtcct caaacgttgc atagaagttt     22216
cccacttcgc ctacccggcc ctcaacctgc cgcccaaagt tatgaaatcg gtcatggacc    22276
agctactcat caagagagct gagccctga atcccgacca ccctgaggcg gaaaactcag     22336
aggacggaaa gcccgtcgtc agcgacgagg agctcgagcg gtggctggaa accagggacc    22396
cccagcagtt gcaagagagg cgcaagatga tgatggcggc cgtgctggtc acggtggagc    22456
tagaatgcct gcaacggttt ttcagcgacg tggagacgct acgcaaaatc ggggagtccc    22516
tgcactacac cttccgccag ggctacgttc gccaggcctg caaaatctcc aacgtagagc    22576
tcagcaacct ggtttcctac atgggcatcc tccacgagaa ccggctgggg cagagcgtgc    22636
tgcactgcac cttgcaaggc gaggcgcgaa gggactacgt ccgagactgc gtctacctct    22696
tcctcacccct cacctggcag accgccatgg gcgtgtggca gcagtgcttg gaagagagaa    22756
acctcaaaga gctggacaaa ctcctctgcc gccagcggcg ggccctctgg accggcttca    22816
gcgagcgcac ggtcgcctgc gccctggcag acatcatttt cccagaacgc ctgatgaaaa    22876
ccttgcagaa cggcctgccg gatttcatca gtcagagcat cttgcaaaac ttccgctcct    22936
tcgtcctgga gcgctccggg atcttgcccg ccatgagctg cgcgctgcct tctgactttg    22996
tcccccttttc ctaccgcgag tgccctcccc cactgtggag ccactgctac ctcttccaac    23056
tggccaactt tctggcctac cactccgacc tcatggaaga cgtgagcgga gaggggctgc    23116
tcgagtgcca ctgccgctgc aacctctgca cccccacag atcgctggcc tgcaacaccg      23176
agctgctcag cgaaacccag gtcataggta ccttcgagat ccaggggccc cagcagcaag    23236
agggtgcttc cggcttgaag ctcactccgg cgctgtggac ctcggcttac ttacgcaaat    23296
ttgtagccga ggactaccac gcccacaaaa ttcagttttta cgaagaccaa tctcgaccac    23356
cgaaagcccc cctcacggcc tgcgtcatca cccagagcaa aatcctggcc caattgcaat    23416
ccatcaacca agcgcgccga gatttccttt tgaaaaaggg tcgggggtg tacctggacc     23476
cccagaccgg cgaggaactc aacccgtcca cactttccgt cgaagcagcc cccccgagac    23536
atgccaccca agggaaccgc caagcagctg atcgctcggc agagagcgaa gaagcaagag    23596
ctgctccagc agcaggtgga ggacgaggaa gagctgtggg acagccaggc agaggaggtg    23656
tcagaggacg aggaggagat ggaaagctgg gacagcctag acgaggagga cgagctttca    23716
```

| | |
|---|---|
| gaggaagagg cgaccgaaga aaaaccacct gcatccagcg cgccttctct gagccgacag | 23776 |
| ccgaagcccc ggcccccgac gccccggcc ggctcactca aagccagccg taggtgggac | 23836 |
| gccaccggat ctccagcggc agcggcaacg gcagcgggta aggccaaacg cgagcggcgg | 23896 |
| gggtattgct cctggcggac ccacaaaagc agtatcgtga actgcttgca acactgcggg | 23956 |
| ggaaacatct cctttgcccg acgctacctc ctcttccatc acggtgtggc cttccctcgc | 24016 |
| aacgttctct attattaccg tcatctctac agccccctacg aaacgctcgg agaaaaaagc | 24076 |
| taaggcctcc tctgccgcga ggaaaaactc cgccgccgct gccgccaagg atccgccggc | 24136 |
| caccgaggag ctgagaaagc gcatctttcc cactctgtat gctatctttc agcaaagccg | 24196 |
| cgggcagcac cctcagcgcg aactgaaaat aaaaaaccgc tccttccgct cactcacccg | 24256 |
| cagctgtctg taccacaaga gagaagacca gctgcagcgc accctggacg acgccgaagc | 24316 |
| actgttcagc aaatactgct cagcgtctct taaagactaa aagacccgcg ctttttcccc | 24376 |
| ctcgggcgcc aaaacccacg tcatcgccag catgagcaag gagattccca ccccttacat | 24436 |
| gtggagctat cagccccaga tgggcctggc cgcgggggcc gcccaggact actccagcaa | 24496 |
| aatgaactgg ctcagcgccg gcccccacat gatctcacga gttaacggca tccgagccca | 24556 |
| ccgaaaccag atcctcttag aacaggcggc aatcaccgcc acaccccggc gccaactcaa | 24616 |
| cccgcccagt tggcccgccg cccaggtgta tcaggaaact ccccgcccga ccacagtcct | 24676 |
| cctgccacgc gacgcggagg ccgaagtcct catgactaac tctggggtac aattagcggg | 24736 |
| cgggtccagg tacgccaggt acagaggtcg ggccgctcct tactctcccg ggagtataaa | 24796 |
| gagggtgatc attcgaggcc gaggtatcca gctcaacgac gaggcggtga gctcctcaac | 24856 |
| cggtctcaga cctgacggag tcttccagct cggaggagcg ggccgctctt ccttcaccac | 24916 |
| tcgccaggcc tacctgaccc tgcagagctc ttcctcgcag ccgcgctccg ggggaatcgg | 24976 |
| cactctccag ttcgtggaag agttcgtccc ctccgtctac ttcaacccgt tttccggctc | 25036 |
| acctggacgc tacccggacg ccttcattcc caactttgac gcagtgagtg aatccgtgga | 25096 |
| cggctacgac tgatgacaga tggtgcggcc gtgagagctc ggctgcgaca tctgcatcac | 25156 |
| tgccgccagc ctcgctgcta cgctcgggag gcgatcgtgt tcagctactt tgagctgccg | 25216 |
| gacgagcacc ctcagggacc ggctcacggg ttgaaactcg agattgagaa cgcgcttgag | 25276 |
| tctcacctca tcgacgcctt caccgcccgg cctctcctgg tagaaaccga acgcgggatc | 25336 |
| actaccatca ccctgttctg catctgcccc acgcccggat tac atg aag atc tgt<br>                                                                                                     Met Lys Ile Cys<br>                                                                                                            1430 | 25391 |
| gtt gtc atc ttt gcg ctc agt tta ata aaa act gaa ctt ttt gcc<br>Val Val Ile Phe Ala Leu Ser Leu Ile Lys Thr Glu Leu Phe Ala<br>             1435                     1440                     1445 | 25436 |
| gta cct tca acg cca cgc gtt gtt tct cct tgt gaa aaa acc cca<br>Val Pro Ser Thr Pro Arg Val Val Ser Pro Cys Glu Lys Thr Pro<br>             1450                     1455                     1460 | 25481 |
| gga gtc ctt aac tta cac ata gca aaa ccc ttg tat ttt acc ata<br>Gly Val Leu Asn Leu His Ile Ala Lys Pro Leu Tyr Phe Thr Ile<br>             1465                     1470                     1475 | 25526 |
| gaa aaa caa cta gcc ctt tca att gga aaa ggg tta aca att tct<br>Glu Lys Gln Leu Ala Leu Ser Ile Gly Lys Gly Leu Thr Ile Ser<br>             1480                     1485                     1490 | 25571 |
| gct aca gga cag ttg gaa agc aca gca agc gta cag gac agc gct<br>Ala Thr Gly Gln Leu Glu Ser Thr Ala Ser Val Gln Asp Ser Ala<br>             1495                     1500                     1505 | 25616 |
| aca cca ccc cta cgt ggt att tcc cct tta aag ctg aca gac aac<br>| 25661 |

|   |   |   |   |   |   |   |   |   |   |   |   |   |
|---|---|---|---|---|---|---|---|---|---|---|---|---|
| Thr | Pro | Pro | Leu | Arg | Gly | Ile | Ser | Pro | Leu | Lys | Leu | Thr | Asp | Asn |
|   |   |   |   | 1510 |   |   |   | 1515 |   |   |   | 1520 |

```
ggt tta aca tta agc  tat tca gat ccc ctg  cgt gtg gta ggt gac       25706
Gly Leu Thr Leu Ser  Tyr Ser Asp Pro Leu  Arg Val Val Gly Asp
            1525                  1530                  1535 caa ctt acg ttt aat  ttt act tct cca ctg  cgt tac gaa aat ggc       25751
Gln Leu Thr Phe Asn  Phe Thr Ser Pro Leu  Arg Tyr Glu Asn Gly
            1540                  1545                  1550 agt ctt aca ttc aac  tac act tct ccc atg  aca cta ata aac aac       25796
Ser Leu Thr Phe Asn  Tyr Thr Ser Pro Met  Thr Leu Ile Asn Asn
            1555                  1560                  1565 agt ctt gct att aac  gtc aat acc tcc aaa  ggc ctc agt agt gac       25841
Ser Leu Ala Ile Asn  Val Asn Thr Ser Lys  Gly Leu Ser Ser Asp
            1570                  1575                  1580 aac ggc aca ctc gct  gta aat gtt act cca  gat ttt aga ttt aac       25886
Asn Gly Thr Leu Ala  Val Asn Val Thr Pro  Asp Phe Arg Phe Asn
            1585                  1590                  1595 agc tct ggt gcc tta  act ttt ggc ata caa  agt cta tgg act ttt       25931
Ser Ser Gly Ala Leu  Thr Phe Gly Ile Gln  Ser Leu Trp Thr Phe
            1600                  1605                  1610 cca acc aaa act cct  aac tgt acc gtg ttt  acc gaa agt gac tcc       25976
Pro Thr Lys Thr Pro  Asn Cys Thr Val Phe  Thr Glu Ser Asp Ser
            1615                  1620                  1625 ctg ctg agt ctt tgc  ttg act aaa tgc gga  gct cac gta ctt gga       26021
Leu Leu Ser Leu Cys  Leu Thr Lys Cys Gly  Ala His Val Leu Gly
            1630                  1635                  1640 agc gtg agt tta agc  gga gtg gca gga acc  atg cta aaa atg acc       26066
Ser Val Ser Leu Ser  Gly Val Ala Gly Thr  Met Leu Lys Met Thr
            1645                  1650                  1655 cac act tct gtt acc  gtt cag ttt tcg ttt  gat gac agt ggt aaa       26111
His Thr Ser Val Thr  Val Gln Phe Ser Phe  Asp Asp Ser Gly Lys
            1660                  1665                  1670 cta ata ttc tct cca  ctt gcg aac aac act  tgg ggt gtt cga caa       26156
Leu Ile Phe Ser Pro  Leu Ala Asn Asn Thr  Trp Gly Val Arg Gln
            1675                  1680                  1685 agc gag agt ccg ttg  ccc aac cca tcc ttc  aac gct ctc acg ttt       26201
Ser Glu Ser Pro Leu  Pro Asn Pro Ser Phe  Asn Ala Leu Thr Phe
            1690                  1695                  1700 atg cca aac agt acc  att tat tct aga gga  gca agt aac gaa cct       26246
Met Pro Asn Ser Thr  Ile Tyr Ser Arg Gly  Ala Ser Asn Glu Pro
            1705                  1710                  1715 caa aac aat tat tat  gtc cag acg tat ctt  aga ggc aac gtg cga       26291
Gln Asn Asn Tyr Tyr  Val Gln Thr Tyr Leu  Arg Gly Asn Val Arg
            1720                  1725                  1730 aag cca att cta cta  act gtt acc tac aac  tca gtt aat tca gga       26336
Lys Pro Ile Leu Leu  Thr Val Thr Tyr Asn  Ser Val Asn Ser Gly
            1735                  1740                  1745 tat tcc tta act ttt  aaa tgg gat gct gtc  gcc aat gaa aaa ttt       26381
Tyr Ser Leu Thr Phe  Lys Trp Asp Ala Val  Ala Asn Glu Lys Phe
            1750                  1755                  1760 gcc act cct aca tct  tcg ttt tgc tat gtt  gca gag caa taa          26423
Ala Thr Pro Thr Ser  Ser Phe Cys Tyr Val  Ala Glu Gln
            1765                  1770 aaccctgtta ccccaccgtc tcgttttttt cag atg aaa cga gcg aga gtt        26474
                                     Met Lys Arg Ala Arg Val
                                              1775 gat gaa gac ttc aac cca gtg tac cct tat gac ccc cca tac gct        26519
Asp Glu Asp Phe Asn  Pro Val Tyr Pro Tyr  Asp Pro Pro Tyr Ala
1780                  1785                  1790
```

```
ccc gtc atg ccc ttc att act ccg cct ttt acc tcc tcg gat ggg      26564
Pro Val Met Pro Phe Ile Thr Pro Pro Phe Thr Ser Ser Asp Gly
1795                1800                1805 ttg cag gaa aaa cca ctt gga gtg tta agt tta aac tac agg gat      26609
Leu Gln Glu Lys Pro Leu Gly Val Leu Ser Leu Asn Tyr Arg Asp
1810                1815                1820 ccc att act aca caa aat ggg tct ctc acg tta aaa cta gga aac      26654
Pro Ile Thr Thr Gln Asn Gly Ser Leu Thr Leu Lys Leu Gly Asn
1825                1830                1835 ggc ctc act cta aac aac cag gga cag tta aca tca act gct ggc      26699
Gly Leu Thr Leu Asn Asn Gln Gly Gln Leu Thr Ser Thr Ala Gly
1840                1845                1850 gaa gtg gag cct ccg ctc act aat gct aac aac aaa ctt gca cta      26744
Glu Val Glu Pro Pro Leu Thr Asn Ala Asn Asn Lys Leu Ala Leu
1855                1860                1865 gcc tat agc gaa cca tta gca gta aaa agc aac cgc cta act cta      26789
Ala Tyr Ser Glu Pro Leu Ala Val Lys Ser Asn Arg Leu Thr Leu
1870                1875                1880 tca cac acc gct ccc ctt gtc atc gct aat aat tct tta gcg ttg      26834
Ser His Thr Ala Pro Leu Val Ile Ala Asn Asn Ser Leu Ala Leu
1885                1890                1895 caa gtt tca gag cct att ttt gta aat gac gat gac aag cta gcc      26879
Gln Val Ser Glu Pro Ile Phe Val Asn Asp Asp Asp Lys Leu Ala
1900                1905                1910 ctg cag aca gcc gcc ccc ctt gta acc aac gct ggc acc ctt cgc      26924
Leu Gln Thr Ala Ala Pro Leu Val Thr Asn Ala Gly Thr Leu Arg
1915                1920                1925 tta cag agc gct gcc cct tta gga ttg gtt gaa aat act ctt aaa      26969
Leu Gln Ser Ala Ala Pro Leu Gly Leu Val Glu Asn Thr Leu Lys
1930                1935                1940 ctg ctg ttt tct aaa ccc ttg tat ttg caa aat gat ttt ctt gca      27014
Leu Leu Phe Ser Lys Pro Leu Tyr Leu Gln Asn Asp Phe Leu Ala
1945                1950                1955 tta gcc att gaa cgc ccc ctg gct gta gca gcc gca ggt act ctg      27059
Leu Ala Ile Glu Arg Pro Leu Ala Val Ala Ala Gly Thr Leu
1960                1965                1970 acc cta caa ctt act cct cca tta aag act aac gat gac ggg cta      27104
Thr Leu Gln Leu Thr Pro Pro Leu Lys Thr Asn Asp Asp Gly Leu
1975                1980                1985 aca cta tcc aca gtc gag cca tta act gta aaa aac gga aac cta      27149
Thr Leu Ser Thr Val Glu Pro Leu Thr Val Lys Asn Gly Asn Leu
1990                1995                2000 ggc ttg caa ata tcg cgc cct tta gtt gtt caa aac aac ggc ctt      27194
Gly Leu Gln Ile Ser Arg Pro Leu Val Val Gln Asn Asn Gly Leu
2005                2010                2015 tcg ctt gct att acc ccc ccg ctg cgt ttg ttt aac agc gac ccc      27239
Ser Leu Ala Ile Thr Pro Pro Leu Arg Leu Phe Asn Ser Asp Pro
2020                2025                2030 gtt ctt ggt ttg ggc ttc act ttt ccc cta gct gtc aca aac aac      27284
Val Leu Gly Leu Gly Phe Thr Phe Pro Leu Ala Val Thr Asn Asn
2035                2040                2045 ctc ctc tcc tta aac atg gga gac gga gtt aaa ctt acc tat aat      27329
Leu Leu Ser Leu Asn Met Gly Asp Gly Val Lys Leu Thr Tyr Asn
2050                2055                2060 aaa cta aca gcc aat ttg ggt agg gat tta caa ttt gaa aac ggt      27374
Lys Leu Thr Ala Asn Leu Gly Arg Asp Leu Gln Phe Glu Asn Gly
2065                2070                2075 gcg att gcc gta acg ctt act gcc gaa tta cct ttg caa tac act      27419
Ala Ile Ala Val Thr Leu Thr Ala Glu Leu Pro Leu Gln Tyr Thr
2080                2085                2090
```

```
aac aaa ctt caa ctg aat att gga gct ggc ctt cgt tac aat gga      27464
Asn Lys Leu Gln Leu Asn Ile Gly Ala Gly Leu Arg Tyr Asn Gly
2095            2100                2105 gcc agc aga aaa cta gat gta aac att aac caa aat aaa ggc tta      27509
Ala Ser Arg Lys Leu Asp Val Asn Ile Asn Gln Asn Lys Gly Leu
2110            2115                2120 act tgg gac aac gat gca gtt att ccc aaa cta gga tcg ggc tta      27554
Thr Trp Asp Asn Asp Ala Val Ile Pro Lys Leu Gly Ser Gly Leu
2125            2130                2135 caa ttt gac cct aat ggc aac atc gct gtt atc cct gaa acc gtg      27599
Gln Phe Asp Pro Asn Gly Asn Ile Ala Val Ile Pro Glu Thr Val
2140            2145                2150 aag ccg caa acg tta tgg acg act gca gat ccc tcg cct aac tgc      27644
Lys Pro Gln Thr Leu Trp Thr Thr Ala Asp Pro Ser Pro Asn Cys
2155            2160                2165 tca gtg tac cag gac ttg gat gcc agg ctg tgg ctc gct ctt gtt      27689
Ser Val Tyr Gln Asp Leu Asp Ala Arg Leu Trp Leu Ala Leu Val
2170            2175                2180 aaa agt ggc gac atg gtg cat gga agc att gcc cta aaa gcc cta      27734
Lys Ser Gly Asp Met Val His Gly Ser Ile Ala Leu Lys Ala Leu
2185            2190                2195 aaa ggg acg ttg cta aat cct aca gcc agc tac att tcc att gtg      27779
Lys Gly Thr Leu Leu Asn Pro Thr Ala Ser Tyr Ile Ser Ile Val
2200            2205                2210 ata tat ttt tac agc aac gga gtc agg cgt acc aac tat cca acg      27824
Ile Tyr Phe Tyr Ser Asn Gly Val Arg Arg Thr Asn Tyr Pro Thr
2215            2220                2225 ttt gac aac gaa ggc acc tta gct aac agc gcc act tgg gga tac      27869
Phe Asp Asn Glu Gly Thr Leu Ala Asn Ser Ala Thr Trp Gly Tyr
2230            2235                2240 cga cag ggg caa tct gct aac act aat gtg acc aat gcc act gaa      27914
Arg Gln Gly Gln Ser Ala Asn Thr Asn Val Thr Asn Ala Thr Glu
2245            2250                2255 ttt atg ccc agc tca agc agg tac ccc gtg aat aaa gga gac aac      27959
Phe Met Pro Ser Ser Ser Arg Tyr Pro Val Asn Lys Gly Asp Asn
2260            2265                2270 att caa aat caa tct ttt tca tac acc tgt att aaa gga gat ttt      28004
Ile Gln Asn Gln Ser Phe Ser Tyr Thr Cys Ile Lys Gly Asp Phe
2275            2280                2285 gct atg cct gtc ccg ttc cgt gta aca tat aat cac gcc ctg aa      28049
Ala Met Pro Val Pro Phe Arg Val Thr Tyr Asn His Ala Leu Glu
2290            2295                2300 ggg tat tcc ctt aag ttc acc tgg cgc gtt gta gcc aat cag gcc      28094
Gly Tyr Ser Leu Lys Phe Thr Trp Arg Val Val Ala Asn Gln Ala
2305            2310                2315 ttt gat att cct tgc tgt tca ttt tca tac atc aca gaa taa          28136
Phe Asp Ile Pro Cys Cys Ser Phe Ser Tyr Ile Thr Glu
2320            2325                2330 aaaaccactt tttcatttta attctttttt attttacacg aacagtgaga cttcctccac 28196 ccttccattt gacagcatac accagcctct cccccttcat agcagtaaac tgttgtgaat 28256 cagtccggta tttgggagtt aaaatccaaa cagtctcttt ggtgatgaaa cgtcgatcag 28316 taatggacac aaatccctgg gacaggtttt ccaacgtttc ggtgaaaaac tgcacaccgc 28376 cctacaaaac aaacaggttc aggctctcca cgggttatct ccccgatcaa actcagacag 28436 ggtaaaggtg cggtggtgtt ccactaaacc acgcaggtgg cgctgtctga acctctcggt 28496 gcgactcctg tgaggctggt aagaagttag attgtccagt agcctcacag catgtatcat 28556
```

-continued

```
cagtctacga gtgcgtctgg cgcagcagcg catctgaatc tcactgagat tccggcaaga   28616
atcgcacacc atcacaatca ggttgttcat gatcccatag ctgaacacgc tccagccaaa   28676
gctcattcgc tccaacagcg ccaccgcgtg tccgtccaac cttactttaa cataaatcag   28736
gtgtctgccg cgtacaaaca tgctacccac atacagaact tcccggggca ggcccctgtt   28796
caccacctgt ctgtaccagg gaaacctcac atttatcagg gagccataga tggccatttt   28856
aaaccaatta gctaataccg ccccaccagc tctacactga agagaaccgg gagagttaca   28916
atgacagtga ataatccatc tctcataacc cctgatggtc tgatgaaaat ctagatctaa   28976
cgtggcacaa caaatacaca ctttcatata cattttcata acatgttttt cccaggccgt   29036
taaaatacaa tcccaataca cgggccactc ctgcagtaca ataaagctaa tacaagatgg   29096
tatactcctc acctcactga cactgtgcat gttcatattt tcacattcta agtaccgaga   29156
gttctcctct acagcagcac tgctgcggtc ctcacaaggt ggtagctggt gatgattgta   29216
gggggccagt ctgcagcgat accgtctgtc gcgttgcatc gtagaccagg aaccgacgca   29276
cctcctcgta cttgtggtag cagaaccacg tccgctgcca gcacgtctcc acgtaacgcc   29336
ggtccctgcg tcgctcacgc tccctcctca atgcaaagtg caaccactct tgtaatccac   29396
acagatccct ctcggcctcc ggggtgatgc acacctcaaa cctacagatg tctcggtaca   29456
gttccaaaca cgtagtgagg gcgagttcca accaagacag acagcctgat ctatcccgac   29516
acactggagg tggaggaaga cacggaagag gcatgttatt ccaagcgatt caccaacggg   29576
tcgaaatgaa gatcccgaag atgacaacgg tcgcctccgg agccctgatg gaatttaaca   29636
gccagatcaa acgttatgcg attctccaag ctatcgatcg ccgcttccaa aagagcctgg   29696
acccgcactt ccacaaacac cagcaaagca aaagcactat tatcaaactc ttcaatcatc   29756
aagctgcagg actgtacaat gcctaagtaa ttttcgtttc tccactcgcg aatgatgtcg   29816
cggcagatag tctgaaggtt catcccgtgc agggtaaaaa gctccgaaag ggcgccctct   29876
acagccatgc gtagacacac catcatgact gcaagatatc gggctcctga cacacctgca   29936
gcagatttaa cagatcaagg tcaggttgct ctccgcgatc acgaatctcc atccgcaagg   29996
tcatttgcaa aaaattaaat aaatctatgc cgactagatc tgtcaactcc gcattaggaa   30056
ccaaatcagg tgtggctacg cagcacaaaa gttccaggga tggtgccaaa ctcactagaa   30116
ccgctcccga gtaacaaaac tgatgaatgg gagtaacaca gtgtaaaatg tgcaaccaaa   30176
aatcactaag gtgctccttt aaaaagtcca gtacttctat attcagtccg tgcaagtact   30236
gaagcaactg tgcgggaata tgcacaacaa aaaaaatagg gcggctcaga tacatgttga   30296
cctaaaataa aaagaatcat taaactaaag aagcttggcg aacggtggga taaatgacac   30356
gctccagcag cagacaggca accggctgtc cccgggaacc gcggtaaaat tcatccgaat   30416
gattaaaaag aacaacagaa acttcccacc atgtactcgg ttggatctcc tgagcacaca   30476
gcaatacccc cctcacattc atgtccgcca cagaaaaaaa acgtcccaga tacccagcgg   30536
ggatatccaa cgacagctgc aaagacagca aaacaatccc tctgggagcg atcacaaaat   30596
cctccggtga aaaagcaca tacatattag ataaccctg ttgctggggc aaaaaggccc   30656
ggcgtcccag caaatgcaca taaatatgtt catcagccat tgccccgtct taccgcgtaa   30716
tcagccacga aaaatcgag ctaaaattca cccaacagcc tatagctata tatacactcc   30776
gcccaatgac gctaataccg caccaccac gaccaaagtt cacccacacc cacaaaaccc   30836
gcgaaaatcc agcgccgtca gcacttccgc aatttcagtc tcacaacgtc acttccgcgc   30896
gccttttcac attcccacac acacccgcgc ccttcgcccc gccctcgcgc caccccgcgt   30956
```

```
caccgcacgt caccccggcc ccgcctcgct cctccccgct cattatcata ttggcacgtt    31016
tccagaataa ggtatattat tgatgatg                                       31044
```

<210> SEQ ID NO 33
<211> LENGTH: 505
<212> TYPE: PRT
<213> ORGANISM: simian adenovirus SV-25

<400> SEQUENCE: 33

| | | | | | | | | | | | | | | |
|---|---|---|---|---|---|---|---|---|---|---|---|---|---|---|
Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Thr Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Ser Thr Asn Lys Phe Arg Ala Lys Leu Met
    130                 135                 140

Val Glu Lys Ser Asn Ala Glu Thr Arg Gln Pro Arg Tyr Glu Trp Phe
145                 150                 155                 160

Glu Phe Thr Ile Pro Glu Gly Asn Tyr Ser Glu Thr Met Thr Ile Asp
                165                 170                 175

Leu Met Asn Asn Ala Ile Val Asp Asn Tyr Leu Gln Val Gly Arg Gln
            180                 185                 190

Asn Gly Val Leu Glu Ser Asp Ile Gly Val Lys Phe Asp Thr Arg Asn
        195                 200                 205

Phe Arg Leu Gly Trp Asp Pro Val Thr Lys Leu Val Met Pro Gly Val
    210                 215                 220

Tyr Thr Asn Glu Ala Phe His Pro Asp Ile Val Leu Leu Pro Gly Cys
225                 230                 235                 240

Gly Val Asp Phe Thr Gln Ser Arg Leu Ser Asn Leu Leu Gly Ile Arg
                245                 250                 255

Lys Arg Arg Pro Phe Gln Glu Gly Phe Gln Ile Met Tyr Glu Asp Leu
            260                 265                 270

Glu Gly Gly Asn Ile Pro Ala Leu Leu Asp Val Ser Lys Tyr Glu Ala
        275                 280                 285

Ser Ile Gln Arg Ala Lys Ala Glu Gly Arg Glu Ile Arg Gly Asp Thr
    290                 295                 300

Phe Ala Val Ala Pro Gln Asp Leu Glu Ile Val Pro Leu Thr Lys Asp
305                 310                 315                 320

Ser Lys Asp Arg Ser Tyr Asn Ile Ile Asn Asn Thr Thr Asp Thr Leu
                325                 330                 335

Tyr Arg Ser Trp Phe Leu Ala Tyr Asn Tyr Gly Asp Pro Glu Lys Gly
            340                 345                 350

```
Val Arg Ser Trp Thr Ile Leu Thr Thr Asp Val Thr Cys Gly Ser
        355                 360                 365

Gln Gln Val Tyr Trp Ser Leu Pro Asp Met Met Gln Asp Pro Val Thr
370                 375                 380

Phe Arg Pro Ser Thr Gln Val Ser Asn Phe Pro Val Val Gly Thr Glu
385                 390                 395                 400

Leu Leu Pro Val His Ala Lys Ser Phe Tyr Asn Glu Gln Ala Val Tyr
                405                 410                 415

Ser Gln Leu Ile Arg Gln Ser Thr Ala Leu Thr His Val Phe Asn Arg
            420                 425                 430

Phe Pro Glu Asn Gln Ile Leu Val Arg Pro Ala Pro Thr Ile Thr
        435                 440                 445

Thr Val Ser Glu Asn Val Pro Ala Leu Thr Asp His Gly Thr Leu Pro
    450                 455                 460

Leu Arg Ser Ser Ile Ser Gly Val Gln Arg Val Thr Ile Thr Asp Ala
465                 470                 475                 480

Arg Arg Arg Thr Cys Pro Tyr Val Tyr Lys Ala Leu Gly Val Val Ala
                485                 490                 495

Pro Lys Val Leu Ser Ser Arg Thr Phe
            500                 505

<210> SEQ ID NO 34
<211> LENGTH: 921
<212> TYPE: PRT
<213> ORGANISM: simian adenovirus SV-25

<400> SEQUENCE: 34

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ser Glu Trp Thr Thr Ser Asp Asn Lys Leu Lys
    130                 135                 140

Ala Tyr Ala Gln Ala Pro Tyr Gln Ser Gln Gly Leu Thr Lys Asp Gly
145                 150                 155                 160

Ile Gln Val Gly Leu Val Val Thr Glu Ser Gly Gln Thr Pro Gln Tyr
                165                 170                 175

Ala Asn Lys Val Tyr Gln Pro Glu Pro Gln Ile Gly Glu Asn Gln Trp
            180                 185                 190

Asn Leu Glu Gln Glu Asp Lys Ala Ala Gly Arg Val Leu Lys Lys Asp
        195                 200                 205

Thr Pro Met Phe Pro Cys Tyr Gly Ser Tyr Ala Arg Pro Thr Asn Glu
    210                 215                 220
```

-continued

```
Gln Gly Gly Gln Ala Lys Asn Gln Glu Val Asp Leu Gln Phe Phe Ala
225                 230                 235                 240

Thr Pro Gly Asp Thr Gln Asn Thr Ala Lys Val Val Leu Tyr Ala Glu
            245                 250                 255

Asn Val Asn Leu Glu Thr Pro Asp Thr His Leu Val Phe Lys Pro Asp
        260                 265                 270

Asp Asp Ser Thr Ser Ser Lys Leu Leu Leu Gly Gln Gln Ala Ala Pro
    275                 280                 285

Asn Arg Pro Asn Tyr Ile Gly Phe Arg Asp Asn Phe Ile Gly Leu Met
290                 295                 300

Tyr Tyr Asn Ser Thr Gly Asn Met Gly Val Leu Ala Gly Gln Ala Ser
305                 310                 315                 320

Gln Leu Asn Ala Val Val Asp Leu Gln Asp Arg Asn Thr Glu Leu Ser
            325                 330                 335

Tyr Gln Leu Met Leu Asp Ala Leu Gly Asp Arg Ser Arg Tyr Phe Ser
        340                 345                 350

Met Trp Asn Gln Ala Val Asp Ser Tyr Asp Pro Asp Val Arg Ile Ile
    355                 360                 365

Glu Asn His Gly Val Glu Asp Glu Leu Pro Asn Tyr Cys Phe Pro Leu
370                 375                 380

Gly Gly Met Val Val Thr Asp Asn Tyr Asn Ser Val Thr Pro Gln Asn
385                 390                 395                 400

Gly Gly Ser Gly Asn Thr Trp Gln Ala Asp Asn Thr Thr Phe Ser Gln
            405                 410                 415

Arg Gly Ala Gln Ile Gly Ser Gly Asn Met Phe Ala Leu Glu Ile Asn
        420                 425                 430

Leu Gln Ala Asn Leu Trp Arg Gly Phe Leu Tyr Ser Asn Ile Gly Leu
    435                 440                 445

Tyr Leu Pro Asp Ser Leu Lys Ile Thr Pro Asp Asn Ile Thr Leu Pro
450                 455                 460

Glu Asn Lys Asn Thr Tyr Gln Tyr Met Asn Gly Arg Val Thr Pro Pro
465                 470                 475                 480

Gly Leu Ile Asp Thr Tyr Val Asn Val Gly Ala Arg Trp Ser Pro Asp
            485                 490                 495

Val Met Asp Ser Ile Asn Pro Phe Asn His His Arg Asn Ala Gly Leu
        500                 505                 510

Arg Tyr Arg Ser Met Leu Leu Gly Asn Gly Arg Tyr Val Pro Phe His
    515                 520                 525

Ile Gln Val Pro Gln Lys Phe Phe Ala Ile Lys Asn Leu Leu Leu Leu
530                 535                 540

Pro Gly Ser Tyr Thr Tyr Glu Trp Asn Phe Arg Lys Asp Val Asn Met
545                 550                 555                 560

Ile Leu Gln Ser Ser Leu Gly Asn Asp Leu Arg Val Asp Gly Ala Ser
            565                 570                 575

Ile Arg Phe Asp Ser Ile Asn Leu Tyr Ala Asn Phe Phe Pro Met Ala
        580                 585                 590

His Asn Thr Ala Ser Thr Leu Glu Ala Met Leu Arg Asn Asp Thr Asn
    595                 600                 605

Asp Gln Ser Phe Asn Asp Tyr Leu Cys Ala Ala Asn Met Leu Tyr Pro
610                 615                 620

Ile Pro Ala Asn Ala Thr Ser Val Pro Ile Ser Ile Pro Ser Arg Asn
625                 630                 635                 640
```

```
Trp Ala Ala Phe Arg Gly Trp Ser Phe Thr Arg Leu Lys Thr Lys Glu
                    645                 650                 655

Thr Pro Ser Leu Gly Ser Gly Phe Asp Pro Tyr Phe Val Tyr Ser Gly
            660                 665                 670

Ser Ile Pro Tyr Leu Asp Gly Thr Phe Tyr Leu Asn His Thr Phe Lys
            675                 680                 685

Lys Val Ser Ile Met Phe Asp Ser Ser Val Ser Trp Pro Gly Asn Asp
        690                 695                 700

Arg Leu Leu Thr Pro Asn Glu Phe Glu Ile Lys Arg Ser Val Asp Gly
705                 710                 715                 720

Glu Gly Tyr Asn Val Ala Gln Ser Asn Met Thr Lys Asp Trp Phe Leu
                725                 730                 735

Ile Gln Met Leu Ser His Tyr Asn Ile Gly Tyr Gln Gly Phe Tyr Val
            740                 745                 750

Pro Glu Asn Tyr Lys Asp Arg Met Tyr Ser Phe Phe Arg Asn Phe Gln
            755                 760                 765

Pro Met Ser Arg Gln Val Val Asp Thr Val Thr Tyr Thr Asp Tyr Lys
        770                 775                 780

Asp Val Lys Leu Pro Tyr Gln His Asn Asn Ser Gly Phe Val Gly Tyr
785                 790                 795                 800

Met Gly Pro Thr Met Arg Glu Gly Gln Ala Tyr Pro Ala Asn Tyr Pro
                805                 810                 815

Tyr Pro Leu Ile Gly Glu Thr Ala Val Pro Ser Leu Thr Gln Lys Lys
            820                 825                 830

Phe Leu Cys Asp Arg Val Met Trp Arg Ile Pro Phe Ser Ser Asn Phe
            835                 840                 845

Met Ser Met Gly Ser Leu Thr Asp Leu Gly Gln Asn Met Leu Tyr Ala
        850                 855                 860

Asn Ser Ala His Ala Leu Asp Met Thr Phe Glu Val Asp Pro Met Asp
865                 870                 875                 880

Glu Pro Thr Leu Leu Tyr Val Leu Phe Glu Val Phe Asp Val Val Arg
                885                 890                 895

Ile His Gln Pro His Arg Gly Val Ile Glu Ala Val Tyr Leu Arg Thr
            900                 905                 910

Pro Phe Ser Ala Gly Asn Ala Thr Thr
            915                 920

<210> SEQ ID NO 35
<211> LENGTH: 347
<212> TYPE: PRT
<213> ORGANISM: simian adenovirus SV-25

<400> SEQUENCE: 35

Met Lys Ile Cys Val Val Ile Phe Ala Leu Ser Leu Ile Lys Thr Glu
1               5                   10                  15

Leu Phe Ala Val Pro Ser Thr Pro Arg Val Val Ser Pro Cys Glu Lys
            20                  25                  30

Thr Pro Gly Val Leu Asn Leu His Ile Ala Lys Pro Leu Tyr Phe Thr
        35                  40                  45

Ile Glu Lys Gln Leu Ala Leu Ser Ile Gly Lys Gly Leu Thr Ile Ser
    50                  55                  60

Ala Thr Gly Gln Leu Glu Ser Thr Ala Ser Val Gln Asp Ser Ala Thr
65                  70                  75                  80

Pro Pro Leu Arg Gly Ile Ser Pro Leu Lys Leu Thr Asp Asn Gly Leu
                85                  90                  95
```

Thr Leu Ser Tyr Ser Asp Pro Leu Arg Val Gly Asp Gln Leu Thr
            100                 105                 110

Phe Asn Phe Thr Ser Pro Leu Arg Tyr Glu Asn Gly Ser Leu Thr Phe
            115                 120                 125

Asn Tyr Thr Ser Pro Met Thr Leu Ile Asn Asn Ser Leu Ala Ile Asn
130                 135                 140

Val Asn Thr Ser Lys Gly Leu Ser Ser Asp Asn Gly Thr Leu Ala Val
145                 150                 155                 160

Asn Val Thr Pro Asp Phe Arg Phe Asn Ser Ser Gly Ala Leu Thr Phe
            165                 170                 175

Gly Ile Gln Ser Leu Trp Thr Phe Pro Thr Lys Thr Pro Asn Cys Thr
            180                 185                 190

Val Phe Thr Glu Ser Asp Ser Leu Leu Ser Leu Cys Leu Thr Lys Cys
            195                 200                 205

Gly Ala His Val Leu Gly Ser Val Ser Leu Ser Gly Val Ala Gly Thr
            210                 215                 220

Met Leu Lys Met Thr His Thr Ser Val Thr Val Gln Phe Ser Phe Asp
225                 230                 235                 240

Asp Ser Gly Lys Leu Ile Phe Ser Pro Leu Ala Asn Asn Thr Trp Gly
            245                 250                 255

Val Arg Gln Ser Glu Ser Pro Leu Pro Asn Pro Ser Phe Asn Ala Leu
            260                 265                 270

Thr Phe Met Pro Asn Ser Thr Ile Tyr Ser Arg Gly Ala Ser Asn Glu
            275                 280                 285

Pro Gln Asn Asn Tyr Tyr Val Gln Thr Tyr Leu Arg Gly Asn Val Arg
            290                 295                 300

Lys Pro Ile Leu Leu Thr Val Thr Tyr Asn Ser Val Asn Ser Gly Tyr
305                 310                 315                 320

Ser Leu Thr Phe Lys Trp Asp Ala Val Ala Asn Glu Lys Phe Ala Thr
            325                 330                 335

Pro Thr Ser Ser Phe Cys Tyr Val Ala Glu Gln
            340                 345

<210> SEQ ID NO 36
<211> LENGTH: 559
<212> TYPE: PRT
<213> ORGANISM: simian adenovirus SV-25

<400> SEQUENCE: 36

Met Lys Arg Ala Arg Val Asp Glu Asp Phe Asn Pro Val Tyr Pro Tyr
1               5                   10                  15

Asp Pro Pro Tyr Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Arg Asp Pro Ile Thr Thr Gln Asn Gly Ser Leu Thr Leu Lys Leu
    50                  55                  60

Gly Asn Gly Leu Thr Leu Asn Asn Gln Gly Gln Leu Thr Ser Thr Ala
65                  70                  75                  80

Gly Glu Val Glu Pro Pro Leu Thr Asn Ala Asn Lys Leu Ala Leu
            85                  90                  95

Ala Tyr Ser Glu Pro Leu Ala Val Lys Ser Asn Arg Leu Thr Leu Ser
            100                 105                 110

His Thr Ala Pro Leu Val Ile Ala Asn Asn Ser Leu Ala Leu Gln Val

```
            115                 120                 125
Ser Glu Pro Ile Phe Val Asn Asp Asp Lys Leu Ala Leu Gln Thr
130                 135                 140

Ala Ala Pro Leu Val Thr Asn Ala Gly Thr Leu Arg Leu Gln Ser Ala
145                 150                 155                 160

Ala Pro Leu Gly Leu Val Glu Asn Thr Leu Lys Leu Leu Phe Ser Lys
                165                 170                 175

Pro Leu Tyr Leu Gln Asn Asp Phe Leu Ala Leu Ala Ile Glu Arg Pro
            180                 185                 190

Leu Ala Val Ala Ala Ala Gly Thr Leu Thr Leu Gln Leu Thr Pro Pro
        195                 200                 205

Leu Lys Thr Asn Asp Asp Gly Leu Thr Leu Ser Thr Val Glu Pro Leu
    210                 215                 220

Thr Val Lys Asn Gly Asn Leu Gly Leu Gln Ile Ser Arg Pro Leu Val
225                 230                 235                 240

Val Gln Asn Asn Gly Leu Ser Leu Ala Ile Thr Pro Pro Leu Arg Leu
                245                 250                 255

Phe Asn Ser Asp Pro Val Leu Gly Leu Gly Phe Thr Phe Pro Leu Ala
            260                 265                 270

Val Thr Asn Asn Leu Leu Ser Leu Asn Met Gly Asp Gly Val Lys Leu
        275                 280                 285

Thr Tyr Asn Lys Leu Thr Ala Asn Leu Gly Arg Asp Leu Gln Phe Glu
    290                 295                 300

Asn Gly Ala Ile Ala Val Thr Leu Thr Ala Glu Leu Pro Leu Gln Tyr
305                 310                 315                 320

Thr Asn Lys Leu Gln Leu Asn Ile Gly Ala Gly Leu Arg Tyr Asn Gly
                325                 330                 335

Ala Ser Arg Lys Leu Asp Val Asn Ile Asn Gln Asn Lys Gly Leu Thr
            340                 345                 350

Trp Asp Asn Asp Ala Val Ile Pro Lys Leu Gly Ser Gly Leu Gln Phe
        355                 360                 365

Asp Pro Asn Gly Asn Ile Ala Val Ile Pro Glu Thr Val Lys Pro Gln
    370                 375                 380

Thr Leu Trp Thr Thr Ala Asp Pro Ser Pro Asn Cys Ser Val Tyr Gln
385                 390                 395                 400

Asp Leu Asp Ala Arg Leu Trp Leu Ala Leu Val Lys Ser Gly Asp Met
                405                 410                 415

Val His Gly Ser Ile Ala Leu Lys Ala Leu Lys Gly Thr Leu Leu Asn
            420                 425                 430

Pro Thr Ala Ser Tyr Ile Ser Ile Val Ile Tyr Phe Tyr Ser Asn Gly
        435                 440                 445

Val Arg Arg Thr Asn Tyr Pro Thr Phe Asp Asn Glu Gly Thr Leu Ala
    450                 455                 460

Asn Ser Ala Thr Trp Gly Tyr Arg Gln Gly Gln Ser Ala Asn Thr Asn
465                 470                 475                 480

Val Thr Asn Ala Thr Glu Phe Met Pro Ser Ser Arg Tyr Pro Val
                485                 490                 495

Asn Lys Gly Asp Asn Ile Gln Asn Gln Ser Phe Ser Thr Cys Ile
            500                 505                 510

Lys Gly Asp Phe Ala Met Pro Val Pro Phe Arg Val Thr Tyr Asn His
        515                 520                 525

Ala Leu Glu Gly Tyr Ser Leu Lys Phe Thr Trp Arg Val Val Ala Asn
    530                 535                 540
```

Gln Ala Phe Asp Ile Pro Cys Cys Ser Phe Ser Tyr Ile Thr Glu
545                 550                 555

<210> SEQ ID NO 37
<211> LENGTH: 34115
<212> TYPE: DNA
<213> ORGANISM: simian adenovirus SV-39
<220> FEATURE:
<221> NAME/KEY: CDS
<222> LOCATION: (13448)..(14959)
<223> OTHER INFORMATION: L2 Penton
<220> FEATURE:
<221> NAME/KEY: CDS
<222> LOCATION: (17785)..(20538)
<223> OTHER INFORMATION: L3 Hexon
<220> FEATURE:
<221> NAME/KEY: CDS
<222> LOCATION: (29515)..(31116)
<223> OTHER INFORMATION: L5 Fiber #1

<400> SEQUENCE: 37

| | | | | | |
|---|---|---|---|---|---|
| catcatcaat | ataacaccgc | aagatggcga | ccgagttaac | atgcaaatga | ggtgggcgga | 60 |
| gttacgcgac | ctttgtcttg | ggaacgcgga | agtgggcgcg | gcgggtttcg | gggaggagcg | 120 |
| cggggcgggg | cgggcgtgtc | gcgcggcggt | gacgcgccgg | ggacccggaa | attgagtagt | 180 |
| ttttattcat | tttgcaagtt | tttctgtaca | ttttggcgcg | aaaactgaaa | cgaggaagtg | 240 |
| aaaagtgaaa | aatgccgagg | tagtcaccgg | gtggagatct | gacctttgcc | gtgtggagtt | 300 |
| tacccgctga | cgtgtgggtt | tcggtctcta | ttttttcact | gtggttttcc | gggtacggtc | 360 |
| aaaggtcccc | attttatgac | tccacgtcag | ctgatcgcta | gggtatttaa | tgcgcctcag | 420 |
| accgtcaaga | ggccactctt | gagtgccggc | gagaagagtt | ttctcctccg | cgttccgcca | 480 |
| actgtgaaaa | aatgaggaac | ttcttgctat | ctccggggct | gccagcgacc | gtagccgccg | 540 |
| agctgttgga | ggacattgtt | accggagctc | tgggagacga | tcctcaggtg | atttctcact | 600 |
| tttgtgaaga | ttttagtctt | catgatctct | atgatattga | tccgggtgtt | gaggggcaag | 660 |
| aggatgaatg | gctggagtct | gtggatgggt | tttttccgga | cgctatgctg | ctagaggctg | 720 |
| atttgccacc | acctcacaac | tctcacactg | agcccgagtc | agctgctatt | cctgaattgt | 780 |
| catcaggtga | acttgacttg | gcttgttacg | agactatgcc | tccggagtcg | gatgaggagg | 840 |
| acagcgggat | cagcgatccc | acggctttta | tggtctctaa | ggcgattgct | atactaaaag | 900 |
| aagatgatga | tggcgatgat | ggatttcgac | tggacgctcc | ggcggtgccg | gggagagact | 960 |
| gtaagtcctg | tgaataccac | cgggatcgta | ccggagaccc | gtctatgttg | tgttctctgt | 1020 |
| gttatctccg | tcttaacgct | gcttttgtct | acagtaagtg | ttttgtgctt | ttttacccct | 1080 |
| tggctttgtt | gagtttattt | ttttctgtgt | ctcataggg | gttgtttatt | ataggtcctg | 1140 |
| tttcagatgt | ggaggaacct | gatagtacta | ctggaaatga | ggaggaaaag | ccctccccgc | 1200 |
| cgaaactaac | tcagcgctgc | agacctaata | ttttgagacc | ctcggcccag | cgtgtgtcat | 1260 |
| cccggaaacg | tgctgctgtt | aattgcatag | aagatttatt | ggaagagccc | actgaacctt | 1320 |
| tggacttgtc | cttaaagcga | ccccgcccgc | agtagggcgc | ggtgccagtt | ttttctctct | 1380 |
| agcttccggg | tgactcagtg | caataaaaat | tttcttggca | acaggtgtat | gtgtttactt | 1440 |
| tacgggcggg | aagggattag | gggagtataa | agctggaggg | gaaaaatctg | aggctgtcag | 1500 |
| atcgagtgag | aagttccatg | gacttgtacg | agagcctaga | gaatctaagt | tctttgcgac | 1560 |
| gtttgctgga | ggaggcctcc | gacagaacct | cttacatttg | gaggtttctg | ttcggttccc | 1620 |
| ctctgagtcg | cttttttgcac | cgggtgaagc | gagagcacct | gacggaattt | gatgggcttt | 1680 |

```
tagagcagct gcctggactg tttgattctt tgaatctcgg ccaccggacg ctgctagagg    1740
agaggctttt tccacaattg gacttttcct ctccaggccg tctgtgttca gcgcttgctt    1800
ttgctgtaca tctgttggac agatggaacg agcagacgca gctcagcccg ggttacactc    1860
tggacttcct gacgctatgc ctatggaagt tcggaatcag gagggggagg aagctgtacg    1920
ggcgcttggt ggagaggcat ccgtctctgc gccagcagcg tctgcaagct caagtgctgc    1980
tgaggcggga ggatctggaa gccatttcgg aggaggagag cggcatggaa gagaagaatc    2040
cgagagcggg gctggaccct ccggcggagg agtaggggg ataccggacc cttttcctga     2100
gttggctttg ggggcggtgg ggggcgcttc tgtggtacgt gaggatgaag aggggcgcca    2160
acgcggtcag aagagggagc attttgagtc ctcgactttc ttggctgatg taaccgtggc    2220
cctgatggcg aaaaacaggc tggaggtggt gtggtacccg gaagtatggg aggactttga    2280 gaaggggac ttgcacctgc tggaaaaata aactttgag caggtgaaaa catactggat      2340
gaacccggat gaggactggg aagtggtttt gaaccgatac ggcaaggtag ctctgcgtcc    2400
cgactgtcgc taccaggttc gcgacaaggt ggtcctgcga cgcaacgtgt acctgttggg    2460
caacggcgcc accgtggaga tggtggaccc cagaagggg gtgtttttgtgg ccaatatgca   2520 agaaatgtgc cctggggtgg tgggcttgtc tggggtgact tttcatagtg tgaggtttag    2580
cggtagcaat tttgggggtg tggttattac cgcgaacact cctgtggtcc tgcataattg    2640
ctactttttt ggcttcagca acacctgtgt ggaaatgagg gtgggaggca aagtgcgcgg    2700
gtgttccttt tacgcttgct ggaagggggt ggtgagccag ggtaaggcta aagtgtctgt    2760
tcacaagtgt atgttggaga gatgcacctt gggcatttcc agtgagggct tcctccacgc    2820
cagcgacaac gtggcttctg acaacggctg cgcctttctt atcaagggag ggggtcgcat    2880
ctgtcacaac atgatatgcg gccctgggga tgtccccca aagccttacc agatggttac     2940
ctgcacagat ggcaaggtgc gcatgctcaa gcctgtgcac attgtgggcc accgcgcca     3000 ccgctggcca gagtttgaac acaatgtgat gacccgctgt agcttgtacc tgggaggcag    3060
gcgaggagtt ttcttgccca gacagtgtaa cctggcccac tgcaacgtga tcatggaaca    3120
atccgccgct acccaggttt gctttggagg aatatttgat ataagcatgg tggtgtataa    3180
gatcctgcgc tacgacgact gtcgggctcg tactcgaacc tgcgactgcg gagcctctca    3240
cctgtgtaac ctgactgtga tggggatggt gactgaggag gtgcgactgg accactgtca    3300
gcactcttgc ctgcgggagg agttttcttc ctcggacgag gaggactagg taggtggttg    3360
gggcgtggcc agcgagaggg tgggctataa aggggaggtg tcggctgacg ctgtcttctg    3420
tttttcaggt accatgagcg gatcaagcag ccagaccgcg ctgagcttcg acggggccgt    3480
gtacagcccc tttctgacgg ggcgcttgcc tgcctgggcc ggagtgcgtc agaatgttac    3540
cggttcgacc gtggacggac gtcccgtgga tccatctaac gctgcttcta tgcgctacgc    3600
tactatcagc acatctactc tggacagcgc cgctgccgcc gcagccgcca cctcagccgc    3660
tctctccgcc gccaagatca tggctattaa cccaagcctt tacagccctg tatccgtgga    3720
cacctcagcc ctggagcttt accggcgaga tctagctcaa gtggtggacc aactcgcagc    3780
cgtgagccaa cagttgcagc tggtgtcgac ccgagtggag caactttccc gccctcccca    3840
gtaaccgcaa aaattcaata aacagaattt aataaacagc acttgagaaa agtttaaact    3900
tgtggttgac tttattcctg gatagctggg gggagggaac ggcgggaacg gtaagacctg    3960
gtccatcgtt cccggtcgtt gagaacacgg tggattttttt ccaagacccg atagaggtgg    4020
```

```
gtctgaacgt tgagatacat gggcatgagc ccgtctcggg ggtggaggta ggcccactgc   4080
agggcctcgt tttcaggggt ggtgttgtaa atgatccagt cgtaggcccc ccgctgggcg   4140
tggtgctgga agatgtcctt cagcagcaag ctgatggcaa cgggaagacc cttggtgtag   4200
gtgttgacaa agcggttgag ttgggagggg tgcatgcggg gactgatgag gtgcattttg   4260
gcctggatct tgaggttggc tatgttgccg cccagatcgc gcctgggatt catgttatgc   4320
aagaccacca gcaccgagta accggtgcag cgggggaatt tgtcgtgcag cttgaaggg    4380
aaagcgtgga agaatttgga gacccctcgg tgcccgccta ggttttccat gcactcatcc   4440
atgatgatgg cgatgggccc ccgggaggca gcctgggcaa aaacgttgcg ggggtccgtg   4500
acatcgtagt tgtggtcctg ggtgagttca tcataggaca ttttgacaaa gcgcgggcag   4560
agggtcccag actggggaat gatggttcca tccggtccgg gggcgtagtt gccctcgcag   4620
atttgcattt cccaggcttt gatttcagag ggagggatca tgtcaacctg ggggcgatg    4680
aaaaaaatgg tctctggggc gggggtgatg agctgggtgg aaagcaggtt gcgcaagagc   4740
tgtgacttgc cgcagccggt gggcccgtag atgacagcta tgacgggttg cagggtgtag   4800
tttagagagc tacaactgcc atcatccttc aaaagcgggg ccacactgtt taaaagttct   4860
ctaacatgta agttttcccg cactaagtcc tgcaggagac gtgaccctcc tagggagaga   4920
agttcaggaa gcgaagcaaa gttttaagt ggcttgaggc catcggccaa gggcaagttc    4980
ctgagagttt gactgagcag ttccagccgg tcccagagct cggttacgtg ctctacggca   5040
tctcgatcca gcagacctcc tcgtttcggg ggttggggcg gctctggctg tagggaatga   5100
ggcggtgggc gtccagctgg gccatggtgc ggtccctcca tgggcgcagg gttctcttca   5160
gggtggtctc ggtcacggtg aatgggtggg ccccgggctg ggcgctggcc agggtgcgct   5220
tgaggctgag gcggctggtg gcgaaccgtt gcttttcgtc tccctgcaag tcagccaaat   5280
agcaacggac catgagctca tagtccaggc tctctgcggc atgtcctttg gcgcgaagct   5340
tgcctttgga aacgtgcccg cagtttgagc agagcaagca ttttagcgcg tagagttttg   5400
gcgccaagaa cacggattcc ggggaataag catccccacc gcagttggag caaacggttt   5460
cgcattccac cagccaggtc agctgaggat cttttgggtc aaaaaccaag cgcccgccgt   5520
ttttttttgat gcgcttccta cctcgggtct ccatgaggcg gtgcccgcgt tcggtgacga   5580
agaggctgtc ggtgtctccg tagacggagg tcagggcgcg ctcctccagg ggggtcccgc   5640
ggtcctcggc gtagagaaac tcgcaccact ctgacataaa cgcccgggtc caggctagga   5700
cgaatgaggc gatgtgggaa gggtaccggt cgttatcgat gagggggtcg gtttttttcca   5760
aggtgtgcag gcacatgtcc ccctcgtccg cttccaaaaa tgtgattggc ttgtaggtgt   5820
aagtcacgtg atcctgtcct tccgcggggg tataaaaggg ggcgtttccc ccctcctcgt   5880
cactctcttc cggttcgctg tcgccaaagg ccagctgttg gggtacgtaa acgcgggtga   5940
aggcgggcat gacctgtgcg ctgaggttgt cagtttctat atacgaggaa gatttgatgg   6000
cgagcgcccc cgtggagatg cccttgaggt gctcggggcc catttggtca gaaaacacaa   6060
tctgtcggtt atcaagcttg gtggcaaaag acccgtagag ggcgttggag agcaacttgg   6120
cgatggagcg ctgggtttgg tttttttccc ggtcggcttt ttccttggcc gcgatgttga   6180
gctggacgta ctccctggcc acgcacttcc agccgggaaa acggccgtg cgctcgtccg    6240
gcaccagcct cacgctccat ccgcggttgt gcagggtgat gacgtcgatg ctggtggcca   6300
cctctccgcg caggggctcg ttggtccagc agaggcgacc gcccttgcga gagcagaagg   6360
ggggcagggg gtcaagcagg cgctcgtccg gggggtcggc gtcgatggta aagatggcgg   6420
```

```
gcagcaggtg tttgtcaaag taatcgatct gatgcccggg gcaacgcagg gcggtttccc   6480
agtcccgcac cgccaaggcg cgctcgtatg gactgagggg ggcgccccag ggcatgggat   6540
gcgtcagggc cgaggcgtac atgccgcaga tgtcatagac gtaaaggggc tcctccagga   6600
cgccgaggta ggtggggtag cagcgccccc cgcggatgct ggcccgtacg tagtcgtaga   6660
gctcgtgcga gggggccaga aggtggcggc tgaggtgagc gcgctggggc ttttcatctc   6720
ggaagaggat ctgcctgaag atggcgtggg agttggagga gatggtgggc cgctgaaaaa   6780
tgttgaagcg ggcgtcgggc agacccacgg cctcgccgat aaagtgggcg taggactctt   6840
gcagcttttc caccagggag gcggtgacca gcacgtccag agcgcagtag tccagggttt   6900
cccgcacgat gtcataatgc tcttcctttt tttccttcca gaggtctcgg ttgaagagat   6960
actcttcgcg gtctttccag tactcttgga gaggaaaccc gttttcgtct ccacggtaag   7020
agcccaacat gtaaaactgg ttgacggcct gatagggaca gcatcccttc tccacgggca   7080
gcgagtaggc cagggcggcc ttgcgcaggg aggtgtgagt cagggcaaag gtgtcgcgga   7140
ccataacttt tacaaactgg tacttaaagt cccggtcgtc gcacatgcct cgctcccagt   7200
ctgagtagtc tgtgcgcttt ttgtgcttgg ggttaggcag ggagtaggtg acgtcgttaa   7260
agaggatttt gccacatctg ggcataaagt tgcgagagat tctgaagggg ccgggcacct   7320
ccgagcggtt gttgatgact tgggcagcca ggagaatttc gtcgaagccg ttgatgttgt   7380
gccccacgac gtagaactct atgaaacgcg gagcgccgcg cagcagggg cacttttcaa   7440 gttgctggaa agtaagttcc cgcggctcga cgccgtgttc cgtgcggctc cagtcctcca   7500
ccgggtttcg ctccacaaaa tcctgccaga tgtggtcgac tagcaagagc tgcagtcggt   7560
cgcgaaattc gcggaatttt ctgccgatgg cttgcttctg ggggttcaag caaaaaagg   7620 tgtctgcgtg gtcgcgccag cgtcccagc cgagctcgcg agccagattc agggccagca   7680
gcaccagagc cggctcaccg gtgattttca tgacgaggag aaaggggcacc agctgttttc   7740 cgaacgcgcc catccaggtg taggtctcca cgtcgtaggt gagaaacaga cgttcggtcc   7800
gcgggtgcga tcccaggggg aaaaacttga tgggctgcca ccattgggag ctctgggcgt   7860
ggatgtgatg gaagtaaaag tcccggcggc gcgtggaaca ttcgtgctgg ttttttgtaaa   7920 agcggccgca gtggtcgcag cgcgagacgg agtgaaggct gtgaatcagg tgaatcttgc   7980
gtcgctgagg gggccccaga gccaaaaagc ggagcgggaa cgaccgcgcg gccacttcgg   8040
cgtccgcagg caagatggat gagggttcca ccgttccccg cccgcggacc gaccagactt   8100
ccgccagctg cggcttcagt tcttgcacca gctctcgcag cgtttcgtcg ctgggcgaat   8160
cgtgaatacg gaagttgtcg ggtagaggcg ggaggcggtg gacttccagg aggtgtgtga   8220 gggcggcag gagatgcagg tggtacttga tttcccacgg atgacggtcg cgggcgtcca   8280
aggcgaagag atgaccgtgg ggccgcggcg ccaccagcgt tccgcgggg gtctttatcg   8340 gcggcgggga cgggctcccg gcggcagcgg cggctcggga cccgcgggca agtcgggcag   8400
cggcacgtcg gcgtggagct cgggcagggg ctggtgctgc gcgcggagct gactggcaaa   8460
ggctatcacc cggcgattga cgtcctggat ccggcggcgc tgcgtgaaga ccaccggacc   8520
cgtggtcttg aacctgaaag agagttcgac agaatcaatc tcggcatcgt taaccgcggc   8580
ctggcgcagg atttcggcca cgtccccgga gttgtcttga tacgcgattt ctgccatgaa   8640
ctggtcgatt tcctcttcct gcaagtctcc gtgaccggcg cgttcgacgg tggccgcgag   8700
atcgttggag atgcggccca tgagctggga aaaggcattg atgccgacct cgttccacac   8760
```

```
tcggctgtac accacctctc cgtgaacgtc gcgggcgcgc atcaccacct gggcgagatt    8820
gagttccacg tggcgggcga aaaccggata gtttcggagg cgctgataca gatagttgag    8880
ggtggtggcg gcgtgctcgg ccacaaaaaa atacatgatc cagcggcgga gggtcagctc    8940
gttgatgtcg cccagcgcct ccaggcgttc catggcctcg taaaagtcca cggcaaagtt    9000
gaaaaattgg ctgttcctgg ccgagaccgt gagctcttct tccaagagcc gaatgagatc    9060
cgccacggtg gccctgactt cgcgttcgaa agccccgggt gcctcctcca cctcttcctc    9120
ctcgacttct tcgaccgctt cgggcacctc ctcttcctcg accaccacct caggcggggc    9180
tcggcggcgc cggcggcgga cgggcaggcg gtcgacgaaa cgctcgatca tttccccccct   9240
ccgtcgacgc atggtctcgg tgacggcgcg accctgttcg cgaggacgca gggtgaaggc    9300
gccgccgccg agcggaggta acagggagat cgggggggcgg tcgtggggga gactgacggc   9360
gctaactatg catctgatca atgtttgcgt agtgacctcg ggtcggagcg agctcagcgc    9420
ttgaaaatcc acgggatcgg aaaaccgttc caggaacgcg tctagccaat cacagtcgca    9480
aggtaagctg aggaccgtct cgggggcttg tctgttctgt cttcccgcgg tggtgctgct    9540
gatgaggtag ttgaagtagg cgctcttgag gcggcggatg gtggacagga gaaccacgtc    9600
tttgcgccca gcttgctgta tccgcaggcg gtcggccatg ccccacactt ctccttgaca    9660
gcggcggagg tccttgtagt attcttgcat cagccttcc acgggcacct cgtcttcttc     9720
ttccgctcgg ccggacgaga gccgcgtcag gccgtacccg cgctgcccct gtggttggag    9780
cagggccagg tcggccacga cgcgctcggc cagcacggcc tgctggatgc gggtgagggt    9840
gtcctgaaag tcgtcgagat ccacaaagcg gtggtacgcg ccagtgttga tggtgtaggt    9900
gcagttgctc atgacggacc agtttacggt ctgggtgcca tggcccacgg tttccaggta    9960
gcggagacgc gagtaggccc gcgtctcgaa gatgtagtcg ttgcaggtcc gcagcagta    10020
ctggtagccc accagcagat gcggcggcgg ctggcggtag aggggccacc gctgggtggc   10080
gggggcgttg gggcgagat cttccaacat gaggcggtga tagccgtaga tgtagcgcga    10140
catccaagtg atgccgctgg ccgtggtgct ggcgcgggcg tagtcgcgaa cgcggttcca   10200
gatgtttcgc agcggctgga agtactcgat ggtggggcga ctctgccccg tgaggcgggc   10260
gcagtcggcg atgctctacg gggaaaaaga agggccagtg aacaaccgcc ttccgtagcc   10320
ggaggagaac gcaaggggt caaagaccac cgaggctcgg gttcgaaacc cgggtggcgg    10380
cccgaatacg gagggcggtt ttttgctttt ttctcagatg catcccgtgc tgcggcagat   10440
gcgtccgaac gcggggtccc agtccccggc ggtgcctgcg gccgtgacgg cggcttctac   10500
ggccacgtcg cgctccaccc cgcctaccac ggcccaggcg gcggtggctc tgcgcggcgc   10560
aggggaaccc gaagcagagg cggtgttgga cgtggaggag ggccagggt tggctcggct    10620
gggggccctg agtcccgagc ggcacccgcg cgtggctctg aagcgcgacg cggcggaggc   10680
gtacgtgccg cggagcaatc tgtttcgcga ccgcagcggc gaggaggccg aggagatgcg   10740
agacttgcgt tttcgggcgg ggaggagtt cgtcacggg ctggaccggc agagggttct     10800
gagagaggag gactttgagg cggacgagcg cacgggggtg agtcccgcgc gggctcacgt   10860
ggcggccgcc aacctggtga gcgcgtacga gcagacggtc aaggaggaga tgaacttcca   10920
gaagagcttc aatcatcacg tgcgcacgct gattgcgcgc gaagaggtgg ccatcggcct   10980
catgcatctg tgggatttgg tggaggcgta cgttcagaac cccagcagca agccgctgac   11040
ggctcagctg ttcctcatcg tgcaacatag tcgacacaac gaaacgttca gggaggccat    11100
gctgaacatt gcagagcctg aggggcgctg gctcttggat ctcattaaca tcttgcagag   11160
```

```
tatcgtagtg caggagcgct cgctgagcct ggccgacaag gtggctgcca tcaactacag   11220
catgctgtcg ctgggcaaat tttacgcccg caagatctac aagtctccgt tcgtccccat   11280
agacaaggag gtgaagatag acagcttta catgcgcatg cgctcaagg tgctgactct   11340 aagcgacgac ctgggggtgt accgcaacga ccgcatacac aaggcggtga gcgccagccg   11400
ccggcgcgag ctgagcgacc gcgagctttt gcacagcctg catcgggcgt tgactggtgc   11460
cggcagcgcc gaggcggccg agtactttga cgccggagcg gacttgcgct ggcagccatc   11520
ccgacgcgcg ctggaggcgg ctggcgtcgg ggagtacggg gtcgaggacg acgatgaagc   11580
ggacgacgag ttgggcattg acttgtagcc gttttcgtt agatatgtcg gcgaacgagc   11640
cgtctgcggc cgccatggtg acggcggcgg gcgcgcccca ggacccggcc acgcgcgcgg   11700
cgctgcagag tcagccttcc ggagtgacgc ccgcggacga ctggtccgag gccatgcgtc   11760
gcatcctggc gctgacggcg cgcaaccccg aggcttttcg gcagcagccg caggcaaacc   11820
ggtttgcggc cattttggaa gcggtggtgc cctccagacc caaccccacc cacgaaaagg   11880
tgctggccat cgtcaacgcc ctggcggaga ccaaggccat ccgcccagac gaggccgggc   11940
aggtttacaa cgcgctgcta gaaagggtgg gacgctacaa cagctccaac gtgcagacca   12000
atctggaccg cttggtgacg gacgtgaagg aggccgtagc ccagcgagag cggtttttca   12060
aggaagccaa tctgggctcg ctggtggccc tcaacgcctt cctgagcacg ctgccggcga   12120
acgtgccccg cggtcaggag gactacgtga actttctgag cgccctccgc ctgatggtgg   12180
ccgaggtgcc gcagagcgag gtgtaccagt ctggccccaa ctactacttc cagacctccc   12240
ggcagggcct gcagacggta aacctgacgc aggcctttca gaacctgcag gcctttggg   12300 gggtgcgcgc tccgctgggc gaccgcagca cggtgtccag cctgctgacc cccaatgccc   12360
ggctgctctt gcttctcatt gctccgttca ccgacagcgg ttccatcagc cgcgactctt   12420
acctgggaca cctgctcacc ctgtaccggg aggccatcgg gcaggcgcgg gtggacgagc   12480
agacgtacca ggaaatcacc agcgtgagcc gcgcgctggg gcaggaggac acgggcagct   12540
tggaggcgac tctgaacttc ctgctgacca accggcggca gcgcctacct ccccagtacg   12600
cgctgaacgc ggaggaggag cgcatcctgc gtttcgtgca gcagagcacc cgcgctgtact   12660 tgatgcggga aggcgcctct cccagcgctt cgctggacat gacggcgcc aacatggagc   12720 catcgttcta cgccgccaac cgtcccttcg tcaaccggct aatggactat ttgcatcggg   12780
cggcggccct gaacccggaa tactttacta acgtcatcct gaacgaccgt tggctgccac   12840
ctcccggctt ctacacgggg gagttcgacc tcccggaggc caacgacggt tcatgtgggg   12900
acgacgtgga cagcgtgttc ctgcccggca gaaggaggc gggtgactct cagagccacc   12960
gcgcgagcct cgcagacctg ggggcgaccg ggcccgcgtc tccgctgcct cgcctgccga   13020
gcgccagcag cgccagcgtg gggcgggtga gccgtccgcg cctcagcggt gaggaggact   13080
ggtggaacga tccgctgctc cgtccggccc gcaacaaaaa cttccccaac aacgggatag   13140
aggatttggt agacaaaatg aaccgttgga agacgtatgc ccaggagcat cgggagtggc   13200
aggcgaggca acccatgggc cctgttctgc cgccctctcg gcgcccgcgc agggacgaag   13260
acgccgacga ttcagccgat gacagcagcg tgttggatct gggcgggagc gggaacccct   13320
ttgcccacct gcaacctcgc ggcgtgggtc ggcggtggcg ctaggaaaaa aaattattaa   13380
aagcacttac cagagccatg gtaagaagag caacaaggt gtgtcctgct ttcttcccgg   13440 tagcaaa atg cgt cgg gcg gtg gca gtt ccc tcc gcg gca atg gcg tta   13489
        Met Arg Arg Ala Val Ala Val Pro Ser Ala Ala Met Ala Leu
```

| | | | | | | | | | | | | | | | |
|---|---|---|---|---|---|---|---|---|---|---|---|---|---|---|---|
| ggc | ccg | ccc | cct | tct | tac | gaa | agc | gtg | atg | gca | gcg | gcc | acc | ctg | caa | 13537 |
| Gly | Pro | Pro | Pro | Ser | Tyr | Glu | Ser | Val | Met | Ala | Ala | Ala | Thr | Leu | Gln | |
| 15 | | | | 20 | | | | | 25 | | | | | 30 | | |

| gcg | ccg | ttg | gag | aat | cct | tac | gtg | ccg | ccg | cga | tac | ctg | gag | cct | acg | 13585 |
|---|---|---|---|---|---|---|---|---|---|---|---|---|---|---|---|---|
| Ala | Pro | Leu | Glu | Asn | Pro | Tyr | Val | Pro | Pro | Arg | Tyr | Leu | Glu | Pro | Thr | |
| | | | | | 35 | | | | 40 | | | | | 45 | | |

| ggc | ggg | aga | aac | agc | att | cgt | tac | tcg | gag | ctg | acg | ccc | ctg | tac | gac | 13633 |
|---|---|---|---|---|---|---|---|---|---|---|---|---|---|---|---|---|
| Gly | Gly | Arg | Asn | Ser | Ile | Arg | Tyr | Ser | Glu | Leu | Thr | Pro | Leu | Tyr | Asp | |
| | | | 50 | | | | | 55 | | | | 60 | | | | |

| acc | acc | cgc | ctg | tac | ctg | gtg | gac | aac | aag | tca | gca | gat | atc | gcc | acc | 13681 |
|---|---|---|---|---|---|---|---|---|---|---|---|---|---|---|---|---|
| Thr | Thr | Arg | Leu | Tyr | Leu | Val | Asp | Asn | Lys | Ser | Ala | Asp | Ile | Ala | Thr | |
| | | 65 | | | | 70 | | | | 75 | | | | | | |

| ttg | aac | tac | cag | aac | gac | cac | agc | aac | ttt | ctc | acg | tcc | gtg | gtg | cag | 13729 |
|---|---|---|---|---|---|---|---|---|---|---|---|---|---|---|---|---|
| Leu | Asn | Tyr | Gln | Asn | Asp | His | Ser | Asn | Phe | Leu | Thr | Ser | Val | Val | Gln | |
| 80 | | | | | 85 | | | | 90 | | | | | | | |

| aac | agc | gac | tac | acg | ccc | gcc | gaa | gcg | agc | acg | cag | acc | att | aac | ttg | 13777 |
|---|---|---|---|---|---|---|---|---|---|---|---|---|---|---|---|---|
| Asn | Ser | Asp | Tyr | Thr | Pro | Ala | Glu | Ala | Ser | Thr | Gln | Thr | Ile | Asn | Leu | |
| 95 | | | | 100 | | | | | 105 | | | | | 110 | | |

| gac | gac | cgc | tcg | cgc | tgg | ggc | ggg | gac | ttg | aaa | acc | att | ctg | cac | act | 13825 |
|---|---|---|---|---|---|---|---|---|---|---|---|---|---|---|---|---|
| Asp | Asp | Arg | Ser | Arg | Trp | Gly | Gly | Asp | Leu | Lys | Thr | Ile | Leu | His | Thr | |
| | | | | 115 | | | | | 120 | | | | | 125 | | |

| aac | atg | ccc | aac | gtg | aac | gag | ttc | atg | ttt | acc | aac | tcg | ttc | agg | gct | 13873 |
|---|---|---|---|---|---|---|---|---|---|---|---|---|---|---|---|---|
| Asn | Met | Pro | Asn | Val | Asn | Glu | Phe | Met | Phe | Thr | Asn | Ser | Phe | Arg | Ala | |
| | | 130 | | | | | 135 | | | | | 140 | | | | |

| aaa | ctt | atg | gtg | gcg | cac | gag | gcc | gac | aag | gac | ccg | gtt | tat | gag | tgg | 13921 |
|---|---|---|---|---|---|---|---|---|---|---|---|---|---|---|---|---|
| Lys | Leu | Met | Val | Ala | His | Glu | Ala | Asp | Lys | Asp | Pro | Val | Tyr | Glu | Trp | |
| | | 145 | | | | | 150 | | | | | 155 | | | | |

| gtg | cag | ctg | acg | ctg | ccg | gag | ggg | aac | ttt | tca | gag | att | atg | acc | ata | 13969 |
|---|---|---|---|---|---|---|---|---|---|---|---|---|---|---|---|---|
| Val | Gln | Leu | Thr | Leu | Pro | Glu | Gly | Asn | Phe | Ser | Glu | Ile | Met | Thr | Ile | |
| 160 | | | | | 165 | | | | | 170 | | | | | | |

| gac | ctg | atg | aac | aac | gcc | att | atc | gac | cac | tac | ctg | gcg | gta | gcc | aga | 14017 |
|---|---|---|---|---|---|---|---|---|---|---|---|---|---|---|---|---|
| Asp | Leu | Met | Asn | Asn | Ala | Ile | Ile | Asp | His | Tyr | Leu | Ala | Val | Ala | Arg | |
| 175 | | | | 180 | | | | | 185 | | | | | 190 | | |

| cag | cag | ggg | gtg | aaa | gaa | agc | gag | atc | ggc | gtc | aag | ttt | gac | acg | cgc | 14065 |
|---|---|---|---|---|---|---|---|---|---|---|---|---|---|---|---|---|
| Gln | Gln | Gly | Val | Lys | Glu | Ser | Glu | Ile | Gly | Val | Lys | Phe | Asp | Thr | Arg | |
| | | | 195 | | | | | 200 | | | | | 205 | | | |

| aac | ttt | cgt | ctg | ggc | tgg | gac | ccg | gag | acg | ggg | ctt | gtg | atg | ccg | ggg | 14113 |
|---|---|---|---|---|---|---|---|---|---|---|---|---|---|---|---|---|
| Asn | Phe | Arg | Leu | Gly | Trp | Asp | Pro | Glu | Thr | Gly | Leu | Val | Met | Pro | Gly | |
| | | | 210 | | | | | 215 | | | | | 220 | | | |

| gtg | tac | acg | aac | gaa | gct | ttc | cat | ccc | gac | gtg | gtc | ctc | ttg | ccg | ggc | 14161 |
|---|---|---|---|---|---|---|---|---|---|---|---|---|---|---|---|---|
| Val | Tyr | Thr | Asn | Glu | Ala | Phe | His | Pro | Asp | Val | Val | Leu | Leu | Pro | Gly | |
| | | 225 | | | | | 230 | | | | | 235 | | | | |

| tgc | ggg | gtg | gac | ttt | acc | tac | agc | cgg | tta | aac | aac | ctg | cta | ggc | ata | 14209 |
|---|---|---|---|---|---|---|---|---|---|---|---|---|---|---|---|---|
| Cys | Gly | Val | Asp | Phe | Thr | Tyr | Ser | Arg | Leu | Asn | Asn | Leu | Leu | Gly | Ile | |
| 240 | | | | | 245 | | | | | 250 | | | | | | |

| cgc | aag | aga | atg | ccc | ttt | cag | gaa | ggg | ttt | cag | atc | ctg | tac | gag | gac | 14257 |
|---|---|---|---|---|---|---|---|---|---|---|---|---|---|---|---|---|
| Arg | Lys | Arg | Met | Pro | Phe | Gln | Glu | Gly | Phe | Gln | Ile | Leu | Tyr | Glu | Asp | |
| 255 | | | | 260 | | | | | 265 | | | | | 270 | | |

| ctg | gag | ggc | ggt | aac | atc | ccg | gcc | ctg | ctg | gac | gtg | ccg | gcg | tac | gag | 14305 |
|---|---|---|---|---|---|---|---|---|---|---|---|---|---|---|---|---|
| Leu | Glu | Gly | Gly | Asn | Ile | Pro | Ala | Leu | Leu | Asp | Val | Pro | Ala | Tyr | Glu | |
| | | | | 275 | | | | | 280 | | | | | 285 | | |

| gag | agc | atc | gcc | aac | gca | agg | gag | gcg | gcg | atc | agg | ggc | gat | aat | ttc | 14353 |
|---|---|---|---|---|---|---|---|---|---|---|---|---|---|---|---|---|
| Glu | Ser | Ile | Ala | Asn | Ala | Arg | Glu | Ala | Ala | Ile | Arg | Gly | Asp | Asn | Phe | |
| | | | 290 | | | | | 295 | | | | | 300 | | | |

| gcg | gcg | cag | ccc | cag | gcg | gct | cca | acc | ata | aaa | ccc | gtt | ttg | gaa | gac | 14401 |
|---|---|---|---|---|---|---|---|---|---|---|---|---|---|---|---|---|
| Ala | Ala | Gln | Pro | Gln | Ala | Ala | Pro | Thr | Ile | Lys | Pro | Val | Leu | Glu | Asp | |
| | | 305 | | | | | 310 | | | | | 315 | | | | |

| tcc | aaa | ggg | cgg | agc | tac | aac | gta | ata | gcc | aac | acc | aac | aac | acg | gct | 14449 |

```
Ser Lys Gly Arg Ser Tyr Asn Val Ile Ala Asn Thr Asn Asn Thr Ala
    320                 325                 330 tac agg agc tgg tat ctg gct tat aac tac ggc gac ccg gag aag ggg    14497
Tyr Arg Ser Trp Tyr Leu Ala Tyr Asn Tyr Gly Asp Pro Glu Lys Gly
335                 340                 345                 350 gtt agg gcc tgg acc ctg ctc acc act ccg gac gtg acg tgc ggt tca    14545
Val Arg Ala Trp Thr Leu Leu Thr Thr Pro Asp Val Thr Cys Gly Ser
                355                 360                 365 gag cag gtc tac tgg tcg ctg cct gac atg tac gtg gac cct gtg acg    14593
Glu Gln Val Tyr Trp Ser Leu Pro Asp Met Tyr Val Asp Pro Val Thr
            370                 375                 380 ttt cgc tcc acg cag caa gtt agc aac tac cca gtg gtg gga gcg gag    14641
Phe Arg Ser Thr Gln Gln Val Ser Asn Tyr Pro Val Val Gly Ala Glu
        385                 390                 395 ctt atg ccg att cac agc aag agc ttt tac aac gag cag gcc gtc tac    14689
Leu Met Pro Ile His Ser Lys Ser Phe Tyr Asn Glu Gln Ala Val Tyr
    400                 405                 410 tca cag ctc att cgt cag acc acc gcc cta acg cac gtt ttc aac cgc    14737
Ser Gln Leu Ile Arg Gln Thr Thr Ala Leu Thr His Val Phe Asn Arg
415                 420                 425                 430 ttc ccc gag aac caa atc cta gtg cga cct cca gcg ccc acc atc acc    14785
Phe Pro Glu Asn Gln Ile Leu Val Arg Pro Pro Ala Pro Thr Ile Thr
                435                 440                 445 acc gtc agc gag aac gtg ccc gct cta acc gat cac ggg acg ctg cct    14833
Thr Val Ser Glu Asn Val Pro Ala Leu Thr Asp His Gly Thr Leu Pro
            450                 455                 460 ttg cag aac agc atc cgc gga gtt cag cga gtt acc atc acg gac gcc    14881
Leu Gln Asn Ser Ile Arg Gly Val Gln Arg Val Thr Ile Thr Asp Ala
        465                 470                 475 cgt cgt cgg acc tgt ccc tac gtc tac aaa gcc ttg gga atc gtg gcc    14929
Arg Arg Arg Thr Cys Pro Tyr Val Tyr Lys Ala Leu Gly Ile Val Ala
    480                 485                 490 ccg cgc gtc ctg tcg agt cgc act ttc tag atgtccatcc tcatctctcc      14979
Pro Arg Val Leu Ser Ser Arg Thr Phe
495                 500 cagcaacaat accggttggg gtctgggcgt gaccaaaatg tacggaggcg ccaaacgacg   15039
gtccccacaa catcccgtgc gagtgcgcgg gcactttaga gccccatggg ggtcgcacac   15099
gcgcgggcgc accggccgaa ccaccgtcga cgacgtgatc gatagcgtgg tggccgacgc   15159
ccgcaactac cagcccgctc gatccacggt ggacgaagtc atcgacgcg tggtggccga   15219 cgccagggcc tacgcccgca gaaagtctcg tctgcgccgc cgccgttcgc taaagcgccc   15279
cacggccgcc atgaaagccg ctcgctctct gctgcgtcgc gcacgtatcg tgggtcgccg   15339
cgccgccaga cgcgcagccg ccaacgccgc cgccggccga gtgcgccgcc gggccgccca   15399
gcaggccgcc gccgccatct ccagtctatc cgcccccga cgcgggaatg tgtactgggt   15459
cagggactcg gccaccggcg tgcgagttcc cgtgagaacc cgtcctcctc gtccctgaat   15519
aaaaagttct aagcccaatc ggtgttccgt tgtgtgttca gctcgtcatg accaaacgca   15579
agtttaaaga ggagctgctg caagcgctgg tccccgaaat ctatgcgccg cgccggacg    15639 tgaaaccgcg tcgcgtgaaa cgcgtgaaga agcaggaaaa gctagagaca aaagaggagg   15699
cggtggcgtt gggagacggg gaggtggagt ttgtgcgctc gttcgcgccg cgtcggcgag   15759
tgaattggaa ggggcgcaag gtgcaacggg tgctgcgtcc cggcacggtg gtgtctttca   15819
ccccgggtga aaaatccgcc tggaagggca taaagcgcgt gtacgatgag gtgtacgggg   15879
acgaagacat tctggagcag gcgctggata gaagcgggga gtttgcttac ggcaagaggg   15939
```

```
cgaggacggg cgagatcgcc atcccgctgg acacttccaa ccccacccc  agtctgaaac   15999
ccgtgacgct gcaacaggtg ttgccggtga gcgcccctc  gcgacgcggc ataaaacgcg   16059
agggcggcga gctgcagccc accatgcagc tcctggttcc caagaggcag aaactagagg   16119
acgtactgga catgataaaa atggagcccg acgtgcagcc cgatattaaa atccgtccca   16179
tcaaagaagt ggcgccggga tgggcgtgc  agaccgtgga catccagatt cccatgacca   16239
gcgccgcaca gcggtagag  gccatgcaga ccgacgtggg gatgatgacg gacctgcccg   16299
cagctgctgc cgccgtggcc agcgccgcga cgcaaacgga agccggcatg cagaccgacc   16359
cgtggacgga ggcgcccgtg cagccggcca aagacgcgt  cagacggacg tacgcccccg   16419
tttctggcat aatgccggag tacgcgctgc atccttccat catccccacc cccggctacc   16479
gggggcgcac ctaccgtccg cgacgcagca ccactcgccg ccgtcgccgc acggcacgag   16539
tcgccaccgc cagagtgaga cgcgtaacga cacgtcgcgg ccgccgcttg accctgcccg   16599
tggtgcgcta ccatcccagc attctttaaa aaaccgctcc tacgttgcag atgggcaagc   16659
ttacttgtcg actccgtatg gccgtgcccg gctaccgagg aagatcccgc cgacgacgga   16719
ctttgggagg cagcggtttg cgccgccgtc gggcggttca ccggcgcctc aaggaggca    16779
ttctgccggc cctgatcccc ataatcgccg cagccatcgg ggccattccc ggaatcgcca   16839
gcgtagcggt gcaggctagc cagcgccact gattttacta accctgtcgg tcgcgccgtc   16899
tctttcggca gactcaacgc ccagcatgga agacatcaat ttctcctctc tggccccgcg   16959
gcacggcacg cggccgtata tgggacgtg  gagcgagatc ggcacgaacc agatgaacgg   17019
gggcgctttc aattggagcg gtgtgtggag cggcttgaaa aatttcggtt ccactctgaa   17079
aacttacggc aaccgggtgt ggaactccag cacggggcag atgctgaggg acaagctaaa   17139
ggacacgcag tttcagcaaa aggtggtgga cggcatcgct tcgggcctca acggcgccgt   17199
cgacctggcc aaccaggcca ttcaaaagga aattaacagc cgcctggagc cgcggccgca   17259
ggtggaggag aacctgcccc ctctggaggc gctgccccc  aagggagaga agcgcccgcg   17319
gcccgacatg gaggagacgc tagttactaa gagcgaggag ccgccatcat acgaggaggc   17379
ggtgggtagc tcgcagctgc cgtccctcac gctgaagccc accacctatc ccatgaccaa   17439
gcccatcgcc tccatggcgc gcccccgtggg agtcgacccg cccatcgacg cggtggccac   17499
tttggacctg ccgcgccccg aaccggcaa  ccgcgtgcct cccgtcccca tcgctccgcc   17559
ggtttctcgc cccgccatcc gccccgtcgc cgtggccact ccccgctatc cgagccgcaa   17619
cgccaactgg cagaccaccc tcaacagtat tgtcggactg ggggtgaagt ctctgaagcg   17679
ccgtcgctgt ttttaaagca caatttatta aacgagtagc cctgtcttaa tccatcgttg   17739
tatgtgtgcc tatatcacgc gttcagagcc tgaccgtccg tcaag atg gcc act ccg   17796
                                                  Met Ala Thr Pro
                                                  505
```

```
tcg atg atg ccg cag tgg tcg tac atg cac atc gcc ggg cag gac gcc   17844
Ser Met Met Pro Gln Trp Ser Tyr Met His Ile Ala Gly Gln Asp Ala
    510                 515                 520 tcg gag tac ctg agc ccg ggt ctg gtg cag ttt gcc cgt gcg acg gaa   17892
Ser Glu Tyr Leu Ser Pro Gly Leu Val Gln Phe Ala Arg Ala Thr Glu
525                 530                 535 acc tac ttc tca ctg ggc aac aag ttc agg aac ccc acc gtg gcg ccc   17940
Thr Tyr Phe Ser Leu Gly Asn Lys Phe Arg Asn Pro Thr Val Ala Pro
540                 545                 550                 555 acc cac gac gtc acc acc gat cgg tcc cag cga ctg aca atc cgc ttc   17988
Thr His Asp Val Thr Thr Asp Arg Ser Gln Arg Leu Thr Ile Arg Phe
                560                 565                 570
```

```
gtc ccc gtg gac aag gaa gac acc gct tac tcc tac aaa acc cgc ttc      18036
Val Pro Val Asp Lys Glu Asp Thr Ala Tyr Ser Tyr Lys Thr Arg Phe
            575                 580                 585 acg ctg gcc gtg ggc gac aac cgg gtg cta gac atg gcc agt acc tac      18084
Thr Leu Ala Val Gly Asp Asn Arg Val Leu Asp Met Ala Ser Thr Tyr
        590                 595                 600 ttt gac atc cgc ggc gtg atc gac cgc gga cct agc ttc aag cct tac      18132
Phe Asp Ile Arg Gly Val Ile Asp Arg Gly Pro Ser Phe Lys Pro Tyr
605                 610                 615 tcc ggc acg gct tac aac tca ctg gct ccc aaa ggg gcg ccc aac aac      18180
Ser Gly Thr Ala Tyr Asn Ser Leu Ala Pro Lys Gly Ala Pro Asn Asn
620                 625                 630                 635 agc caa tgg aac gcc aca gat aac ggg aac aag cca gtg tgt ttt gct      18228
Ser Gln Trp Asn Ala Thr Asp Asn Gly Asn Lys Pro Val Cys Phe Ala
                640                 645                 650 cag gca gct ttt ata ggt caa agc att aca aaa gac gga gtg caa ata      18276
Gln Ala Ala Phe Ile Gly Gln Ser Ile Thr Lys Asp Gly Val Gln Ile
            655                 660                 665 cag aac tca gaa aat caa cag gct gct gcc gac aaa act tac caa cca      18324
Gln Asn Ser Glu Asn Gln Gln Ala Ala Ala Asp Lys Thr Tyr Gln Pro
        670                 675                 680 gag cct caa att gga gtt tcc acc tgg gat acc aac gtt acc agt aac      18372
Glu Pro Gln Ile Gly Val Ser Thr Trp Asp Thr Asn Val Thr Ser Asn
685                 690                 695 gct gcc gga cga gtg tta aaa gcc acc act ccc atg ctg cca tgt tac      18420
Ala Ala Gly Arg Val Leu Lys Ala Thr Thr Pro Met Leu Pro Cys Tyr
700                 705                 710                 715 ggt tca tat gcc aat ccc act aat cca aac ggg ggt cag gca aaa aca      18468
Gly Ser Tyr Ala Asn Pro Thr Asn Pro Asn Gly Gly Gln Ala Lys Thr
                720                 725                 730 gaa gga gac att tcg cta aac ttt ttc aca aca act gcg gca gca gac      18516
Glu Gly Asp Ile Ser Leu Asn Phe Phe Thr Thr Thr Ala Ala Ala Asp
            735                 740                 745 aat aat ccc aaa gtg gtt ctt tac agc gaa gat gta aac ctt caa gcc      18564
Asn Asn Pro Lys Val Val Leu Tyr Ser Glu Asp Val Asn Leu Gln Ala
        750                 755                 760 ccc gat act cac tta gta tat aag cca acg gtg gga gaa aac gtt atc      18612
Pro Asp Thr His Leu Val Tyr Lys Pro Thr Val Gly Glu Asn Val Ile
765                 770                 775 gcc gca gaa gcc ctg cta acg cag cag gcg tgt ccc aac aga gca aac      18660
Ala Ala Glu Ala Leu Leu Thr Gln Gln Ala Cys Pro Asn Arg Ala Asn
780                 785                 790                 795 tac ata ggt ttc cga gat aac ttt atc ggt tta atg tat tat aac agc      18708
Tyr Ile Gly Phe Arg Asp Asn Phe Ile Gly Leu Met Tyr Tyr Asn Ser
                800                 805                 810 aca ggg aac atg gga gtt ctg gca ggt cag gcc tcg cag tta aac gca      18756
Thr Gly Asn Met Gly Val Leu Ala Gly Gln Ala Ser Gln Leu Asn Ala
            815                 820                 825 gtt gta gac ctg caa gat cga aac acg gaa ctg tcc tat cag cta atg      18804
Val Val Asp Leu Gln Asp Arg Asn Thr Glu Leu Ser Tyr Gln Leu Met
        830                 835                 840 cta gat gct ctg ggt gac aga act cga tat ttc tca atg tgg aat cag      18852
Leu Asp Ala Leu Gly Asp Arg Thr Arg Tyr Phe Ser Met Trp Asn Gln
845                 850                 855 gcc gtg gac agc tac gat cca gac gtt agg att atc gag aac cat ggg      18900
Ala Val Asp Ser Tyr Asp Pro Asp Val Arg Ile Ile Glu Asn His Gly
860                 865                 870                 875 gtg gaa gac gag ctg ccc aat tac tgt ttt cca ctc cca ggc atg ggt      18948
Val Glu Asp Glu Leu Pro Asn Tyr Cys Phe Pro Leu Pro Gly Met Gly
```

-continued

```
            880                 885                 890
att ttt aac tcc tac aag ggg gta aaa cca caa aat ggc ggt aat ggt    18996
Ile Phe Asn Ser Tyr Lys Gly Val Lys Pro Gln Asn Gly Gly Asn Gly
            895                 900                 905 aac tgg gaa gca aac ggg gac cta tca aat gcc aat gag atc gct tta    19044
Asn Trp Glu Ala Asn Gly Asp Leu Ser Asn Ala Asn Glu Ile Ala Leu
        910                 915                 920 gga aac att ttt gcc atg gaa att aac ctc cac gca aac ctg tgg cgc    19092
Gly Asn Ile Phe Ala Met Glu Ile Asn Leu His Ala Asn Leu Trp Arg
925                 930                 935 agc ttc ttg tac agc aat gtg gcg ctg tac ctg cca gac agc tat aaa    19140
Ser Phe Leu Tyr Ser Asn Val Ala Leu Tyr Leu Pro Asp Ser Tyr Lys
940                 945                 950                 955 ttc act ccc gct aac atc act ctg ccc gcc aac caa aac acc tac gag    19188
Phe Thr Pro Ala Asn Ile Thr Leu Pro Ala Asn Gln Asn Thr Tyr Glu
            960                 965                 970 tat atc aac ggg cgc gtc act tct cca acc ctg gtg gac acc ttt gtt    19236
Tyr Ile Asn Gly Arg Val Thr Ser Pro Thr Leu Val Asp Thr Phe Val
        975                 980                 985 aac att gga gcc cga tgg tcg ccg gat ccc atg gac aac gtc aac ccc    19284
Asn Ile Gly Ala Arg Trp Ser Pro Asp Pro Met Asp Asn Val Asn Pro
990                 995                 1000 ttt aac cat cac cgg aac gcg ggc ctc cgt tac cgc tcc atg ctg        19329
Phe Asn His His Arg Asn Ala Gly Leu Arg Tyr Arg Ser Met Leu
1005                1010                1015 ctg gga aat gga cgc gtg gtg cct ttc cac ata caa gtg ccg caa        19374
Leu Gly Asn Gly Arg Val Val Pro Phe His Ile Gln Val Pro Gln
1020                1025                1030 aaa ttt ttc gcg att aag aac ctc ctg ctt ttg ccc ggc tcc tac        19419
Lys Phe Phe Ala Ile Lys Asn Leu Leu Leu Leu Pro Gly Ser Tyr
1035                1040                1045 act tac gag tgg agc ttc aga aaa gac gtg aac atg att ctg cag        19464
Thr Tyr Glu Trp Ser Phe Arg Lys Asp Val Asn Met Ile Leu Gln
1050                1055                1060 agc acc ctg ggc aat gat ctt cga gtg gac ggg gcc agc gtc cgc        19509
Ser Thr Leu Gly Asn Asp Leu Arg Val Asp Gly Ala Ser Val Arg
1065                1070                1075 att gac agc gtc aac ttg tac gcc aac ttt ttc ccc atg gcg cac        19554
Ile Asp Ser Val Asn Leu Tyr Ala Asn Phe Phe Pro Met Ala His
1080                1085                1090 aac acc gct tct acc ttg gaa gcc atg ctg cga aac gac acc aac        19599
Asn Thr Ala Ser Thr Leu Glu Ala Met Leu Arg Asn Asp Thr Asn
1095                1100                1105 gac cag tcg ttt aac gac tac ctc agc gcg gcc aac atg ctt tat        19644
Asp Gln Ser Phe Asn Asp Tyr Leu Ser Ala Ala Asn Met Leu Tyr
1110                1115                1120 ccc att ccg gcc aac gcc acc aac gtt ccc att tcc att ccc tcc        19689
Pro Ile Pro Ala Asn Ala Thr Asn Val Pro Ile Ser Ile Pro Ser
1125                1130                1135 cgc aac tgg gcg gcc ttc cgg gga tgg agc ttc acc cgc ctt aaa        19734
Arg Asn Trp Ala Ala Phe Arg Gly Trp Ser Phe Thr Arg Leu Lys
1140                1145                1150 gcc aag gaa acg cct tcc ttg ggc tcc ggc ttt gac ccc tac ttt        19779
Ala Lys Glu Thr Pro Ser Leu Gly Ser Gly Phe Asp Pro Tyr Phe
1155                1160                1165 gtg tac tca ggc acc att cct tac ctg gac ggc agc ttt tac ctc        19824
Val Tyr Ser Gly Thr Ile Pro Tyr Leu Asp Gly Ser Phe Tyr Leu
1170                1175                1180 aac cac act ttc aaa cgt ctg tcc atc atg ttc gat tct tcc gta        19869
```

```
                Asn His Thr Phe Lys Arg Leu Ser Ile Met Phe Asp Ser Ser Val
                    1185                1190                1195 agt tgg ccg ggc aac gac cgc ctc ctg acg ccg aac gag ttc gaa          19914
Ser Trp Pro Gly Asn Asp Arg Leu Leu Thr Pro Asn Glu Phe Glu
    1200                1205                1210 att aag cgc att gtg gac ggg gaa ggc tac aac gtg gct caa agt          19959
Ile Lys Arg Ile Val Asp Gly Glu Gly Tyr Asn Val Ala Gln Ser
    1215                1220                1225 aac atg acc aaa gac tgg ttt tta att caa atg ctc agc cac tac          20004
Asn Met Thr Lys Asp Trp Phe Leu Ile Gln Met Leu Ser His Tyr
    1230                1235                1240 aac atc ggc tac caa ggc ttc tat gtt ccc gag ggc tac aag gat          20049
Asn Ile Gly Tyr Gln Gly Phe Tyr Val Pro Glu Gly Tyr Lys Asp
    1245                1250                1255 cgg atg tat tct ttc ttc cga aac ttt cag ccc atg agc cgc cag          20094
Arg Met Tyr Ser Phe Phe Arg Asn Phe Gln Pro Met Ser Arg Gln
    1260                1265                1270 gtg ccg gat ccc acc gct gcc ggc tat caa gcg gtt ccc ctg ccc          20139
Val Pro Asp Pro Thr Ala Ala Gly Tyr Gln Ala Val Pro Leu Pro
    1275                1280                1285 aga caa cac aac aac tcg ggc ttt gtg ggg tac atg ggc ccg acc          20184
Arg Gln His Asn Asn Ser Gly Phe Val Gly Tyr Met Gly Pro Thr
    1290                1295                1300 atg cgc gaa gga cag cca tac ccg gcc aac tac ccc tat ccc ctg          20229
Met Arg Glu Gly Gln Pro Tyr Pro Ala Asn Tyr Pro Tyr Pro Leu
    1305                1310                1315 atc ggc gct acc gcc gtc ccc gcc att acc cag aaa aag ttt ttg          20274
Ile Gly Ala Thr Ala Val Pro Ala Ile Thr Gln Lys Lys Phe Leu
    1320                1325                1330 tgc gac cgc gtc atg tgg cgc ata cct ttt tcc agc aac ttt atg          20319
Cys Asp Arg Val Met Trp Arg Ile Pro Phe Ser Ser Asn Phe Met
    1335                1340                1345 tca atg ggg gcc ctg acc gac ctc gga cag aac atg ctt tac gct          20364
Ser Met Gly Ala Leu Thr Asp Leu Gly Gln Asn Met Leu Tyr Ala
    1350                1355                1360 aac tcc gcc cat gcc ctg gat atg act ttt gag gtg gac ccc atg          20409
Asn Ser Ala His Ala Leu Asp Met Thr Phe Glu Val Asp Pro Met
    1365                1370                1375 aac gag ccc acg ttg ctg tac atg ctt ttt gag gtg ttc gac gtg          20454
Asn Glu Pro Thr Leu Leu Tyr Met Leu Phe Glu Val Phe Asp Val
    1380                1385                1390 gtc aga gtg cac cag ccg cac cgc ggt att atc gag gcc gtg tac          20499
Val Arg Val His Gln Pro His Arg Gly Ile Ile Glu Ala Val Tyr
    1395                1400                1405 ctg cgc acc ccc ttc tct gcg ggc aat gcc acc aca taa gccgctgaac       20548
Leu Arg Thr Pro Phe Ser Ala Gly Asn Ala Thr Thr
    1410                1415                1420 tagctggttt ttaccccaga tcccatgggc tccacggaag acgaactgcg ggccattgtg    20608
cgagacctgg gctgcggacc ctacttcctg ggcacctttg acaagcggtt tcccgggttc    20668
gtgtctcctc gcaaactcgc gtgcgcgatc gtgaataccg ccggccgaga gaccggagga    20728
gagcattggc tagctctggg ctggaacccc cgctcgtcca cgttttttcct gttcgacccc    20788 tttggctttt cagaccaacg cttgaagcag atctatgcat ttgaatatga gggtctactc    20848
aagcgaagcg cgctggcctc ctccgccgat cactgtctaa ccctggtaaa gagcactcag    20908
acggttcagg gccctcacag cgccgcctgt ggcttttttt gttgcatgtt tttgcacgcc    20968
tttgtgaact ggccggacac ccccatggaa aacaaccccca ccatggacct cctgactggc    21028
```

-continued

```
gttcccaact ccatgctcca aagccccagc gtgcagacca ccctcctcca aaaccagaaa   21088
aatctgtacg cctttctgca caagcactct ccctactttc gccgccatcg ggaacaaata   21148
gaaaatgcaa ccgcgtttaa caaaactctg taacgtttaa taaatgaact ttttattgaa   21208
ctggaaaacg ggtttgtgat ttttaaaaat caaaggggtt gagctggaca tccatgtggg   21268
aggccggaag ggtggtgttc ttgtactggt acttgggcag ccacttaaac tctggaatca   21328
caaacttggg cagcggtatt tctgggaagt tgtcgtgcca cagctggcgg gtcagctgaa   21388
gtgcctgcag aacatcgggg gcggagatct tgaagtcgca gtttatctgg ttcacggcac   21448
gcgcgttgcg gtacatggga ttggcacact gaaacaccag caggctggga ttcttgatgc   21508
tagccagggc cacggcgtcg gtcacgtcac cggtgtcttc tatgttggac agcgaaaaag   21568
gcgtgacttt gcaaagctgg cgtcccgcgc gaggcacgca atctcccagg tagttgcact   21628
cacagcggat gggcagaaga agatgcttgt ggccgcgggt catgtaggga taggccgctg   21688
ccataaaagc ttcgatctgc ctgaaagcct gcttggcctt gtgcccttcg gtataaaaaa   21748
caccgcagga cttgttggaa aaggtattac tggcgcaagc ggcatcgtga aagcaagcgc   21808
gtgcgtcttc gtttcgtaac tgcaccacgc tgcggcccca ccggttctga atcaccttgg   21868
ccctgccggg gttttccttg agagcgcgct ggccggcttc gctgcccaca tccatttcca   21928
cgacatgctc cttgttaatc atggccagac cgtggaggca gcgcagctcc tcgtcatcgt   21988
cggtgcagtg atgctcccac acgacgcagc cagtgggctc ccacttgggc ttggaggcct   22048
cggcaatgcc agaatacagg agaacgtagt ggtgcagaaa acgtcccatc atggtgccaa   22108
aggttttctg gctgctgaag gtcatcgggc agtacctcca gtcctcgtta agccaagtgt   22168
tgcagatctt cctgaagacc gtgtactgat cgggcataaa gtggaactca ttgcgctcgg   22228
tcttgtcgat cttatacttt tccatcagac tatgcataat ctccatgccc ttttcccagg   22288
cgcaaacaat cttggtgcta cacgggttag gtatggccaa agtggttggc ctctgaggcg   22348
gcgcttgttc ttcctcttga gccctctccc gactgacggg ggttgaaaga gggtgccccct   22408 tggggaacgg cttgaacacg gtctggcccg aggcgtcccg aagaatctgc atcggggat   22468 tgctggccgt catggcgatg atctgacccc ggggctcctc cacttcgtcc tcctcgggac   22528
tttcctcgtg cttttcgggg gacggtacgg gagtaggggg aagagcgcgg cgcgccttct   22588
tcttgggcgg cagttccgga gcctgctctt gacgactggc cattgtcttc tcctaggcaa   22648
gaaaaacaag atggaagact ctttctcctc ctcctcgtca acgtcagaaa gcgagtcttc   22708
caccttaagc gccgagaact cccagcgcat agaatccgat gtgggctacg agactccccc   22768
cgcgaacttt tcgccgcccc ccataaacac taacgggtgg acggactacc tggccctagg   22828
agacgtactg ctgaagcaca tcaggcggca gagcgttatc gtgcaagatg ctctcaccga   22888
gcgactcgcg gttccgctgg aagtggcgga acttagcgcc gcctacgagc gaaccctctt   22948
ctccccaaag actcccccca agaggcaggc taacggcacc tgcgagccta accctcgact   23008
caacttctac cctgcctttg ccgtgccaga ggtactggct acgtaccaca tttttttcca   23068
aaaccacaaa atccctctct cgtgccgcgc caaccgcacc aaagccgatc gcgtgctgcg   23128
actggaggaa ggggctcgca tacctgagat tgcgtgtctg gaggaagtcc caaaatcttt   23188
tgaaggtctg ggccgcgacg aaaagcgagc agcaaacgct ctggaagaga acgcagagag   23248
tcacaacagc gccttggtag aactcgaggg cgacaacgcc agactggccg tcctcaaacg   23308
gtccatagaa gtcacgcact tcgcctaccc cgccgttaac ctccctccaa aagttatgac   23368
agcggtcatg gactcgctgc tcataaagcg cgctcagccc ttagacccag agcacgaaaa   23428
```

```
caacagtgac gaaggaaaac cggtggtttc tgatgaggag ttgagcaagt ggctgtcctc    23488
caacgacccc gccacgttgg aggaacgaag aaaaaccatg atggccgtgg tgctagttac    23548
cgtgcaatta gaatgtctgc agaggttctt ttcccaccca gagaccctga gaaaagtgga    23608
ggaaacgctg cactacacat ttaggcacgg ctacgtgaag caagcctgca agatttccaa    23668
cgtagaactt agcaacctca tctcctacct ggggatcttg cacgaaaacc gcctcggaca    23728
aaacgtgctg cacagcacac tgaaaggaga agcccgccga gactatgtgc gagactgcgt    23788
gttcctagcg ctagtgtaca cctggcagag cggaatggga gtctggcagc agtgcctgga    23848
ggacgaaaac ctcaaagagc ttgaaaagct gctggtgcgc tccagaaggg cactgtggac    23908
cagttttgac gagcgcaccg ccgcgcgaga cctagctgat attattttc ctcccaagct    23968 ggtgcagact ctccgggaag gactgccaga ttttatgagt caaagcatct tgcaaaactt    24028
ccgctctttc atcttggaac gctcgggaat cttgcccgcc actagctgcg ccctacccac    24088
agattttgtg cctctccact accgcgaatg cccaccgccg ctgtggccgt acacttactt    24148
gcttaaactg gccaactttc taatgttcca ctctgacctg gcagaagacg ttagcggcga    24208
ggggctgcta gaatgccact gccgctgcaa cctgtgcacc ccccaccgct ctctagtatg    24268
caacactccc ctgctcaatg agacccagat catcggtacc tttgaaatcc agggaccctc    24328
cgacgcggaa aacggcaagc aggggtctgg gctaaaactc acagccggac tgtggacctc    24388
cgcctacttg cgcaaatttg taccagaaga ctatcacgcc caccaaatta aattttacga    24448
aaaccaatca aaaccaccca aaagcgagtt aacggcttgc gtcattacgc agagcagcat    24508
agttgggcag ttgcaagcca ttaacaaagc gcggcaagag tttctcctaa aaaaaggaaa    24568
aggggtctac ttggaccccc agaccggcga ggaactcaac ggaccctcct cagtcgcagg    24628
ttgtgtgccc catgccgccc aaaaagaaca cctcgcagtg gaacatgcca gagacggagg    24688
aagaggagtg gagcagtgtg agcaacagcg aaacggagga agagccgtgg cccgaggggt    24748
gcaacgggga agaggacacg gagggacggc gaagtcttcg ccgaagaact ctcgccgctg    24808
cccccgaagt cccagccggc cgcctcggcc caagatcccg cacacacccg tagatgggat    24868
agcaagacca aaaagccggg taagagaaac gctcgccccc gccagggcta ccgctcgtgg    24928
agaaagcaca aaaactgcat cttatcgtgc ttgctccagt gcggcggaga cgtttcgttc    24988
acccgtagat acttgctttt taacaaaggg gtggccgtcc cccgtaacgt cctccactac    25048
taccgtcact cttacagctc cgaagcggac ggctaagaaa acgcagcagt gccggcgggg    25108
aggactgcgt ctcagcgccc gagaaccccc agccaccagg gagctccgaa accgcatatt    25168 tcccacccatc tacgctatct ttcagcaaag ccgggggcag cagcaagaac tgaaaataaa    25228
aaaccgcacg ctgaggtcgc ttacccgaag ctgcctctat cacaagagcg aagagcagct    25288
gcagcgaacc ctggaggacg cagaagcgct gttccagaag tactgcgcga ccaccctaaa    25348
taactaaaaa agcccgcgcg cgggacttca aaccgtctga cgtcaccagc cgcgcgccaa    25408
aatgagcaaa gagattccca cgccttacat gtggagttac cagccgcaga tgggattagc    25468
cgccggcgcc gccccaggat actccacgaa aatgaactgg ctcagcgccg gcccccacat    25528
gatttcccgc gtaaacgaca ttcgcgccca ccgcaatcag ctattgttag aacaggctgc    25588
tctgaccgcc acgccccgta ataacctgaa ccctcccagc tggccagctg ccctggtgta    25648
ccaggaaacg cctccaccca ccagcgtact tttgccccgt gacgcccagg cggaagtcca    25708
gatgactaac gcgggcgcgc aattagcggg cggatcccgg tttcggtaca gagttcacgg    25768
```

```
cgccgcaccc tatagcccag gtataaagag gctgatcatt cgaggcagag gtgtccagct   25828
caacgacgag acagtgagct cttcgcttgg tctacgacca gacggagtgt tccagctcgc   25888
gggctcgggc cgctcttcgt tcacgcctcg ccaggcatac ctgactctgc agagctctgc   25948
ctctcagcct cgctcgggag gaatcggacc ccttcagttt gtggaggagt tgtgccctc    26008
ggtctacttt cagcctttct ccggatcgcc cggccagtac ccggacgagt tcatccccaa   26068
cttcgacgcg gtgagtgact ctgtggacgg ttatgactga tgtcgagccc gcttcagtgc   26128
tagtggaaca agcgcggctc aatcacctgg ttcgttgccg ccgccgctgc tgcgtggctc   26188
gcgacttgag cttagctctc aagttttgtaa aaaacccgtc cgaaaccggg agcgctgtgc   26248
acgggttgga gctagtgggt cctgagaagg ccaccatcca cgttctcaga aactttgtgg   26308
aaaaacccat tttggttaaa cgagatcagg ggccttttgt aatcagctta ctctgcacct   26368
gtaaccatgt tgaccttcac gactatttta tggatcattt gtgcgctgaa ttcaataagt   26428
aaagcgaatt cttaccaaga ttatgatgtc catgactgtt cctcgccact atacgatgtt   26488
gtgccagtaa actctcttgt cgacatctat ctgaactgtt cctttggtc cgcacagctt    26548
acttggtact acggtgacac cgtccttct ggctcactgg gcagctcaca cggaataaca    26608
cttcacctct tttcgccgtt tcgatacgga aactacagct gtcgtgccgg tacctgcctc   26668
cacgttttca atcttcagcc ctgtccaccg accaaacttg tatttgtcga ctctaagcac   26728
ttacagctca actgcagcat tctaggcccc agtatcttgt ggacatacaa taaatcagg    26788
ttggtggaat tgtctactta cccacccagc gcccgcggtt tggggaaat tcctttccag    26848
atctactaca actatcttgc cacacattat gcaagtcaac agcaactaaa cttgcaagca   26908
cccttcacgc caggagagta ctcctgtcac gtaggctcct gcacagaaac ttttattctc   26968
ttcaacagat cttctgccat tgaacgcttc actactaact actttagaaa ccaagttgtg   27028
cttttcactg acgaaacccc taacgtcacc ctggactgtg catgttttc tcatgacacc    27088
gtaacttgga ctcttaacaa tactctctgg ctcgcgttcg ataaccaaag cttgattgtt   27148
aaaaattttg atttaacctt tactaaaccc tctcctcgcg aaatagttat ctttgctcct   27208
tttaatccaa aaactacctt agcctgtcag gttttgttta agccttgcca aacaaacttt   27268
aagtttgttt atttgcctcc gcaatctgtc aaactcatag aaaaatacaa caaagcgccc   27328
gtcttggctc ctaaaacctt ctaccactgg ctaacctaca cggggctgtt tgcactaatt   27388
gttttttcc taattaacat ttttatatgt ttcttgcctt cctccttctt ttcgcgaaca    27448
ccgttgccgc agaaagacct ctccttatta ctgtagcgct tgctatacaa accaagagt    27508
ggtcaaccgt gctctcaatc tatttcaat ttttcatttt gtccttaata ctttctctta    27568
ttgtcgttaa caatgatctg gagcattggt ctcgcctttt tttggctgct tagtgcaaaa   27628
gccactattt ttcacaggta tgtggaagaa ggaactagca ccctctttac gatacctgaa   27688
acaattaagg cggctgatga gtttcttgg tacaaaggct cgctctcaga cggcaaccac    27748
tcattctcag acagaccct ttgcatccaa gaaacttatt ttaaatcaga actacaatac    27808
agctgcataa aaaactttt ccatctctac aacatctcaa accctatga gggtatttac     27868
aatgccaagg tttcagacaa ctccagcaca cggaactttt actttaatct gacagttatt   27928
aaagcaattt ccattcctat ctgtgagttt agctcccagt ttctttctga aacctactgt   27988
ttaattacta taaactgcac taaaaatcgc cttcacacca ccataatcta caatcacaca   28048
caatcacctt gggttttaaa cctaaaattt tctccacaca tgccttcgca atttctcacg   28108
caagttaccg tctctaacat aagcaagcag tttggctttt actatccttt ccacgaactg   28168
```

```
tgcgaaataa ttgaagccga atatgaacca gactacttta cttacattgc cattggtgta   28228
atcgttgttt gcctttgctt tgttattggg gggtgtgttt atttgtacat tcagagaaaa   28288
atattgctct cgctgtgctc ctgcggttac aaagcagaag aaagaattaa aatctctaca   28348
ctttattaat gttttccaga aatggcaaaa ctaacgctcc tacttttgct tctcacgccg   28408
gtgacgcttt ttaccatcac ttttctgcc gccgccacac tcgaacctca atgtttgcca    28468
ccggttgaag tctactttgt ctacgtgttg ctgtgctgcg ttagcgtttg cagtataaca   28528
tgttttacct ttgttttct tcagtgcatt gactacttct gggtcagact ctactaccgc    28588
agacacgcgc ctcagtatca aaatcaacaa attgccagac tactcggtct gccatgattg   28648
tcttgtattt taccctgatt tttttcacc ttacttgcgc ttgtgatttt cacttcactc    28708
aatttttggaa aacgcaatgc ttcgacccgc gcctctccaa cgactggatg atggctcttg  28768
caattgccac gcttggggcg tttggacttt ttagtggttt tgctttgcat tacaaattta   28828
agactccatg gacacatggc tttctttcag attttccagt tacacctact ccgccgcctc   28888
ccccggccat cgacgtgcct caggttccct caccttctcc atctgtctgc agctactttc   28948
atctgtaatg gccgacctag aatttgacgg agtgcaatct gagcaaaggg ctatacactt   29008
ccaacgccag tcggaccgcg aacgcaaaaa cagagagctg caaaccatac aaaacaccca   29068
ccaatgtaaa cgcgggatat tttgtattgt aaaacaagct aagctccact cgagcttct   29128
atctggcaac gaccacgagc tccaatacgt ggtcgatcag cagcgtcaaa cctgtgtatt   29188
cttaattgga gtttccccca ttaaagttac tcaaaccaag ggtgaaacca agggaaccat   29248
aaggtgctca tgtcacctgt cagaatgcct ttacactcta gttaaaaccc tatgtggctt   29308
acatgattct atccccttta attaaataaa cttactttaa atctgcaatc acttcttcgt   29368
ccttgttttt gtcgccatcc agcagcacca ccttcccctc ttcccaactt tcatagcata   29428
ttttccgaaa agaggcgtac tttcgccaca ccttaaaggg aacgttact tcgctttcaa    29488
gctctcccac gattttcatt gcagat atg aaa cgc gcc aaa gtg gaa gaa gga    29541
                              Met Lys Arg Ala Lys Val Glu Glu Gly
                                                      1425
ttt aac ccc gtt tat ccc tat gga tat tct act ccg act gac gtg          29586
Phe Asn Pro Val Tyr Pro Tyr Gly Tyr Ser Thr Pro Thr Asp Val
1430                1435                    1440
gct cct ccc ttt gta gcc tct gac ggt ctt caa gaa aac cca cct          29631
Ala Pro Pro Phe Val Ala Ser Asp Gly Leu Gln Glu Asn Pro Pro
1445                1450                    1455
ggg gtc ttg tcc cta aaa ata tcc aaa cct tta act ttt aat gcc          29676
Gly Val Leu Ser Leu Lys Ile Ser Lys Pro Leu Thr Phe Asn Ala
1460                1465                    1470
tcc aag gct cta agc ctg gct att ggt cca gga tta aaa att caa          29721
Ser Lys Ala Leu Ser Leu Ala Ile Gly Pro Gly Leu Lys Ile Gln
1475                1480                    1485
gat ggt aaa cta gtg ggg gag gga caa gca att ctt gca aac ctg          29766
Asp Gly Lys Leu Val Gly Glu Gly Gln Ala Ile Leu Ala Asn Leu
1490                1495                    1500
ccg ctt caa atc acc aac aac aca att tca cta cgt ttt ggg aac          29811
Pro Leu Gln Ile Thr Asn Asn Thr Ile Ser Leu Arg Phe Gly Asn
1505                1510                    1515
aca ctt gcc ttg aat gac aat aat gaa ctc caa acc aca cta aaa          29856
Thr Leu Ala Leu Asn Asp Asn Asn Glu Leu Gln Thr Thr Leu Lys
1520                1525                    1530
tct tca tcg ccc ctt aaa atc aca gac cag act ctg tcc ctt aac          29901
Ser Ser Ser Pro Leu Lys Ile Thr Asp Gln Thr Leu Ser Leu Asn
```

| | | | | | | | | |
|---|---|---|---|---|---|---|---|---|
| | | 1535 | | 1540 | | 1545 | | |

```
ata ggg gac agc ctt gca att aaa gat gac aaa cta gaa agc gct    29946
Ile Gly Asp Ser Leu Ala Ile Lys Asp Asp Lys Leu Glu Ser Ala
1550                1555                1560 ctt caa gcg acc ctc cca ctc tcc att agc aac aac acc atc agc    29991
Leu Gln Ala Thr Leu Pro Leu Ser Ile Ser Asn Asn Thr Ile Ser
1565                1570                1575 ctc aac gtg ggc acc gga ctc acc ata aat gga aac gtt tta caa    30036
Leu Asn Val Gly Thr Gly Leu Thr Ile Asn Gly Asn Val Leu Gln
1580                1585                1590 gct gtt ccc tta aat gct cta agt ccc cta act att tcc aac aat    30081
Ala Val Pro Leu Asn Ala Leu Ser Pro Leu Thr Ile Ser Asn Asn
1595                1600                1605 aac atc agc ctg cgc tat ggc agt tcc ctg acg gtg ctt aac aat    30126
Asn Ile Ser Leu Arg Tyr Gly Ser Ser Leu Thr Val Leu Asn Asn
1610                1615                1620 gaa ctg caa agc aac ctc aca gtt cac tcc cct tta aaa ctc aac    30171
Glu Leu Gln Ser Asn Leu Thr Val His Ser Pro Leu Lys Leu Asn
1625                1630                1635 tcc aac aac tca att tct ctc aac act cta tct ccg ttt aga atc    30216
Ser Asn Asn Ser Ile Ser Leu Asn Thr Leu Ser Pro Phe Arg Ile
1640                1645                1650 gag aat ggt ttc ctc acg ctc tat ttg gga aca aaa tct ggc ttg    30261
Glu Asn Gly Phe Leu Thr Leu Tyr Leu Gly Thr Lys Ser Gly Leu
1655                1660                1665 cta gtt caa aac agt ggc tta aaa gtt caa gcg ggc tac ggc ctg    30306
Leu Val Gln Asn Ser Gly Leu Lys Val Gln Ala Gly Tyr Gly Leu
1670                1675                1680 caa gta aca gac acc aat gct ctc aca tta aga tat ctc gct cca    30351
Gln Val Thr Asp Thr Asn Ala Leu Thr Leu Arg Tyr Leu Ala Pro
1685                1690                1695 ctg acc att cca gac tcg ggc tca gaa caa ggc att ctt aaa gta    30396
Leu Thr Ile Pro Asp Ser Gly Ser Glu Gln Gly Ile Leu Lys Val
1700                1705                1710 aac act gga cag ggc cta agt gtg aac caa gct gga gcg ctt gaa    30441
Asn Thr Gly Gln Gly Leu Ser Val Asn Gln Ala Gly Ala Leu Glu
1715                1720                1725 aca tcc cta gga ggt gga tta aaa tat gct gat aac aaa ata acc    30486
Thr Ser Leu Gly Gly Gly Leu Lys Tyr Ala Asp Asn Lys Ile Thr
1730                1735                1740 ttt gat aca gga aac gga ctg aca tta tct gaa aat aaa ctt gca    30531
Phe Asp Thr Gly Asn Gly Leu Thr Leu Ser Glu Asn Lys Leu Ala
1745                1750                1755 gta gct gca ggt agt ggt cta act ttt aga gat ggt gcc ttg gta    30576
Val Ala Ala Gly Ser Gly Leu Thr Phe Arg Asp Gly Ala Leu Val
1760                1765                1770 gcc acg gga acc gca ttt acg caa aca ctg tgg act acg gct gat    30621
Ala Thr Gly Thr Ala Phe Thr Gln Thr Leu Trp Thr Thr Ala Asp
1775                1780                1785 ccg tct ccc aac tgc aca att ata cag gac cgc gac aca aaa ttt    30666
Pro Ser Pro Asn Cys Thr Ile Ile Gln Asp Arg Asp Thr Lys Phe
1790                1795                1800 act ttg gcg ctt acc att agt ggg agc caa gtg ctg ggg acg gtt    30711
Thr Leu Ala Leu Thr Ile Ser Gly Ser Gln Val Leu Gly Thr Val
1805                1810                1815 tcc att att gga gta aaa ggc ccc ctt tca agt agc ata ccg tca    30756
Ser Ile Ile Gly Val Lys Gly Pro Leu Ser Ser Ser Ile Pro Ser
1820                1825                1830 gct acc gtt aca gta caa ctt aac ttt gat tcc aac gga gcc cta    30801
```

```
Ala  Thr  Val  Thr  Val  Gln  Leu  Asn  Phe  Asp  Ser  Asn  Gly  Ala  Leu
1835                1840                    1845 ttg  agc  tcc  tct  tca  ctt  aaa  ggt  tac  tgg  ggg  tat  cgc  caa  ggt       30846
Leu  Ser  Ser  Ser  Ser  Leu  Lys  Gly  Tyr  Trp  Gly  Tyr  Arg  Gln  Gly
1850                1855                    1860 ccc  tca  att  gac  cct  tac  ccc  ata  att  aat  gcc  tta  aac  ttt  atg       30891
Pro  Ser  Ile  Asp  Pro  Tyr  Pro  Ile  Ile  Asn  Ala  Leu  Asn  Phe  Met
1865                1870                    1875 cca  aac  tca  ctg  gct  tat  ccc  ccg  gga  caa  gaa  atc  caa  gca  aaa       30936
Pro  Asn  Ser  Leu  Ala  Tyr  Pro  Pro  Gly  Gln  Glu  Ile  Gln  Ala  Lys
1880                1885                    1890 tgt  aac  atg  tac  gtt  tct  act  ttt  tta  cga  gga  aat  cca  caa  aga       30981
Cys  Asn  Met  Tyr  Val  Ser  Thr  Phe  Leu  Arg  Gly  Asn  Pro  Gln  Arg
1895                1900                    1905 cca  ata  gtt  tta  aac  atc  act  ttt  aat  aat  caa  acc  agc  ggg  ttt       31026
Pro  Ile  Val  Leu  Asn  Ile  Thr  Phe  Asn  Asn  Gln  Thr  Ser  Gly  Phe
1910                1915                    1920 tcc  att  aga  ttt  aca  tgg  aca  aat  tta  acc  aca  gga  gaa  gca  ttt       31071
Ser  Ile  Arg  Phe  Thr  Trp  Thr  Asn  Leu  Thr  Thr  Gly  Glu  Ala  Phe
1925                1930                    1935 gca  atg  ccc  cca  tgc  act  ttt  tcc  tac  att  gct  gaa  caa  caa  taa       31116
Ala  Met  Pro  Pro  Cys  Thr  Phe  Ser  Tyr  Ile  Ala  Glu  Gln  Gln
1940                1945                    1950 actatgtaac cctcaccgtt aacccgcctc cgcccttcca tttttattta taaaccaccc            31176
gatccacctt ttcagcagta aacaattgca tgtcagtagg ggcagtaaaa cttttgggag            31236
ttaaaatcca cacaggttct tcacaagcta agcgaaaatc agttacactt ataaaaccat            31296
cgctaacatc ggacaaagac aagcatgagt ccaaagcttc cggttctgga tcagattttt            31356
gttcattaac agcgggagaa acagcttctg gaggattttc catctccatc tccttcatca            31416
gttccaccat gtccaccgtg gtcatctggg acgagaacga cagttgtcat acacctcata            31476
agtcaccggt cgatgacgaa cgtacagatc tcgaagaatg tcctgtcgcc gcctttcggc            31536
agcactgggc cgaaggcgaa agcgcccatg tttaacaatg ccagcaccg cccgcttcat             31596
caggcgccta gttctttag cgcaacagcg catgcgcagc tcgctaagac tggcgcaaga            31656
aacacagcac agaaccacca gattgttcat gatcccataa gcgtgctgac accagccat             31716
actaacaaat tgtttcacta ttctagcatg aatgtcatat ctgatgttca agtaaattaa            31776
atggcgcccc cttatgtaaa cacttccac gtacaacacc tcctttggca tctgataatt             31836
aaccacctcc cgataccaaa tacatctctg attaatagtc gccccgtaca ctacccgatt            31896
aaaccaagtt gccaacataa tcccccctgc catacactgc aaagaacctg acggctaca             31956
atgacagtgc aaagtccaca cctcgttgcc atggataact gaggaacgcc ttaagtcaat            32016
agtggcacaa ctaatacaaa catgtaaata gtgtttcaac aagtgccact cgtatgaggt            32076
gagtatcatg tcccagggaa cgggccactc cataaacact gcaaaccaa cacatcctac             32136
catccccgc acggcactca catcgtgcat ggtgttcata tcacagtccg gaagctgagg             32196
acaaggaaaa gtctcgggag catttcata gggcggtagt gggtactcct tgtagggtt              32256
cagtcggcac cggtatctcc tcaccttctg ggccataaca cacaagttga gatctgattt            32316
caaggtactt tctgaatgaa aaccaagtgc tttcccaaca atgtatccga tgtcttcggt            32376
ccccgcgtcg gtagcgctcc ttgcagtaca cacggaacaa ccactcacgc aggcccagaa            32436
gacagtttc cgcggacggt gacaagttaa tcccctcag tctcagagcc aatatagttt              32496
cttccacagt agcataggcc aaacccaacc aggaaacaca agctggcacg tcccgttcaa            32556
```

```
cgggaggaca aggaagcaga ggcagaggca taggcaaagc aacagaattt ttattccaac    32616
tggtcacgta gcacttcaaa caccaggtca cgtaaatggc agcgatcttg ggtttcctga    32676
tggaacataa cagcaagatc aaacatgaga cgattctcaa ggtgattaac cacagctgga    32736
attaaatcct ccacgcgcac atttagaaac accagcaata caaaagcccg gttttctccg    32796
ggatctatca tagcagcaca gtcatcaatt agtcccaagt aattttcccg tttccaatct    32856
gttataattt gcagaataat gccctgtaaa tccaagccgg ccatggcgaa agctcagat     32916 aatgcacttt ccacgtgcat tcgtaaacac accctcatct tgtcaatcca aaaagtcttc    32976
ttcttgagaa acctgtagta aattaagaat cgccaggtta ggctcgatgc ctacatcccg    33036
gagcttcatt ctcagcatgc actgcaaatg atccagcaga tcagaacagc aattagcagc    33096
cagctcatcc ccggtttcca gttccggagt tcccacggca attatcactc gaaacgtggg    33156
acaaatcgaa ataacatgag ctcccacgtg agcaaaagcc gtagggccag tgcaataatc    33216
acagaaccag cggaaaaaag attgcagctc atgtttcaaa aagctctgca gatcaaaatt    33276
cagctcatgc aaataacaca gtaaagtttg cggtatagta accgaaaacc acacgggtcg    33336
acgttcaaac atctcggctt acctaaaaaa gaagcacatt tttaaaccac agtcgcttcc    33396
tgaacaggag gaaatatggt gcggcgtaaa accgacgcg ccaccggatc tccggcagag     33456
ccctgataat acagccagct gtggttaaac agcaaaacct ttaattcggc aacggttgag    33516
gtctccacat aatcagcgcc cacaaaaatc ccatctcgaa cttgctcgcg tagggagcta    33576
aaatggccag tatagcccca tggcacccga acgctaatct gcaagtatat gagagccacc    33636
ccattcggcg ggatcacaaa atcagtcgga gaaaacaacg tatacacccc ggactgcaaa    33696
agctgttcag gcaaacgccc ctgcggtccc tctcggtaca ccagcaaagc ctcgggtaaa    33756
gcagccatgc caagcgctta ccgtgccaag agcgactcag acgaaaaagt gtactgaggc    33816
gctcagagca gcggctatat actctacctg tgacgtcaag aaccgaaagt caaaagttca    33876
cccggcgcgc ccgaaaaaac ccgcgaaaat ccacccaaaa agcccgcgaa aaacacttcc    33936
gtataaaatt tccgggttac cggcgcgtca ccgccgcgcg acacgcccgc cccgccccgc    33996
gctcctcccc gaaacccgcc gcgcccactt ccgcgttccc aagacaaagg tcgcgtaact    34056
ccgcccacct catttgcatg ttaactcggt cgccatcttg cggtgttata ttgatgatg    34115
```

<210> SEQ ID NO 38  
<211> LENGTH: 503  
<212> TYPE: PRT  
<213> ORGANISM: simian adenovirus SV-39

<400> SEQUENCE: 38

Met Arg Arg Ala Val Ala Val Pro Ser Ala Ala Met Ala Leu Gly Pro  
1               5                   10                  15

Pro Pro Ser Tyr Glu Ser Val Met Ala Ala Thr Leu Gln Ala Pro  
            20                  25                  30

Leu Glu Asn Pro Tyr Val Pro Pro Arg Tyr Leu Glu Pro Thr Gly Gly  
        35                  40                  45

Arg Asn Ser Ile Arg Tyr Ser Glu Leu Thr Pro Leu Tyr Asp Thr Thr  
    50                  55                  60

Arg Leu Tyr Leu Val Asp Asn Lys Ser Ala Asp Ile Ala Thr Leu Asn  
65                  70                  75                  80

Tyr Gln Asn Asp His Ser Asn Phe Leu Thr Ser Val Val Gln Asn Ser  
                85                  90                  95

Asp Tyr Thr Pro Ala Glu Ala Ser Thr Gln Thr Ile Asn Leu Asp Asp

```
                100                 105                 110
Arg Ser Arg Trp Gly Gly Asp Leu Lys Thr Ile Leu His Thr Asn Met
        115                 120                 125

Pro Asn Val Asn Glu Phe Met Phe Thr Asn Ser Phe Arg Ala Lys Leu
        130                 135                 140

Met Val Ala His Glu Ala Asp Lys Asp Pro Val Tyr Glu Trp Val Gln
145                 150                 155                 160

Leu Thr Leu Pro Glu Gly Asn Phe Ser Glu Ile Met Thr Ile Asp Leu
                165                 170                 175

Met Asn Asn Ala Ile Ile Asp His Tyr Leu Ala Val Ala Arg Gln Gln
                180                 185                 190

Gly Val Lys Glu Ser Glu Ile Gly Val Lys Phe Asp Thr Arg Asn Phe
        195                 200                 205

Arg Leu Gly Trp Asp Pro Glu Thr Gly Leu Val Met Pro Gly Val Tyr
        210                 215                 220

Thr Asn Glu Ala Phe His Pro Asp Val Leu Leu Pro Gly Cys Gly
225                 230                 235                 240

Val Asp Phe Thr Tyr Ser Arg Leu Asn Asn Leu Leu Gly Ile Arg Lys
                245                 250                 255

Arg Met Pro Phe Gln Glu Gly Phe Gln Ile Leu Tyr Glu Asp Leu Glu
                260                 265                 270

Gly Gly Asn Ile Pro Ala Leu Leu Asp Val Pro Ala Tyr Glu Glu Ser
        275                 280                 285

Ile Ala Asn Ala Arg Glu Ala Ala Ile Arg Gly Asp Asn Phe Ala Ala
        290                 295                 300

Gln Pro Gln Ala Ala Pro Thr Ile Lys Pro Val Leu Glu Asp Ser Lys
305                 310                 315                 320

Gly Arg Ser Tyr Asn Val Ile Ala Asn Thr Asn Thr Ala Tyr Arg
                325                 330                 335

Ser Trp Tyr Leu Ala Tyr Asn Tyr Gly Asp Pro Glu Lys Gly Val Arg
                340                 345                 350

Ala Trp Thr Leu Leu Thr Thr Pro Asp Val Thr Cys Gly Ser Glu Gln
        355                 360                 365

Val Tyr Trp Ser Leu Pro Asp Met Tyr Val Asp Pro Val Thr Phe Arg
        370                 375                 380

Ser Thr Gln Gln Val Ser Asn Tyr Pro Val Val Gly Ala Glu Leu Met
385                 390                 395                 400

Pro Ile His Ser Lys Ser Phe Tyr Asn Glu Gln Ala Val Tyr Ser Gln
                405                 410                 415

Leu Ile Arg Gln Thr Thr Ala Leu Thr His Val Phe Asn Arg Phe Pro
                420                 425                 430

Glu Asn Gln Ile Leu Val Arg Pro Ala Pro Thr Ile Thr Thr Val
        435                 440                 445

Ser Glu Asn Val Pro Ala Leu Thr Asp His Gly Thr Leu Pro Leu Gln
        450                 455                 460

Asn Ser Ile Arg Gly Val Gln Arg Val Thr Ile Thr Asp Ala Arg Arg
465                 470                 475                 480

Arg Thr Cys Pro Tyr Val Tyr Lys Ala Leu Gly Ile Val Ala Pro Arg
                485                 490                 495

Val Leu Ser Ser Arg Thr Phe
                500

<210> SEQ ID NO 39
```

<211> LENGTH: 917
<212> TYPE: PRT
<213> ORGANISM: simian adenovirus SV-39

<400> SEQUENCE: 39

```
Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Ile Arg Phe Val Pro Val Asp Lys Glu Asp Thr Ala Tyr Ser Tyr
65                  70                  75                  80

Lys Thr Arg Phe Thr Leu Ala Val Gly Asp Asn Arg Val Leu Asp Met
                85                  90                  95

Ala Ser Thr Tyr Phe Asp Ile Arg Gly Val Ile Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Asn Ser Gln Trp Asn Ala Thr Asp Asn Gly Asn Lys Pro
    130                 135                 140

Val Cys Phe Ala Gln Ala Ala Phe Ile Gly Gln Ser Ile Thr Lys Asp
145                 150                 155                 160

Gly Val Gln Ile Gln Asn Ser Glu Asn Gln Gln Ala Ala Ala Asp Lys
                165                 170                 175

Thr Tyr Gln Pro Glu Pro Gln Ile Gly Val Ser Thr Trp Asp Thr Asn
            180                 185                 190

Val Thr Ser Asn Ala Ala Gly Arg Val Leu Lys Ala Thr Thr Pro Met
        195                 200                 205

Leu Pro Cys Tyr Gly Ser Tyr Ala Asn Pro Thr Asn Pro Asn Gly Gly
    210                 215                 220

Gln Ala Lys Thr Glu Gly Asp Ile Ser Leu Asn Phe Phe Thr Thr Thr
225                 230                 235                 240

Ala Ala Ala Asp Asn Asn Pro Lys Val Val Leu Tyr Ser Glu Asp Val
                245                 250                 255

Asn Leu Gln Ala Pro Asp Thr His Leu Val Tyr Lys Pro Thr Val Gly
            260                 265                 270

Glu Asn Val Ile Ala Ala Glu Ala Leu Leu Thr Gln Gln Ala Cys Pro
        275                 280                 285

Asn Arg Ala Asn Tyr Ile Gly Phe Arg Asp Asn Phe Ile Gly Leu Met
    290                 295                 300

Tyr Tyr Asn Ser Thr Gly Asn Met Gly Val Leu Ala Gly Gln Ala Ser
305                 310                 315                 320

Gln Leu Asn Ala Val Val Asp Leu Gln Asp Arg Asn Thr Glu Leu Ser
                325                 330                 335

Tyr Gln Leu Met Leu Asp Ala Leu Gly Asp Arg Thr Arg Tyr Phe Ser
            340                 345                 350

Met Trp Asn Gln Ala Val Asp Ser Tyr Asp Pro Asp Val Arg Ile Ile
        355                 360                 365

Glu Asn His Gly Val Glu Asp Glu Leu Pro Asn Tyr Cys Phe Pro Leu
    370                 375                 380

Pro Gly Met Gly Ile Phe Asn Ser Tyr Lys Gly Val Lys Pro Gln Asn
```

```
            385                 390                 395                 400
Gly Gly Asn Gly Asn Trp Glu Ala Asn Gly Asp Leu Ser Asn Ala Asn
                    405                 410                 415
Glu Ile Ala Leu Gly Asn Ile Phe Ala Met Glu Ile Asn Leu His Ala
                420                 425                 430
Asn Leu Trp Arg Ser Phe Leu Tyr Ser Asn Val Ala Leu Tyr Leu Pro
            435                 440                 445
Asp Ser Tyr Lys Phe Thr Pro Ala Asn Ile Thr Leu Pro Ala Asn Gln
        450                 455                 460
Asn Thr Tyr Glu Tyr Ile Asn Gly Arg Val Thr Ser Pro Thr Leu Val
465                 470                 475                 480
Asp Thr Phe Val Asn Ile Gly Ala Arg Trp Ser Pro Asp Pro Met Asp
                485                 490                 495
Asn Val Asn Pro Phe Asn His His Arg Asn Ala Gly Leu Arg Tyr Arg
                500                 505                 510
Ser Met Leu Leu Gly Asn Gly Arg Val Val Pro Phe His Ile Gln Val
            515                 520                 525
Pro Gln Lys Phe Phe Ala Ile Lys Asn Leu Leu Leu Pro Gly Ser
        530                 535                 540
Tyr Thr Tyr Glu Trp Ser Phe Arg Lys Asp Val Asn Met Ile Leu Gln
545                 550                 555                 560
Ser Thr Leu Gly Asn Asp Leu Arg Val Asp Gly Ala Ser Val Arg Ile
                565                 570                 575
Asp Ser Val Asn Leu Tyr Ala Asn Phe Phe Pro Met Ala His Asn Thr
            580                 585                 590
Ala Ser Thr Leu Glu Ala Met Leu Arg Asn Asp Thr Asn Asp Gln Ser
        595                 600                 605
Phe Asn Asp Tyr Leu Ser Ala Ala Asn Met Leu Tyr Pro Ile Pro Ala
    610                 615                 620
Asn Ala Thr Asn Val Pro Ile Ser Ile Pro Ser Arg Asn Trp Ala Ala
625                 630                 635                 640
Phe Arg Gly Trp Ser Phe Thr Arg Leu Lys Ala Lys Glu Thr Pro Ser
                645                 650                 655
Leu Gly Ser Gly Phe Asp Pro Tyr Phe Val Tyr Ser Gly Thr Ile Pro
            660                 665                 670
Tyr Leu Asp Gly Ser Phe Tyr Leu Asn His Thr Phe Lys Arg Leu Ser
        675                 680                 685
Ile Met Phe Asp Ser Ser Val Ser Trp Pro Gly Asn Asp Arg Leu Leu
    690                 695                 700
Thr Pro Asn Glu Phe Glu Ile Lys Arg Ile Val Asp Gly Glu Gly Tyr
705                 710                 715                 720
Asn Val Ala Gln Ser Asn Met Thr Lys Asp Trp Phe Leu Ile Gln Met
                725                 730                 735
Leu Ser His Tyr Asn Ile Gly Tyr Gln Gly Phe Tyr Val Pro Glu Gly
            740                 745                 750
Tyr Lys Asp Arg Met Tyr Ser Phe Phe Arg Asn Phe Gln Pro Met Ser
        755                 760                 765
Arg Gln Val Pro Asp Pro Thr Ala Ala Gly Tyr Gln Ala Val Pro Leu
    770                 775                 780
Pro Arg Gln His Asn Asn Ser Gly Phe Val Gly Tyr Met Gly Pro Thr
785                 790                 795                 800
Met Arg Glu Gly Gln Pro Tyr Pro Ala Asn Tyr Pro Tyr Pro Leu Ile
                805                 810                 815
```

```
Gly Ala Thr Ala Val Pro Ala Ile Thr Gln Lys Lys Phe Leu Cys Asp
                820                 825                 830

Arg Val Met Trp Arg Ile Pro Phe Ser Ser Asn Phe Ser Met Gly
            835                 840                 845

Ala Leu Thr Asp Leu Gly Gln Asn Met Leu Tyr Ala Asn Ser Ala His
850                 855                 860

Ala Leu Asp Met Thr Phe Glu Val Asp Pro Met Asn Glu Pro Thr Leu
865                 870                 875                 880

Leu Tyr Met Leu Phe Glu Val Phe Asp Val Val Arg Val His Gln Pro
                885                 890                 895

His Arg Gly Ile Ile Glu Ala Val Tyr Leu Arg Thr Pro Phe Ser Ala
            900                 905                 910

Gly Asn Ala Thr Thr
            915

<210> SEQ ID NO 40
<211> LENGTH: 533
<212> TYPE: PRT
<213> ORGANISM: simian adenovirus SV-39

<400> SEQUENCE: 40

Met Lys Arg Ala Lys Val Glu Glu Gly Phe Asn Pro Val Tyr Pro Tyr
1               5                   10                  15

Gly Tyr Ser Thr Pro Thr Asp Val Ala Pro Pro Phe Val Ala Ser Asp
            20                  25                  30

Gly Leu Gln Glu Asn Pro Pro Gly Val Leu Ser Leu Lys Ile Ser Lys
        35                  40                  45

Pro Leu Thr Phe Asn Ala Ser Lys Ala Leu Ser Leu Ala Ile Gly Pro
50                  55                  60

Gly Leu Lys Ile Gln Asp Gly Lys Leu Val Gly Glu Gly Gln Ala Ile
65                  70                  75                  80

Leu Ala Asn Leu Pro Leu Gln Ile Thr Asn Asn Thr Ile Ser Leu Arg
                85                  90                  95

Phe Gly Asn Thr Leu Ala Leu Asn Asp Asn Asn Glu Leu Gln Thr Thr
            100                 105                 110

Leu Lys Ser Ser Ser Pro Leu Lys Ile Thr Asp Gln Thr Leu Ser Leu
        115                 120                 125

Asn Ile Gly Asp Ser Leu Ala Ile Lys Asp Asp Lys Leu Glu Ser Ala
130                 135                 140

Leu Gln Ala Thr Leu Pro Leu Ser Ile Ser Asn Asn Thr Ile Ser Leu
145                 150                 155                 160

Asn Val Gly Thr Gly Leu Thr Ile Asn Gly Asn Val Leu Gln Ala Val
                165                 170                 175

Pro Leu Asn Ala Leu Ser Pro Leu Thr Ile Ser Asn Asn Ile Ser
            180                 185                 190

Leu Arg Tyr Gly Ser Ser Leu Thr Val Leu Asn Glu Leu Gln Ser
        195                 200                 205

Asn Leu Thr Val His Ser Pro Leu Lys Leu Ser Asn Asn Ser Ile
    210                 215                 220

Ser Leu Asn Thr Leu Ser Pro Phe Arg Ile Glu Asn Gly Phe Leu Thr
225                 230                 235                 240

Leu Tyr Leu Gly Thr Lys Ser Gly Leu Leu Val Gln Asn Ser Gly Leu
                245                 250                 255

Lys Val Gln Ala Gly Tyr Gly Leu Gln Val Thr Asp Thr Asn Ala Leu
```

```
            260                 265                 270
Thr Leu Arg Tyr Leu Ala Pro Leu Thr Ile Pro Asp Ser Gly Ser Glu
        275                 280                 285

Gln Gly Ile Leu Lys Val Asn Thr Gly Gln Gly Leu Ser Val Asn Gln
        290                 295                 300

Ala Gly Ala Leu Glu Thr Ser Leu Gly Gly Leu Lys Tyr Ala Asp
305                 310                 315                 320

Asn Lys Ile Thr Phe Asp Thr Gly Asn Gly Leu Thr Leu Ser Glu Asn
                    325                 330                 335

Lys Leu Ala Val Ala Ala Gly Ser Gly Leu Thr Phe Arg Asp Gly Ala
                340                 345                 350

Leu Val Ala Thr Gly Thr Ala Phe Thr Gln Thr Leu Trp Thr Thr Ala
            355                 360                 365

Asp Pro Ser Pro Asn Cys Thr Ile Ile Gln Asp Arg Asp Thr Lys Phe
        370                 375                 380

Thr Leu Ala Leu Thr Ile Ser Gly Ser Gln Val Leu Gly Thr Val Ser
385                 390                 395                 400

Ile Ile Gly Val Lys Gly Pro Leu Ser Ser Ile Pro Ser Ala Thr
                405                 410                 415

Val Thr Val Gln Leu Asn Phe Asp Ser Asn Gly Ala Leu Leu Ser Ser
                420                 425                 430

Ser Ser Leu Lys Gly Tyr Trp Gly Tyr Arg Gln Gly Pro Ser Ile Asp
            435                 440                 445

Pro Tyr Pro Ile Ile Asn Ala Leu Asn Phe Met Pro Asn Ser Leu Ala
        450                 455                 460

Tyr Pro Pro Gly Gln Glu Ile Gln Ala Lys Cys Asn Met Tyr Val Ser
465                 470                 475                 480

Thr Phe Leu Arg Gly Asn Pro Gln Arg Pro Ile Val Leu Asn Ile Thr
                485                 490                 495

Phe Asn Asn Gln Thr Ser Gly Phe Ser Ile Arg Phe Thr Trp Thr Asn
                500                 505                 510

Leu Thr Thr Gly Glu Ala Phe Ala Met Pro Pro Cys Thr Phe Ser Tyr
            515                 520                 525

Ile Ala Glu Gln Gln
    530

<210> SEQ ID NO 41
<211> LENGTH: 50
<212> TYPE: DNA
<213> ORGANISM: Artificial sequence
<220> FEATURE:
<223> OTHER INFORMATION: oligomer SV25T

<400> SEQUENCE: 41
aatttaaata cgtagcgcac tagtcgcgct aagcgcggat atcatttaaa          50

<210> SEQ ID NO 42
<211> LENGTH: 49
<212> TYPE: DNA
<213> ORGANISM: Artificial sequence
<220> FEATURE:
<223> OTHER INFORMATION: oligomer SV25B

<400> SEQUENCE: 42
tatttaaatg atatccgcgc ttaagcgcga ctagtgcgct acgtattta           49

<210> SEQ ID NO 43
```

<211> LENGTH: 338
<212> TYPE: PRT
<213> ORGANISM: hexon protein of Hu5

<400> SEQUENCE: 43

Ala Pro Lys Gly Ala Pro Asn Pro Cys Glu Trp Asp Glu Ala Ala Thr
1               5                   10                  15

Ala Leu Glu Ile Asn Leu Glu Glu Asp Asp Asn Glu Asp Glu
            20                  25                  30

Val Asp Glu Gln Ala Glu Gln Lys Thr His Val Phe Gly Gln Ala
        35                  40                  45

Pro Tyr Ser Gly Ile Asn Ile Thr Lys Glu Gly Ile Gln Ile Gly Val
    50                  55                  60

Glu Gly Gln Thr Pro Lys Tyr Ala Asp Lys Thr Phe Gln Pro Glu Pro
65                  70                  75                  80

Gln Ile Gly Glu Ser Gln Trp Tyr Glu Thr Glu Ile Asn His Ala Ala
                85                  90                  95

Gly Arg Val Leu Lys Lys Thr Thr Pro Met Lys Pro Cys Tyr Gly Ser
                100                 105                 110

Tyr Ala Lys Pro Thr Asn Glu Asn Gly Gly Gln Gly Ile Leu Val Lys
            115                 120                 125

Gln Gln Asn Gly Lys Leu Glu Ser Gln Val Glu Met Gln Phe Phe Ser
130                 135                 140

Thr Thr Glu Ala Thr Ala Gly Asn Gly Asp Asn Leu Thr Pro Lys Val
145                 150                 155                 160

Val Leu Tyr Ser Glu Asp Val Asp Ile Glu Thr Pro Asp Thr His Ile
                165                 170                 175

Ser Tyr Met Pro Thr Ile Lys Glu Gly Asn Ser Arg Glu Leu Met Gly
            180                 185                 190

Gln Gln Ser Met Pro Asn Arg Pro Asn Tyr Ile Ala Phe Arg Asp Asn
        195                 200                 205

Phe Ile Gly Leu Met Tyr Tyr Asn Ser Thr Gly Asn Met Gly Val Leu
210                 215                 220

Ala Gly Gln Ala Ser Gln Leu Asn Ala Val Val Asp Leu Gln Asp Arg
225                 230                 235                 240

Asn Thr Glu Leu Ser Tyr Gln Leu Leu Leu Asp Ser Ile Gly Asp Arg
                245                 250                 255

Thr Arg Tyr Phe Ser Met Trp Asn Gln Ala Val Asp Ser Tyr Asp Pro
            260                 265                 270

Asp Val Arg Ile Ile Glu Asn His Gly Thr Glu Asp Glu Leu Pro Asn
        275                 280                 285

Tyr Cys Phe Pro Leu Gly Gly Val Ile Asn Thr Glu Thr Leu Thr Lys
    290                 295                 300

Val Lys Pro Lys Thr Gly Gln Glu Asn Gly Trp Glu Lys Asp Ala Thr
305                 310                 315                 320

Glu Phe Ser Asp Lys Asn Glu Ile Arg Val Gly Asn Asn Phe Ala Met
                325                 330                 335

Glu Ile